US006960471B2

(12) United States Patent
Pecker et al.

(10) Patent No.: US 6,960,471 B2
(45) Date of Patent: Nov. 1, 2005

(54) POLYNUCLEOTIDE ENCODING A POLYPEPTIDE HAVING HEPARANASE ACTIVITY AND EXPRESSION OF SAME IN GENETICALLY MODIFIED CELLS

(75) Inventors: Iris Pecker, Rishon LeZion (IL); Israel Vlodavsky, Mevaseret Zion (IL); Elena Feinstein, Rehovot (IL)

(73) Assignees: InSight Biopharmaceuticals Ltd., Rehovot (IL); Hadasit Medical Research Services and Development Ltd., Jerusalem (IL)

( * ) Notice: Subject to any disclaimer, the term of this patent is extended or adjusted under 35 U.S.C. 154(b) by 0 days.

(21) Appl. No.: 10/384,450

(22) Filed: Mar. 10, 2003

(65) Prior Publication Data

US 2003/0190737 A1 Oct. 9, 2003

Related U.S. Application Data

(60) Division of application No. 09/988,113, filed on Nov. 19, 2001, which is a continuation of application No. 09/776,874, filed on Feb. 6, 2001, which is a continuation of application No. 09/258,892, filed on Mar. 1, 1999, now abandoned, which is a continuation-in-part of application No. PCT/US98/17954, filed on Aug. 31, 1998, which is a continuation-in-part of application No. 09/109,386, filed on Jul. 2, 1998, now abandoned, which is a continuation-in-part of application No. 08/922,170, filed on Sep. 2, 1997, now Pat. No. 5,968,822.

(51) Int. Cl.$^7$ .......................... C12N 15/56; C12N 5/10; C12N 15/63; C12N 9/24; C07H 21/04

(52) U.S. Cl. .................... 435/325; 435/252.3; 435/200; 435/320.1; 435/348; 536/23.1; 536/23.2; 536/23.5

(58) Field of Search .............................. 435/325, 320.1, 435/252.3, 200; 536/23.1, 23.2; 530/350

(56) References Cited

PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*

* cited by examiner

*Primary Examiner*—Richard Hutson
(74) *Attorney, Agent, or Firm*—G. E. Ehrlich (1995) Ltd.

(57) ABSTRACT

A polynucleotide (hpa) encoding a polypeptide having heparanase activity, vectors including same, genetically modified cells expressing heparanase, a recombinant protein having heparanase activity and antisense oligonucleotides and constructs for modulating heparanase expression.

27 Claims, 34 Drawing Sheets

1 CTAGAGCTTTCGACTCTCCGCTGCGCGGCAGCTGGCGGGGGGAGCAGCCAGGTGAGCCCA

61 AGATGCTGCTGCGCTCGAAGCCTGCGCTGCCGCCGCCGCTGATGCTGCTGCTCCTGGGGC
M L L R S K P A L P P P L M L L L L G P

121 CGCTGGGTCCCCTCTCCCCTGGCGCCCTGCCCCGACCTGCGCAAGCACAGGACGTCGTGG
L G P L S P G A L P R P A Q A Q D V V D

181 ACCTGGACTTCTTCACCCAGGAGCCGCTGCACCTGGTGAGCCCCTCGTTCCTGTCCGTCA
L D F F T Q E P L H L V S P S F L S V T

241 CCATTGACGCCAACCTGGCCACGGACCCGCGGTTCCTCATCCTCCTGGGTTCTCCAAAGC
I D A N L A T D P R F L I L L G S P K L

301 TTCGTACCTTGGCCAGAGGCTTGTCTCCTGCGTACCTGAGGTTTGGTGGCACCAAGACAG
R T L A R G L S P A Y L R F G G T K T D

361 ACTTCCTAATTTTCGATCCCAAGAAGGAATCAACCTTTGAAGAGAGAAGTTACTGGCAAT
F L I F D P K K E S T F E E R S Y W Q S

421 CTCAAGTCAACCAGGATATTTGCAAATATGGATCCATCCCTCCTGATGTGGAGGAGAAGT
Q V N Q D I C K Y G S I P P D V E E K L

481 TACGGTTGGAATGGCCCTACCAGGAGCAATTGCTACTCCGAGAACACTACCAGAAAAAGT
R L E W P Y Q E Q L L L R E H Y Q K K F

541 TCAAGAACAGCACCTACTCAAGAAGCTCTGTAGATGTGCTATACACTTTTGCAAACTGCT
K N S T Y S R S S V D V L Y T F A N C S

601 CAGGACTGGACTTGATCTTTGGCCTAAATGCGTTATTAAGAACAGCAGATTTGCAGTGGA
G L D L I F G L N A L L R T A D L Q W N

661 ACAGTTCTAATGCTCAGTTGCTCCTGGACTACTGCTCTTCCAAGGGGTATAACATTTCTT
S S N A Q L L L D Y C S S K G Y N I S W

721 GGGAACTAGGCAATGAACCTAACAGTTTCCTTAAGAAGGCTGATATTTTCATCAATGGGT
E L G N E P N S F L K K A D I F I N G S (T)
781 CGCAGTTAGGAGAAGATTATATTCAATTGCATAAACTTCTAAGAAAGTCCACCTTCAAAA
Q L G E D Y I Q L H K L L R K S T F K N (F)
841 ATGCAAAACTCTATGGTCCTGATGTTGGTCAGCCTCGAAGAAAGACGGCTAAGATGCTGA
A K L Y G P D V G Q P R R K T A K M L K

901 AGAGCTTCCTGAAGGCTGGTGGAGAAGTGATTGATTCAGTTACATGGCATCACTACTATT
S F L K A G G E V I D S V T W H H Y Y L

961 TGAATGGACGGACTGCTACCAGGGAAGATTTTCTAAACCCTGATGTATTGGACATTTTTA
N G R T A T R E D F L N P D V L D I F I

1021 TTTCATCTGTGCAAAAAGTTTTCCAGGTGGTTGAGAGCACCAGGCCTGGCAAGAAGGTCT
S S V Q K V F Q V V E S T R P G K K V W

1081 GGTTAGGAGAAACAAGCTCTGCATATGGAGGCGGAGCGCCCTTGCTATCCGACACCTTTG
L G E T S S A Y G G G A P L L S D T F A

1141 CAGCTGGCTTTATGTGGCTGGATAAATTGGGCCTGTCAGCCCGAATGGGAATAGAAGTGG
A G F M W L D K L G L S A R M G I E V V

1201 TGATGAGGCAAGTATTCTTTGGAGCAGGAAACTACCATTTAGTGGATGAAAACTTCGATC
M R Q V F F G A G N Y H L V D E N F D P

1261 CTTTACCTGATTATTGGCTATCTCTTCTGTTCAAGAAATTGGTGGGCACCAAGGTGTTAA
L P D Y W L S L L F K K L V G T K V L M

1321 TGGCAAGCGTGCAAGGTTCAAAGAGAAGGAAGCTTCGAGTATACCTTCATTGCACAAACA
A S V Q G S K R R K L R V Y L H C T N T

1381 CTGACAATCCAAGGTATAAAGAAGGAGATTTAACTCTGTATGCCATAAACCTCCATAACG
D N P R Y K E G D L T L Y A I N L H N V

1441 TCACCAAGTACTTGCGGTTACCCTATCCTTTTTCTAACAAGCAAGTGGATAAATACCTTC
T K Y L R L P Y P F S N K Q V D K Y L L

1501 TAAGACCTTTGGGACCTCATGGATTACTTTCCAAATCTGTCCAACTCAATGGTCTAACTC
R P L G P H G L L S K S V Q L N G L T L

1561 TAAAGATGGTGGATGATCAAACCTTGCCACCTTTAATGGAAAAACCTCTCCGGCCAGGAA
K M V D D Q T L P P L M E K P L R P G S

1621 GTTCACTGGGCTTGCCAGCTTTCTCATATAGTTTTTTTGTGATAAGAAATGCCAAAGTTG
S L G L P A F S Y S F F V I R N A K V A

1681 CTGCTTGCATCTGAAAATAAAATATACTAGTCCTGACACTG
A C I

Fig. 1

```
mouse  CTGGCAAGAAGGTCTGGTTGGGAGAGACGAGCTCAGCTTACGGTGGCGGT 50
human  CTGGCAAGAAGGTCTGGTTAGGAGAAACAAGCTCTGCATATGGAGGCGGA 1115

mouse  GCACCCTTGCTGTCCAACACCTTTGCAGCTGGCTTTATGTGGCTGGATAA 100
human  GCGCCCTTGCTATCCGACACCTTTGCAGCTGGCTTTATGTGGCTGGATAA 1165

mouse  ATTGGGCCTGTCAGCCCAGATGGGCATAGAAGTCGTGATGAGGCAGGTGT 150
human  ATTGGGCCTGTCAGCCCGAATGGGAATAGAAGTGGTGATGAGGCAAGTAT 1215

mouse  TCTTCGGAGCAGGCAACTACCACTTAGTGGATGAAAACTTTGAGCCTTTA 200
human  TCTTTGGAGCAGGAAACTACCATTTAGTGGATGAAAACTTCGATCCTTTA 1265

mouse  CCTGATTACTGGCTCTCTCTTCTGTTCAAGAAACTGGTAGGTCCCAGGGT 250
human  CCTGATTATTGGCTATCTCTTCTGTTCAAGAAATTGGTGGGCACCAAGGT 1315

mouse  GTTACTGTCAAGAGTGAAAGGCCCAGACAGGAGCAAACTCCGAGTGTATC 300
human  GTTAATGGCAAGCGTGCAAGGTTCAAAGAGAAGGAAGCTTCGAGTATACC 1365

mouse  TCCACTGCACTAACGTCTATCACCCACGATATCAGGAAGGAGATCTAACT 350
human  TTCATTGCACAAACACTGACAATCCAAGGTATAAAGAAGGAGATTTAACT 1415

mouse  CTGTATGTCCTGAACCTCCATAATGTCACCAAGCACTTGAAGGTACCGCC 400
human  CTGTATGCCATAAACCTCCATAACGTCACCAAGTACTTGCGGTTACCCTA 1465

mouse  TCCGTTGTTCAGGAAACCAGTGGATACGTACCTTCTGAAGCCTTCGGGGC 450
human  TCCTTTTTCTAACAAGCAAGTGGATAAATACCTTCTAAGACCTTTGGGAC 1515

mouse  CGGATGGATTACTTTCCAAATCTGTCCAACTGAACGGTCAAATTCTGAAG 500
human  CTCATGGATTACTTTCCAAATCTGTCCAACTCAATGGTCTAACTCTAAAG 1565

mouse  ATGGTGGATGAGCAGACCCTGCCAGCTTTGACAGAAAAACCTCTCCCCGC 550
human  ATGGTGGATGATCAAACCTTGCCACCTTTAATGGAAAAACCTCTCCGGCC 1615

mouse  AGGAAGTGCACTAAGCCTGCCTGCCTTTTCCTATGGTTTTTTTGTCATAA 600
human  AGGAAGTTCACTGGGCTTGCCAGCTTTCTCATATAGTTTTTTTGTGATAA 1665

mouse  GAAATGCCAAAATCGCTGCTTGTATATGAAAATAAAA 637
human  GAAATGCCAAAGTTGCTGCTTGCATCTGAAAATAAAA 1702
```

Fig. 13

```
ggatcttggctcactgcaatctctgcctcccatgcaattcttatgcatca   50
gcctcctgagtagcttggattataggtctgcgccaccactcctggctaca   100
ccatgttgcccaggctggtcttgaactcttgggctctagtgatccacccg   150
ccttggcctcccaaagtgctgggattacaggtgtgagccatcacacccgg   200
ccccccgtttccatattagtaactcacatgtagaccacaaggatgcacta   250
tttagaaaacttgcaatggtccacttttcaaatcacccaaacatgttaaa   300
gaaattggtatgactgggcatggcacagtggctcatgcctgcaatcctag   350
cattttgtgaggctgagacgggcagatcacgaggtcaggagattgagacc   400
atcctgacagacatggtgaaatcccatctctactaaaaatacaaaacaat   450
tagccgggggtgatggcaggcccctgtagtcccagctactcgggaggctg   500
aggcaggagaatggcgtgaatccaggaggcagagcttgcagtgagccgag   550
atggtgccactgcactccagcctgggcgacagagcgagactccgtctcaa   600
aaaaaaaaaaaagaaagaaattggtatgactgttgactcacaacaggag   650
tcaggggcatggggtggggtgtaagattaatgtcatgacaaatgtggaaa   700
agaaacttctgtttttccaactccacgtctgctaccatattattacactc   750
ttctggtagtgtggtgtttatgtgtgaattttttttcatatgtatacagt   800
aattgtaggatatgaacctgattctagttgcaaaactcactatgagctta   850
gcttttaagttgcttaagaataggtagatctatgcaaataatgataatta   900
ttattattattttaagagagggtctcactttgtcacccaggctggagtgc   950
agtggtgtgattaagggtcactgcaacctccacctcccaggctcaaataa   1000
acctcccacctcagcctccccagtagctggaaccacaggcacgggccacc   1050
acgcctggctaatttttttgtatttttttgtagagatggggtttcatcatgt   1100
tgcccaggctgttcttgaattcctcggctcaagcaatcctcccaccttgg   1150
cctcccaaaatgctggcatcacaggcatgatggcatcactggcatcacat   1200
accatgcctggcctgatttatgcaaattagatatgcatttcaaaataatc   1250
tatttttatttgttgccttattggtggtacaatctcaagtggaaaaatct   1300
aagggttttggtgttatttgcttactcaaccaatatttattagactctta   1350
ctaagcaccaacatgatcacatgcctgagctatggctagcatagcgtgtg   1400
agacaaacttaatctctgttttggtggagcatataatctagtagatgaag   1450
ccaatgttgagcaacatcacaatactaacaaattgaggatgctacgagag   1500
tgtctaacaaattgaggatgctacgagagtgtctaacaaattgaggatgc   1550
tatgagagtgtgtcatggagagctgcctggagattgagagaaagcttcct   1600
tgagggaagttacatttcagctgaaacacactgccatctgctcgaggttt   1650
tgtaactgcattcacatcccgattctgacacttcacatcccgattctgac   1700
acttcacccagttactgtctcagagcttgggtccgcatgtgtaaaacaag   1750
gacagtatgcacttggcagggttgtgagaagggaagagaacacaagtaaa   1800
gcacctgtatcaggcatacagtaggcactaagcgtgcgatgcttgctatg   1850
attatacatcagtgtaagcatcaaggaaaagctgaagaaaagtctgacca   1900
acagcgaaagataaatgcgcagaggagaaatttggcaaaggctccaaatt   1950
caggggcagtccgtactctacactttgtatgggggcttcaggtcctgagt   2000
tccagacattggagcaactaaccctttaagattgctaaatattgtcttaa   2050
tgagaagttgataaagaattttgggtggttgatctctttccagctgcagt   2100
ttagcgtatgctgaggccagatttttttcaagcaaaagtaaaatacctgag   2150
aaactgcctggccagaggacaatcagattttggctggctcaagtgacaag   2200
caagtgtttataagctagatgggagaggaagggatgaatactccattgga   2250
ggttttactcgagggtcagagggatacccggcgccatcagaatgggatct   2300
gggagtcggaaacgctgggttcccacgagagcgcgcagaacacgtgcgtc   2350
aggaagcctggtccgggatgcccagcgctgctccccgggcgctcctcccc   2400
gggcgctcctccccaggcctcccgggcgcttggatcccggccatctccgc   2450
acccttcaagtgggtgtgggtgatttcgtaagtgaacgtgaccgccaccg   2500
aggggaaagcgagcaaggaagtaggagagagccgggcaggcggggcgggg   2550
ttggattgggagcagtgggagggatgcagaagaggagtgggagggatgga   2600
gggcgcagtgggaggggtgaggaggcgtaacgggGCGGAGGAAAGGAGAA   2650
AAGGGCGCTGGGGCTCGGCGGGAGGAAGTGCTAGAGCTCTCGACTCTCCG   2700
CTGCGCGGCAGCTGGCGGGGGGAGCAGCCAGGTGAGCCCAAGATGCTGCT   2750
                                          M  L  L
GCGCTCGAAGCCTGCGCTGCCGCCGCCGCTGATGCTGCTGCTCCTGGGGC   2800
 R  S  K  P  A  L  P  P  P  L  M  L  L  L  L  G
CGCTGGGTCCCCTCTCCCCTGGCGCCCTGCCCCGACCTGCGCAAGCACAG   2850
```

Fig. 16

```
P  L  G  P  L  S  P  G  A  L  P  R  P  A  Q  A  Q
GACGTCGTGGACCTGGACTTCTTCACCCAGGAGCCGCTGCACCTGGTGAG   2900
 D  V  V  D  L  D  F  F  T  Q  E  P  L  H  L  V  S
CCCCTCGTTCCTGTCCGTCACCATTGACGCCAACCTGGCCACGGACCCGC   2950
  P  S  F  L  S  V  T  I  D  A  N  L  A  T  D  P
GGTTCCTCATCCTCCTGGGgtaagcgccagcctcctggtcctgtcccctt   3000
R  F  L  I  L  L  G
tcctgtcctcctgacacctatgtctgccccgccagcggctctccttcttt   3050
tgcgcggaaacaacttcacaccggaacctccccgcctgtctctccccacc   3100
ccacttcccgcctctcattctccctctccctcccttactctcagacccca   3150
aaccgcttttgggggtatcatttaaaaatagatttaggggttacaag   3200
tgcagttctgttccatgggtatattgcattgtggtggcatctgggctctt   3250
agtgtaactgtcacccgaatgttgtacattgtatctaataggtaatttct   3300
catccctcatccctctcccaccctcccacctttggagtctccagtgtct   3350
actattccactaagtccatgtgtacacattgtttagcgcccactctaaat   3400
gagcctttttgtttcattcattctgtaagtgttgaataggcaccacctaa   3450
ggtcaggtataagtggaaatttgaaaaagaaactgcccacttgccccagt   3500
acttccctagccaagaggagggaaaccaggcaggtgcacctgaaggcctg   3550
tgagtgcttgatttgctgtgcagtgtaggacaagtaagattgtgcatagc   3600
cttctgtatttaagactgtgttaggaagatttctctttcttttcttttct   3650
ttttctttttttcttttcttttttttttttaggcagatgaaaagggcgtca   3700
cagaacaggaataaaaatctaaatattcaataaatgagacctaggagact   3750
actgcagtgacttacaaagtcctaataaaagatgtctctccaaaatggg   3800
gctgcaaaatgtggtgctgccttatcagctctaagtttttccttacctg   3850
agaaagaaggaacctgatgcaggttcagggctcctgccccatgaatgcag   3900
gctgactccaagatggggagctacagggacaatcccaggtcttctaggcc   3950
tcttatttaggccctgggagcctccagagatggccacatcttgaccagcc   4000
cagatagagggaaagatcaccattatctcacctctgtgtcaaatacctag   4050
atgctgtcctccctgagcccacactatagttgccagcgctaatttaatgg   4100
gtagtgtactggttaagagatggacagaccatcctggcttgactctcagc   4150
tctggcaaagatgagtgacttggtttttccatatctcttggccacaccaa   4200
ccttgatttcttcagctgtagaatggaatttctcaagcttgcctcaagga   4250
ttattgcccgaggatttgatgatatggtaagagcttctcagtgtttgacc   4300
catagtaagtgtttgacgtttcaaacgaattgtttctttctaggacatgg   4350
tgagcatttggtagccattcaccggttttctgtttctttggatcatagtt   4400
aacctctccttttccttctggcactacaattttctggtggggaagaatcc   4450
ttactttctgcccttccccttaaggataggaagctgatactaggcagcaa   4500
ctagttgggggataggaagattgttccagagaaatgctgaaccatagggc   4550
tccagatcacaggaccccagtcttagcttgctggggtgtggggtgggggg   4600
gggcggttactgaacatgggtatgaagtagatgtccatttactgaaatgt   4650
gaggacctgaggcctcttctattgctgtagccagcatattccccaacctc   4700
tccccaagaaaggacagatgggggttccccccctggagtaacaggtccaaa   4750
agaaaaaacatacagtgggacttccaggatctgggcctgatcacccagca   4800
gtcaagctccccgcaattgactaacaccccccctaacacgtagaaattcca   4850
atctgcaatttagtgaggatgatacctttattcttcttaaatacatctct   4900
tcatttcccagagcaccctttttttcccctcctctgcaccttttttgttaaa   4950
gactggagtataatgaaataccaagagagcataacatgtgatacataaaa   5000
ctttttttctggtttacaaaacagttcattcttgtccatacgtgcttctc   5050
tccaaggctggctgctgtctgttccagcccgcttcgcttggagaggccat   5100
ctgccatacctgctccccagacgcatcgacaagcacacccagagtgttat   5150
ctgctaagacctaaaagagggaggaacccccctctcctcatctaagaccta   5200
gcttctaaattagagtgtgagggtccatctccccaggagggggcacagggc   5250
ccaaacagcccagccatctcagaagacaacactaagctttgtaggggtcc   5300
acagtagaggagagtaagacgcctgttgtttaatttattacagttcctca   5350
aaagtgaagatgtgtgggcgggatggcaagagctgagcagacgaaagctg   5400
aaggaataaggaaagagaggaggacacaaacagctgacacttcctcagtt   5450
cttgtcatttgcctggccctgttctaagcaccttctaggtattaatccat   5500
ttagtcttggctacaacactgtgagtaactagttttgtcaccccccatttt   5550
aaaaatgaagaaagtgaggctcagggaggttaagtaacttggccacagtt   5600
tgaaactagactctgatcacatgagataatagtgcccataaaagggaaa   5650
gcagattatatttttaaaggaaagagagtaggatatggtagaaaaagat   5700
```

Fig. 16 (continued)

tgtttggaaaggaattgagagattgatataatgaaaagaagcattcacat 5750
gagagtaacagtatcagggcccaaaccttcatctaaggtacttcaaagag 5800
gcctaagcaaacttagtcactggcgtggttctagtctccatgatggcaaa 5850
tacattgtgtacagcccaactccacacaaacttaaataccaatgataga 5900
gcaatctaaaatttgaaagaaaaaatctttcaatttgtcgtcttcccaga 5950
gggacttaatcaagaaaccaatcaaaatacttcctaagcctaactgtgtg 6000
cagaactccaaagagagcccagccctaaatcaacactgtccaatggaaat 6050
ataatataatgtgggcctcatatgcaaggtcatatgtaattttaaatttt 6100
ctagtagccatattaaaaggtaaaagaaacaagtgaaattaattttaa 6150
taattttatttagttcaatagatccaaaatgttttctcagcatgtaatca 6200
atataaaaatattaatgaggtatttattattcctttttctcaaaccaagtc 6250
tattctataatctggcgtgtattatttacagcacttctcagactatattt 6300
ctttctttctttttttttttccgagacaatttgctcttgtcacccaagct 6350
agagtacaatggcgttacctcggctcactgcaacctccgcctcccgggtt 6400
caagttattctcctgcctcagtctcccaagtagctgggactagaggcatg 6450
caccaccacgcctggctaattgtgtatttttagtagagacagggtttcac 6500
catgttggccaggctaatctcaaactcctgagctcaggtgatatgcccac 6550
ctcggcctcccaaagtgttgggattacaggcgtgagccactgcacccggc 6600
ctcagattaactatatttcaagcgttcagtagccacatgtagctagtgct 6650
atggtagtggacagtacagatctgcatttcaattaagacacgtatacaag 6700
catagttcactaatgcacggtaaaaaaagtatagtgctgagtcggtggt 6750
agaaatcctaaatactgcagagcaaaagtggtacgaacagcaatctcagt 6800
gataatgcaaccatgcttgcttttcattgcaatttgcttattttccttca 6850
gcaaagttcatccatttttgccaattcaataaatatttactgataaaaac 6900
tttcaatattagattcttgcatcttcatagacagagttgcttttcacatt 6950
tagaaaattacttatcaatgttaaacacacgttttgataaccagtgttgg 7000
aaagaggtgcagactccccatgtgcctattgatggcagaaatattcacag 7050
ccaaagggaaacaaagggctggggacaatcacacacctcatgtctcctaa 7100
ctcctgggaagtgctgtccctctgattgagctcttattattgccttcccc 7150
actaaccctgtccactgtgccctggagccctttgcagggttacctgctct 7200
gtcctcctcacagaatatctcctctacctccttgtccaagctacaacttg 7250
gctattctctgatgacactgtcttccctgtagcccttttgagtaatggct 7300
gcatattctcccatagtccagttcttttcctgttctccagtctggcttct 7350
ggatgacagcccactagtttgaactccatactgctatagttcaagtccct 7400
tttgacttgttaccttgggcaaattacctcctttttgttcaggttccttgt 7450
ttgtaaaatgacgataataatgccatttgcttcagtgggttattttgaaa 7500
ttgagtgaaagaaggcgggtagcttccctacacgctcagtgtagactagc 7550
ctgatgtgcattacgggtgatgccatgactcagtgtgttttcctcatctc 7600.
cacatctggctctcatccagtgctcctgcttacggcactctgtcccccctc 7650
ttacttactcccccttattaactgaagactggcactgatctcacagtttc 7700
ctctccacttcctagtctcaccatcatcctagatgacttcaagtcaccta 7750
gataaactgtctcagtttcttcactcacatttttttataacagataatgt 7800
tacactcaagttgtaacagaaccagcttatccagctcatgaaatgtatgc 7850
atttcatctcaactctgtattcagtgacatcctgtgggtatctggaaatc 7900
agccatggtgagaatatttaccatggaaattggcaaatactaaaaagcag 7950
agcacctttttttctgagagccagaccatagctcttctactccatagcac 8000
ccatcataacaattttttaaatacctccactgaacagcttcttcctctctc 8050
tacttcttccatatctgatttgagcttcttaatttatcatgtgaaccact 8100
cttgtaataataaccccaaatccctgttccattgttcttcctgctaaaat 8150
actaaacctggtttagtccaaccatatttctctctttggaatctacagg 8200
gtggcccaaaaacctggaaatggaaaaatattacttattaattttaatgt 8250
atattaataagccattttaatgcttcatttccagtctcagtggccaccct 8300
gtatagctgggctattgagctcttgcgggaggagggagtggacagtctcc 8350
cagccacacagactgatgttgcaccaaacatttttagcttccagacttc 8400
cctggccccttagtgttacccttaactctccatttctctgcctttcacatt 8450
ctctacttttttaaaaatctctgactccaccttcaccttatcattcttagc 8500
acatgaccatacttctgcttcccaaagaaaatgagcaattacttcctttt 8550
cctttttcctcctgtcatcaaatctgcagacatgtcatgcctaagtccagc 8600
tttcctcctttctctgatctcagtctgcttcttccatttctgccctgaat 8650
cccgtcccctccccaacccccaaggacttcgctctatcagtcacctcttc 8700
cctctcctgtatcttcaactcctcccatttttactggcttcttcctcaagc 8750

Fig. 16
(continued)

```
ctttccccaagcctttcccatctcaattacctcctcgcacatgcctctgc    8800
agaaaccaccccgtttcttccctcccctcggcagcctgttcttcctgttc    8850
tgccctcatgatggcaccatcattgtgtcactaaaatcaatctctccgac    8900
atcatcaatggccttcctttgttgggaaacctaataaacactttatctta    8950
tttggtctttgttatgggttgaatgaggttaccccgaaatccatattaga    9000
agtcctaacccccagtacctcagaatgtgactttatttgggaatagggtc    9050
attgcagacgttattagttaggatgaggtcatactggaatgtgatgggct    9100
gcttatctaatatgactgatgtccttataacaaggagaaatttggagaca    9150
gacacgcacatagggagaataccatgtgatgacaggagttatggagttgg    9200
agtcaaaagctatgggaacttaggagaaagacctggaacaaatcctttc    9250
ctgcgcctagagagggagtatggccctgccactaccttgaattcaacgtt    9300
tcggcttttcaaaactgtaagacaatacatttctgttgttcaaaccaatt    9350
agtttgcagtactctgcgactgcagccctaacaaactaatacagtctctt    9400
ggaggcatttggcaaggttgacaatggaagcactttcttacccctttagg    9450
tctgtcgcctttcttgttgggggtgttttctaacaattcctctccatct    9500
ctctctctctagtttgtcttaaacattggtgttcttcagacttctgacct    9550
aggccttctttttcacttcacatattcccctgggtggtctcacccacttcc    9600
agaaattacttaaattactgctcatgcagtactgtgctggaaactgttta    9650
acaactggctctctgggaagaggggagactggttgatggttttgctgat    9700
ttctgtggtgtaaatactccctccatggccaattccaaactgccaacagt    9750
ttaacaactggctcacaaatttctccaaatttaacatttggctttcaca    9800
ggccaacaacgtggtacagccaactccagcacacctctgcttttgtgtca    9850
gagagaagtaacttatttttgtacaaaaggtaaaataaaaacacctgcag    9900
gcccccttttttccttaacaaactgctctagaaatagaatagctgaagc    9950
ttcttttatgcattcatctgttatttccatgtcactgtggtggtgggatt    10000
atttttcctttatttttcttgtatatggttgaaatactgtacctttgatc    10050
agttttagttttatggcatgttttgcacccatattaaatctagtttttgt    10100
cagagggcgtcaatattatttctcaaaacaagaaaatatttcattgcaa    10150
aggagacaaacaaaaaggtccttaataccaaaactttgaaatgtgatttc    10200
ttgtacttggcagtgtccaagtggtaaacccaaacagtattgggttttca    10250
ttttgttcaggaaagtctttgtctggcagcgacttacccttacatcaggc    10300
gggccttgctcattcattcacttaagtatttattaaacaccagcggtgtg    10350
ccaagtacttatctaggtatcgggtagattctgataagtcagtcaggtcc    10400
ctgctctcagggagcttgcagcagagatgggggctgcaatagagagtaag    10450
ccaaggaaatgaaaaaggaagttgatttcagagagtgatgaatgctatga    10500
agaaaatgaaggcagcgcagtgtgatggagagtgacccaaggtggtacag    10550
tttgtacctctaaggaccagactgtgacccaggtcactcacagatgcccg    10600
tcatgtgatgccacagcaacttttccaggtgctcgtttcctcccacttcc    10650
cagtctcttgcccagccgcgactgcttacaaatacagctagaggaatcta    10700
aatgaggttcctctatcatcaaacccaatcaaaatgccaaggaacagaat    10750
cagtgcctggctgaaggcagtggaacagggccagcctggagtggttctct    10800
ctgaggaagttcctcatcttggttttagggccataccttgtgacctgtga    10850
gctaggggttgccagtccctgacatttctactgaggactcgcctgtctat    10900
attcccggcctgtatgtgtctcctgagttccagacacacagggcgaagcg    10950
cctgatggatggaagtatgtttttttggtgttccattggtatctcaaattc    11000
tacaaaacttagtgccccttctcctccctgttcctccccatcttcagtct    11050
atcacctgttcctcatccagcaaatgatattaccatcttccaaggagctt    11100
cccaggagtaatccttgactcctcctcaacatccaattaataatcaaatc    11150
taggccaggtacaatagctcacgcctataatcccagcactttgggaggct    11200
gaggcaggtggatcatttgaggccaggagttcaagaccagcctggccaac    11250
aaggtgaaacctgtctcatttaaaaaaagttattttaaaaactcaaatct    11300
attatttctacctctaagtgtgtcttgaatttatccatctctctccatct    11350
ctgagctgttaccttacctcagtccatcacgttttgtctacgttaacatg    11400
accagagtcttgttcttagtctggtgaggtcactccagctgcttcagatc    11450
cttccatggctcaccgttgccctcatataaagttggcactcctggacatg    11500
tggcttacggggccctccgtgatgtggccctatttgcttctccattctgt    11550
tctctcccagcctctctgcccccatctctaggcaccaaccacacccttct    11600
gctcgtcaatggtgccagcttctcttctatctctggtctttggacagact    11650
tttcccttcacctggaatgctttcttcaatcctaccccactctctttaat    11700
ctagataaggtttattctttttgaatgtctagcagtgaaaccatttcccc    11750
tgaaaaaccttctctaaccaacccccctaccctcagcccaaggtctagatt    11800
```

Fig. 16 (continued)

aggagtccctctgaatgtttccatagcattttaaagaattgcctattta 11850
cttgttcgtatctatcactaaactacaaattgtatgagaacagccactat 11900
ctctgcctggttcaccattcatctccagcaactagcataatgcctggcag 11950
agtcagcctgcaacaaatatttgttgaataaattaacagatggctttatc 12000
tccttaagtaaatcttgctttttcacctattaaaacagacgcacaggcc 12050
aggtgtggtggcccatgcctgtaatcccagcactttggcaggctgaggtg 12100
ggcggatcacctgaggtcaggagttcaagaccagcctggccaacatggtg 12150
aaaccccatctctaataaaaatacaaaaattagctgggcatggtggtggg 12200
tgcgtatagtcccagctactagggaggctgaggcaagagaatcgcttgaa 12250
cccaggaggcagaggtggcagtgagccgagatcatgccactgtactccag 12300
cctggatgacagagaccctgtctcaaaacacacacacacacacacacaca 12350
cacacacacacacacacacacacacaccaagttgtataatttaaaata 12400
taacgtgcttgttatggaacacttgtaaaatacaggaaagtaatgaaaaa 12450
gtctaccatctagctcaccacataatgaccattgctatcatcctggcata 12500
attctctcctgtatataaatatatattcttttattgttaaaattacacta 12550
tgagtactatttatttattttactgtggcaaaatgcgcaaaacataaaat 12600
cttgccattttaaggtatgcagtttggtgcattcaccacactcacattgt 12650
tgtgcaaatatcaccactatctatctcagaacttcttcgtcttcccaaac 12700
tgaaactctgtacccattaaacaatagtgcatcctctgtttttcccctccc 12750
tacaatttattttatttgggtttgtaccaaactgaaaatagctgcttct 12800
tccttacttagttcagattagcatttccatttatttagccgtggttttga 12850
ggatgccatgacagatgccatccttcctagagctctttggggctgtcagg 12900
tatttcagtcagggtgaattcgggttgataacattttaaaatctcacttt 12950
attctgaggttcctagtgtcagagcccaccgtatttttagggactcccaa 13000
gttacaaacaaaaatatggtgaggaggaatcactgaagttttaacacaag 13050
agacttacattttgttcaatttctatcttttagtttatttcctaagcata 13100
aagaaatactttgaaaattttacatagcattatacatatttaattaagca 13150
tgagcacatcttaaaactttaaattttagatcagatctttaattcctagg 13200
atattaagaggtactggcaatttggccaggtgtggtggttcacgcctata 13250
atcccaacactttgggagggtgaagtgggcgaattgctagagcccaggag 13300
gtggaggctgcaatggcctgagatcacgccatcgtactccagcctggatg 13350
atgagaatgaaatcctgtctcaaaaaaaaaaaaaaaaaaaaagaagaa 13400
gaagaagtattggcaatcagtgctccaggaataatttcctgacttgaaat 13450
aaacctacatgtagacaaactaattaggccattccaagagttgctagcat 13500
tggtttaatatgttttcagagcattccaggaagcagtgtggccagcattg 13550
catgtttgatacttcagaaatgtatgacaggtgtttctcttacccaggtc 13600
ttctgttttcttagttttgctcatgtaaatatttatgaacatcctcatct 13650
ttttgagggaagggattatagatcattctaattccattttctagcatttg 13700
gtaccattctaagcacatgataggcacccatttggagcatttttggcttg 13750
acagaatatgcatttagaattgttcaaattagaggtgtcagtgatgggaa 13800
ttagaatactatataattctaagtcatttgacttaaatacaaaagaatga 13850
ttttccttggtggggaatggtgaagggaggcaggagttaagaagaggaga 13900
agagatcctaagtcatttataaacttctctggaaagacaggtgtgtgaag 13950
acttttaaaaagtcattcaccaaattgtgtgtgtgtgtgtgtgtgtt 14000
ttaaatagactttatttttttagagcagttttaggttcacagcaaaattga 14050
atgcaaggacagagatttcccataaacccccctgcccacacacatgcatag 14100
cctccctcattatcaacatccccaccagagaggtgtttgttctagttgat 14150
gaacctacactgacacatcattatcacccaaagtccatagttcacggcag 14200
ggttcactgtcggtgtacattctatgggtttgagcaaatgtataatgaca 14250
tgtatccaccattatagtaacatacagagtattttcagtgccctgcaaat 14300
cccctgttctccacctattcatccctccctctctgcatttccacccccag 14350
cccctggtaaccgctgatctttttactgtcccatagtttcggacgatcta 14400
tttttcagacagacacagagctgtctttcccttagtttctattctatcat 14450
ttctttctccccatccatcataaaaggctatgagtttttttttaagtgttg 14500
aacaccatcctacttgtcaagttaaaacataagctcctggctgggtacag 14550
tggctcatgcctgtaatctcagcattttgggaggctgtggcagaagcatc 14600
acttgaagccagaagtttgagaccagcctgggcaacatagcaagacccca 14650
tccctccacacacaaacacacacacacacacacacacacacacacaca 14700
cacacacacacacaaaaacaagctcttgccagaattagagctacaaattg 14750
ccctcaggttcctagaagatcagtccttcaattagattcagattgagatg 14800
cttcctcttttaaacaatgattccctttctatcatgcccaataagaaaac 14850

Fig. 16
(continued)

```
aaataaaaattaaacaatactgcctgtaatctcagctacccaggaggcag  14900
aagcagaactgcttcaacccggcaagcagaagttgcagtgaagtgagatc  14950
gcgccactgcactccagcctgggaaacagagcaagattctgtctcaaaaa  15000
caaaacaatgtgatttcctcctctaagtcctgcacagggaaatgttaaga  15050
aataggtccaccaggaaagaaggaagtaagaatgtttgactagattgtct  15100
tggaaaaaatagttatactttcttgcttgtcttcctaacagTTCTCCAAA  15150
                                          S  P  K
GCTTCGTACCTTGGCCAGAGGCTTGTCTCCTGCGTACCTGAGGTTTGGTG  15200
 L  R  T  L  A  R  G  L  S  P  A  Y  L  R  F  G
GCACCAAGACAGACTTCCTAATTTTCGATCCCAAGAAGGAATCAACCTTT  15250
G  T  K  T  D  F  L  I  F  D  P  K  K  E  S  T  F
GAAGAGAGAAGTTACTGGCAATCTCAAGTCAACCAGGgtgaaaatttta  15300
 E  E  R  S  Y  W  Q  S  Q  V  N  Q
aagattcactctatattttaattaacgtcagtccgtcatgagaatgcttt  15350
gagaaaactgttatttctcacacctaacaattaatgagattaacttcctc  15400
tcccctcatctgacctgtggaggaatctgaacaagaggaggaggcagtgg  15450
gcaggtttccttatcatgatgtttgtcatgttcagtgtgaggcctcacaa  15500
aaaaaaaaaaaaaaaaaaggcgtcctggatataactgagagctcattg  15550
tacagtaaatattaataaaacagtgattgtagctgaaggatagaactgct  15600
tggagggagcaagtgggtagaatcgcgtcaaactaaagagcatttctagc  15650
caaagacacaatgatagattgaaggatatttattctaaatatagaatatg  15700
ggtgaacgagatctgtggacttctgggctccaacgttagattctgatttt  15750
agcaagcttgtcaggggattctgatattgaaaggctgtggccttcacctg  15800
agaaacctgccctagggggccatgaaaatttgtcctgtctttcagaagtg  15850
ctatcagacatcaaatggaagttaaatcgtatcttaacaattactaggat  15900
gggcgcagtgactcacacctgtaatcccaacactttgggaggctgaggca  15950
ggaggatcacttgagcccaggagttcgggaccagcctgggcaacatagag  16000
agacgttgtctctatttttttaataatttaaagagaaaaaaatactgaaaa  16050
tattgtatacaccactgaattataataatgtgtatataatgtatatattc  16100
attatgaggaatatttgattatttcatatattatatcttttccttctgtt  16150
tattttatccagttatgaagtatttagaacaattcatcagtaattggggc  16200
taaattgacagaatagtaatcagagaaaatagaaaaagacagatgggtta  16250
tctttgaataccaggttggagttgtttatgggtttgtttttttgttttggg  16300
ggcgtttttttagacagagtcccactctgttgcccaggctggagtgcagt  16350
ggcacaagcatggcccactgcatccttgacctcttgggctcaagcaatct  16400
tcccaccttagcctcctgagtagctgggaccacaggtgcatgtcaccaca  16450
cccagctaatttttttattttttgtagagacagtctttctatgttatcca  16500
ggctgatctcaaactcctgcactcaagtgatccccctgccttggcgtccc  16550
aaagtattgggattataggcatagccaccacacccaacctagtttctatt  16600
tagacttggccctttcccaccagtcatttgtgtccaaaagatctcataaa  16650
tgtagacaggaaactgtcctttgctcatcagttttcttcatcctgtgtct  16700
aggggggatggtcggtgggggaaactggggttatgcaagttcctctgaaac  16750
atcctctgtgagcccagggatggatgaggcaccagccgccagcgagtcag  16800
tgtgcagctttccagaaaggaagtcatcagccagtcagccggccctggca  16850
gccagcacccggcaaccctgctgtcttgtgataaagaaatggtctgcctg  16900
acaggatggtgtggatttttctttttcttttttttttttttgagacagg  16950
gtctggctctgtcgcccaggctggagtgcaatggcgggatcttggctcac  17000
tgcagcctctgcctcccaggctcaaggcatcctcccacctcggtctcccg  17050
agtagctgggaccacaggcacacaccaccacgcccaactaagttttcgta  17100
tttttagtagaggcagggtttactatgttgtccaggctagtctcaaact  17150
cctgagctcaagctatccatctgccttggcctcccaaagagctggaatta  17200
caagcgtgagccactgtgcctgaccagggtggatttttttcaagtgcacat  17250
gttgtggtcccagaagctctgatggtaccaaattccaagcgaaaaaaagt  17300
caatggttcccacccatcctacctcccatgatggcaagaggaaatcacca  17350
cactgcagatacagtccatgtaaaacaaattgctatggattttgaaagtg  17400
aaccttaagagaactgcactatgttttcttcattagagttctctggtaat  17450
ttccagcttttttttttttttttttttagacagtgtctcgctttgtcgccc  17500
agtgtcacccaggctggagtgcagtgacgtgatctcggctcactgcaacc  17550
tccgcctcgtgggttgaagtgattctcctgcctcagcctcctgagtagct  17600
gtattttagtagagacgaggtttcaccatttggccaggctggtctcgaac  17650
tcctgacctcaagtgattcgcccatctcagcctcccaaagtgctgggatt  17700
```

Fig. 16 (continued)

acaggtgtgagccactgcacccggccagtaatttcaagcttctgaggagc 17750
cctttgaattgttaaataacttgtagctatgtccaacatatccatgttca 17800
gtgtatgttcgatatttcttaggaaacctgcccttggttgttttctttgt 17850
ggtaattcatgagccggcaaatttgacatgtgttacagaatatacctttt 17900
ctctgctctcctacctcataaccagaacttaattatcctgctttagtcac 17950
ataaatagctaactaaataaatatatgagatttcagtctgctcactgtga 18000
aaatagaccttctaaatgatctcttccacttgcagATATTTGCAAATATG 18050
D I C K Y
GATCCATCCCTCCTGATGTGGAGGAGAAGTTACGGTTGGAATGGCCCTAC 18100
G S I P P D V E E K L R L E W P Y
CAGGAGCAATTGCTACTCCGAGAACACTACCAGAAAAAGTTCAAGAACAG 18150
Q E Q L L L R E H Y Q K K F K N S
CACCTACTCAAgtaagaaatgaaaggcaccctagagatgttccagcccca 18200
T Y S
aagatatttgaataggttggactcgggcaccaatctagcaagtcctacgg 18250
aagttgtataaagctgaaaatactgaagcatttcccaaatgggaaatcct 18300
aaactcaaaacttgcttttggtttttttgtttgtttgtttttttcttcat 18350
ctgacattgcttagtagtcacagaatgaaagataaatcaatcattcatga 18400
tctaacaatgaccttcagtgctctaaaaactacggagtcaaggaaaaca 18450
tgaatatattcctcatgtaaaattaaaatacagacatataaagggcaaaa 18500
catgaacatcattcataccttgaggtccgtcccccctcccagaaataaccc 18550
ccagtatgccttggtttagagcattaagcaggagggccctgagtcactcc 18600
agacagtcttgaccaccaagcagcattctctttttgtttcctctgtggct 18650
tttgcaaacacagggctagctcagctacccattagtatgttttcagtcac 18700
taaaacagtcttccagtcttcaaattaggatgacattgtcacatggggct 18750
ttaaagcaagtgaaacaaggaacccccttttttttttttttgagatgga 18800
atctcactcttgtcgcccagcctggagtgcaatggcgcaatcttggctca 18850
ctgcaacctccacctcccaggttcaagagattctcctgccttagcctcct 18900
attcattatgaggaatatttgattattcagttcctgtagggtaaagatat 18950
taccccccgatcatattattgattattgagtagctgagattacaggtgcct 19000
gccaccacgaccggctaatttttgtatttttagtagagacagggtttc 19050
accatgttggccaggctccaggctcgtctcgaactcctgacctcaggtga 19100
tccacccacctcagcctcccaaagttctgggattacaggcgtgagccacc 19150
actcctggccacaatcctttttttaactatgaaatatatttttatctgaag 19200
tttgatgtttatacccaactgagggatgatgttcccatatctcagttaaa 19250
gaaataacctgctcagatacttcaagctcttcttttgacttttgaaaata 19300
aatgatcttgaagttactatactttgtttgggttagttaacattatttaa 19350
agtatattattttaattaattatctttgtaagatttactgtatactacc 19400
tggagttcaatgtatcagatggatttcaaatttatgtacatttttttatgt 19450
atatggtacagaaaaaaatgtgatccataagaaatcagaaaatagcgcat 19500
atgctaatagctaatgttgtcctctaaaaacttatttttgcatttttaa 19550
gaggggggatatactctgacactttaataagtgtaattaattattgactgg 19600
aatttggcatgaggcagggccatttcagatcccattaaaggaatgacaca 19650
taccagagaaccacagaagtaaggccacatttgtaataaatcattatagc 19700
tctgctaggagaagacccagttgtattaggtaattaatggatttgctctt 19750
aaaacacatgtcccggaagatataggtgagtcttgggggccgcattaaa 19800
cattataccaatgtatcttacatttctaagaaagttttactactttacag 19850
gatctttctgttaccaaaatggaaggtttccaactccaggacttggcttt 19900
catagttcctacaccaggggaaatgccttcctttgctaactatgcaacca 19950
ggttagttagtgtaagtccagccaccctgttggcaatgctaaaaggtaca 20000
acaaacacagaattttatttgcatttgtaaacatttgatttctggctcga 20050
aattttcagttttcatgggcacgtcatggaaacagaaatcttctgtgttt 20100
agtttgggcacctactcattgtagtgacaaatatttcagaagccaatagg 20150
ggattccacaaattgttctgaacctgtggctgagactggtaatggctgag 20200
tgacatggggacataccacaaaagaagaggtagcaaaaggctgctgagat 20250
aaggacatgttcattgcttagctagtggcctgcacccttaaaacacatgt 20300
cccaggctgggtgctgtggctcacgcctgtaatcccagcactttgggagg 20350
ctgaggcgggtggattacctgaggtcaggagttcgagaccaacctggcca 20400
acatagtgaaacctcatttctactaaaaatacaaaaattagccaggcatg 20450
gtggcgggcgcctgtagtcccagctactcaggaggcaggcaggagaatta 20500
cttgaatctgggaggcagaggttgtggtgagccgagattgcgccaccgca 20550

Fig. 16 (continued)

```
cgctagcctgggcgacaaagtgagactctgtctcaaaaaacaaaaacaa  20600
aaaacaaacaaacaaaaacaacaacaacaaaaaacgggtatcccagaa  20650
gatacaggtaagtttctaacacaggtcctcttgtatggtgcgttccact  20700
taagtagaagatgacaaaaacatttgtcatgagaatatagactcacattt  20750
taaacctgtttgagcaggaaaaggaagcaatgttacagatgtaattctgg  20800
gtgtgactgcagaaaggatgactcccttattaaagtagtcatcctgagtg  20850
agctaactctttgtacttcctcttctcctcctgttcccctcatcacccca  20900
ttcttccgttgcctacacccaggcccacattggatgctgacatagactta  20950
catggtacagtccaagggaaagatctgccatttttttcaatgtgtcatct  21000
tggttatcttcattccaaggatctctccactctttatacagtaagagatg  21050
agagtctggaaaggattgggaataagataatgaattgtaagttttaaatt  21100
gttcttcgtattttggggaaggagtaggctaggtggtccttctgtttttt  21150
ttttgttttttttttttaaagtagatgtggccagacgtggtggctcacgcc  21200
tgtaatcccagcactttgagaggctgaggcaggtggatcacttgatgtca  21250
ggagttcaagaccagcctggccaacacagtgaaaccccgtctttactaaa  21300
aatacaaaaactagccgggcttggtggcgtccacctgtagtcccagctac  21350
tgcagaggtggaggcaggagaatcacttgaacccgggaggtggaggttgc  21400
agtgagccaagatcatgccattgtactccagcctgggcgacagaacaata  21450
ctctgtctcaaaaaaaaagagaaaagaaaagaaaaaaagaatggatttga  21500
actcagtcgtcaatagcctctattccaggagatgttacagttgattatgt  21550
tataggggggtgtataatagaatttcgagctatgtaaattccaagtgcatt  21600
tggaagaatgaagaaatggaggaagggtaaagtatgagtgcaagcattcc  21650
aggtttttgaaaatgctataatctttgttcagggctagtacaaagtgct  21700
atttagctgtaagggtttttgtgatttacagacagttttcacatgtgtc  21750
atttcaaccttggttttatggcgaaggcatgtgatggtgcttgtcccagg  21800
actttagatccatatctgaggttcctgtcgggcaaagatattacccctga  21850
tcatattatagtctataagtgggagagttgtgcctggagctcaagtctta  21900
tgatttctgatccagggcacttcctacaacatgattttgcaatataaaag  21950
cctataatgtgtgactaaagcaggtcactcaccccttgtaacagactcta  22000
gtaatggtactgccaccaaacggctgcgtgatattgggcaaagacttacc  22050
ttatttgaatctcagtttcctcctagaaaaatgagggtggaggttaagca  22100
taggctgatgatcctaaagcctccatactgccctaaactgtggctctaag  22150
atccagtagaatgctgggtcacaggactctagggagcttttcaaacccaa  22200
atgtctgtcattccttgatggtaggcagcagtttatggaagtgggcgaca  22250
cagcaaatatcaaaatacctaaagcagcttgcaagagttgtttctgccta  22300
gtggtctttatagttaatattaaatagttaatttttttttttttttgagac  22350
agagtcttgctctgttacccaggctgcagtgcagtggcacaatctcggct  22400
cactgcaacctccacctcccgggtttgagcaattctgtctcagcctccca  22450
agtagctgggactacaggtgcatgccactgcacccagctaatttttgtat  22500
ttttagtagagacggggtttcaccatattgggcaggctggtctcgaactc  22550
ttgacctcaggtgatccacctgcctcagcctcccaaagtgctgggattac  22600
aggcatgagccactgcacccagcttaaatagctaatatttaatattattc  22650
tatagttattcaagtaattcaggccaaagacttagaaacaaaacaaaaag  22700
ccactttttaaggagaaagggtgtaagtttgccagatagatagagatcttt  22750
ctttttaactacaagagttcaggaatgaattactctttaacaaacgact  22800
atagatatacatgaaaattggaaggacttattatgcatatgataatcaat  22850
ttaaagacaacacttaaaattatattgttgccactctcaaaaagtggtaa  22900
tagaacagctaatggtttaaaaagcagagtacagaagttcccaaacttat  22950
ggcaccttaatatcgcagaaaacttttaaagcatgcctaggccacaaaa  23000
aatacctgtattttgattattaaattgtaaggtctacacaacctaatagt  23050
aataggtccaatagtaatgctgtccaatagatgttgatgtttttttcctt  23100
gcaaacttaaaagatcctacagtgcctctgtaaatagcactgcctggtta  23150
gagttgaatttcagataaataatttttttcatgttaattatttttctttt  23200
ctttactttttttttttgtttttttgtttttttgttttttttttttgagaca  23250
gggtctcattctgttgcccaggctgctgtgcaatggcatgatcatggctc  23300
actgcagccttgacctccctgggctcaggtgatcctcccacctcagcctc  23350
ccaagtagctagctgggactacaggtgcttaccatcatgcccggctaatt  23400
tttgtgtttttttgtagagatgtggttttgccatgttgcccaggctggtct  23450
tgaactcctgggctcaagtgatccgcccgcctcggcctcccaaagtgcta  23500
ggatgacaggcatgagccactgcacctggcccctgggcgaagtatttctt  23550
aatggttacataggacatacactaaacattatttattgtctatatgaagt  23600
```

Fig. 16 (continued)

tcaagtttaactaggtgccctgcactttagttgctaaatcctgtagctg 23650
tacccatgcattcactggtgctccccagcttgccttgcacagagtttgga 23700
aaccatagtcctataactctaggccaatttttaatgtaaaatttgattc 23750
attttaaattaataaataataacaggaattttttttaaaaattgttttaaa 23800
tataattaaattatcaaatattttttttaactgaacttgtgactagagat 23850
atttagattatgaagagtggggtttatgctaactaatgacagtctggcta 23900
tgcatgtggagcactgagctataaattgtggcttccccaattctcctgat 23950
gtcacttgaacaaaacctaagtgtcagaccagagcttctggtatcttcca 24000
tgggatttcattcaacagctggagcaaatgaagtcagattgatttttttt 24050
aatttgtccaattttgttgtctcaaaaacataattataatcatttattag 24100
aactagaatttcttcagtttaacaacagaaatagttattcattatgaaaa 24150
gcgaatctggaggccttcattgtggtgccaatctaaccattaaattgtga 24200
cgtttttcttttagGAAGCTCTGTAGATGTGCTATACACTTTTGCAAACT 24250
R S S V D V L Y T F A N
GCTCAGGACTGGACTTGATCTTTGGCCTAAATGCGTTATTAAGAACAGCA 24300
C S G L D L I F G L N A L L R T A
GATTTGCAGTGGAACAGTTCTAATGCTCAGTTGCTCCTGGACTACTGCTC 24350
D L Q W N S S N A Q L L L D Y C S
TTCCAAGGGGTATAACATTTCTTGGGAACTAGGCAATGgtgagtacccca 24400
S K G Y N I S W E L G N
gggaacaattcattaataaggagattccccactagcattatttcttttct 24450
tttctttttcttttcttttttttttttttttgagacagagtctcgcactgc 24500
tgcccaggctggagtgcagtggcgccacctcggctcacttgaagctctgc 24550
ctcccaaaacgccattctcctgcctcagcctcccgagtagctgggactac 24600
aggcacccgccaccgcgcccggctaatttttttttttttttttttttttt 24650
ttttttttgcattttagtagagacggggtttcaccgtgttagccaggatg 24700
gtcttgatctcctgacctcgtgatctgccctcctcggcctcccaaagtgc 24750
tgggattacaggcgtgagccaccaggcccggctagcattatttcttatga 24800
cacttttttttttttttgagacggagtctcgctctgtcgcccaggctgg 24850
agtgcagtggcgccatctcggctcactgcaagctccacctcccaggttca 24900
cgccattctcctgcctcagcctcccgagtagctgggactacacgcacccg 24950
ccaccacgcccggctaatttttttgtatttttagtagagacggggtttca 25000
ccgtgttagccaggatggtctctatatcctgaccccatgatctgcccgcc 25050
tcggcctcccaaagtggtgggattacaggcgtgagccactgcgcccggcc 25100
aacactcttttattattagcaaatatacttctgcctgggcacattcttg 25150
caagtgctcaacaatgcaacttttggaagtgcatgtggcagaaactcctg 25200
ctgtatttattccagaacctattattgctaatcccagtttatgttacatt 25250
tgaagtgagaaccagttggagccagcaacgttcccagctccaaagttccc 25300
ttgagattttcagaatcacttaaccctattatgcttggcaacctggactc 25350
agcaaaactgggaagtcagcagtttgttttattcatcccttcctttctca 25400
gtttctcaaatgtgtcagttaatctcagtaaccccattgcaaccttcatt 25450
acctgcccaagcggtctagaacttgccagtatagaatcctacgtgggtca 25500
agctcctgactgtctccttcttcactcttttttttgcaaagaacttgtaaa 25550
ttttaactataagtattcatgattcgccacatttattcaaaacatagagt 25600
gctttttccacatatcagccaatggaaataaggattaaatgggaaatgaa 25650
atgtagtaataggataagcacaagtcttcttcctgctcaaactttttttt 25700
ttttttttttcagacaagatcttgctctgttacccaggctggagtgcagt 25750
ggcgtgttcatagctcaatgtaacctccaactcctgggctcatgcaatct 25800
ctcacacctcagccccctgattagctaggactacactatgcctagccaat 25850
tttttttcttttgtctggttgtgttgcccaggctgtctcgatctcctggc 25900
ctcaagtaatcctcctgcctcggccttctaaagtgctgggattataggca 25950
tgagccactgtgcccggtctcaaaccttttttttccaaagtaaatgaagtt 26000
attagatatggaatatagtctagttcccagatatccatatccattggttt 26050
attaccctcattattaacttcaaattgtttaatagaccctcatatctcag 26100
ttatacagttaaaattttgttttgtttttctggagtatcttatttataa 26150
ctatgagttttactttacttatttattttatttttttgagacagacgcttg 26200
ctctgtcactcaggctggagtgcggttgcgtgatcatggctcactatggc 26250
ctcgaccttctgggctcaagtgatcctctccctcagcctcccaagctgag 26300
actacaggcatgcaccaccacatctagctaattttttttttttccccatgg 26350
aacaaggctttactatgttacccagagtggtctcaaactcctggcctcag 26400
gggatcctcctgtctcagcctaccaaaatgctgggattacaggcatgagc 26450

Fig. 16 (continued)

```
catagcgccagacctggttttactttcttgactttgaattacaagtttt  26500
tgtaatttggaaaatgttttgttgcttttaaatactgctgtatgtttgct  26550
tttaaatacaacatttctcgatatatattttgagaattgctgtctttcag  26600
AACCTAACAGTTTCCTTAAGAAGGCTGATATTTTCATCAATGGGTCGCAG  26650
E  P  N  S  F  L  K  K  A  D  I  F  I  N  G  S  Q
TTAGGAGAAGATTTTATTCAATTGCATAAACTTCTAAGAAAGTCCACCTT  26700
 L  G  E  D  F  I  Q  L  H  K  L  L  R  K  S  T  F
CAAAAATGCAAAACTCTATGGTCCTGATGTTGGTCAGCCTCGAAGAAAGA  26750
  K  N  A  K  L  Y  G  P  D  V  G  Q  P  R  R  K
CGGCTAAGATGCTGAAGAGgtaggaactagaggatgcagaatcactttac  26800
T  A  K  M  L  K  S
ttttcttcttttttcctttttgagacagagtctcactctgtcagccagactg  26850
gagtgcagtggtacaatcatggctcactgcaacttcgacctcccaggctc  26900
aagcaatcctcccatctcagtcccacaaatagctgggactacaggtgcac  26950
atcaccacacctggctactttaaaaaaatttttttgtagagatggggtct  27000
ccctgtgttgcccaggctggtctcttgaattcctgtgctcaagccatcct  27050
tccacctcagcctcccagagtgccaggattacaggcatgagccaccacac  27100
ccagccaccactttttcttaaaaaaaaaaaaagattctctctggtagacaa  27150
tcctcaatagtccacatgttattaaacaatctgctgcctgaatacatgat  27200
ttaccaaaaaaaggaaatttgacgggttcagaatatcaagggatctgag  27250
gcaaatgtcacctatgataaaatttgctatcaaaattaggaagtttgtgt  27300
ttacctgatcctaaagcagtaaccagcccatttctagggaataaaactct  27350
catgcgtatattgtgcatatatatgtattatatgactgagtgataataaa  27400
atttttttttctagCTTCCTGAAGGCTGGTGGAGAAGTGATTGATTCAGTT  27450
              F  L  K  A  G  G  E  V  I  D  S  V
ACATGGCATCAgtaagtatgtctcctattcttaatactaggaaagtaagg  27500
T  W  H  H
ctagctttatttattacctagtattcaaaaagttagttcatttaactgcc  27550
aattgactgcagttcaaataagaaacaaatagtgtctcaagtagcactgt  27600
actccaattttaatattaataaaaaaaattttaagttattttaaataatg  27650
tagtggtttctataaagatcactttatacagaagaacagtgccaattaac  27700
ccatggaacatataagtagctaaaaccaattgcttgccaaagaaccagta  27750
acccaggagtacatgtccttgccactgtgtttttcaagacagagtaact  27800
gatttctagttacttgcatagaatggactcctcctcataactcccttcca  27850
tcttggtctttccctagtagaacttctacctttttttagtaacaggtgag  27900
tgggagaggtaagaaggagaataaggtcagcaattaacctaaaagcagaa  27950
agtaaaatttgttattttttttctgaatattttctgtgtaatttagCTAC  28000
                                                 Y
TATTTGAATGGACGGACTGCTACCAGGGAAGATTTTCTAAACCCTGATGT  28050
 Y  L  N  G  R  T  A  T  R  E  D  F  I  N  P  D  V
ATTGGACATTTTTATTTCATCTGTGCAAAAAGTTTTCCAGgtaatagtct  28100
  L  D  I  F  I  S  S  V  Q  K  V  F  Q
ttttaaacttttttaatgtaaaaccagaatccttattttatagtctagcta  28150
gttctaaattctataggtatgtatatttacatgtttttctaattttagag  28200
aacaagcactatgacttatccactgttagtttcccccttagcattgggtc  28250
ttaccccatgtacgtgattagaaatttgaaatatttccaatagcctttag  28300
tagaattaactcacatagatgataagaatgggttggttcacttcatgttc  28350
cttccacagcctactatttcaataaaagaaagtttcccaagacctaaatg  28400
actatgaacatattttataactatataggaggggtgggtctaggaataca  28450
aagttttgaatgctgttaatcttcaacaccacagttgaaaccacaggtca  28500
gctttttgcaattaccatggatacttttctgttctatagGTGGTTGAGA  28550
                                        V  V  E
GCACCAGGCCTGGCAAGAAGGTCTGGTTAGGAGAAACAAGCTCTGCATAT  28600
S  T  R  P  G  K  K  V  W  L  G  E  T  S  S  A  Y
GGAGGCGGAGCGCCCTTGCTATCCGACACCTTTGCAGCTGGCTTTATgtg  28650
 G  G  G  A  P  L  L  S  D  T  F  A  A  G  F  M
agtgaagcagcgctggccttaggggtcagagtgcagctcttctccatcct  28700
tctattctgctgaaatagctccccagccaaaaagcagatcaaagaccgtt  28750
tcagtggctgagccccaaaattcatgccagattttgcaagaaaatgattt  28800
actaaagcttgagggacatctttaacaagtgttccaaattaatcactata  28850
aggatgaattgtttcagaaattttggcctttaattatggcccataaatat  28900
```

Fig. 16 (continued)

gtcaagtagtccttactctaaagaagtacactgtaaaagaatgcatatag 28950
ccggatatggtagttccctgtaatcccaatactttgggaggccaaggtgg 29000
gaggattgcttgagcccaggagtttgaggctgcagtgagttatgatggtg 29050
ccactgcactctagactgggcaacagagtgagactgtcttttttttccc 29100
ctctgtcacccagactggagggcagtggcacgatctcacctcactgcaac 29150
ctctgcctcccggattgaagcgattctcctgcctcagcgtcctgagtagc 29200
tgggactacaggagtatcaccgcactgggctaattttgtatttttagta 29250
gagacggggtttgacatgttgcccaggctggtctgaaacccatgagctc 29300
aagtgatctgcctacctcagccttccaaatgctgggattacggacatga 29350
gctaccacgcccggccacaccctgtctcttaaaaaaaaaaaaatgcaag 29400
ttagagcatattacagctttgtctctcaggaggatacttagtgtatgtag 29450
ctataattcatagattcccaagaagtttagagcctaaagtatgaggtccc 29500
accagaggggctatcattaaatttaaagatttgttaaatcatctcattgt 29550
ccaacaccacaaacttgattgctttaaaatactggtttagttacatttag 29600
taactctattagtgcttttaatctatactgctatatcctcacattgagat 29650
tttttttcttttctcttccatcttcattctttttctctcatcctcattc 29700
ttataagcctagaatacatcacaaatcctttatgcccatggaagcaagag 29750
gaataaagaatggagatgtttgttttgccattaactaaagatctggggtg 29800
tcggggagaaggggatagagaaggagaagtgggaagaggtgtccataat 29850
agcttaggtgcaattctgcttatttacatttaccccgctgactgcca 29900
ctttttcttcagccctcacacattgtttgtgcagggacctcataggacca 29950
ggaattgtctatagaggtgggaatttgtctcaccctgaaagggatacctc 30000
tagcatggtaatagtcttctaggatttgttatcatatggaaagatgtaaa 30050
gggagggattctgctgctgctgctgctgcatgcagttgccatttcat 3 100
ttaaatgacttatttataattgatgacacttttctggcttcctgttaatt 30150
cctcccctcaaagatcaataaaccagaaccaggcatggtggcatgcacttg 30200
tggtcctgtaaccacccaacaggttcaccttgcctgctgtctagatagag 30250
ccaattatcaagacaggggaattgcaaaggagaaagagtaatttatgcag 30300
agccagctgtgcaggagaccagagttttattattactcaaatcagtctcc 30350
ccgaacattcgaggatcagagcttttaaggataatttggccggtaggggc 30400
ttaggaagtggagagtgctggttggtcaggttggagatggaatcacaggg 30450
agtggaagtgaggtttcttgctgtcttctgttcctggatgggatggcag 30500
aactggttgggccagattaccggtctgggtggtctcaaatgatccaccca 30550
gttcagggtctgcaagatatctcaagcactgatcttaggtttacaacag 30600
tgatgttatccccaggaacaatttggggaggttcagactcttggagccag 30650
aggctgcattatccctaaaccgtaatctctaatgttgtagctaatttgtt 30700
agtcctgcaaaggtagacttgtccccaggcaagaagggggtcttttcaga 30750
aaagggctattatcatttttgtttcagagtcaaaccatgaactgaatttc 30800
ttcccaaagttagttcagcctacacccaggaatgaagaaggacagcttaa 30850
aggttagaagcaagatggagtcaatgaggtctgatctctttcactgtcat 30900
aatttcctcagttataatttttgcaaaggcggtttcagtcccagctactt 30950
gggaggctgagacaggaggattaatggagcccaggagtttgaggttgcag 31000
agagctatgatcacgccactgcactccagcctgggtgacagagtgagacc 31050
ctgtctctaaataaataaataagtaaataaataaatacataaataaaatc 31100
aagatggtgtgcaattagaattgagcgattttgtttccaaacctcaagaa 31150
agcttggtcttgctctgtcccagGTGGCTGGATAAATTGGGCCTGTCAGC 31200
W L D K L G L S A
CCGAATGGGAATAGAAGTGGTGATGAGGCAAGTATTCTTTGGAGCAGGAA 31250
R M G I E V V M R Q V F F G A G
ACTACCATTTAGTGGATGAAAACTTCGATCCTTTACCTgtaagtgaccat 31300
N Y H L V D E N F D P L P
tatttcctaattctagtggagtagattaaagtcaactcaggacctctgg 31350
tgttaacctcctatgaacagtcagtcctctcagtaactagccaaatcatg 31400
agatgatgaattagaaggagccttagatagcatccaatctaacattttt 31450
tgtgtgtttgaagagaagaaatcaagagctaggaataactttttaaaggt 31500
aagccatttgcagtatagtgtggatttgtttaaaaggggataatttgaa 31550
attttatgactcattatacaagacaaaataagttggattttcaaatgttt 51600
tacaaagtaaatcaaagttataattgcctacagtacgcaaagcttcaaaa 31650
catttttatgttatgaaattgtaatttatttaaccttaaaatgagccag 31700
taccatgtgtttgcttaaaaatctcatgctaagaatttactatgttgtta 31750
ataatcttcaagatatttatgaataaagtcttatttctaatccttcctcc 31800

Fig. 16 (continued)

```
aactgtatctggtgctaaatcaggaaatgtttcttcccaaaaagcctcgt 31850
ggaagatctgtatgtctaaatatatgtcagggataatacagatgtagccc 31900
tgcgaagcatgaccttgattttatagtctaaaatgtcatttgcagatat 31950
ctattttctaagaataattcctaaaagaattatttgaatgttgtaggaaa 32000
gctaagaaattttgcaaagagcgtacgtgaaaatataagctaggcttttg 32050
tggtttgtggatagacttcccaacaaaattgcttttttatctatagtgatc 32100
caagcttgtggaacatattagtcatcttttttagaaaattcttagaaaa 32150
gtgatcttgcaaaaatggaatttatctttccccaagtatattctgtcatg 32200
tatagagttaaactaagcatagtaatttcaccagacaaacattcaaaatc 32250
tactcctgaccttttatctcatccaaatttcccagggcccagacataa 32300
acctttgccttacgaactctttgtatatgcactaaatatgcttctccttc 32350
aaggttctcagtcagctagaaaaatgtgcaagagtaaatggtacccttct 32400
cacttgtagatccaagagaattagacttaaactcactctacatgtctgtg 32450
actttattttatttgcatgacagtcctgtgaggtggcaaggcaggtatct 32500
tggatccattttttagataaggaagttcaaattgagaagaggttgcatga 32550
tttacaggaagccatactgtagtcctatgttactcttaaaaatcccattc 32600
aaatcctgcttctgaggcctgcatactttctaccctaccagtcattgacc 32650
catgcttatgtctcctttgaaaacattgattccactcttgtctccagtga 32700
aaaagtggaatttaagcagagaaacaaaagccatttgtcttgttaagtct 32750
actttccctctactttcaagaaggaaagttggggtatgtgttgaatggtg 32800
atttatttatttatttattattttaaaaattgatacaaggtcttactgta 32850
ttgtgcaggctggtctcaaactcctgggctcaagtgatcatcccacctca 32900
gcctcccagtgttgggattacagcatgaaccattgtgcccaccaccgatc 32950
cgcagtttttttaagaaaaactttactatagaaaattttaatcatataca 33000
aaatacagaggaaagtatatgaacccactttaggagactagaatatgcca 33050
ccccaaaatatgccactttggcataaggattatttcgagctaaaggcaac 33100
tgggaagaaacacatagaagaaaagttctctgtccttctccatttgccta 33150
aaagcaggacatgaatcttaaaagtccccctccttccctttctaccagga 33200
aaaacaagagttaatcactgaagataacttcagacccttatcagtgtaga 33250
gatggcactagaagaatctatattacatactcatttattttccttcccac 33300
aacttgccaccccagagactaaaaatccttttcctttgtcatgtctcttg 33350
tccaaaaatttgctctataagctggagttctaagccacctctttgagaat 33400
tacttgttccctggtattttctgttaacatacatgtattaatatacatgt 33450
taacaagcttctgtttgtttttctcctgttttctgtcttgttacagaggt 33500
ccatcccaactaagaactaaagagtaggaggaaaatataatttcctcctg 33550
catactttgatcttgtttaatccgtaacccttcccacttttcacctccta 33600
cctattagattactttgaagcaaatttcagatatattactttatctataa 33650
atatttcagtatgtgctaggtgtggtggctcacacctgtaatcccaacac 33700
tttgggaagctgaggcaggaggatcacttgagcccaggagttcaagacca 33750
gctacggcaacaaaaaatcaaaaacttatctgggcatggtggcacatgcc 33800
tgtggtcccagctacatgagaggctgaggcaggaggatcgctttagccca 33850
ggaggttgaggctgcagtaagctgcattcacaccactgcactccagcctg 33900
ggtgacagagtaagaccatgtctcaaaaaaatacatatttagtatgtat 33950
ccttttttgtaaaaacacaatactttatcatactttaaataataacaata 34000
attccttagtatcaccaaatatttgtcagtgtctcacattttccttatt 34050
gtctaaaatattgttgatagttattcaaatcagaatccaaacaaggtcca 34100
tatattacatttggttgacaagtctcttaagtttgttcatctttaagttc 34150
ttcctccctctctttcatctcttgtaatttattaatgtgaaaaaacaggt 34200
aatttgttctatagtatttcctacattatagagtttgctacatttattcc 34250
ctatgatatcatttagcatgttcctctgtcccctgtgtttcctgtaaact 34300
ggtagttatacctagaagcttgagtttattcaggtttttaattgtatttt 34350
ttttgcaagaattctttattatctgcttctggaagcacagaatgtctggt 34400
tgtgtctggttttgatcttgacagctactgatgaccattgcctaatccat 34450
tactttattggggtgggggaataaggttttaaaataaatttttttttaaa 34500
gatttttttaactgttattttgagacagtgtctcatttcgtttcccaggc 34550
tggagtgcagtggcacaatcacggctcactgcagccttgacctcctggga 34600
tcaggtgatcttctcacctcagcctcctgggtacctggaactacaggtgc 34650
acaccaccacacctggctaatttttttgtatttttgtgtacagaaggggttt 34700
catcatgtttcccagactggtcttgaactcctgggttcaagtgatctacc 34750
cacttcagcttcccaaaatcctgggattacactttggccaccgtgcctgg 34800
cctaaatgaaattatttgtctctaaacagacagaagttttactttaaaaa 34850
```

Fig. 16 (continued)

```
tttgtctttgtgtgtacatgtgtttgtgtatgtgtgtgtgtctaaaagtt  34900
tggctttgagctttgctttgaattcttggatgaacaataaccaagaatac  34950
ttaaactctgatcattcttgacagatatcccctacaggctatggcctttt  35000
gaattgtgtcctccagtgataaaaagcagcaagcacgatactgctctcag  35050
attcatggtggtcacatgtgaggtgaaaaaaaaaaaaagatgaatccta  35100
tttaaatgccccccaggataacagtgatactctttgtaggataactatttg  35150
cttgccactggtttcattaaataaggacataagtaaagatctatttttgt  35200
ctctttctccccaaccaccacaactagGATTATTGGCTATCTCTTCTGTT  35250
                            D  Y  W  L  S  L  L  F
CAAGAAATTGGTGGGCACCAAGGTGTTAATGGCAAGCGTGCAAGGTTCAA  35300
 K  K  L  V  G  T  K  V  L  M  A  S  V  Q  G  S
AGAGAAGGAAGCTTCGAGTATACCTTCATTGCACAAACACTGACAAgtaa  35350
K  R  R  K  L  R  V  Y  L  H  C  T  N  T  D  N
gtatgaaacacacccctttaccaatcatcaagttttagtgggtaagcctgt  35400
aactttactcaaacacccctgttgcatgtgtctatacattgcataagtata  35450
ggcagttgcaatttagtaaagttttatacaacgattttattttattttat  35500
ttttagaagaaaaatgctacttttgttgttgttgtttttgagacggggc  35550
ctcgctcgtcacccaggctggagtgcagtggtgcaatctcagctcactgc  35600
aacctccgcctcccgggttcaagtgattcttgaagaggagaacaataata  35650
acaacaatattattttcaaaagttgtgaccgcagtttctggagttgagaa  35700
gacatcgagattttgtagcctcatactcttgctttaggtagcaaaaaat  35750
gttcctaaatctcaggaatattctctagataggtttcaatctatcattcc  35800
tgataagatgatgctgaaatactaattctagccaaaaaagaccagctacc  35850
atttccgattgttggggactgggaactctggatagtgaggaccccagtag  35900
gaagtagcgaggggaatggtttgaatggataaattcataaaaaatgtcag  35950
tagatttaattttcttatacatttcagtctttttataaggctaggaaaag  36000
cccctgtttttatggtttataatttgaattcacatgaacccacaaaattt  36050
gccttttaccttcctatgtctgaaaatggatagtctggctggcctcttaa  36100
caacccagctggcagagctgtgaggatctcagtgtgctctagcccagaca  36150
ttggtagcatgaacggcaacatttttaattgtgttttcaaaataggagca  36200
cactagcggtctaaaacgatcataaaagaaggatactaagagggcccact  36250
gtcattatggatcctaatacttaggatgcattatggattgtcattatgga  36300
tactaatacttaggatcacatttgtaattgagtttttaattgcttaaatt  36350
agatacatatttctattaagttaacctctttgcttttagTCCAAGGTATA  36400
                                        P  R  Y
AAGAAGGAGATTTAACTCTGTATGCCATAAACCTCCATAATGTCACCAAG  36450
K  E  G  D  L  T  L  Y  A  I  N  L  H  N  V  T  K
TACTTGCGGTTACCCTATCCTTTTTCTAACAAGCAAGTGGATAAATACCT  36500
 Y  L  R  L  P  Y  P  F  S  N  K  Q  V  D  K  Y  L
TCTAAGACCTTTGGGACCTCATGGATTACTTTCCAAgtaagtaattttcc  36550
  L  R  P  L  G  P  H  G  L  L  S  K
ttgttcattccaaactttcaataaatttattggtgtttatcagaatagag  36600
agtttggacagggagcaaaagacaaagtcaactatatcaagttctaataa  36650
ttcttaatattcaggaaatttatgtatgaatacttactaatatgagtata  36700
actcatcctaagagtctaaagcaaaaggatgtgaacacaaactagcagtt  36750
atcttagagaataagtttgcatttcaaaataacttgacatatcaagatcc  36800
actcaacgcatttaaattatttactctaaaaagacataattcttggtaac  36850
acattcactaaagcaaaatatacctttatataattgctatcaaaggtatg  36900
tgggttggtataaaatatcataccatgtgagatcagtgtgattcctttac  36950
agcattaatttttattggttagagtaagaaaaagaatagctagagtatat  37000
ttcttaagtagattctcatacactttggtttcaaaaccaattattgact  37050
acatcttataaaagcctgtattcaatggagtgccaaaaaatgactatgag  37100
tcttaaagagttaggcatataaatatttaaggtttctgttcaatgtatg  37150
ttggaaggagttcctttctcatgactattctcatattggagcataaaaag  37200
agtttacaggcttggcgcagtggctcatgcctgtaatcccaatactttgg  37250
gaagctgaagcaggcagatcacttcagcccaggagtttgagaccagcctg  37300
ggcaatatggcaaaactctctctacaaaatataccaaaattagccaggcg  37350
tggtggtgcatgcctgtagtcccagctacttgggaagctgaggtgggagg  37400
attgcttgagcccaggggggtcatggctgcagtgagctgtgatggtgcct  37450
ctgtcacccagcctgggtgacagagtgagaccctgtctcaaaaaaataaa  37500
taaataaaaattaagagtttacaaaattctcaccatctcctcccatcttt  37550
```

Fig. 16 (continued)

gcaaatgccacataagtgatgtgttccaggactattagcctcggaacctg 37600
aggcagtacagtaagcacgctttctccaaagtcctgtcccccacagacaa 37650
acattatttacactgggtactgctctttatttttcccctctatgcttt 37700
attttactataactataatcatataacatgtaataggaaaaaggcagggt 37750
cggggagagatccagaagtcttcccaagagcctttccaacatagcctct 37800
gtagacatttttctttcttctttttttttttttttttttttctgagaca 37850
gagtctcactctgttgtccaggctagagtgcagtggcgtgatctaggctc 37900
actgcaacctccgcctcctgggttcaagcaattctcccacctcagcctcc 37950
ctagtagctgggattagaggcatgcatcaccacgcctggctaatttttgt 38000
atttttagtagagatgaggtttcaccatgtgggccaggctggtcttgaac 38050
tcctgacctcaagtgatccacctgccttagcctcccaaagtgctaggatt 38100
acacgagtgagccaccgtgccctgcccctattacattctgatcacacatt 38150
tcatgttttataattggaaaactggtgaaattatagacaatgttttgttc 38200
ccctaaattctctttgatgagtatatattacttacactcttctgtcttta 38250
aaattttgcaaaatagtatcctagataagtttatgagtgcacagtctgta 38300
cgcttactcatattaatgacctcggagagttaaacaacagtcacctttaa 38350
aaattattactatcattatcattatttttgaggcgggggtctcattctgt 38400
ctcccaggctggagagtagtggtgcggtcacagctcactgcagccaccgc 38450
tacctgggctcaagtgatccttcctcctcagccttctgagtagctgagac 38500
cacaggcttatgctaccacacctggctaatttttttaactttttgtagaga 38550
cgatgtctcattatgttgcccaggctggtctcaaactcctaagctcaagt 38600
gatcttcctcagcctcccaaagtgctgggattacaggcatgaaaaactgc 38650
acccagccctaaaaattattagggtcctgcatagtaagactttaataaat 38700
atttaaatgaacatctggtttttttaaaaaaaaaatagagacaaggtctc 38750
actatattgcccaagctggtctcgaactcctggactcacgcaatcctgct 38800
gccttagccgcccaaagtgctgggattacaggcatgacccacctcatctg 38850
ggctgagtgaacatattttaacataaaggccgtattttatatttatctc 38900
atacatttgcccagcatccccatttccgccgaatctgttgcttgctaat 38950
tccttccagcttcatttcatctgaaatttgacaaacatcttctatttctt 39000
tgtcgtcatgttattgacttcagaatataaaataaaacactatacccaaa 39050
ttaaaccccaccctcattgcccagcctgatgtgaaaataatcagcataca 39100
ttaagcttacccttgatatatgtgtagcatcttttagataaatatacagc 39150
tgattaagcaatatagcctgatggtataatatcttgcccatgtacctcat 39200
cttatctccagcaggattaattcacagtgatcagatttacctttaaactt 39250
tgtagcaaaatatcctctccaaaagcatatctaaaacttttgtgtgtact 39300
cttgcaagtttcttaatttcatgcagaacaggctcttaccactgttagct 39350
ggagatattttcaagacctatttttgtttgtggtttcctgatgatggtca 39400
tggcatttccccctcactccatctaaaaattgaggtgatacaggctttt 39450
aaacaaaaccaactcatatagactgagtacaactgcaatgcaggcatgct 39500
aacctctgctacaatcatgggcgtgctattgatatgtcttaagttacaga 39550
acacagggctgagcgtctcattaggtcaaaatgtaaaccagtttttctgc 39600
tcactgatgcttaatgaggacagggtgtgagagatttctttaaggaaaac 39650
aaatatataataatgctacatggaaaaatatctaacattagagaattaag 39700
taaataaactaatatactcacaccatggaatcttgtgcagacattaaaat 39750
tatgtagtggatggatgtttaatggtgtgagaaaaagttaggatgtgctg 39800
gggtgggggaagaatcaagttttaagaaaatacagtatacccatactta 39850
agtaaaaaaaaaaaaaaaggtatgtacagtcatgtgttgcttaatgatgg 39900
ggatacattccgagaaatgtgtcgataggtgatttcatccttgtgtgaac 39950
atcatagagtgaacttacacaaacctagatggtctagcctactatgtatc 40000
taggctatatgactagcctgttgctcctaggctacaaacctgtaaagcat 40050
gttactgtagcgaatatacaaatacttaacacaatggcaagctatcattg 40100
tgttaagtagttgtgtatctaaacatatctaaaacatagaaaactaatgt 40150
gttgtgctacaatgttacaatgactatgacattgctaggcaataggaatt 40200
ataattttatccttttatggaaccacacttatatatgcggtccatggtgg 40250
accaaaacatccttatgtggcatatgactgtatacatgtacacaaaaaat 40300
agatgaaagaatgaatatacatcaaaatatttaaaatggttataatgact 40350
taggttactttttatttatcttagtaataataatgatgatagataatactt 40400
ttatagtgtttactatataaaagacactgttataagtgttctacatactt 40450
tacatgtattacctaaatgatataaatataactctgacagtaactaatct 40500
tatacgttctcttttctttttttttttttctttttttagacagaatctt 40550
gctctaccaggctggagtgcagggtgcaatctcggctcactgcaacctcc 40600

Fig. 16 (continued)

```
gcctcccaggttcaaacgattctcatgtctcagcctcctgagtagctggg  40650
actacaggcacacaccaccatgcccggctaatttttgtatttttgggtag  40700
agatggagttttgccatgttggccaggctgatcttgaactcctggcctca  40750
agtgatctgcctgcctcagcctcccaaagtgctgggattacaggtgtgaa  40800
ccactgtgctcggcctaatcttacaagttttcaatatttaaagagtgcta  40850
actttgttgacaatataaaacatatttgagaaaaagagatataagcatct  40900
tatttagaattatgaaaatatcaatagacctacagccgactaaagctttt  40950
cttcataagctcttgcctatattgattcgctcctgtgaatatgcattaat  41000
ttgatttaaataataagtatgtataagaaataacacttttccttaatttt  41050
taagaacgttcaacagttttaatttgaattccaatagtgaaatacatag  41100
aaaatataaaatttctgtagtttagccaaattgtttttgtttcaccaca  41150
gcattctaccaaatttcttaataacagtaagaaaatgaatgcatacctc  41200
ctgcagggagaggggagttaggcagtttatgggcatagttacaagtgaga  41250
aatttcattggctaccatttacgctaaattcataaaaactgcattcaatt  41300
ctatatatctatttctttacataaaaaggtttcaattattggccatta  41350
aataaaatagccaccattccagaagttgtgtcatgtttatcctttttata  41400
ccaccatcatattgcctattatatagattgtgtgtgttccatttttctgta  41450
atgggccagacagtaagtatttctggctttggagtccatatggtctctat  41500
cataactactcatctctgccattgtagcttaaagattatctaggtcaaat  41550
gcctaagtgatatagtgttgaaatacaagttatataatataggctgccac  41600
aaaaaaaatttatttggtctaaaaaagatttcatgacttttgtagcagc  41650
atgggtggggcatgcaccacttggttaactcggtgtatctttctcctttg  41700
cagATCTGTCCAACTCAATGGTCTAACTCTAAAGATGGTGGATGATCAAA  41750
    S  V  Q  L  N  G  L  T  L  K  M  V  D  D  Q

CCTTGCCACCTTTAATGGAAAAACCTCTCCGGCCAGGAAGTTCACTGGGC  41800
T  L  P  P  L  M  E  K  P  L  R  P  G  S  S  L  G

TTGCCAGCTTTCTCATATAGTTTTTTTGTGATAAGAAATGCCAAAGTTGC  41850
 L  P  A  F  S  Y  S  F  F  V  I  R  N  A  K  V  A

TGCTTGCATCTGAAAATAAAATATACTAGTCCTGACACTGaatttttcaa  41900
  A  C  I  *
gtatactaagagtaaagcaactcaagttataggaaaggaagcagatacct  41950
tgcaaagcaactagtgggtgcttgagagacactgggacactgtcagtgct  42000
agatttagcacagtattttgatctcgctaggtagaacactgctaataata  42050
atagctaataataccttgttccaaatactgcttagcattttgcatgtttt  42100
acttttatctaaagttttgttttgttttattatttatttatttatttatt  42150
ttgagacagaatctctctctgtcacccaggctggagtgccatggtgcgat  42200
cttggctcactgcaactttaagcaattctcctgcctcagcttcctgagta  42250
gctgggattataggcgtgtgccaccacgcccagctactttctatattttt  42300
tgtagagatggagtttcgccatattggccaagctggtctcgaactcctgt  42350
cctcgaactcctgtcctcaagtgatccacccgcctcagcctctcaaagtg  42400
ctgggattacaggtgtgagccaccacacccagcagtgttttattttttgag  42450
acagggtatcattctgttgcccaggcttgagtgcagtggtgcaatcatag  42500
atcactgcagcctttttaactcctgggctcaagtcatcctcctgcttagcc  42550
tcccaagtagctaggaccacagacacatgccatcacacttggctattttt  42600
aaaaaatttttttgtagagatggggtctcgctatgttacccaaactggtcc  42650
tgaactcctggactcaattgatcctcccaccttggccttccaggtgctgg  42700
gatttctttgggagtacagcatggtacagcaggagatcatttgatgttac  42750
ctctgtgcagtgttgctagtcagcgaaagactataatacctgtggggaca  42800
gcgattagccaccacaaccagtctttatttaaagttattaaaaatggctg  42850
ggcgcagtggctcacacctgtaatcctagcactttgggaggccgaggcag  42900
atggatcacctgacgtgaggaatttgagaccagcctggccaacatggtga  42950
aaccccatctctactaaaaatacaaaaattagctgggtgtggtcctgta  43000
gtcccagctacttgggaggctggggcaggagaattacttgaacccaggag  43050
gcagaggttgcagtgagccgagattgtgccactgcactccagcctgggtg  43100
acagagagagattccatctcaaaaaaacaagttattaaaaatgtatatga  43150
atgctcctaatatggtcaggaagcaaggaagcgaaggatatattatgagt  43200
tttaagaaggtgcttagctgtatatttatctttcaaaatgtattagaaga  43250
ttttagaattctttccttcatgtgccatctctacaggcacccatcagaaa  43300
aagcatactgccgttaccgtgaaactggttgtaaaagagaaactatctat  43350
ttgcaccttaaaagacagctagattttgctgatttcttctttcggtttt  43400
```

Fig. 16 (continued)

```
ctttgtcagcaataatatgtgagaggacagattgttagatatgatagtat  43450
aaaaaatggttaatgacaattcagaggcgaggagattctgtaaacttaaa  43500
attactataaatgaaattgatttgtcaagaggataaattttagaaaacac  43550
ccaataccttataactgtctgttaatgcttgctttttctctacctttctt  43600
ccttgtttcagttgggaagcttttggctgcaagtaacagaaactcctaat  43650
tcaaatggcttaagcaataaggaaatgtatattcccacataactagacgt  43700
tcaaacaggccaggctccagcacttcagtacgtcaccagggatctgggtt  43750
cttcccagctctctgctctgccatctttagcgctggcttcattctcagac  43800
tctggtagcatgatggctgtagctgtttcatggccccttcaaacctcat   43850
agcaaccagaggaagaaaatgagccatttttttgagtctccttcatagact  43900
tgaataactcttttcagagcttctcacagcaaacctctcctcatgtctc   43950
ctcatgtcttattgttcagaaatgggtaatgtggccatttcaccagtcac  44000
tgccaacaacaacgaggttcctataattgtctctgagtaaccctttggaa  44050
tggagagggtgttggtcagtctacaaactgaacactgcagttctgcgctt  44100
tttaccagtgaaaaaatgtaattattttcccctcttaaggattaatattc  44150
ttcaaatgtatgcctgttatggatatagtatctttaaaatttttttatttt 44200
aatagctttaggggtacacactttttgcttacaggggtgaattgtgtagt  44250
ggtgaagactcggcttttaatgtacttgtcacctgagtgatgtacattgt  44300
acccaataggtaatttttcatccattaccctccttccgccctcttccctt  44350
ctgagtctccaacatccccttataccactgtgtatgttcttgtgtacctac 44400
agctaagcttccacttataagtgagaacatgcagtatttggtttttccatt 44450
cctgagttacttccccttaggataacagcccccagttccgtccaagttgct 44500
gcaaaatacattattcttctttatggctgagtaatagtccatggtacata  44550
tataccacattttctttatccacttatcagttgatggacacttaggttaa  44600
ttccattcaatttcattcaatttaagtatatttgtaaggagctaaagctg  44650
aaaattaaattttagatctttcaatactcttaaattttatatgtaagtgg  44700
ttttatattttcacatttgaaataaagtaatttttataaccttgatatt   44750
gtatgactattcttttagtaatgtaaagcctacagactcctacatttgga  44800
accactagtgtgttgtttcaccccttgttatactatcaggatcctcga    44898
```

Fig. 16
(continued)

```
                                                                50
human   MLLRSKPALP PPLMLLLLGP LGPLSPGALP RPAQAQDVVD LDFFTQEPLH
mouse   ~~~~~~~~ML RLLLLWLWGP LGALAQGAPA GTAPTDDVVD LEFYTKRPLR
rat     ~~~~~~~~~~ ~LLLLWLWGR LRALTQGTPA GTAPTKDVVD LEFYTKRLFQ

                                                               100
human   LVSPSFLSVT IDANLATDPR FLILLGSPKL RTLARGLSPA YLRFGGTKTD
mouse   SVSPSFLSIT IDASLATDPR FLTFLGSPRL RALARGLSPA YLRFGGTKTD
rat     SVSPSFLSIT IDASLATDPR FLTFLSSPRL RALSRGLSPA YLRFGGTKTD

                                                               150
human   FLIFDPKKES TFEERSYWQS QVNQDICKYG SIPPDVEEKL RLEWPYQEQL
mouse   FLIFDPDKEP TSEERSYWKS QVNHDICRSE PVSAAVLRKL QVEWPFQELL
rat     FLIFDPNNEP TSEERSYWQS QDNNDICGSD RVSADVL~~~ ~~~~~~~~~~

                                                               200
human   LLREHYQKKF KNSTYSRSSV DVLYTFANCS GLDLIFGLNA LLRTADLQWN
mouse   LLREQYQKEF KNSTYSRSSV DMLYSFAKCS GLDLIFGLNA LLRTPDLRWN
rat     ~~~~~~~~~~ ~~~~~~~~~~ ~~~~~~~~~~ ~~~~~~~~~~ ~~~~~~~~~~

                                                               250
human   SSNAQLLLDY CSSKGYNISW ELGNEPNSFL KKADIFINGS QLGEDYIQLH
mouse   SSNAQLLLDY CSSKGYNISW ELGNEPNSFW KKAHILIDGL QLGEDFVELH
rat     ~~~~~~~~~~ ~~~~~~~~~~ ~~~~~~~~~~ ~~~~~~~~~~ ~~~~~~~~~~

                                                               300
human   KLLRKSTFKN AKLYGPDVGQ PRRKTAKMLK SFLKAGGEVI DSVTWHHYYL
mouse   KLLQRSAFQN AKLYGPDIGQ PRGKTVKLLR SFLKAGGEVI DSLTWHHYYL
rat     ~~~~~~~~~~ ~~~~~~~~~~ ~~~~~~~~~~ ~~~~~~~~~~ ~~~~~~~~~~

                                                               350
human   NGRTATREDF LNPDVLDIFI SSVQKVFQVV ESTRPGKKVW LGETSSAYGG
mouse   NGRIATKEDF LSSDALDTFI LSVQKILKVT KEITPGKKVW LGETSSAYGG
rat     ~~~~~~~~~~ ~~~~~~~~~~ ~~~~~~~~~~ ~~~~~~~~~~ ~~~~~~~~~~

                                                               400
human   GAPLLSDTFA AGFMWLDKLG LSARMGIEVV MRQVFFGAGN YHLVDENFDP
mouse   GAPLLSNTFA AGFMWLDKLG LSAQMGIEVV MRQVFFGAGN YHLVDENFEP
rat     ~~~~~~~~~~ ~~~~~~~~~~ ~~~~~~~~~~ ~~~~~~~~~~ ~~~~~~~~~~

                                                               450
human   LPDYWLSLLF KKLVGTKVLM ASVQGSKRRK LRVYLHCTNT DNPRYKEGDL
mouse   LPDYWLSLLF KKLVGPRVLL SRVKGPDRSK LRVYLHCTNV YHPRYQEGDL
rat     ~~~~~~~~~~ ~~~~~~~~~~ ~~~~~~~~~~ ~~~~~~~~~~ ~~~~~~~~~~

                                                               500
human   TLYAINLHNV TKYLRLPYPF SNKQVDKYLL RPLGPHGLLS KSVQLNGLTL
mouse   TLYVLNLHNV TKHLKVPPPL FRKPVDTYLL KPSGPDGLLS KSVQLNGQIL
rat     ~~~~~~~~~~ ~~~~~~~~~~ ~~~~~~~~~~ ~~~~~~~~~~ ~~~~~~~~~L

                                                    543
human   KMVDDQTLPP LMEKPLRPGS SLGLPAFSYS FFVIRNAKVA ACI~
mouse   KMVDEQTLPA LTEKPLPAGS ALSLPAFSYG FFVIRNAKIA ACI~
rat     KMVDEQTXPA LTEKPLPAGS SLSVPAFSYG FFVIRNAKIA ACI~
```

Fig. 17

```
    |MLLRSKPALPPPLMLLLLGPLGPLSPGALPRPAQAQDVVDLDFFTQEPLHLVSPSFLSVT|  60
PHD |                  EEEEE                       HHH         EEEE     EEE|

    |IDANLATDPRFLILLGSPKLRTLARGLSPAYLRFGGTKTDFLIFDPKKESTFEERSYWQS| 120
PHD |EEE          EEEEE    HHHHHH    HHHHE     EEEEE            HHHHHH|

    |QVNQDICKYGSIPPDVEEKLRLEWPYQEQLLLREHYQKKFKNSTYSRSSVDVLYTFANCS| 180
PHD |HHHHHHHH       HHHHHHH   HHHHHHHHHHHHHHHH      EEEEEEEEEEEE    |

    |GLDLIFGLNALLRTADLQWNSSNAQLLLDYCSSKGYNISWELGNEPNSFLKKADIFINGS| 240
PHD |  HHHHHHHHHHHHHHHHHHHHHHHHHHHHHHH     EEEEE     HHHHHHH EEEE    |

    |QLGEDYIQLHKLLRKSTFKNAKLYGPDVGQPRRKTAKMLKSFLKAGGEVIDSVTWHHYYL| 300
PHD |   HHHHHHHHHHHHHHHHH            HHHHHHHHHHHHH   EEEEEEEEEEE |

    |NGRTATREDFLNPDVLDIFISSVQKVFQVVESTRPGKKVWLGETSSAYGGGAPLLSDTFA| 360
PHD |              HHHHHHHHHHHHEEEEEEE     EEEEEE          HHHHHHH|

    |AGFMWLDKLGLSARMGIEVVMRQVFFGAGNYHLVDENFDPLPDYWLSLLFKKLVGTKVLM| 420
PHD |HHHHHHHH   HHHH HHHHHHHHHHH    EEEEE      HHHHHHHHHHHH   EEEEE|

    |ASVQGSKRRKLRVYLHCTNTDNPRYKEGDLTLYAINLHNVTKYLRLPYPFSNKQVDKYLL| 480
PHD |EEE     E  EEEEEEEE                   EEEEEE     EEEEE     HHHHHHH|

    |RPLGPHGLLSKSVQLNGLTLKMVDDQTLPPLMEKPLRPGSSLGLPAFSYSFFVIRNAKVA| 540
PHD |HH        EEEEEEE   EEEEE                                 EEEEEEEE EE |

     |ACI|                                                           543
PHD |    |
```

Fig. 19

POLYNUCLEOTIDE ENCODING A POLYPEPTIDE HAVING HEPARANASE ACTIVITY AND EXPRESSION OF SAME IN GENETICALLY MODIFIED CELLS

This is a divisional of U.S. patent application Ser. No. 09/988,113, filed Nov. 19, 2001, which is a continuation of U.S. patent application Ser. No. 09/776,874, filed Feb. 6, 2001, which is a continuation of U.S. patent application Ser. No. 09/258,892, filed Mar. 1, 1999 now abandoned, which is a continuation-in-part of PCT/US98/17954, filed Aug. 31, 1998, which is a continuation in part of U.S. patent application Ser. No. 09/109,386, filed Jul. 2, 1998, now abandoned, which is a continuation-in-part of U.S. patent application Ser. No. 08/922,170, filed Sep. 2, 1997, now, U.S. Pat. No. 5,968,822.

FIELD AND BACKGROUND OF THE INVENTION

The present invention relates to a polynucleotide, referred to hereinbelow as hpa, encoding a polypeptide having heparanase activity, vectors (nucleic acid constructs) including same and genetically modified cells expressing heparanase. The invention further relates to a recombinant protein having heparanase activity and to antisense oligonucleotides, constructs and ribozymes for down regulating heparanase activity. In addition, the invention relates to heparanase promoter sequences and their uses.

Heparan sulfate proteoglycans: Heparan sulfate proteoglycans (HSPG) are ubiquitous macromolecules associated with the cell surface and extra cellular matrix (ECM) of a wide range of cells of vertebrate and invertebrate tissues (1–4). The basic HSPG structure includes a protein core to which several linear heparan sulfate chains are covalently attached. These polysaccharide chains are typically composed of repeating hexuronic and D-glucosamine disaccharide units that are substituted to a varying extent with N- and O-linked sulfate moieties and N-linked acetyl groups (1–4). Studies on the involvement of ECM molecules in cell attachment, growth and differentiation revealed a central role of HSPG in embryonic morphogenesis, angiogenesis, neurite outgrowth and tissue repair (1–5). HSPG are prominent components of blood vessels (3). In large blood vessels they are concentrated mostly in the intima and inner media, whereas in capillaries they are found mainly in the subendothelial basement membrane where they support proliferating and migrating endothelial cells and stabilize the structure of the capillary wall. The ability of HSPG to interact with ECM macromolecules such as collagen, laminin and fibronectin, and with different attachment sites on plasma membranes suggests a key role for this proteoglycan in the self-assembly and insolubility of ECM components, as well as in cell adhesion and locomotion. Cleavage of the heparan sulfate (HS) chains may therefore result in degradation of the subendothelial ECM and hence may play a decisive role in extravasation of blood-borne cells. HS catabolism is observed in inflammation, wound repair, diabetes, and cancer metastasis, suggesting that enzymes which degrade HS play important roles in pathologic processes. Heparanase activity has been described in activated immune system cells and highly metastatic cancer cells (6–8), but research has been handicapped by the lack of biologic tools to explore potential causative roles of heparanase in disease conditions.

Involvement of Heparanase in Tumor Cell Invasion and Metastasis: Circulating tumor cells arrested in the capillary beds of different organs must invade the endothelial cell lining and degrade its underlying basement membrane (BM) in order to invade into the extravascular tissue(s) where they establish metastasis (9, 10). Metastatic tumor cells often attach at or near the intercellular junctions between adjacent endothelial cells. Such attachment of the metastatic cells is followed by rupture of the junctions, retraction of the endothelial cell borders and migration through the breach in the endothelium toward the exposed underlying BM (9). Once located between endothelial cells and the BM, the invading cells must degrade the subendothelial glycoproteins and proteoglycans of the BM in order to migrate out of the vascular compartment. Several cellular enzymes (e.g., collagenase IV, plasminogen activator, cathepsin B, elastase, etc.) are thought to be involved in degradation of BM (10). Among these enzymes is an endo-β-D-glucuronidase (heparanase) that cleaves HS at specific intrachain sites (6, 8, 11). Expression of a HS degrading heparanase was found to correlate with the metastatic potential of mouse lymphoma (11), fibrosarcoma and melanoma (8) cells. Moreover, elevated levels of heparanase were detected in sera from metastatic tumor bearing animals and melanoma patients (8) and in tumor biopsies of cancer patients (12).

The control of cell proliferation and tumor progression by the local microenvironment, focusing on the interaction of cells with the extracellular matrix (ECM) produced by cultured corneal and vascular endothelial cells, was investigated previously by the present inventors. This cultured ECM closely resembles the subendothelium in vivo in its morphological appearance and molecular composition. It contains collagens (mostly type III and IV, with smaller amounts of types I and V), proteoglycans (mostly heparan sulfate- and dermatan sulfate-proteoglycans, with smaller amounts of chondroitin sulfate proteoglycans), laminin, fibronectin, entactin and elastin (13, 14). The ability of cells to degrade HS in the cultured ECM was studied by allowing cells to interact with a metabolically sulfate labeled ECM, followed by gel filtration (Sepharose 6B) analysis of degradation products released into the culture medium (11). While intact HSPG are eluted next to the void volume of the column ($Kav<0.2$, $Mr \sim 0.5 \times 10^6$), labeled degradation fragments of HS side chains are eluted more toward the $V_t$ of the column ($0.5<kav<0.8$, $Mr=5–7 \times 10^3$) (11).

The heparanase inhibitory effect of various non-anticoagulant species of heparin that might be of potential use in preventing extravasation of blood-borne cells was also investigated by the present inventors. Inhibition of heparanase was best achieved by heparin species containing 16 sugar units or more and having sulfate groups at both the N and O positions. While O-desulfation abolished the heparanase inhibiting effect of heparin, O-sulfated, N-acetylated heparin retained a high inhibitory activity, provided that the N-substituted molecules had a molecular size of about 4,000 daltons or more (7). Treatment of experimental animals with heparanase inhibitors (e.g., non-anticoagulant species of heparin) markedly reduced (>90%) the incidence of lung metastases induced by B16 melanoma, Lewis lung carcinoma and mammary adenocarcinoma cells (7, 8, 16). Heparin fractions with high and low affinity to anti-thrombin III exhibited a comparable high anti-metastatic activity, indicating that the heparanase inhibiting activity of heparin, rather than its anticoagulant activity, plays a role in the anti-metastatic properties of the polysaccharide (7).

Heparanase activity in the urine of cancer patients: In an attempt to further elucidate the involvement of heparanase in tumor progression and its relevance to human cancer, urine samples for heparanase activity were screened (16a).

Heparanase activity was detected in the urine of some, but not all, cancer patients. High levels of heparanase activity were determined in the urine of patients with an aggressive metastatic disease and there was no detectable activity in the urine of healthy donors.

Heparanase activity was also found in the urine of 20% of normal and microalbuminuric insulin dependent diabetes mellitus (IDDM) patients, most likely due to diabetic nephropathy, the most important single disorder leading to renal failure in adults.

Possible involvement of heparanase in tumor angiogenesis: Fibroblast growth factors are a family of structurally related polypeptides characterized by high affinity to heparin (17). They are highly mitogenic for vascular endothelial cells and are among the most potent inducers of neovascularization (17, 18). Basic fibroblast growth factor (bFGF) has been extracted from the subendothelial ECM produced in vitro (19) and from basement membranes of the cornea (20), suggesting that ECM may serve as a reservoir for bFGF. Immunohistochemical staining revealed the localization of bFGF in basement membranes of diverse tissues and blood vessels (21). Despite the ubiquitous presence of bFGF in normal tissues, endothelial cell proliferation in these tissues is usually very low, suggesting that bFGF is somehow sequestered from its site of action. Studies on the interaction of bFGF with ECM revealed that bFGF binds to HSPG in the ECM and can be released in an active form by HS degrading enzymes (15, 20, 22). It was demonstrated that heparanase activity expressed by platelets, mast cells, neutrophils, and lymphoma cells is involved in release of active bFGF from ECM and basement membranes (23), suggesting that heparanase activity may not only function in cell migration and invasion, but may also elicit an indirect neovascular response. These results suggest that the ECM HSPG provides a natural storage depot for bFGF and possibly other heparin-binding growth promoting factors (24, 25). Displacement of bFGF from its storage within basement membranes and ECM may therefore provide a novel mechanism for induction of neovascularization in normal and pathological situations.

Recent studies indicate that heparin and HS are involved in binding of bFGF to high affinity cell surface receptors and in bFGF cell signaling (26, 27). Moreover, the size of HS required for optimal effect was similar to that of HS fragments released by heparanase (28). Similar results were obtained with vascular endothelial cells growth factor (VEGF) (29), suggesting the operation of a dual receptor mechanism involving HS in cell interaction with heparin-binding growth factors. It is therefore proposed that restriction of endothelial cell growth factors in ECM prevents their systemic action on the vascular endothelium, thus maintaining a very low rate of endothelial cells turnover and vessel growth. On the other hand, release of bFGF from storage in ECM as a complex with HS fragment, may elicit localized endothelial cell proliferation and neovascularization in processes such as wound healing, inflammation and tumor development (24, 25).

Expression of heparanase by cells of the immune system: Heparanase activity correlates with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of HS by a specific heparanase activity (6). The enzyme is released from intracellular compartments (e.g., lysosomes, specific granules, etc.) in response to various activation signals (e.g., thrombin, calcium ionophore, immune complexes, antigens, mitogens, etc.), suggesting its regulated involvement in inflammation and cellular immunity.

Some of the Observations Regarding the Heparanase Enzyme were Reviewed in Reference No. 6 and are Listed Hereinbelow:

First, a proteolytic activity (plasminogen activator) and heparanase participate synergistically in sequential degradation of the ECM HSPG by inflammatory leukocytes and malignant cells.

Second, a large proportion of the platelet heparanase exists in a latent form, probably as a complex with chondroitin sulfate. The latent enzyme is activated by tumor cell-derived factor(s) and may then facilitate cell invasion through the vascular endothelium in the process of tumor metastasis.

Third, release of the platelet heparanase from α-granules is induced by a strong stimulant (i.e., thrombin), but not in response to platelet activation on ECM.

Fourth, the neutrophil heparanase is preferentially and readily released in response to a threshold activation and upon incubation of the cells on ECM.

Fifth, contact of neutrophils with ECM inhibited release of noxious enzymes (proteases, lysozyme) and oxygen radicals, but not of enzymes (heparanase, gelatinase) which may enable diapedesis. This protective role of the subendothelial ECM was observed when the cells were stimulated with soluble factors but not with phagocytosable stimulants.

Sixth, intracellular heparanase is secreted within minutes after exposure of T cell lines to specific antigens.

Seventh, mitogens (Con A, LPS) induce synthesis and secretion of heparanase by normal T and B lymphocytes maintained in vitro. T lymphocyte heparanase is also induced by immunization with antigen in vivo.

Eighth, heparanase activity is expressed by pre-B lymphomas and B-lymphomas, but not by plasmacytomas and resting normal B lymphocytes.

Ninth, heparanase activity is expressed by activated macrophages during incubation with ECM, but there was little or no release of the enzyme into the incubation medium. Similar results were obtained with human myeloid leukemia cells induced to differentiate to mature macrophages.

Tenth, T-cell mediated delayed type hypersensitivity and experimental autoimmunity are suppressed by low doses of heparanase inhibiting non-anticoagulant species of heparin (30).

Eleventh, heparanase activity expressed by platelets, neutrophils and metastatic tumor cells releases active bFGF from ECM and basement membranes. Release of bFGF from storage in ECM may elicit a localized neovascular response in processes such as wound healing, inflammation and tumor development.

Twelfth, among the breakdown products of the ECM generated by heparanase is a tri-sulfated disaccharide that can inhibit T-cell mediated inflammation in vivo (31). This inhibition was associated with an inhibitory effect of the disaccharide on the production of biologically active TNFα by activated T cells in vitro (31).

Other potential therapeutic applications: Apart from its involvement in tumor cell metastasis, inflammation and autoimmunity, mammalian heparanase may be applied to modulate: bioavailability of heparin-binding growth factors (15); cellular responses to heparin-binding growth factors (e.g., bFGF, VEGF) and cytokines (IL-8) (31a, 29); cell interaction with plasma lipoproteins (32); cellular susceptibility to certain viral and some bacterial and protozoa infections (33, 33a, 33b); and disintegration of amyloid plaques (34). Heparanase may thus prove useful for conditions such as wound healing, angiogenesis, restenosis, atherosclerosis, inflammation, neurodegenerative diseases and viral infections. Mammalian heparanase can be used to neutralize plasma heparin, as a potential replacement of protamine. Anti-heparanase antibodies may be applied for immunodetection and diagnosis of micrometastases, autoimmune lesions and renal failure in biopsy specimens, plasma samples, and body fluids. Common use in basic research is expected.

The identification of the hpa gene encoding for heparanase enzyme will enable the production of a recombinant enzyme in heterologous expression systems. Availability of the recombinant protein will pave the way for solving the protein structure function relationship and will provide a tool for developing new inhibitors.

Viral Infection: The presence of heparan sulfate on cell surfaces have been shown to be the principal requirement for the binding of Herpes Simplex (33) and Dengue (33a) viruses to cells and for subsequent infection of the cells. Removal of the cell surface heparan sulfate by heparanase may therefore abolish virus infection. In fact, treatment of cells with bacterial heparitinase (degrading heparan sulfate) or heparinase (degrading heparan) reduced the binding of two related animal herpes viruses to cells and rendered the cells at least partially resistant to virus infection (33). There are some indications that the cell surface heparan sulfate is also involved in HIV infection (33b).

Neurodegenerative diseases: Heparan sulfate proteoglycans were identified in the prion protein amyloid plaques of Genstmann-Straussler Syndrome, Creutzfeldt-Jakob disease and Scrape (34). Heparanase may disintegrate these amyloid plaques which are also thought to play a role in the pathogenesis of Alzheimer's disease.

Restenosis and Atherosclerosis: Proliferation of arterial smooth muscle cells (SMCs) in response to endothelial injury and accumulation of cholesterol rich lipoproteins are basic events in the pathogenesis of atherosclerosis and restenosis (35). Apart from its involvement in SMC proliferation (i.e., low affinity receptors for heparin-binding growth factors), HS is also involved in lipoprotein binding, retention and uptake (36). It was demonstrated that HSPG and lipoprotein lipase participate in a novel catabolic pathway that may allow substantial cellular and interstitial accumulation of cholesterol rich lipoproteins (32). The latter pathway is expected to be highly atherogenic by promoting accumulation of apoB and apoE rich lipoproteins (i.e. LDL, VLDL, chylomicrons), independent of feed back inhibition by the cellular sterol content. Removal of SMC HS by heparanase is therefore expected to inhibit both SMC proliferation and lipid accumulation and thus may halt the progression of restenosis and atherosclerosis.

Gene Therapy:

The ultimate goal in the management of inherited as well as acquired diseases is a rational therapy with the aim to eliminate the underlying biochemical defects associated with the disease rather then symptomatic treatment. Gene therapy is a promising candidate to meet these objectives. Initially it was developed for treatment of genetic disorders, however, the consensus view today is that it offers the prospect of providing therapy for a variety of acquired diseases, including cancer, viral infections, vascular diseases and neurodegenerative disorders.

The gene-based therapeutic can act either intracellularly, affecting only the cells to which it is delivered, or extracellularly, using the recipient cells as local endogenous factories for the therapeutic product(s). The application of gene therapy may follow any of the following strategies; (i) prophylactic gene therapy, such as using gene transfer to protect cells against viral infection; (ii) cytotoxic gene therapy, such as cancer therapy, where genes encode cytotoxic products to render the target cells vulnerable to attack by the normal immune response; (iii) biochemical correction, primarily for the treatment of single gene defects, where a normal copy of the gene is added to the affected or other cells.

To allow efficient transfer of the therapeutic genes, a variety of gene delivery techniques have been developed based on viral and non-viral vector systems. The most widely used and most efficient systems for delivering genetic material into target cells are viral vectors. So far, 329 clinical studies (phase I, I/II and II) with over 2,500 patients have been initiated Worldwide since 1989 (50).

The approach of gene addition pose serious barriers. The expression of many genes is tightly regulated and context dependent, so achieving the correct balance and function of expression is challenging. The gene itself is often quite large, containing many exons and introns. The delivery vector is usually a virus, which can infect with a high efficiency but may, on the other hand, induce immunological response and consequently decreases effectiveness, especially upon secondary administration. Most of the current expression vector-based gene therapy protocols fail to achieve clinically significant transgene expression required for treating genetic diseases. Apparently, it is difficult to deliver enough virus to the right cell type to elicit an effective and therapeutic effect (51)

Homologous recombination, which was initially considered to be of limited use for gene therapy because of its low frequency in mammalian cells, has recently emerged as a potential strategy for developing gene therapy. Different approaches have been used to study homologous recombination in mammalian cells; some involve DNA repair mechanisms. These studies aimed at either gene disruption or gene correction and include RNA/DNA chimeric oligonucleotides, small or large homologous DNA fragments, or adeno-associated viral vectors. Most of these studies show a reasonable frequency of homologous recombination, which warrants further in vivo testing (52). Homologous recombination-based gene therapy has the potential to develop into a powerful therapeutic modality for genetic diseases. It can offer permanent expression and normal regulation of corrected genes in appropriate cells or organs and probably can be used for treating dominantly inherited diseases such as polycystic kidney disease.

Genomic Sequences Function in Regulation of Gene Expression:

The efficient expression of therapeutic genes in target cells or tissues is an important component of efficient and safe gene therapy. The expression of genes is driven by the promoter region upstream of the coding sequence, although regulation of expression may be supplemented by farther upstream or downstream DNA sequences or DNA in the introns of the gene. Since this important information is embedded in the DNA, the description of gene structure is crucial to the analysis of gene regulation. Characterization of cell specific or tissue specific promoters, as well as other tissue specific regulatory elements enables the use of such sequences to direct efficient cell specific, or developmental stage specific gene expression. This information provides the basis for targeting individual genes and for control of their expression by exogenous agents, such as drugs. Identification of transcription factors and other regulatory proteins required for proper gene expression will point at new potential targets for modulating gene expression, when so desired or required.

Efficient expression of many mammalian genes depends on the presence of at least one intron. The expression of mouse thymidylate synthase (TS) gene, for example, is greatly influenced by intron sequences. The addition of almost any of the introns from the mouse TS gene to an intronless TS minigene leads to a large increase in expression (42). The involvement of intron 1 in the regulation of expression was demonstrated for many other genes. In human factor IX (hFIX), intron 1 is able to increase the expression level about 3 fold mare as compared to that of the hFIX cDNA (43). The expression enhancing activity of intron 1 is due to efficient functional splicing sequences, present in the precursor mRNA. By being efficiently assembled into spliceosome complexes, transcripts with splicing sequences may be better protected in the nucleus from random degradations, than those without such sequences (44).

A forward-inserted intron1-carrying hFIX expression cassette suggested to be useful for directed gene transfer, while for retroviral-mediated gene transfer system, reversely-inserted intron 1-carrying hFIX expression cassette was considered (43).

A highly conserved cis-acting sequence element was identified in the first intron of the mouse and rat c-Ha-ras, and in the first exon of Ha- and Ki-ras genes of human, mouse and rat. This cis-acting regulatory sequence confers strong transcription enhancer activity that is differentially modulated by steroid hormones in metastatic and nonmetastatic subpopulations. Perturbations in the regulatory activities of such cis-acting sequences may play an important role in governing oncogenic potency of Ha-ras through transcriptional control mechanisms (45).

Intron sequences affect tissue specific, as well as inducible gene expression. A 182 bp intron 1 DNA segment of the mouse Col2a1 gene contains the necessary information to confer high-level, temporally correct, chondrocyte expression on a reporter gene in intact mouse embryos, while Col2a1 promoter sequences are dispensable for chondrocyte expression (46). In Col1A1 gene the intron plays little or no role in constitutive expression of collagen in the skin, and in cultured cells derived from the skin, however, in the lungs of young mice, intron deletion results in decrease of expression to less than 50% (47).

A classical enhancer activity was shown in the 2 kb intron fragment in bovine beta-casein gene. The enhancer activity was largely dependent on the lactogenic hormones, especially prolactin. It was suggested that several elements in the intron-1 of the bovine beta-casein gene cooperatively interact not only with each other but also with its promoter for hormonal induction (48).

Identification and characterization of regulatory elements in genomic non-coding sequences, such as introns, provides a tool for designing and constructing novel vectors for tissue specific, hormone regulated or any other defined expression pattern, for gene therapy. Such an expression cassette was developed, utilizing regulatory elements from the human cytokeratin 18 (K18) gene, including 5' genomic sequences and one of its introns. This cassette efficiently expresses reporter genes, as well as the human cystic fibrosis transmembrane conductance regulator (CFTR) gene, in cultured lung epithelial cells (49).

Alternative Splicing:

Alternative splicing of pre mRNA is a powerful and versatile regulatory mechanism that can effect quantitative control of gene expression and functional diversification of proteins. It contributes to major developmental decisions and also to a fine-tuning of gene function. Genetic and biochemical approaches have identified cis-acting regulatory elements and trans-acting factors that control alternative splicing of specific mRNAs. This mechanism results in the generation of variant isoforms of various proteins from a single gene. These include cell surface molecules such as CD44, receptors, cytokines such as VEGF and enzymes. Products of alternatively spliced transcripts differ in their expression pattern, substrate specificity and other biological parameters.

The FGF receptor RNA undergoes alternative splicing which results in the production of several isoforms, which exhibit different ligand binding specificities. The alternative splicing is regulated in a cell specific manner (53).

Alternative spliced mRNAs are often correlated with malignancy. An increase in specific splice variant of tyrosinase was identified in murine melanomas (54). Multiple splicing variants of estrogen receptor are present in individual human breast tumors. CD44 has various isoform, some are characteristic of malignant tissues.

Identification of tumor specific alternative splice variants provide new tool for cancer diagnostics. CD44 variants have been used for detection of malignancy in urine samples from patients with urothelial cancer by competitive RT-PCR (55). CD44 exon 6 was suggested as prognostic indicator of metastasis in breast cancer (56).

Different enzymes or polypeptides generated by alternative splicing may have different function or catalytic specificity. The identification and characterization of the enzyme forms, which are involved in pathological processes, is crucial for the design of appropriate and efficient drugs.

Modulation of Gene Expression—Antisense Technology:

An antisense oligonucleotide (e.g., antisense oligodeoxyribonucleotide) may bind its target nucleic acid either by Watson-Crick base pairing or Hoogsteen and anti-Hoogsteen base pairing (64). According to the Watson-Crick base pairing, heterocyclic bases of the antisense oligonucleotide form hydrogen bonds with the heterocyclic bases of target single-stranded nucleic acids (RNA or single-stranded DNA), whereas according to the Hoogsteen base pairing, the heterocyclic bases of the target nucleic acid are double-stranded DNA, wherein a third strand is accommodated in the major groove of the B-form DNA duplex by Hoogsteen and anti-Hoogsteen base pairing to form a triple helix structure.

According to both the Watson-Crick and the Hoogsteen base pairing models, antisense oligonucleotides have the potential to regulate gene expression and to disrupt the essential functions of the nucleic acids in cells. Therefore, antisense oligonucleotides have possible uses in modulating a wide range of diseases in which gene expression is altered.

Since the development of effective methods for chemically synthesizing oligonucleotides, these molecules have been extensively used in biochemistry and biological research and have the potential use in medicine, since carefully devised oligonucleotides can be used to control gene expression by regulating levels of transcription, transcripts and/or translation.

Oligodeoxyribonucleotides as long as 100 base pairs (bp) are routinely synthesized by solid phase methods using commercially available, fully automated synthesis machines. The chemical synthesis of oligoribonucleotides, however, is far less routine. Oligoribonucleotides are also much less stable than oligodeoxyribonucleotides, a fact which has contributed to the more prevalent use of oligodeoxyribonucleotides in medical and biological research, directed at, for example, the regulation of transcription or translation levels.

Gene expression involves few distinct and well regulated steps. The first major step of gene expression involves transcription of a messenger RNA (mRNA) which is an RNA sequence complementary to the antisense (i.e., −) DNA strand, or, in other words, identical in sequence to the DNA sense (i.e., +) strand, composing the gene. In eukaryotes, transcription occurs in the cell nucleus.

The second major step of gene expression involves translation of a protein (e.g., enzymes, structural proteins, secreted proteins, gene expression factors, etc.) in which the mRNA interacts with ribosomal RNA complexes (ribosomes) and amino acid activated transfer RNAs (tRNAs) to direct the synthesis of the protein coded for by the mRNA sequence.

Initiation of transcription requires specific recognition of a promoter DNA sequence located upstream to the coding sequence of a gene by an RNA-synthesizing enzyme—RNA polymerase. This recognition is preceded by sequence-specific binding of one or more transcription factors to the promoter sequence. Additional proteins which bind at or close to the promoter sequence may trans upregulate transcription via cis elements known as enhancer sequences. Other proteins which bind to or close to the promoter, but whose binding prohibits the action of RNA polymerase, are known as repressors.

There are also evidence that in some cases gene expression is downregulated by endogenous antisense RNA repressors that bind a complementary mRNA transcript and thereby prevent its translation into a functional protein.

Thus, gene expression is typically upregulated by transcription factors and enhancers and downregulated by repressors.

However, in many disease situation gene expression is impaired. In many cases, such as different types of cancer, for various reasons the expression of a specific endogenous or exogenous (e.g., of a pathogen such as a virus) gene is upregulated. Furthermore, in infectious diseases caused by pathogens such as parasites, bacteria or viruses, the disease progression depends on expression of the pathogen genes, this phenomenon may also be considered as far as the patient is concerned as upregulation of exogenous genes.

Most conventional drugs function by interaction with and modulation of one or more targeted endogenous or exogenous proteins, e.g., enzymes. Such drugs, however, typically are not specific for targeted proteins but interact with other proteins as well. Thus, a relatively large dose of drug must be used to effectively modulate a targeted protein.

Typical daily doses of drugs are from $10^{-5}$–$10^{-1}$ millimoles per kilogram of body weight or $10^{-3}$–10 millimoles for a 100 kilogram person. If this modulation instead could be effected by interaction with and inactivation of mRNA, a dramatic reduction in the necessary amount of drug could likely be achieved, along with a corresponding reduction in side effects. Further reductions could be effected if such interaction could be rendered site-specific. Given that a functioning gene continually produces mRNA, it would thus be even more advantageous if gene transcription could be arrested in its entirety.

Given these facts, it would be advantageous if gene expression could be arrested or downmodulated at the transcription level.

The ability of chemically synthesizing oligonucleotides and analogs thereof having a selected predetermined sequence offers means for downmodulating gene expression. Three types of gene expression modulation strategies may be considered.

At the transcription level, antisense or sense oligonucleotides or analogs that bind to the genomic DNA by strand displacement or the formation of a triple helix, may prevent transcription (64).

At the transcript level, antisense oligonucleotides or analogs that bind target mRNA molecules lead to the enzymatic cleavage of the hybrid by intracellular RNase H (65). In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing (66). As a result, in both cases, the number of the target mRNA intact transcripts ready for translation is reduced or eliminated.

At the translation level, antisense oligonucleotides or analogs that bind target mRNA molecules prevent, by steric hindrance, binding of essential translation factors (ribosomes), to the target mRNA, a phenomenon known in the art as hybridization arrest, disabling the translation of such mRNAs (67).

Thus, antisense sequences, which as described hereinabove may arrest the expression of any endogenous and/or exogenous gene depending on their specific sequence, attracted much attention by scientists and pharmacologists who were devoted at developing the antisense approach into a new pharmacological tool (68).

For example, several antisense oligonucleotides have been shown to arrest hematopoietic cell proliferation (69), growth (70), entry into the S phase of the cell cycle (71), reduced survival (72) and prevent receptor mediated responses (73). For use of antisense oligonucleotides as antiviral agents the reader is referred to reference 74.

For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity.

Unmodified oligonucleotides are impractical for use as antisense sequences since they have short in vivo half-lives, during which they are degraded rapidly by nucleases. Furthermore, they are difficult to prepare in more than milligram quantities. In addition, such oligonucleotides are poor cell membrane penetraters (75).

Thus it is apparent that in order to meet all the above listed requirements, oligonucleotide analogs need to be devised in a suitable manner. Therefore, an extensive search for modified oligonucleotides has been initiated.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases, thereby improving binding conditions with regard to ionic strength and pH.

In addition, in order to improve half-life as well as membrane penetration, a large number of variations in polynucleotide backbones have been done, nevertheless with little success.

Oligonucleotides can be modified either in the base, the sugar or the phosphate moiety. These modifications include, for example, the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester bridges, carbonate bridges, carboxymethyl ester bridges, acetamide bridges, carbamate bridges, thioether bridges, sulfoxy bridges, sulfono bridges, various "plastic" DNAs, α-anomeric bridges and borane derivatives. For further details the reader is referred to reference 76.

International patent application WO 89/12060 discloses various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone ($—SO_2—$). However, the application provides no data supporting the specific binding of an oligonucleotide analog to a target oligonucleotide.

International patent application WO 92/20702 describe an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other (77). PNA oligomers can be synthesized from the four protected monomers containing thymine, cytosine, adenine and guanine by Merrifield solid-phase peptide synthesis. In order to increase solubility in water and to prevent aggregation, a lysine amide group is placed at the C-terminal.

Thus, antisense technology requires pairing of messenger RNA with an oligonucleotide to form a double helix that inhibits translation. The concept of antisense-mediated gene therapy was already introduced in 1978 for cancer therapy. This approach was based on certain genes that are crucial in cell division and growth of cancer cells. Synthetic fragments of genetic substance DNA can achieve this goal. Such molecules bind to the targeted gene molecules in RNA of tumor cells, thereby inhibiting the translation of the genes and resulting in dysfunctional growth of these cells. Other mechanisms has also been proposed. These strategies have been used, with some success in treatment of cancers, as well as other illnesses, including viral and other infectious diseases. Antisense oligonucleotides are typically synthesized in lengths of 13–30 nucleotides. The life span of oligonucleotide molecules in blood is rather short. Thus, they have to be chemically modified to prevent destruction by ubiquitous nucleases present in the body. Phosphorothioates are very widely used modification in antisense oligonucleotide ongoing clinical trials (57). A new generation of antisense molecules consist of hybrid antisense oligonucleotide with a central portion of synthetic DNA while four bases on each end have been modified with 2'O-methyl ribose to resemble RNA. In preclinical studies in laboratory animals, such compounds have demonstrated greater stability to metabolism in body tissues and an improved safety profile when compared with the first-generation unmodified phosphorothioate (Hybridon Inc. news). Dosens of other nucleotide analogs have also been tested in antisense technology.

RNA oligonucleotides may also be used for antisense inhibition as they form a stable RNA-RNA duplex with the target, suggesting efficient inhibition. However, due to their low stability RNA oligonucleotides are typically expressed inside the cells using vectors designed for this purpose. This approach is favored when attempting to target a mRNA that encodes an abundant and long-lived protein (57).

Recent scientific publications have validated the efficacy of antisense compounds in animal models of hepatitis, cancers, coronary artery restenosis and other diseases. The first antisense drug was recently approved by the FDA. This drug Fomivirsen, developed by Isis, is indicated for local treatment of cytomegalovirus in patients with AIDS who are intolerant of or have a contraindication to other treatments for CMV retinitis or who were insufficiently responsive to previous treatments for CMV retinitis (Pharmacotherapy News Network).

Several antisense compounds are now in clinical trials in the United States. These include locally administered antivirals, systemic cancer therapeutics. Antisense therapeutics has the potential to treat many life-threatening diseases with a number of advantages over traditional drugs. Traditional drugs intervene after a disease-causing protein is formed. Antisense therapeutics, however, block mRNA transcription/translation and intervene before a protein is formed, and since antisense therapeutics target only one specific mRNA, they should be more effective with fewer side effects than current protein-inhibiting therapy.

A second option for disrupting gene expression at the level of transcription uses synthetic oligonucleotides capable of hybridizing with double stranded DNA. A triple helix is formed. Such oligonucleotides may prevent binding of transcription factors to the gene's promoter and therefore inhibit transcription. Alternatively, they may prevent duplex unwinding and, therefore, transcription of genes within the triple helical structure.

Another approach is the use of specific nucleic acid sequences to act as decoys for transcription factors. Since transcription factors bind specific DNA sequences it is possible to synthesize oligonucleotides that will effectively compete with the native DNA sequences for available transcription factors in vivo. This approach requires the identification of gene specific transcription factor (57).

Indirect inhibition of gene expression was demonstrated for matrix metalloproteinase genes (MMP-1, -3, and -9), which are associated with invasive potential of human cancer cells. E1AF is a transcription activator of MMP genes. Expression of E1AF antisense RNA in HSC3AS cells showed decrease in mRNA and protein levels of MMP-1, -3, and -9. Moreover, HSC3AS showed lower invasive potential in vitro and in vivo. These results imply that transfection of antisense inhibits tumor invasion by down-regulating MMP genes (58).

Ribozymes:

Ribozymes are being increasingly used for the sequence-specific inhibition of gene expression by the cleavage of mRNAs encoding proteins of interest. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders. Most notably, several ribozyme gene therapy protocols for HIV patients are already in Phase 1 trials (62). More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated-WEB home page).

Gene Disruption in Animal Models:

The emergence of gene inactivation by homologous recombination methodology in embryonic stem cells has revolutionized the field of mouse genetics. The availability of a rapidly growing number of mouse null mutants has represented an invaluable source of knowledge on mammalian development, cellular biology and physiology, and has provided many models for human inherited diseases. Animal models are required for an effective drug delivery development program and evaluation of gene therapy approach. The improvement of the original knockout strategy, as well as exploitation of exogenous enzymatic systems that are active in the recombination process, has been considerably extended the range of genetic manipulations that can be produced. Additional methods have been developed to provide versatile research tools: Double replacement method, sequential gene targeting, conditional cell type specific gene targeting, single copy integration method, inducible gene targeting, gene disruption by viral delivery, replacing one gene with another, the so called knock-in method and the induction of specific balanced chromosomal translocation. It is now possible to introduce a point mutation as a unique change in the entire genome, therefore allowing very fine dissection of gene function in vivo. Furthermore, the advent of methods allowing conditional gene targeting opens the way for analysis of consequence of a particular mutation in a defined organ and at a specific time during the life of the experimental animal (59).

DNA Vaccination:

Observations in the early 1990s that plasmid DNA could directly transfect animal cells in vivo sparked exploration of the use of DNA plasmids to induce immune response by direct injection into animal of DNA encoding antigenic protein. When a DNA vaccine plasmid enters the eukaryotic cell, the protein it encodes is transcribed and translated within the cell. In the case of pathogens, these proteins are presented to the immune system in their native form, mimicking the presentation of antigens during a natural infection. DNA vaccination is particularly useful for the induction of T cell activation. It was applied for viral and bacterial infectious diseases, as well as for allergy and for cancer. The central hypothesis behind active specific immunotherapy for cancer is that tumor cells express unique antigens that should stimulate the immune system. The first DNA vaccine against tumor was carcino-embrionic antigen (CEA). DNA vaccinated animals expressed immunoprotection and immunotherapy of human CEA-expressing syngeneic mouse colon and breast carcinoma (61). In a mouse model of neuroblastoma, DNA immunization with HuD resulted in tumor growth inhibition with no neurological disease (60). Immunity to the brown locus protein, $gp^{75}$ tyrosinase-related protein-1, associated with melanoma, was investigated in a syngeneic mouse model. Priming with human gp75 DNA broke tolerance to mouse gp75. Immunity against mouse gp75 provided significant tumor protection (60).

Glycosyl Hydrolases:

Glycosyl hydrolases are a widespread group of enzymes that hydrolyze the o-glycosidic bond between two or more carbohydrates or between a carbohydrate and a noncarbohydrate moiety. The enzymatic hydrolysis of glycosidic bond occurs by using major one or two mechanisms leading to overall retention or inversion of the anomeric configuration. In both mechanisms catalysis involves two residues: a proton donor and a nucleophile. Glycosyl hydrolyses have been classified into 58 families based on amino acid similarities. The glycosyl hydrolyses from families 1, 2, 5, 10, 17, 30, 35, 39 and 42 act on a large variety of substrates, however, they all hydrolyze the glycosidic bond in a general acid catalysis mechanism, with retention of the anomeric configuration. The mechanism involves two glutamic acid residues, which are the proton donors and the nucleophile, with an aspargine always preceding the proton donor. Analyses of a set of known 3D structures from this group revealed that their catalytic domains, despite the low level of sequence identity, adopt a similar ($\alpha$/$\beta$) 8 fold with the proton donor and the nucleophile located at the C-terminal ends of strands $\beta$4 and $\beta$7, respectively. Mutations in the functional conserved amino acids of lysosomal glycosyl hydrolases were identified in lysosomal storage diseases.

Lysosomal glycosyl hydrolases including $\beta$-glucuronidase, $\beta$-manosidase, $\beta$-glucocerebrosidase, $\beta$-galactosidase and $\alpha$-L iduronidase, are all exo-glycosyl hydrolases, belong to the GH-A clan and share a similar catalytic site. However, many endo-glucanases from various organisms, such as bacterial and fungal xylenases and cellulases share this catalytic domain.

Genomic Sequence of hpa Gene and its Implications:

It is well established that heparanase activity is correlated with cancer metastasis. This correlation was demonstrated at the level of enzymatic activity as well as the levels of protein and hpa cDNA expression in highly metastatic cancer cells as compared with non-metastatic cells. As such, inhibition of heparanase activity is desirable, and has been attempted by several means. The genomic region, encoding the hpa gene and the surrounding, provides a new powerful tool for regulation of heparanase activity at the level of gene expression. Regulatory sequences may reside in noncoding regions both upstream and downstream the transcribed region as well as in intron sequences. A DNA sequence upstream of the transcription start site contains the promoter region and potential regulatory elements. Regulatory factors, which interact with the promoter region may be identified and be used as potential drugs for inhibition of cancer, metastasis and inflammation. The promoter region can be used to screen for inhibitors of heparanase gene expression. Furthermore, the hpa promoter can be used to direct cell specific, particularly cancer cell specific, expression of foreign genes, such as cytotoxic or apoptotic genes, in order to specifically destroy cancer cells.

Cancer and yet unknown related genetic disorders may involve rearrangements and mutations in the heparanase gene, either in coding or non-coding regions. Such mutations may affect expression level or enzymatic activity. The genomic sequence of hpa enables the amplification of specific genomic DNA fragments, identification and diagnosis of mutations.

There is thus a widely recognized need for, and it would be highly advantageous to have genomic, cDNA and composite polynucleotides encoding a polypeptide having heparanase activity, vectors including same, genetically modified cells expressing heparanase and a recombinant protein having heparanase activity, as well as antisense oligonucleotides, constructs and ribozymes which can be used for down regulation heparanase activity.

SUMMARY OF THE INVENTION

Cloning of the human hpa gene which encodes heparanase, and expression of recombinant heparanase by transfected host cells is reported herein, as well as down-regulation of heparanase activity by antisense technology.

A purified preparation of heparanase isolated from human hepatoma cells was subjected to tryptic digestion and microsequencing. The YGPDVGQPR (SEQ ID NO:8) sequence revealed was used to screen EST databases for homology to the corresponding back translated DNA sequence. Two closely related EST sequences were identified and were thereafter found to be identical. Both clones contained an insert of 1020 bp which included an open reading frame of 973 bp followed by a 27 bp of 3' untranslated region and a Poly A tail. Translation start site was not identified.

Cloning of the missing 5' end of hpa was performed by PCR amplification of DNA from placenta Marathon RACE cDNA composite using primers selected according to the EST clones sequence and the linkers of the composite. A 900 bp PCR fragment, partially overlapping with the identified 3' encoding EST clones was obtained. The joined cDNA fragment (hpa), 1721 bp long (SEQ ID NO:9), contained an open reading frame which encodes a polypeptide of 543 amino acids (SEQ ID NO:10) with a calculated molecular weight of 61,192 daltons.

Cloning an extended 5' sequence was enabled from the human SK-hep1 cell line by PCR amplification using the Marathon RACE. The 5' extended sequence of the SK-hep1 hpa cDNA was assembled with the sequence of the hpa cDNA isolated from human placenta (SEQ ID NO:9). The assembled sequence contained an open reading frame, SEQ ID NOs: 13 and 15, which encodes, as shown in SEQ ID NOs:14 and 15, a polypeptide of 592 amino acids with a calculated molecular weight of 66,407 daltons.

The ability of the hpa gene product to catalyze degradation of heparan sulfate in an in vitro assay was examined by expressing the entire open reading frame of hpa in insect cells, using the Baculovirus expression system. Extracts and conditioned media of cells infected with virus containing the hpa gene, demonstrated a high level of heparan sulfate degradation activity both towards soluble ECM-derived HSPG and intact ECM. This degradation activity was inhibited by heparin, which is another substrate of heparanase. Cells infected with a similar construct containing no hpa gene had no such activity, nor did non-infected cells. The ability of heparanase expressed from the extended 5' clone towards heparin was demonstrated in a mammalian expression system.

The expression pattern of hpa RNA in various tissues and cell lines was investigated using RT-PCR. It was found to be expressed only in tissues and cells previously known to have heparanase activity.

A panel of monochromosomal human/CHO and human/mouse somatic cell hybrids was used to localize the human heparanase gene to human chromosome 4. The newly isolated heparanase sequence can be used to identify a chromosome region harboring a human heparanase gene in a chromosome spread.

A human genomic library was screened and the human locus harboring the heparanase gene isolated, sequenced and characterized. Alternatively spliced heparanase mRNAs were identified and characterized. The human heparanase promoter has been isolated, identified and positively tested for activity. The mouse heparanase promoter has been isolated and identified as well. Antisense heparanase constructs were prepared and their influence on cells in vitro tested. A predicted heparanase active site was identified. And finally, the presence of sequences hybridizing with human heparanase sequences was demonstrated for a variety of mammalians and for an avian.

According to one aspect of the present invention there is provided an isolated nucleic acid comprising a genomic, complementary or composite polynucleotide sequence encoding a polypeptide having heparanase catalytic activity.

According to further features in preferred embodiments of the invention described below, the polynucleotide or a portion thereof is hybridizable with SEQ ID NOs: 9, 13, 42, 43 or a portion thereof at 68° C. in 6×SSC, 1% SDS, 5×Denharts, 10% dextran sulfate, 100 $\mu$g/ml salmon sperm DNA, and $^{32}$p labeled probe and wash at 68° C. with 3×SSC and 0.1% SDS.

According to still further features in the described preferred embodiments the polynucleotide or a portion thereof is at least 60% identical with SEQ ID NOs: 9, 13, 42, 43 or portions thereof as determined using the Bestfit procedure of the DNA sequence analysis software package developed by the Genetic Computer Group (GCG) at the university of Wisconsin (gap creation penalty—12, gap extension penalty—4).

According to still further features in the described preferred embodiments the polypeptide is as set forth in SEQ ID NOs:10, 14, 44 or portions thereof.

According to still further features in the described preferred embodiments the polypeptide is at least 60% homologous to SEQ ID NOs:10, 14, 44 or portions thereof as determined with the Smith-Waterman algorithm, using the Bioaccelerator platform developed by Compugene (gapop: 10.0, gapext: 0.5, matrix: blosum62).

According to additional aspects of the present invention there are provided a nucleic acid construct (vector) comprising the isolated nucleic acid described herein and a host cell comprising the construct.

According to a further aspect of the present invention there is provided an antisense oligonucleotide comprising a polynucleotide or a polynucleotide analog of at least 10 bases being hybridizable in vivo, under physiological conditions, with a portion of a polynucleotide strand encoding a polypeptide having heparanase catalytic activity.

According to an additional aspect of the present invention there is provided a method of in vivo downregulating heparanase activity comprising the step of in vivo administering the antisense oligonucleotide herein described.

According to yet an additional aspect of the present invention there is provided a pharmaceutical composition comprising the antisense oligonucleotide herein described and a pharmaceutically acceptable carrier.

According to still an additional aspect of the present invention there is provided a ribozyme comprising the antisense oligonucleotide described herein and a ribozyme sequence.

According to a further aspect of the present invention there is provided an antisense nucleic acid construct comprising a promoter sequence and a polynucleotide sequence directing the synthesis of an antisense RNA sequence of at least 10 bases being hybridizable in vivo, under physiological conditions, with a portion of a polynucleotide strand encoding a polypeptide having heparanase catalytic activity.

According to further features in preferred embodiments of the invention described below, the polynucleotide strand encoding the polypeptide having heparanase catalytic activity is as set forth in SEQ ID NOs: 9, 13, 42 or 43.

According to still further features in the described preferred embodiments the polypeptide having heparanase catalytic activity is as set forth in SEQ ID NOs: 10, 14 or 44.

According to still a further aspect of the present invention there is provided a method of in vivo downregulating heparanase activity comprising the step of in vivo administering the antisense nucleic acid construct herein described.

According to yet a further aspect of the present invention there is provided a pharmaceutical composition comprising the antisense nucleic acid construct herein described and a pharmaceutically acceptable carrier.

According to a further aspect of the present invention there is provided a nucleic acid construct comprising a polynucleotide sequence functioning as a promoter, the polynucleotide sequence is derived from SEQ ID NO:42 and includes at least nucleotides 2535–2635 thereof or from SEQ ID NO:43 and includes at least nucleotides 320–420.

According to a further aspect of the present invention there is provided a method of expressing a polynucleotide sequence comprising the step of ligating the polynucleotide sequence into the nucleic acid construct described above, downstream of the polynucleotide sequence derived from SEQ ID NOs:42 or 43.

According to a further aspect of the present invention there is provided a recombinant protein comprising a polypeptide having heparanase catalytic activity.

According to further features in preferred embodiments of the invention described below, the polypeptide includes at least a portion of SEQ ID NOs:10, 14 or 44.

According to still further features in the described preferred embodiments the protein is encoded by a polynucleotide hybridizable with SEQ ID NOs: 9, 13, 42, 43 or a portion thereof at 68° C. in 6×SSC, 1% SDS, 5×Denharts, 10% dextran sulfate, 100 μg/ml salmon sperm DNA, and $^{32}$p labeled probe and wash at 68° C. with 3×SSC and 0.1% SDS.

According to still further features in the described preferred embodiments the protein is encoded by a polynucleotide at least 60% identical with SEQ ID NOs: 9, 13, 42, 43 or portions thereof as determined using the Bestfit procedure of the DNA sequence analysis software package developed by the Genetic Computer Group (GCG) at the university of Wisconsin (gap creation penalty—12, gap extension penalty—4).

According to a further aspect of the present invention there is provided a pharmaceutical composition comprising, as an active ingredient, the recombinant protein herein described.

According to a further aspect of the present invention there is provided a method of identifying a chromosome region harboring a heparanase gene in a chromosome spread comprising the steps of (a) hybridizing the chromosome spread with a tagged polynucleotide probe encoding heparanase; (b) washing the chromosome spread, thereby removing excess of non-hybridized probe; and (c) searching for signals associated with the hybridized tagged polynucleotide probe, wherein detected signals being indicative of a chromosome region harboring a heparanase gene.

According to a further aspect of the present invention there is provided a method of in vivo eliciting anti-heparanase antibodies comprising the steps of administering a nucleic acid construct including a polynucleotide segment corresponding to at least a portion of SEQ ID NOs:9, 13 or 43 and a promoter for directing the expression of said polynucleotide segment in vivo. Accordingly, there is provided also a DNA vaccine for in vivo eliciting anti-heparanase antibodies comprising a nucleic acid construct including a polynucleotide segment corresponding to at least a portion of SEQ ID NOs:9, 13 or 43 and a promoter for directing the expression of said polynucleotide segment in vivo.

The present invention can be used to develop new drugs to inhibit tumor cell metastasis, inflammation and autoimmunity. The identification of the hpa gene encoding for heparanase enzyme enables the production of a recombinant enzyme in heterologous expression systems. Additional features, advantages, uses and applications of the present invention in biological science and in diagnostic and therapeutic medicine are described hereinafter.

BRIEF DESCRIPTION OF THE DRAWINGS

The invention herein described, by way of example only, with reference to the accompanying drawings, wherein:

FIG. 1 presents nucleotide (SEQ ID NO:9) and deduced amino acid (SEQ ID NO: 10) sequence of hpa cDNA. A single nucleotide difference at position 799 (A to T) between the EST (Expressed Sequence Tag) and the PCR amplified cDNA (reverse transcribed RNA) and the resulting amino acid substitution (Tyr to Phe) are indicated above and below the substituted unit, respectively. Cysteine residues and the poly adenylation consensus sequence are underlined. The asterisk denotes the stop codon TGA.

was found in the high (>50 kDa) (•), but not low (<50 kDa) (○) molecular weight compartment.

Figure 5A:
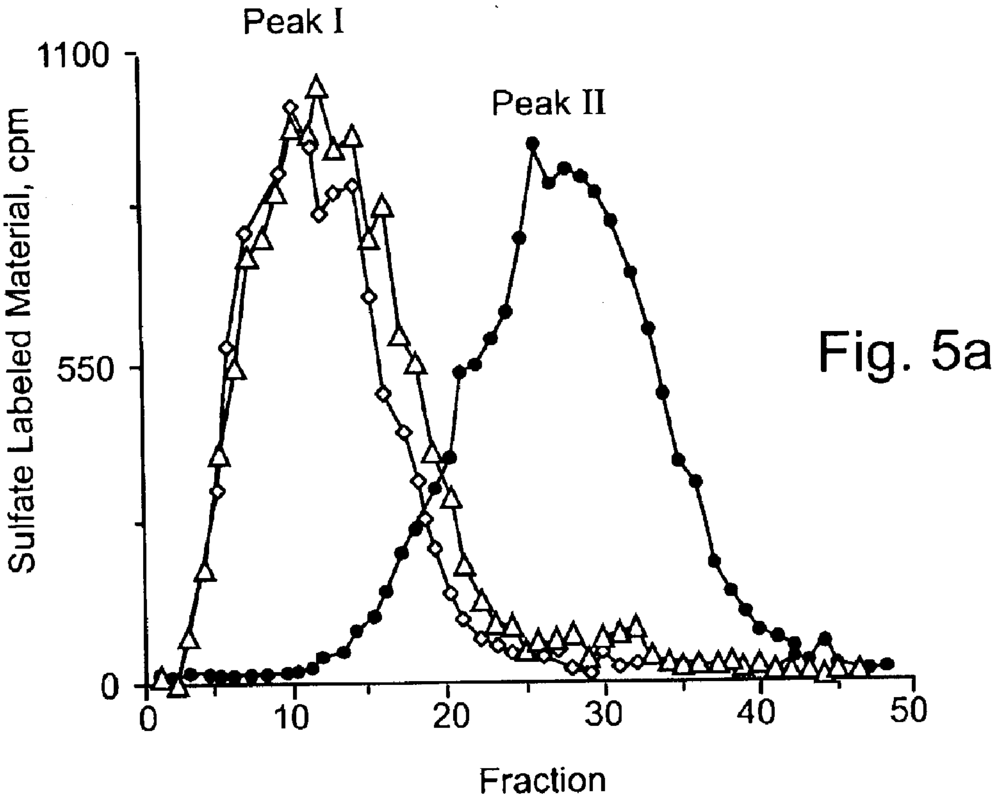
Figure 5B:
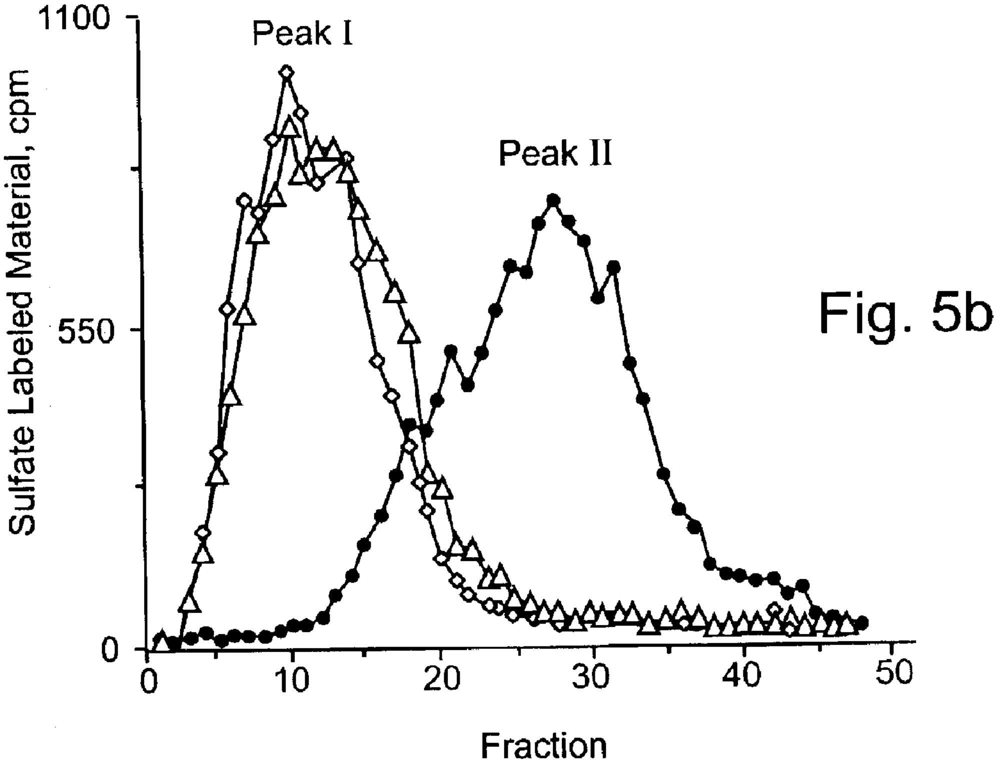

FIGS. 5*a–b* demonstrate the effect of heparin on heparanase activity expressed by pFhpa2 and pFhpa4 infected High Five cells. Culture media of pFhpa2 (5a) and pFhpa4 (5b) infected High Five cells were incubated (18 h, 37° C.) with sulfate labeled ECM-derived soluble HSPG (peak I, ◇) in the absence (•) or presence (Δ) of 10 μg/ml heparin. Production of low molecular weight HS degradation fragments was completely abolished in the presence of heparin, a potent inhibitor of heparanase activity (6, 7).

Figure 6A:
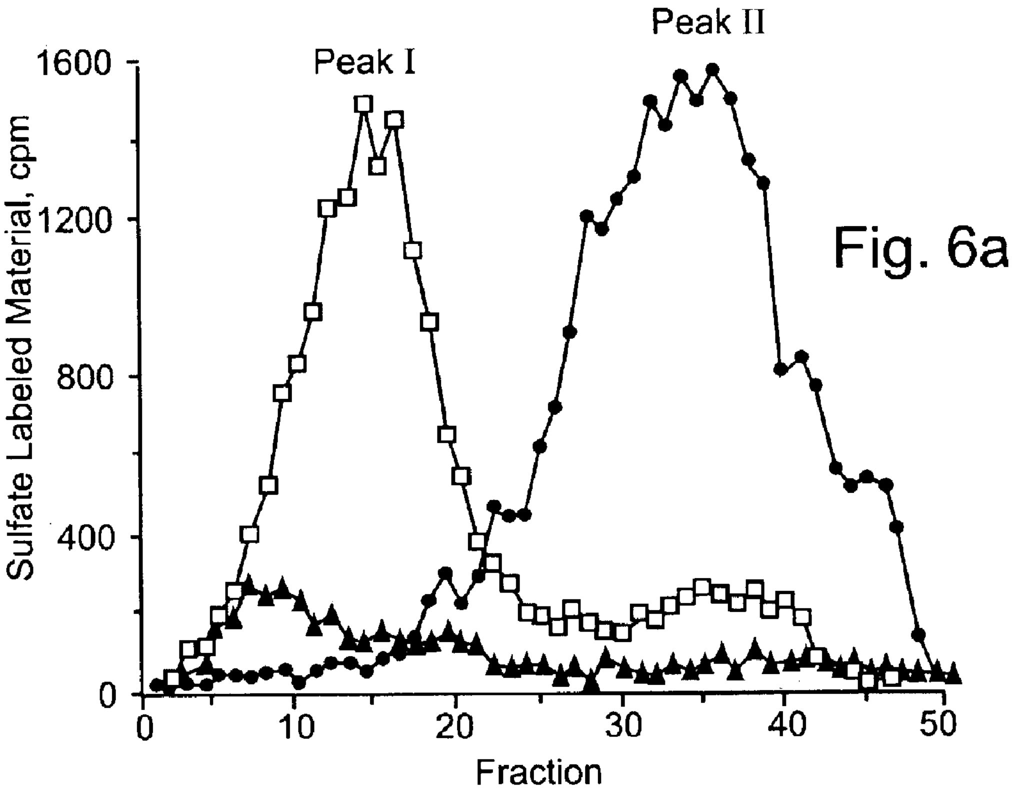
Figure 6B:
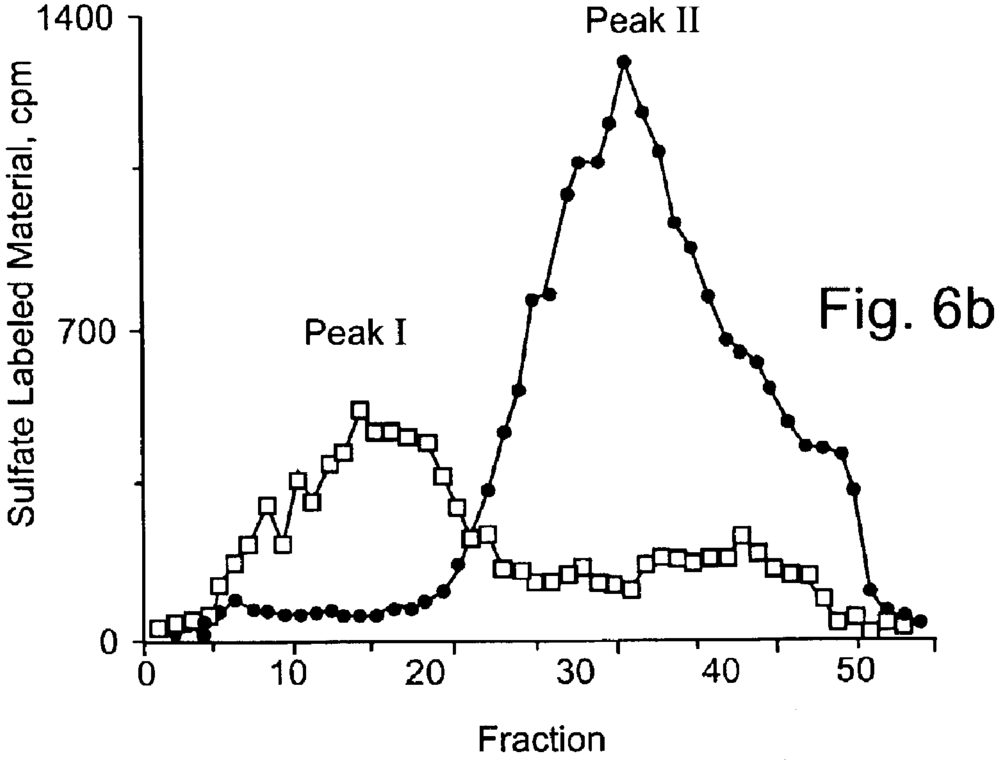

FIGS. 6*a–b* demonstrate degradation of sulfate labeled intact ECM by virus infected High Five and Sf21 cells. High Five (6a) and Sf21 (6b) cells were plated on sulfate labeled ECM and infected (48 h, 28° C.) with pFhpa4 (•) or control pF1 (□) viruses. Control non-infected Sf21 cells (R) were plated on the labeled ECM as well. The pH of the cultured medium was adjusted to 6.0–6.2 followed by 24 h incubation at 37° C. Sulfate labeled material released into the incubation medium was analyzed by gel filtration on Sepharose 6B. HS degradation fragments were produced only by cells infected with the hpa containing virus.

Figure 7A:
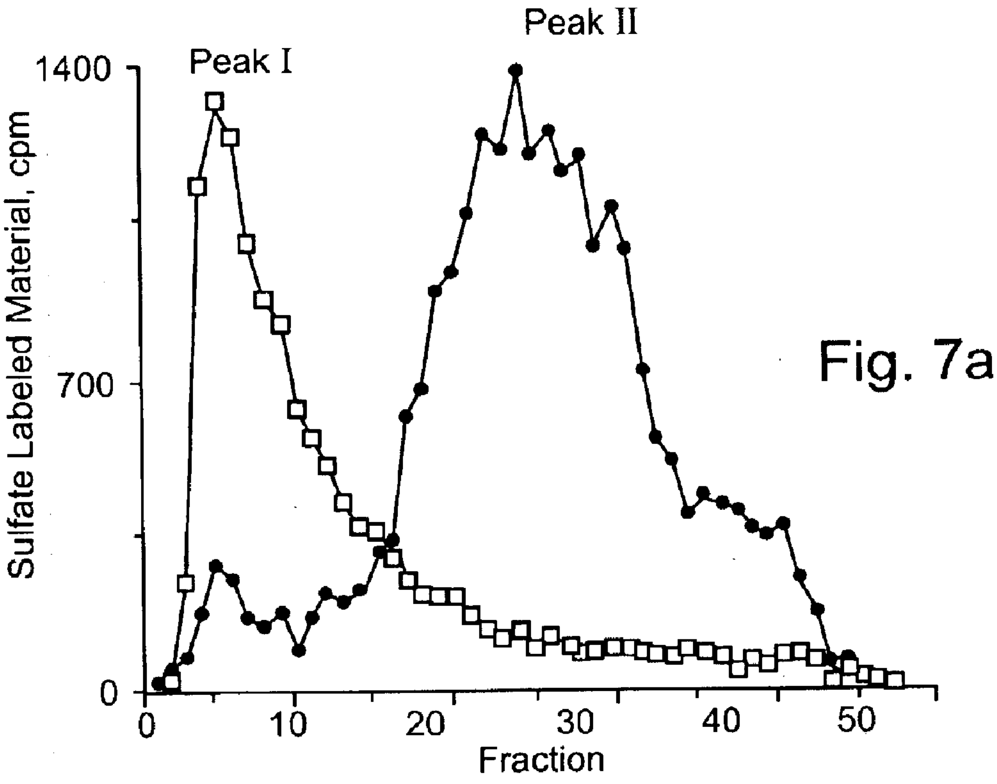
Figure 7B:
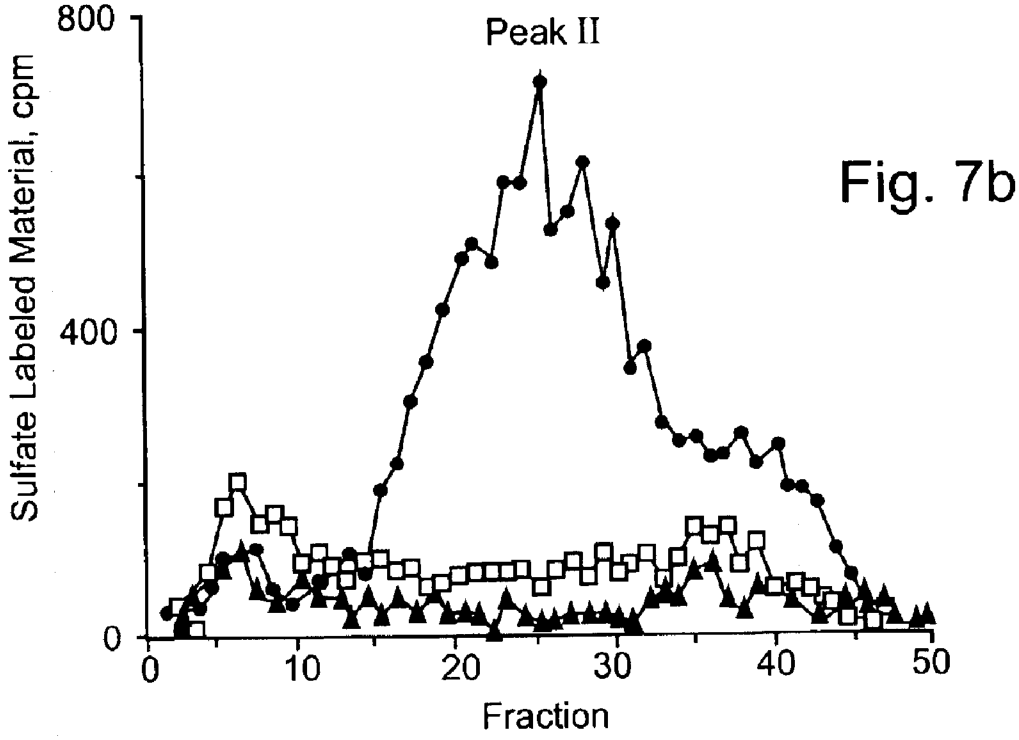

FIGS. 7*a–b* demonstrate degradation of sulfate labeled intact ECM by virus infected cells. High Five (7a) and Sf21 (7b) cells were plated on sulfate labeled ECM and infected (48 h, 28° C.) with pFhpa4 (•) or control pF1 (□) viruses. Control non-infected Sf21 cells (R) were plate on labeled ECM as well. The pH of the cultured medium was adjusted to 6.0–6.2, followed by 48 h incubation at 28° C. Sulfate labeled degradation fragments released into the incubation medium was analyzed by gel filtration on Sepharose 6B. HS degradation fragments were produced only by cells infected with the hpa containing virus.

Figure 8A:
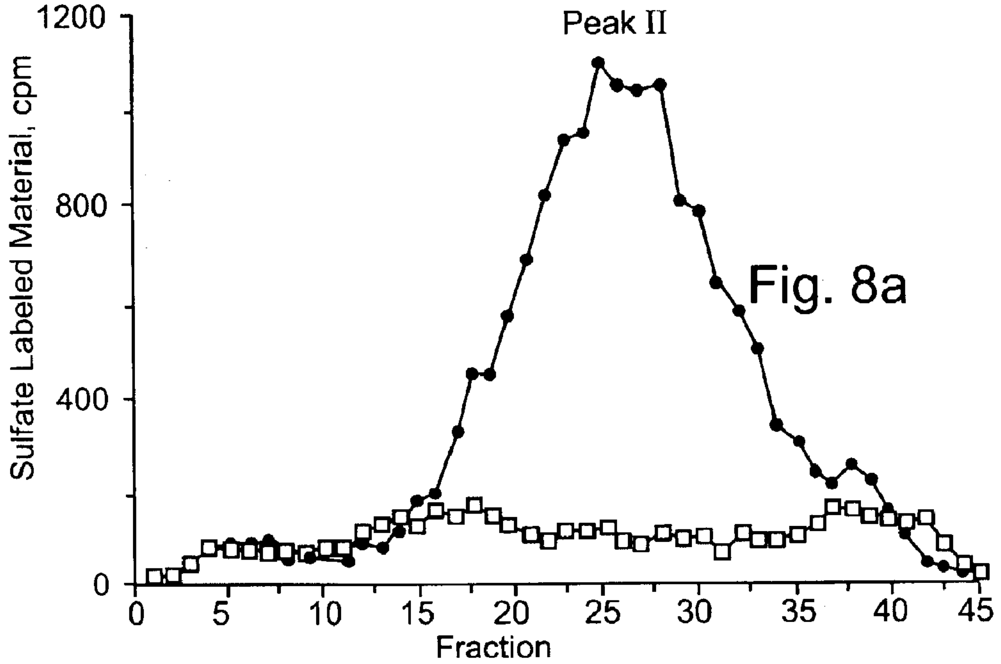
Figure 8B:
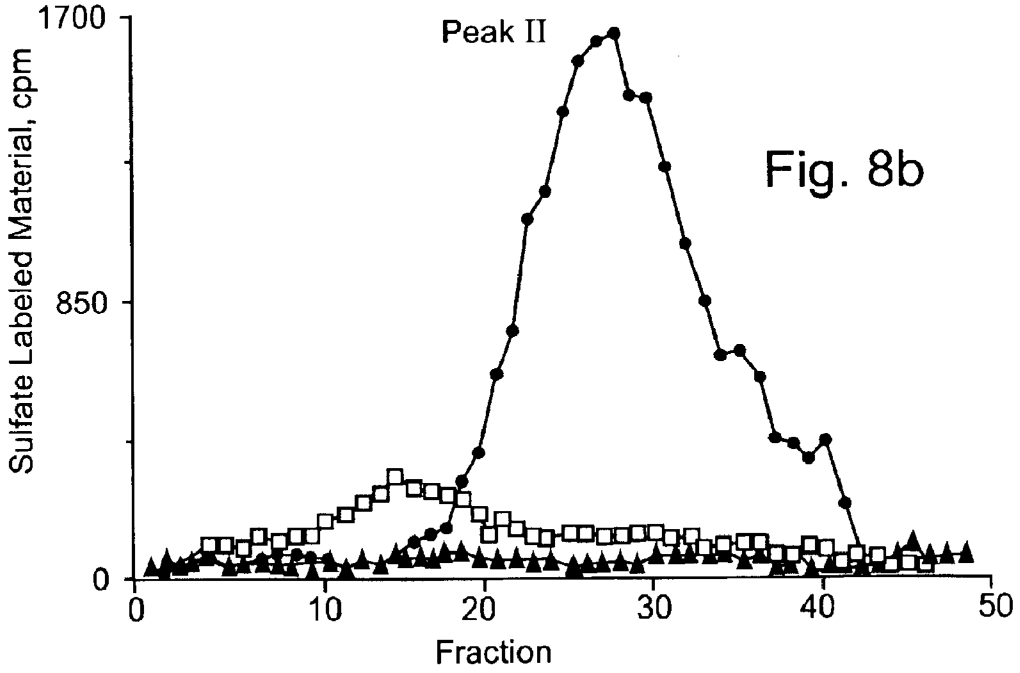

FIGS. 8*a–b* demonstrate degradation of sulfate labeled intact ECM by the culture medium of pFhpa4 infected cells. Culture media of High Five (8a) and Sf21 (8b) cells that were infected with pFhpa4 (•) or control pF1 (□) viruses were incubated (48 h, 37° C., pH 6.0) with intact sulfate labeled ECM. The ECM was also incubated with the culture medium of control non-infected Sf21 cells (R). Sulfate labeled material released into the reaction mixture was subjected to gel filtration analysis. Heparanase activity was detected only in the culture medium of pFhpa4 infected cells.

Figure 9A:
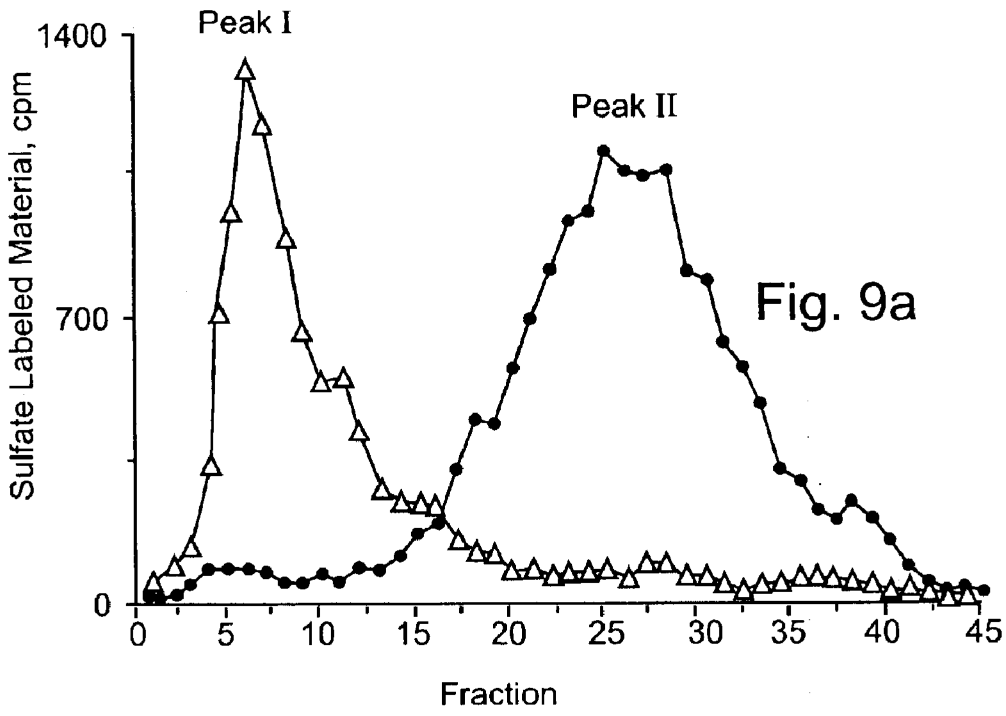
Figure 9B:
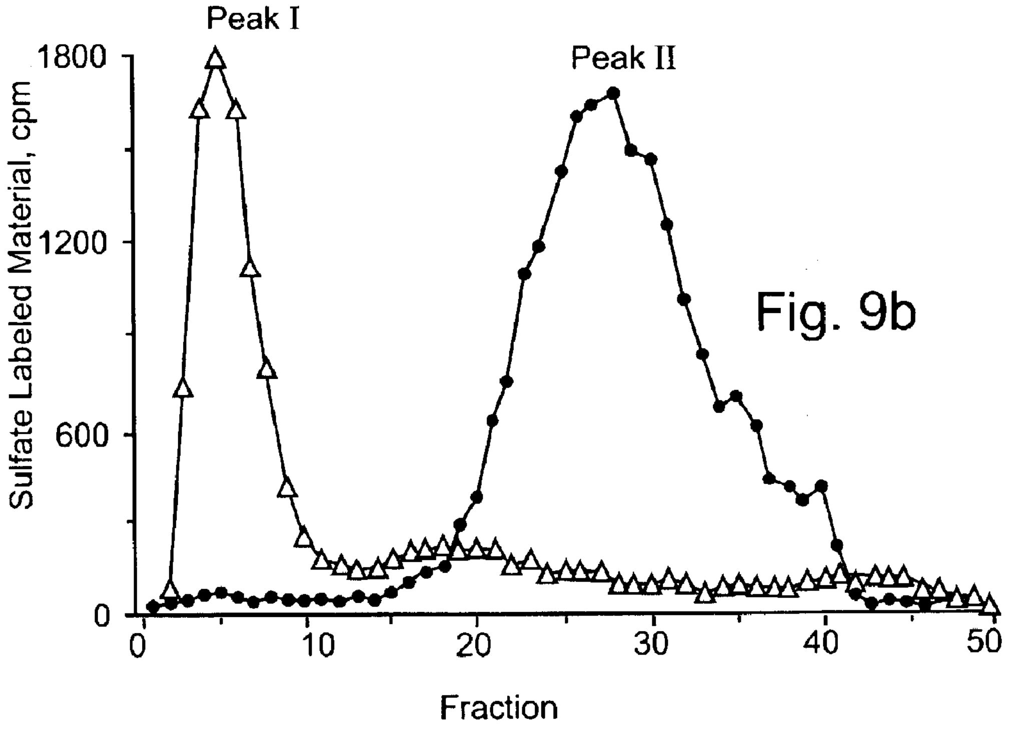

FIGS. 9*a–b* demonstrate the effect of heparin on heparanase activity in the culture medium of pFhpa4 infected cells. Sulfate labeled ECM was incubated (24 h, 37° C., pH 6.0) with culture medium of pFhpa4 infected High Five (9a) and Sf21 (9b) cells in the absence (•) or presence (V) of 10 μg/ml heparin. Sulfate labeled material released into the incubation medium was subjected to gel filtration on Sepharose 6B. Heparanase activity (production of peak II HS degradation fragments) was completely inhibited in the presence of heparin.

Figure 10A:
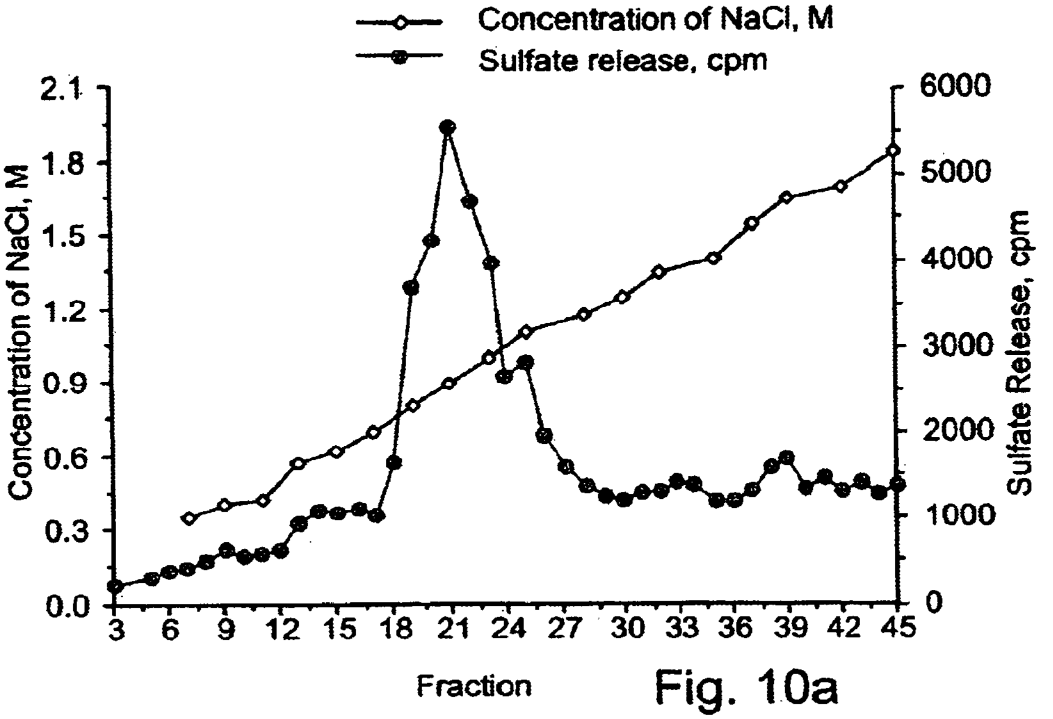
Figure 10B:
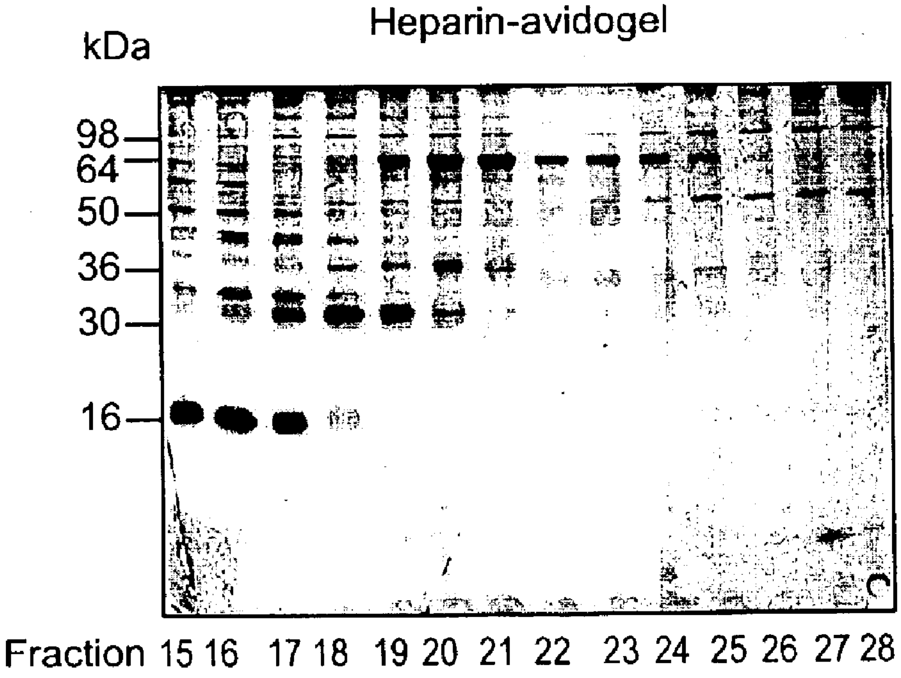

FIGS. 10*a–b* demonstrate purification of recombinant heparanase on heparin-Sepharose. Culture medium of Sf21 cells infected with pFhpa4 virus was subjected to heparin-Sepharose chromatography. Elution of fractions was performed with 0.35–2 M NaCl gradient (◇). Heparanase activity in the eluted fractions is demonstrated in FIG. 10*a* (•). Fractions 15–28 were subjected to 15% SDS-polyacrylamide gel electrophoresis followed by silver nitrate staining. A correlation is demonstrated between a major protein band (MW~63,000) in fractions 19–24 and heparanase activity.

Figure 11A:
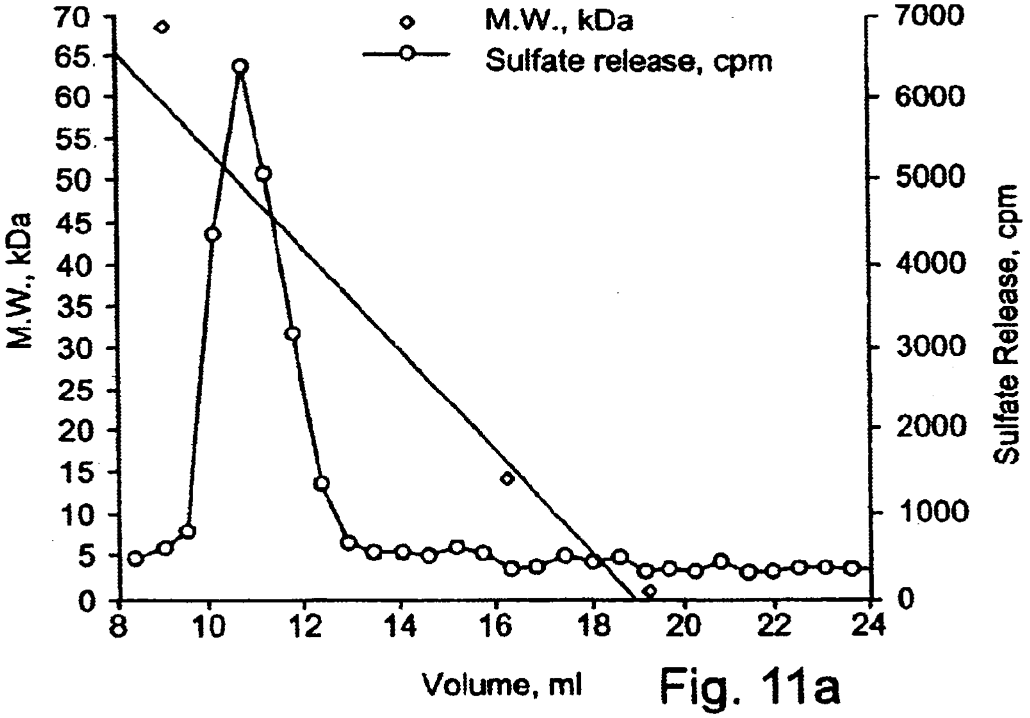
Figure 11B:
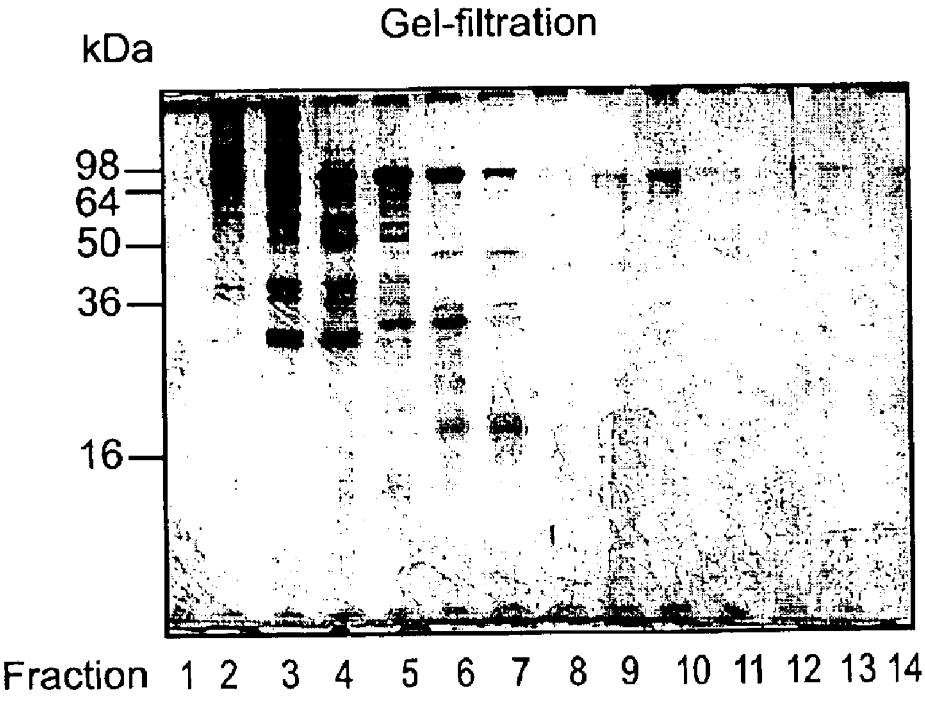

FIGS. 11*a–b* demonstrate purification of recombinant heparanase on a Superdex 75 gel filtration column. Active fractions eluted from heparin-Sepharose (FIG. 10*a*) were pooled, concentrated and applied onto Superdex 75 FPLC column. Fractions were collected and aliquots of each fraction were tested for heparanase activity (C, FIG. 11*a*) and analyzed by SDS-polyacrylamide gel electrophoresis followed by silver nitrate staining (FIG. 11*b*). A correlation is seen between the appearance of a major protein band (MW~63,000) in fractions 4–7 and heparanase activity.

FIGS. 12*a–e* demonstrate expression of the hpa gene by RT-PCR with total RNA from human embryonal tissues (12a), human extra-embryonal tissues (12b) and cell lines from different origins (12c–e). RT-PCR products using hpa specific primers (I), primers for GAPDH housekeeping gene (II), and control reactions without reverse transcriptase demonstrating absence of genomic DNA or other contamination in RNA samples (III). M-DNA molecular weight marker VI (Boehringer Mannheim). For 12a: lane 1—neutrophil cells (adult), lane 2—muscle, lane 3—thymus, lane 4—heart, lane 5—adrenal. For 12b: lane 1—kidney, lane 2—placenta (8 weeks), lane 3—placenta (11 weeks), lanes 4–7—mole (complete hydatidiform mole), lane 8 —cytotrophoblast cells (freshly isolated), lane 9—cytotrophoblast cells (1.5 h in vitro), lane 10—cytotrophoblast cells (6 h in vitro), lane 11—cytotrophoblast cells (18 h in vitro), lane 12—cytotrophoblast cells (48 h in vitro). For 12c: lane 1—JAR bladder cell line, lane 2—NCITT testicular tumor cell line, lane 3—SW-480 human hepatoma cell line, lane 4—HTR (cytotrophoblasts transformed by SV40), lane 5—HPTLP-I hepatocellular carcinoma cell line, lane 6—EJ-28 bladder carcinoma cell line. For 12d: lane 1—SK-hep-1 human hepatoma cell line, lane 2—DAMI human megakaryocytic cell line, lane 3—DAMI cell line +PMA, lane 4—CHRF cell line+PMA, lane 5—CHRF cell line. For 12e: lane 1—ABAE bovine aortic endothelial cells, lane 2—1063 human ovarian cell line, lane 3—human breast carcinoma MDA435 cell line, lane 4—human breast carcinoma MDA231 cell line.

FIG. 13 presents a comparison between nucleotide sequences of the human hpa and a mouse EST cDNA fragment (SEQ ID NO:12) which is 80% homologous to the 3' end (starting at nucleotide 1066 of SEQ ID NO:9) of the human hpa. The aligned termination codons are underlined.

Figure 14:
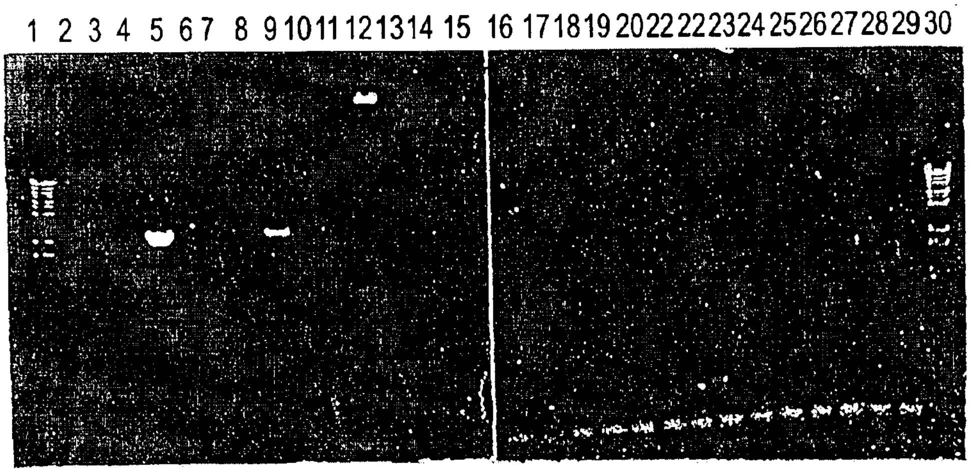

FIG. 14 demonstrates the chromosomal localization of the hpa gene. PCR products of DNA derived from somatic cell hybrids and of genomic DNA of hamster, mouse and human of were separated on 0.7% agarose gel following amplification with hpa specific primers. Lane 1—Lambda DNA digested with BstEII, lane 2—no DNA control, lanes 3—29, PCR amplification products. Lanes 3–5—human, mouse and hamster genomic DNA, respectively. Lanes 6–29, human monochromosomal somatic cell hybrids representing chromosomes 1–22 and X and Y, respectively. Lane 30—Lambda DNA digested with BstEII. An amplification product of approximately 2.8 Kb is observed only in lanes 5 and 9, representing human genomic DNA and DNA derived from cell hybrid carrying human chromosome 4, respectively. These results demonstrate that the hpa gene is localized in human chromosome 4.

Figure 15:
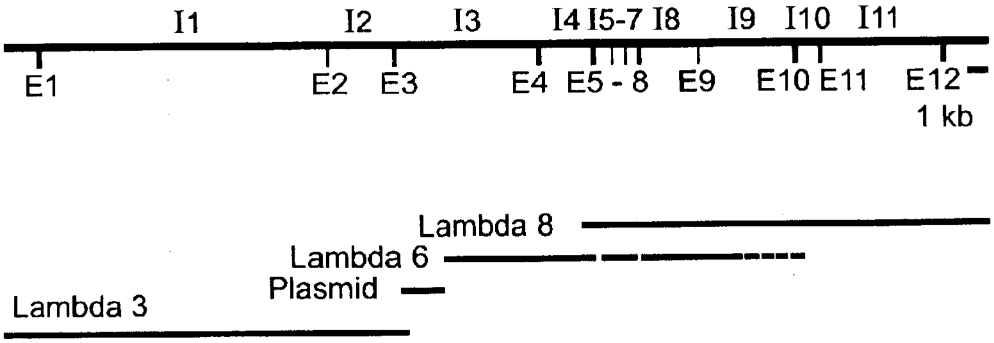

FIG. 15 demonstrates the genomic exon-intron structure of the human hpa locus (top) and the relative positions of the lambda clones used as sequencing templates to sequence the locus (below). The vertical rectangles represent exons (E) and the horizontal lines therebetween represent introns (I), upstream (U) and downstream (D) regions. Continuous lines represent DNA fragments, which were used for sequence analysis. The discontinuous line in lambda 6 represent a region, which overlaps with lambda 8 and hence was not analyzed. The plasmid contains a PCR product, which bridges the gap between L3 and L6.

FIG. 16 presents the nucleotide sequence of the genomic region of the hpa gene (SEQ ID NO:42). Exon sequences appear in upper case and intron sequences in lower case. The deduced amino acid sequence (SEQ ID NO:10) of the exons is printed below the nucleotide sequence. Two predicted transcription start sites are shown in bold.

FIG. 17 presents an alignment of the amino acid sequences of human heparanase (SEQ ID NO:10), mouse (SEQ ID NO:44) and partial sequences of rat (SEQ ID NO:48) homologues. The human and the mouse sequences were determined by sequence analysis of the isolated cDNAs. The rat sequence is derived from two different EST clones, which represent two different regions (5' and 3') of the rat hpa cDNA. The human sequence and the amino acids in the mouse and rat homologues, which are identical to the human sequence, appear in bold.

Figure 18:
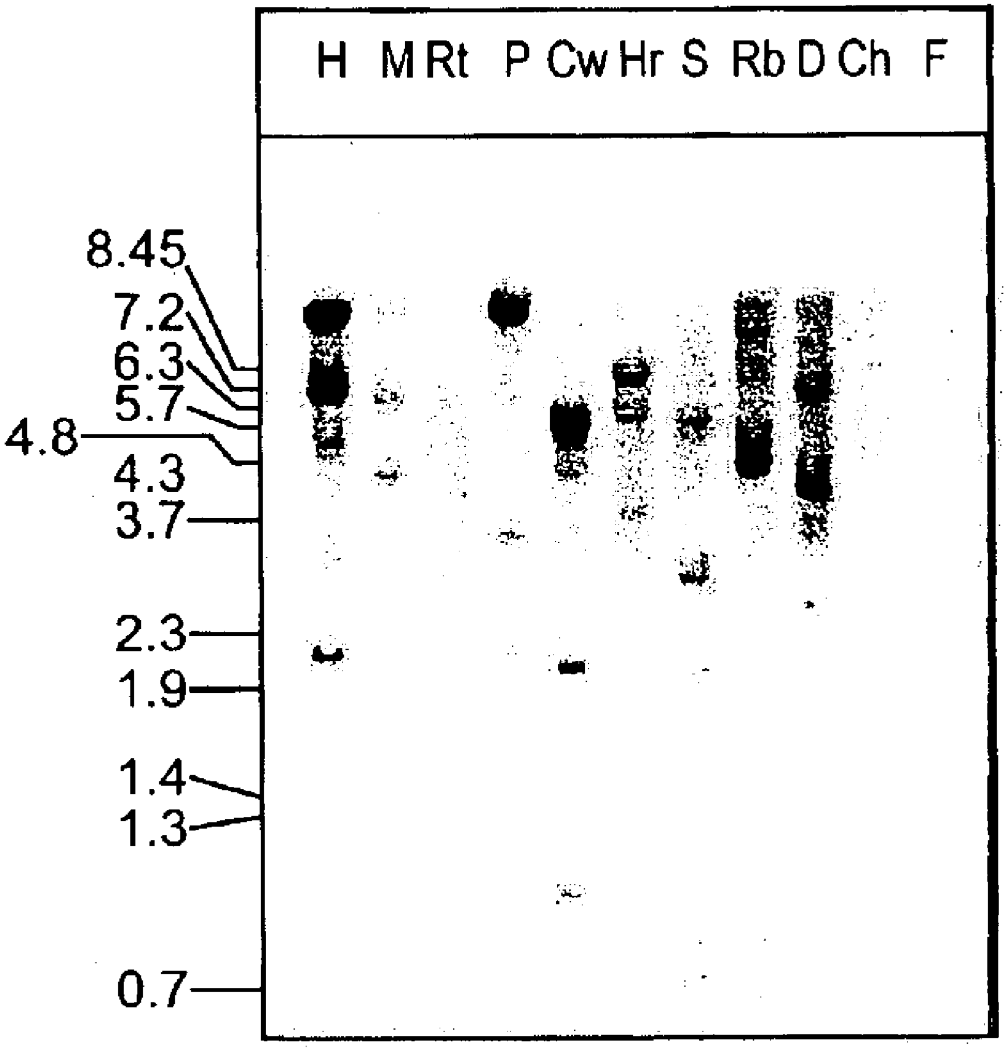

FIG. 18 presents a heparanase Zoo blot. Ten micrograms of genomic DNA from various sources were digested with EcoRI and separated on 0.7% agarose—TBE gel. Following electrophoresis, the was gel treated with HCl and than with NaOH and the DNA fragments were downward transferred to a nylon membrane (Hybond N+, Amersham) with 0.4 N NaOH. The membrane was hybridized with a 1.6 Kb DNA probe that contained the entire hpa cDNA. Lane order: H—Human; M—Mouse; Rt—Rat; P—Pig; Cw—Cow; Hr—Horse; S—Sheep; Rb—Rabbit; D—Dog; Ch—Chicken; F—Fish. Size markers (Lambda BsteII) are shown on the left FIG. 19 demonstrates the secondary structure prediction for heparanase (SEQ ID NO:10) performed using the PHD server—Profile network Prediction Heidelberg. H—helix, E—extended (beta strand), The glutamic acid predicted as the proton donor is marked by asterisk and the possible nucleophiles are underlined.

DESCRIPTION OF THE PREFERRED EMBODIMENTS

The present invention is of a polynucleotide or nucleic acid, referred to hereinbelow interchangeably as hpa, hpa cDNA or hpa gene or identified by its SEQ ID NOs, encoding a polypeptide having heparanase activity, vectors or nucleic acid constructs including same and which are used for over-expression or antisense inhibition of heparanase, genetically modified cells expressing same, recombinant protein having heparanase activity, antisense oligonucleotides and ribozymes for heparanase modulation, and heparanase promoter sequences which can be used to direct the expression of desired genes.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Cloning of the human and mouse hpa genes, cDNAs and genomic sequence (for human), encoding heparanase and expressing recombinant heparanase by transfected cells is reported herein. These are the first mammalian heparanase genes to be cloned.

A purified preparation of heparanase isolated from human hepatoma cells was subjected to tryptic digestion and microsequencing.

The YGPDVGQPR (SEQ ID NO:8) sequence revealed was used to screen EST databases for homology to the corresponding back translated DNA sequences. Two closely related EST sequences were identified and were thereafter found to be identical.

Both clones contained an insert of 1020 bp which includes an open reading frame of 973 bp followed by a 3' untranslated region of 27 bp and a Poly A tail, whereas a translation start site was not identified.

Cloning of the missing 5' end was performed by PCR amplification of DNA from placenta Marathon RACE cDNA composite using primers selected according to the EST clones sequence and the linkers of the composite.

A 900 bp PCR fragment, partially overlapping with the identified 3' encoding EST clones was obtained. The joined cDNA fragment (hpa), 1721 bp long (SEQ ID NO:9), contained an open reading frame which encodes, as shown in FIG. 1 and SEQ ID NO:11, a polypeptide of 543 amino acids (SEQ ID NO:10) with a calculated molecular weight of 61,192 daltons.

A single nucleotide difference at position 799 (A to T) between the EST clones and the PCR amplified cDNA was observed. This difference results in a single amino acid substitution (Tyr to Phe) (FIG. 1). Furthermore, the published EST sequences contained an unidentified nucleotide, which following DNA sequencing of both the EST clones was resolved into two nucleotides (G and C at positions 1630 and 1631 in SEQ ID NO:9, respectively).

The ability of the hpa gene product to catalyze degradation of heparan sulfate in an in vitro assay was examined by expressing the entire open reading frame in insect cells, using the Baculovirus expression system.

Extracts and conditioned media of cells infected with virus containing the hpa gene, demonstrated a high level of heparan sulfate degradation activity both towards soluble ECM-derived HSPG and intact ECM, which was inhibited by heparin, while cells infected with a similar construct containing no hpa gene had no such activity, nor did non-infected cells.

The expression pattern of hpa RNA in various tissues and cell lines was investigated using RT-PCR. It was found to be expressed only in tissues and cells previously known to have heparanase activity.

Cloning an extended 5' sequence was enabled from the human SK-hep1 cell line by PCR amplification using the Marathon RACE. The 5' extended sequence of the SK-hep1 hpa cDNA was assembled with the sequence of the hpa cDNA isolated from human placenta (SEQ ID NO:9). The assembled sequence contained an open reading frame, SEQ ID NOs: 13 and 15, which encodes, as shown in SEQ ID NOs:14 and 15, a polypeptide of 592 amino acids, with a calculated molecular weight of 66,407 daltons. This open reading frame was shown to direct the expression of catalytically active heparanase in a mammalian cell expression system. The expressed heparanase was detectable by anti heparanase antibodies in Western blot analysis.

A panel of monochromosomal human/CHO and human/mouse somatic cell hybrids was used to localize the human heparanase gene to human chromosome 4. The newly isolated heparanase sequence can therefore be used to identify a chromosome region harboring a human heparanase gene in a chromosome spread.

The hpa cDNA was then used as a probe to screen a a human genomic library. Several phages were positive. These phages were analyzed and were found to cover most of the hpa locus, except for a small portion which was recovered by bridging PCR. The hpa locus covers about 50,000 bp. The hpa gene includes 12 exons separated by 11 introns.

RT-PCR performed on a variety of cells revealed alternatively spliced hpa transcripts.

The amino acid sequence of human heparanase was used to search for homologous sequences in the DNA and protein databases. Several human EST's were identified, as well as mouse sequences highly homologous to human heparanase. The following mouse EST's were identified AA177901, AA674378, AA67997, AA047943, AA690179, AI122034, all sharing an identical sequence and correspond to amino acids 336–543 of the human heparanase sequence. The entire mouse heparanase cDNA was cloned, based on the nucleotide sequence of the mouse EST's using Marathon cDNA libraries. The mouse and the human hpa genes share an average homology of 78% between the nucleotide sequences and 81% similarity between the deduced amino acid sequences. hpa homologous sequences from rat were also uncovered (EST's AI060284 and AI237828).

Homology search of heparanase amino acid sequence against the DNA and the protein databases and prediction of its protein secondary structure enabled to identify candidate amino acids that participate in the heparanase active site.

Expression of hpa antisense in mammalian cell lines resulted in about five fold decrease in the number of recoverable cells as compared to controls.

Human Hpa cDNA was shown to hybridize with genomic DNAs of a variety of mammalian species and with an avian.

The human and mouse hpa promoters were identified and the human promoter was tested positive in directing the expression of a reporter gene.

Thus, according to the present invention there is provided an isolated nucleic acid comprising a genomic, complementary or composite polynucleotide sequence encoding a polypeptide having heparanase catalytic activity.

The phrase "composite polynucleotide sequence" refers to a sequence which includes exonal sequences required to encode the polypeptide having heparanase activity, as well as any number of intronal sequences. The intronal sequences can be of any source and typically will include conserved splicing signal sequences. Such intronal sequences may further include cis acting expression regulatory elements.

The term "heparanase catalytic activity" or its equivalent term "heparanase activity" both refer to a mammalian endoglycosidase hydrolyzing activity which is specific for heparan or heparan sulfate proteoglycan substrates, as opposed to the activity of bacterial enzymes (heparinase I, II and III) which degrade heparin or heparan sulfate by means of β-elimination (37).

According to a preferred embodiment of the present invention the polynucleotide or a portion thereof is hybridizable with SEQ ID NOs: 9, 13, 42, 43 or a portion thereof at 68° C. in 6×SSC, 1% SDS, 5×Denharts, 10% dextran sulfate, 100 μg/ml salmon sperm DNA, and $^{32}$p labeled probe and wash at 68° C. with 3, 2, 1, 0.5 or 0.1×SSC and 0.1% SDS.

According to another preferred embodiment of the present invention the polynucleotide or a portion thereof is at least 60%, preferably at least 65%, more preferably at least 70%, more preferably at least 75%, more preferably at least 80%, more preferably at least 85%, more preferably at least 90%, most preferably, 95–100% identical with SEQ ID NOs: 9, 13, 42, 43 or portions thereof as determined using the Bestfit procedure of the DNA sequence analysis software package developed by the Genetic Computer Group (GCG) at the university of Wisconsin (gap creation penalty—12, gap extension penalty—4—which are the default parameters).

According to another preferred embodiment of the present invention the polypeptide encoded by the polynucleotide sequence is as set forth in SEQ ID NOs:10, 14, 44 or portions thereof having heparanase catalytic activity. Such portions are expected to include amino acids Asp-Glu 224–225 (SEQ ID NO:10), which can serve as proton donors and glutamic acid 343 or 396 which can serve as a nucleophile.

According to another preferred embodiment of the present invention the polypeptide encoded by the polynucleotide sequence is at least 60%, preferably at least 65%, more preferably at least 70%, more preferably at least 75%, more preferably at least 80%, more preferably at least 85%, more preferably at least 90%, most preferably, 95–100% homologous (both similar and identical acids) to SEQ ID NOs:10, 14, 44 or portions thereof as determined with the Smith-Waterman algorithm, using the Bioaccelerator platform developed by Compugene (gapop: 10.0, gapext: 0.5, matrix: blosum62, see also the description to FIG. 17).

Further according to the present invention there is provided a nucleic acid construct comprising the isolated nucleic acid described herein. The construct may and preferably further include an origin of replication and trans regulatory elements, such as promoter and enhancer sequences.

The construct or vector can be of any type. It may be a phage which infects bacteria or a virus which infects eukaryotic cells. It may also be a plasmid, phagemid, cosmid, bacmid or an artificial chromosome.

Further according to the present invention there is provided a host cell comprising the nucleic acid construct described herein. The host cell can be of any type. It may be a prokaryotic cell, an eukaryotic cell, a cell line, or a cell as a portion of an organism. The polynucleotide encoding heparanase can be permanently or transiently present in the cell. In other words, genetically modified cells obtained following stable or transient transfection, transformation or transduction are all within the scope of the present invention. The polynucleotide can be present in the cell in low copy (say 1–5 copies) or high copy number (say 5–50 copies or more). It may be integrated in one or more chromosomes at any location or be present as an extrachromosomal material.

The present invention is further directed at providing a heparanase over-expression system which includes a cell overexpressing heparanase catalytic activity. The cell may be a genetically modified host cell transiently or stably transfected or transformed with any suitable vector which includes a polynucleotide sequence encoding a polypeptide having heparanase activity and a suitable promoter and enhancer sequences to direct over-expression of heparanase. However, the overexpressing cell may also be a product of an insertion (e.g., via homologous recombination) of a promoter and/or enhancer sequence downstream to the endogenous heparanase gene of the expressing cell, which will direct over-expression from the endogenous gene.

The term "over-expression" as used herein in the specification and claims below refers to a level of expression which is higher than a basal level of expression typically characterizing a given cell under otherwise identical conditions.

According to another aspect the present invention provides an antisense oligonucleotide comprising a polynucleotide or a polynucleotide analog of at least 10, preferably 11–15, more preferably 16–17, more preferably 18, more preferably 19–25, more preferably 26–35, most preferably 35–100 bases being hybridizable in vivo, under physiological conditions, with a portion of a polynucleotide strand encoding a polypeptide having heparanase catalytic activity. The antisense oligonucleotide can be used for downregulating heparanase activity by in vivo administration thereof to a patient. As such, the antisense oligonucleotide according to the present invention can be used to treat types of cancers which are characterized by impaired (over) expression of heparanase, and are dependent on the expression of heparanase for proliferating or forming metastases.

The antisense oligonucleotide can be DNA or RNA or even include nucleotide analogs, examples of which are provided in the Background section hereinabove. The antisense oligonucleotide according to the present invention can be synthetic and is preferably prepared by solid phase synthesis. In addition, it can be of any desired length which still provides specific base pairing (e.g., 8 or 10, preferably more, nucleotides long) and it can include mismatches that do not hamper base pairing under physiological conditions.

Further according to the present invention there is provided a pharmaceutical composition comprising the antisense oligonucleotide herein described and a pharmaceutically acceptable carrier. The carrier can be, for example, a liposome loadable with the antisense oligonucleotide.

According to a preferred embodiment of the present invention the antisense oligonucleotide further includes a ribozyme sequence. The ribozyme sequence serves to cleave a heparanase RNA molecule to which the antisense oligonucleotide binds, to thereby downregulate heparanase expression.

Further according to the present invention there is provided an antisense nucleic acid construct comprising a promoter sequence and a polynucleotide sequence directing the synthesis of an antisense RNA sequence of at least 10 bases being hybridizable in vivo, under physiological conditions, with a portion of a polynucleotide strand encoding a polypeptide having heparanase catalytic activity. Like the antisense oligonucleotide, the antisense construct can be used for downregulating heparanase activity by in vivo administration thereof to a patient. As such, the antisense construct, like the antisense oligonucleotide, according to the present invention can be used to treat types of cancers which are characterized by impaired (over) expression of heparanase, and are dependent on the expression of heparanase for proliferating or forming metastases.

Thus, further according to the present invention there is provided a pharmaceutical composition comprising the antisense construct herein described and a pharmaceutically acceptable carrier. The carrier can be, for example, a liposome loadable with the antisense construct.

Formulations for topical administration may include, but are not limited to, lotions, ointments, gels, creams, suppositories, drops, liquids, sprays and powders. Conventional pharmaceutical carriers, aqueous, powder or oily bases, thickeners and the like may be necessary or desirable. Coated condoms, stents, active pads, and other medical devices may also be useful. Compositions for oral administration include powders or granules, suspensions or solutions in water or non-aqueous media, sachets, capsules or tablets. Thickeners, diluents, flavorings, dispersing aids, emulsifiers or binders may be desirable. Formulations for parenteral administration may include, but are not limited to, sterile aqueous solutions which may also contain buffers, diluents and other suitable additives.

Dosing is dependent on severity and responsiveness of the condition to be treated, but will normally be one or more doses per day, week or month with course of treatment lasting from several days to several months or until a cure is effected or a diminution of disease state is achieved. Persons ordinarily skilled in the art can easily determine optimum dosages, dosing methodologies and repetition rates.

Further according to the present invention there is provided a nucleic acid construct comprising a polynucleotide sequence functioning as a promoter, the polynucleotide sequence is derived from SEQ ID NO:42 and includes at least nucleotides 2135–2635, preferably 2235–2635, more preferably 2335–2635, more preferably 2435–2635, most preferably 2535–2635 thereof, or SEQ ID NO:43 and includes at least nucleotides 1–420, preferably 120–420, more preferably 220–420, most preferably 320–420, thereof. These nucleotides are shown in the example section that follows to direct the synthesis of a reporter gene in transformed cells. Thus, further according to the present invention there is provided a method of expressing a polynucleotide sequence comprising the step of ligating the polynucleotide sequence downstream to either of the promoter sequences described herein. Heparanase promoters can be isolated from a variety of mammalian an other species by cloning genomic regions present 5' to the coding sequence thereof. This can be readily achievable by one ordinarily skilled in the art using the heparanase polynucleotides described herein, which are shown in the Examples section that follows to participate in efficient cross species hybridization.

Further according to the present invention there is provided a recombinant protein comprising a polypeptide having heparanase catalytic activity. The protein according to the present invention include modifications known as post translational modifications, including, but not limited to, proteolysis (e.g., removal of a signal peptide and of a pro- or preprotein sequence), methionine modification, glycosylation, alkylation (e.g., methylation), acetylation, etc. According to preferred embodiments the polypeptide includes at least a portion of SEQ ID NOs:10, 14 or 44, the portion has heparanase catalytic activity. According to preferred embodiments of the present invention the protein is encoded by any of the above described isolated nucleic acids. Further according to the present invention there is provided a pharmaceutical composition comprising, as an active ingredient, the recombinant protein described herein.

The recombinant protein may be purified by any conventional protein purification procedure close to homogeneity and/or be mixed with additives. The recombinant protein may be manufactured using any of the genetically modified cells described above, which include any of the expression nucleic acid constructs described herein. The recombinant protein may be in any form. It may be in a crystallized form, a dehydrated powder form or in solution. The recombinant protein may be useful in obtaining pure heparanase, which in turn may be useful in eliciting anti-heparanase antibodies, either poly or monoclonal antibodies, and as a screening active ingredient in an anti-heparanase inhibitors or drugs screening assay or system.

Further according to the present invention there is provided a method of identifying a chromosome region harboring a human heparanase gene in a chromosome spread. the method is executed implementing the following method steps, in which in a first step the chromosome spread (either interphase or metaphase spread) is hybridized with a tagged polynucleotide probe encoding heparanase. The tag is preferably a fluorescent tag. In a second step according to the method the chromosome spread is washed, thereby excess of non-hybridized probe is removed. Finally, signals associated with the hybridized tagged polynucleotide probe are searched for, wherein detected signals being indicative of a chromosome region harboring the human heparanase gene. One ordinarily skilled in the art would know how to use the sequences disclosed herein in suitable labeling reactions and how to use the tagged probes to detect, using in situ hybridization, a chromosome region harboring a human heparanase gene.

Further according to the present invention there is provided a method of in vivo eliciting anti-heparanase antibodies comprising the steps of administering a nucleic acid construct including a polynucleotide segment corresponding to at least a portion of SEQ ID NOs:9, 13 or 43 and a promoter for directing the expression of said polynucleotide segment in vivo. Accordingly, there is provided also a DNA vaccine for in vivo eliciting anti-heparanase antibodies comprising a nucleic acid construct including a polynucleotide segment corresponding to at least a portion of SEQ ID NOs:9, 13 or 43 and a promoter for directing the expression of said polynucleotide segment in vivo. The vaccine optionally further includes a pharmaceutically acceptable carrier, such as a virus, liposome or an antigen presenting cell. Alternatively, the vaccine is employed as a naked DNA vaccine The present invention can be used to develop treatments for various diseases, to develop diagnostic assays for these diseases and to provide new tools for basic research especially in the fields of medicine and biology.

Specifically, the present invention can be used to develop new drugs to inhibit tumor cell metastasis, inflammation and autoimmunity. The identification of the hpa gene encoding for the heparanase enzyme enables the production of a recombinant enzyme in heterologous expression systems.

Furthermore, the present invention can be used to modulate bioavailability of heparin-binding growth factors, cellular responses to heparin-binding growth factors (e.g., bFGF, VEGF) and cytokines (e.g., IL-8), cell interaction with plasma lipoproteins, cellular susceptibility to viral, protozoa and some bacterial infections, and disintegration of neurodegenerative plaques. Recombinant heparanase offers a potential treatment for wound healing, angiogenesis, restenosis, atherosclerosis, inflammation, neurodegenerative diseases (such as, for example, Genstmann-Straussler Syndrome, Creutzfeldt-Jakob disease, Scrape and Alzheimer's disease) and certain viral and some bacterial and protozoa infections. Recombinant heparanase can be used to neutralize plasma heparin, as a potential replacement of protamine.

As used herein, the term "modulate" includes substantially inhibiting, slowing or reversing the progression of a disease, substantially ameliorating clinical symptoms of a disease or condition, or substantially preventing the appearance of clinical symptoms of a disease or condition. A "modulator" therefore includes an agent which may modulate a disease or condition. Modulation of viral, protozoa and bacterial infections includes any effect which substantially interrupts, prevents or reduces any viral, bacterial or protozoa activity and/or stage of the virus, bacterium or protozoon life cycle, or which reduces or prevents infection by the virus, bacterium or protozoon in a subject, such as a human or lower animal.

As used herein, the term "wound" includes any injury to any portion of the body of a subject including, but not limited to, acute conditions such as thermal burns, chemical burns, radiation burn, burns caused by excess exposure to ultraviolet radiation such as sunburn, damage to bodily tissues such as the perineum as a result of labor and childbirth, including injuries sustained during medical procedures such as episiotomies, trauma-induced injuries including cuts, those injuries sustained in automobile and other mechanical accidents, and those caused by bullets, knives and other weapons, and post-surgical injuries, as well as chronic conditions such as pressure sores, bedsores, conditions related to diabetes and poor circulation, and all types of acne, etc.

Anti-heparanase antibodies, raised against the recombinant enzyme, would be useful for immunodetection and diagnosis of micrometastases, autoimmune lesions and renal failure in biopsy specimens, plasma samples, and body fluids. Such antibodies may also serve as neutralizing agents for heparanase activity.

The genomic heparanase sequences described herein can be used to construct knock-in and knock-out constructs. Such constructs include a fragment of 10–20 Kb of a heparanase locus and a negative and a positive selection markers and can be used to provide heparanase knock-in and knock-out animal models by methods known to the skilled artisan. Such animal models can be used for studying the function of heparanase in developmental processes, and in normal as well as pathological processes. They can also serve as an experimental model for testing drugs and gene therapy protocols. The complementary heparanase sequence (cDNA) can be used to derive transgenic animals, overexpressing heparanase for same. Alternatively, if cloned in the antisense orientation, the complementary heparanase sequence (cDNA) can be used to derive transgenic animals under-expressing heparanase for same.

The heparanase promoter sequences described herein and other cis regulatory elements linked to the heparanase locus can be used to regulated the expression of genes. For example, these promoters can be used to direct the expression of a cytotoxic protein, such as TNF, in tumor cells. It will be appreciated that heparanase itself is abnormally expressed under the control of its own promoter and other cis acting elements in a variety of tumors, and its expression is correlated with metastasis. It is also abnormally highly expressed in inflammatory cells. The introns of the heparanase gene can be used for the same purpose, as it is known that introns, especially upstream introns include cis acting element which affect expression. A heparanase promoter fused to a reporter protein can be used to study/monitor its activity.

The polynucleotide sequences described herein can also be used to provide DNA vaccines which will elicit in vivo anti heparanase antibodies. Such vaccines can therefore be used to combat inflammatory and cancer.

Antisense oligonucleotides derived according to the heparanase sequences described herein, especially such oligonucleotides supplemented with ribozyme activity, can be used to modulate heparanase expression. Such oligonucleotides can be from the coding region, from the introns or promoter specific. Antisense heparanase nucleic acid constructs can similarly function, as well known in the art.

The heparanase sequences described herein can be used to study the catalytic mechanism of heparanase. Carefully selected site directed mutagenesis can be employed to provide modified heparanase proteins having modified characteristics in terms of, for example, substrate specificity, sensitivity to inhibitors, etc.

While studying heparanase expression in a variety of cell types alternatively spliced transcripts were identified. Such transcripts if found characteristic of certain pathological conditions can be used as markers for such conditions. Such transcripts are expected to direct the synthesis of heparanases with altered functions.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., Molecular Cloning—A Laboratory Manual, Cold Spring Harbor Laboratory, Cold Spring Harbor, N.Y. (1989), which is incorporated herein by reference. Other general references are provided throughout this document. The procedures therein are believed to be well known in the art and are provided for the convenience of the reader. All the information contained therein is incorporated herein by reference.

The following protocols and experimental details are referenced in the Examples that follow:

Purification and characterization of heparanase from a human hepatoma cell line and human placenta: A human hepatoma cell line (Sk-hep-1) was chosen as a source for purification of a human tumor-derived heparanase. Purification was essentially as described in U.S. Pat. No. 5,362,641 to Fuks, which is incorporated by reference as if fully set forth herein. Briefly, 500 liter, $5\times10^{11}$ cells were grown in suspension and the heparanase enzyme was purified about 240,000 fold by applying the following steps: (i) cation exchange (CM-Sephadex) chromatography performed at pH 6.0, 0.3–1.4 M NaCl gradient; (ii) cation exchange (CM-Sephadex) chromatography performed at pH 7.4 in the presence of 0.1% CHAPS, 0.3–1.1 M NaCl gradient; (iii) heparin-Sepharose chromatography performed at pH 7.4 in the presence of 0.1% CHAPS, 0.35–1.1 M NaCl gradient; (iv) ConA-Sepharose chromatography performed at pH 6.0 in buffer containing 0.1% CHAPS and 1 M NaCl, elution with 0.25 M α-methyl mannoside; and (v) HPLC cation exchange (Mono-S) chromatography performed at pH 7.4 in the presence of 0.1% CHAPS, 0.25–1 M NaCl gradient.

Active fractions were pooled, precipitated with TCA and the precipitate subjected to SDS polyacrylamide gel electrophoresis and/or tryptic digestion and reverse phase HPLC. Tryptic peptides of the purified protein were separated by reverse phase HPLC (C8 column) and homogeneous peaks were subjected to amino acid sequence analysis.

The purified enzyme was applied to reverse phase HPLC and subjected to N-terminal amino acid sequencing using the amino acid sequencer (Applied Biosystems).

Cells: Cultures of bovine corneal endothelial cells (BCECs) were established from steer eyes as previously described (19, 38). Stock cultures were maintained in DMEM (1 g glucose/liter) supplemented with 10% newborn calf serum and 5% FCS. bFGF (1 ng/ml) was added every other day during the phase of active cell growth (13, 14).

Preparation of dishes coated with ECM: BCECs (second to fifth passage) were plated into 4-well plates at an initial density of $2\times10^5$ cells/ml, and cultured in sulfate-free Fisher medium plus 5% dextran T-40 for 12 days. $Na_2{}^{35}SO_4$ (25 μCi/ml) was added on day 1 and 5 after seeding and the cultures were incubated with the label without medium change. The subendothelial ECM was exposed by dissolving (5 min., room temperature) the cell layer with PBS containing 0.5% Triton X-100 and 20 mM $NH_4OH$, followed by four washes with PBS. The ECM remained intact, free of cellular debris and firmly attached to the entire area of the tissue culture dish (19, 22).

To prepare soluble sulfate labeled proteoglycans (peak I material), the ECM was digested with trypsin (25 μg/ml, 6 h, 37° C.), the digest was concentrated by reverse dialysis and the concentrated material was applied onto a Sepharose 6B gel filtration column. The resulting high molecular weight material (Kav<0.2, peak I) was collected. More than 80% of the labeled material was shown to be composed of heparan sulfate proteoglycans (11, 39).

Heparanase activity: Cells ($1\times10^6$/35-mm dish), cell lysates or conditioned media were incubated on top of $^{35}$S-labeled ECM (18 h, 37° C.) in the presence of 20 mM phosphate buffer (pH 6.2). Cell lysates and conditioned media were also incubated with sulfate labeled peak I material (10–20 μl). The incubation medium was collected, centrifuged (18,000×g, 4° C., 3 min.), and sulfate labeled material analyzed by gel filtration on a Sepharose CL-6B column (0.9×30 cm). Fractions (0.2 ml) were eluted with PBS at a flow rate of 5 ml/h and counted for radioactivity using Bio-fluor scintillation fluid. The excluded volume ($V_o$) was marked by blue dextran and the total included volume ($V_t$) by phenol red. The latter was shown to comigrate with free sulfate (7, 11, 23). Degradation fragments of HS side chains were eluted from Sepharose 6B at 0.5<Kav<0.8 (peak II) (7, 11, 23). A nearly intact HSPG released from ECM by trypsin—and, to a lower extent, during incubation with PBS alone—was eluted next to $V_o$ (Kav<0.2, peak I). Recoveries of labeled material applied on the columns ranged from 85 to 95% in different experiments (11). Each experiment was performed at least three times and the variation of elution positions (Kav values) did not exceed +/−15%.

Cloning of hpa cDNA: cDNA clones 257548 and 260138 were obtained from the I.M.A.G.E Consortium (2130 Memorial Parkway SW, Hunstville, Ala. 35801). The cDNAs were originally cloned in EcoRI and NotI cloning sites in the plasmid vector pT3T7D-Pac. Although these clones are reported to be somewhat different, DNA sequencing demonstrated that these clones are identical to one another. Marathon RACE (rapid amplification of cDNA ends) human placenta (poly-A) cDNA composite was a gift of Prof. Yossi Shiloh of Tel Aviv University. This composite is vector free, as it includes reverse transcribed cDNA fragments to which double, partially single stranded adapters are attached on both sides. The construction of the specific composite employed is described in reference 39a.

Amplification of hp3 PCR fragment was performed according to the protocol provided by Clontech laboratories. The template used for amplification was a sample taken from the above composite. The primers used for amplification were:

First step: 5'-primer: AP1: 5'-CCATCCTAATACGACTCACT ATAGGGC-3', SEQ ID NO:1; 3'-primer: HPL229: 5'-GTAGTGATGCCA TGTAACTGAATC-3', SEQ ID NO:2.

Second step: nested 5'-primer: AP2: 5'-ACTCACTATAGGGCTCG AGCGGC-3', SEQ ID NO:3; nested 3'-primer: HPL171: 5'-GCATCTTAGCCGTCTTTCTTCG-3', SEQ ID NO:4. The HPL229 and HPL171 were selected according to the sequence of the EST clones. They include nucleotides 933–956 and 876–897 of SEQ ID NO:9, respectively.

PCR program was 94° C.—4 min., followed by 30 cycles of 94° C.—40 sec., 62° C.—1 min., 72° C.—2.5 min. Amplification was performed with Expand High Fidelity (Boehringer Mannheim). The resulting ca. 900 bp hp3 PCR product was digested with BfrI and PvuII. Clone 257548 (phpa1) was digested with EcoRI, followed by end filling and was then further digested with BfrI. Thereafter the PvuII—BfrI fragment of the hp3 PCR product was cloned into the blunt end—BfrI end of clone phpa1 which resulted in having the entire cDNA cloned in pT3T7-pac vector, designated phpa2.

RT-PCR: RNA was prepared using TRI-Reagent (Molecular research center Inc.) according to the manufacturer instructions. 1.25 μg were taken for reverse transcription reaction using MuMLV Reverse transcriptase (Gibco BRL) and Oligo $(dT)_{15}$ primer, SEQ ID NO:5, (Promega). Amplification of the resultant first strand cDNA was performed with Taq polymerase (Promega). The following primers were used:

HPU-355: 5'-TTCGATCCCAAGAAGGAATCAAC-3', SEQ ID NO:6, nucleotides 372–394 in SEQ ID NOs:9 or 11.

HPL-229: 5'-GTAGTGATGCCATGTAACTGAATC-3', SEQ ID NO:7, nucleotides 933–956 in SEQ ID NOs:9 or 11.

PCR program: 94° C.—4 min., followed by 30 cycles of 94° C.—40 sec., 62° C.—1 min., 72° C.—1 min.

Alternatively, total RNA was prepared from cell cultures using Tri-reagent (Molecular Research Center, Inc.) according to the manufacturer recommendation. Poly A+RNA was isolated from total RNA using mRNA separator (Clontech). Reverse transcription was performed with total RNA using Superscript II (GibcoBRL). PCR was performed with Expand high fidelity (Boehringer Mannheim). Primers used for amplification were as follows:

```
Hpu-685,
5'-GAGCAGCCAGGTGAGCCCAAGAT-3',    SEQ ID NO:24

Hpu-355,
5'-TTCGATCCCAAGAAGGAATCAAC-3',    SEQ ID NO:25

Hpu 565,
5'-AGCTCTGTAGATGTGCTATACAC-3',    SEQ ID NO:26

Hpl 967,
5'-TCAGATGCAAGCAGCAACTTTGGC-3',   SEQ ID NO:27

Hpl 171,
5'-GCATCTTAGCCGTCTTTCTTCG-3',     SEQ ID NO:28

Hpl 229,
5'-GTAGTGATGCCATGTAACTGAATC-3',   SEQ ID NO:29
```

PCR reaction was performed as follows: 94° C. 3 minutes, followed by 32 cycles of 94° C. 40 seconds, 64° C. 1 minute, 72° C. 3 minutes, and one cycle 72° C., 7 minutes.

Expression of recombinant heparanase in insect cells: Cells, High Five and Sf21 insect cell lines were maintained as monolayer cultures in SF900II-SFM medium (GibcoBRL).

Recombinant Baculovirus: Recombinant virus containing the hpa gene was constructed using the Bac to Bac system (GibcoBRL). The transfer vector pFastBac was digested with SalI and NotI and ligated with a 1.7 kb fragment of phpa2 digested with XhoI and NotI. The resulting plasmid was designated pFasthpa2. An identical plasmid designated pFasthpa4 was prepared as a duplicate and both independently served for further experimentations. Recombinant bacmid was generated according to the instructions of the manufacturer with pFasthpa2, pFasthpa4 and with pFastBac. The latter served as a negative control. Recombinant bacmid DNAs were transfected into Sf21 insect cells. Five days after transfection recombinant viruses were harvested and used to infect High Five insect cells, $3\times10^6$ cells in T-25 flasks. Cells were harvested 2–3 days after infection. $4\times10^6$ cells were centrifuged and resuspended in a reaction buffer containing 20 mM phosphate citrate buffer, 50 mM NaCl. Cells underwent three cycles of freeze and thaw and lysates were stored at −80° C. Conditioned medium was stored at 4° C.

Partial purification of recombinant heparanase: Partial purification of recombinant heparanase was performed by heparin-Sepharose column chromatography followed by Superdex 75 column gel filtration. Culture medium (150 ml) of Sf21 cells infected with pFhpa4 virus was subjected to heparin-Sepharose chromatography. Elution of 1 ml fractions was performed with 0.35–2 M NaCl gradient in presence of 0.1% CHAPS and 1 mM DTT in 10 mM sodium acetate buffer, pH 5.0. A 25 μl sample of each fraction was tested for heparanase activity. Heparanase activity was eluted at the range of 0.65–1.1 M NaCl (fractions 18–26, FIG. 10*a*). 5 μl of each fraction was subjected to 15% SDS-polyacrylamide gel electrophoresis followed by silver nitrate staining. Active fractions eluted from heparin-Sepharose (FIG. 10*a*) were pooled and concentrated (×6) on YM3 cut-off membrane. 0.5 ml of the concentrated material was applied onto 30 ml Superdex 75 FPLC column equilibrated with 10 mM sodium acetate buffer, pH 5.0, containing 0.8 M NaCl, 1 mM DTT and 0.1% CHAPS. Fractions (0.56 ml) were collected at a flow rate of 0.75 ml/min. Aliquots of each fraction were tested for heparanase activity and were subjected to SDS-polyacrylamide gel electrophoresis followed by silver nitrate staining (FIG. 11*b*).

PCR amplification of genomic DNA: 94° C. 3 minutes, followed by 32 cycles of 94° C. 45 seconds, 64° C. 1 minute, 68° C. 5 minutes, and one cycle at 72° C., 7 minutes. Primers used for amplification of genomic DNA included:

```
GHpu-L3
5'-AGGCACCCTAGAGATGTTCCAG-3',      SEQ ID NO:30

GHpl-L6
5'-GAAGATTTCTGTTTCCATGACGTG-3',    SEQ ID NO:31.
```

Screening of genomic libraries: A human genomic library in Lambda phage EMBLE3 SP6/T7 (Clontech, Paulo Alto, Calif.) was screened. $5\times10^5$ plaques were plated at $5\times10^4$ pfu/plate on NZCYM agar/top agarose plates. Phages were absorbed on nylon membranes in duplicates (Qiagen). Hybridization was performed at 65° C. in 5×SSC, 5×Denhart's, 10% dextran sulfate, 100 μg/ml Salmon sperm, $^{32}p$ labeled probe ($10^6$ cpm/ml). A 1.6 kb fragment, containing the entire hpa cDNA was labeled by random priming (Boehringer Mannheim). Following hybridization membranes were washed once with 2×SSC, 0.1% SDS at 65° C. for 20 minutes, and twice with 0.2×SSC, 0.1% SDS at 65° C. for 15 minutes. Hybridizing plaques were picked, and plated at 100 pfu/plate. Hybridization was performed as above and single isolated positive plaques were picked.

Phage DNA was extracted using a Lambda DNA extraction kit (Qiagen). DNA was digested with XhoI and EcoRI, separated on 0.7% agarose gel and transferred to nylon membrane Hybond N+ (Amersham). Hybridization and washes were performed as above.

cDNA Sequence analysis: Sequence determinations were performed with vector specific and gene specific primers, using an automated DNA sequencer (Applied Biosystems, model 373A). Each nucleotide was read from at least two independent primers.

Genomic sequence analysis: Large-scale sequencing was performed by Commonwealth Biotechnology Incorporation.

Isolation of mouse hpa: Mouse hpa cDNA was amplified from either Marathon ready cDNA library of mouse embryo or from mRNA isolated from mouse melanoma cell line BL6, using the Marathon RACE kit from Clontech. Both procedures were performed according to the manufacturer's recommendation.

Primers Used for PCR Amplification of Mouse hpa:

```
Mhpl773
5'-CCACACTGAATGTAATACTGAAGTG-3',      SEQ ID NO:32

MHpl736
5'-CGAAGCTCTGGAACTCGGCAAG-3',         SEQ ID NO:33

MHpl83
5'-GCCAGCTGCAAAGGTGTTGGAC-3',         SEQ ID NO:34

Mhpl152
5'-AACACCTGCCTCATCACGACTTC-3',        SEQ ID NO:35

Mhpl114
5'-GCCAGGCTGGCGTCGATGGTGA-3',         SEQ ID NO:36

MHpl103
5'-GTCGATGGTGATGGACAGGAAC-3',         SEQ ID NO:37

Ap1
5'-GTAATACGACTCACTATAGGGC-3',         SEQ ID NO:38
(Genome walker)

Ap2
5'-ACTATAGGGCACGCGTGGT-3',            SEQ ID NO:39
(Genome walker)

Ap1
5'-CCATCCTAATACGACTCACTATAGGGC-3',    SEQ ID NO:40
(Marathon RACE)

Ap2
5'-ACTCACTATAGGGCTCGAGCGGC-3',        SEQ ID NO:41
(Marathon RACE)
```

Southern analysis of genomic DNA: Genomic DNA was extracted from animal or from human blood using Blood and cell culture DNA maxi kit (Qiagene). DNA was digested with EcoRI, separated by gel electrophoresis and transferred to a nylon membrane Hybond N+ (Amersham). Hybridization was performed at 68° C. in 6×SSC, 1% SDS, 5×Denharts, 10% dextran sulfate, 100 $\mu$g/ml salmon sperm DNA, and $^{32}$p labeled probe. A 1.6 kb fragment, containing the entire hpa cDNA was used as a probe. Following hybridization, the membrane was washed with 3×SSC, 0.1% SDS, at 68° C. and exposed to X-ray film for 3 days. Membranes were then washed with 1×SSC, 0.1% SDS, at 68° C. and were reexposed for 5 days.

Construction of hpa promoter-GFP expression vector: Lambda DNA of phage L3, was digested with SacI and BglII, resulting in a 1712 bp fragment which contained the hpa promoter (877–2688 of SEQ ID NO:42). The pEGFP-1 plasmid (Clontech) was digested with BglII and SacI and ligated with the 1712 bp fragment of the hpa promoter sequence. The resulting plasmid was designated phpEGL. A second hpa promoter-GFP plasmid was constructed containing a shorter fragment of the hpa promoter region: phpEGL was digested with HindIII, and the resulting 1095 bp fragment (nucleotides 1593–2688 of SEQ ID NO:42) was ligated with HindIII digested pEGFP-1. The resulting plasmid was designated phpEGS.

Computer analysis of sequences: Homology searches were performed using several computer servers, and various databases. Blast 2.0 service, at the NCBI server was used to screen the protein database swplus and DNA databases such as GenBank, EMBL, and the EST databases. Blast 2.0 search was performed using the basic search option of the NCBI server. Sequence analysis and alignments were done using the DNA sequence analysis software package developed by the Genetic Computer Group (GCG) at the university of Wisconsin. Alignments of two sequences were performed using Bestfit (gap creation penalty—12, gap extension penalty—4). Protein homology search was performed with the Smith-Waterman algorithm, using the Bioaccelerator platform developed by Compugene. The protein database swplus was searched using the following parameters: gapop: 10.0, gapext: 0.5, matrix: blosum62. Blocks homology was performed using the Blocks WWW server developed at Fred Hutchinson Cancer Research Center in Seattle, Wash., USA. Secondary structure prediction was performed using the PHD server—Profile network Prediction Heidelberg. Fold recognition (threading) was performed using the UCLA-DOE structure prediction server. The method used for prediction was gonnet+predss. Alignment of three sequences was performed using the pileup application (gap creation penalty—5, gap extension penalty—1). Promoter analysis was performed using TSSW and TSSG programs (BCM Search Launcher Human Genome Center, Baylor College of Medicine, Houston Tex.).

Example 1

Cloning of Human hpa cDNA

Purified fraction of heparanase isolated from human hepatoma cells (SK-hep-1) was subjected to tryptic digestion and microsequencing. EST (Expressed Sequence Tag) databases were screened for homology to the back translated DNA sequences corresponding to the obtained peptides. Two EST sequences (accession Nos. N41349 and N45367) contained a DNA sequence encoding the peptide YGPDVGQPR (SEQ ID NO:8). These two sequences were derived from clones 257548 and 260138 (I.M.A.G.E Consortium) prepared from 8 to 9 weeks placenta cDNA library (Soares). Both clones which were found to be identical contained an insert of 1020 bp which included an open reading frame (ORF) of 973 bp followed by a 3' untranslated region of 27 bp and a Poly A tail. No translation start site (AUG) was identified at the 5' end of these clones.

Cloning of the missing 5' end was performed by PCR amplification of DNA from a placenta Marathon RACE cDNA composite. A 900 bp fragment (designated hp3), partially overlapping with the identified 3' encoding EST clones was obtained.

The joined cDNA fragment, 1721 bp long (SEQ ID NO:9), contained an open reading frame which encodes, as shown in FIG. 1 and SEQ ID NO:11, a polypeptide of 543 amino acids (SEQ ID NO:10) with a calculated molecular weight of 61,192 daltons. The 3' end of the partial cDNA inserts contained in clones 257548 and 260138 started at nucleotide $G^{721}$ of SEQ ID NO:9 and FIG. 1.

As further shown in FIG. 1, there was a single sequence discrepancy between the EST clones and the PCR amplified sequence, which led to an amino acid substitution from $Tyr^{246}$ in the EST to $Phe^{246}$ in the amplified cDNA. The nucleotide sequence of the PCR amplified cDNA fragment was verified from two independent amplification products. The new gene was designated hpa.

As stated above, the 3' end of the partial cDNA inserts contained in EST clones 257548 and 260138 started at nucleotide 721 of hpa (SEQ ID NO:9). The ability of the hpa cDNA to form stable secondary structures, such as stem and loop structures involving nucleotide stretches in the vicinity of position 721 was investigated using computer modeling. It was found that stable stem and loop structures are likely to be formed involving nucleotides 698–724 (SEQ ID NO:9). In addition, a high GC content, up to 70%, characterizes the 5' end region of the hpa gene, as compared to about only 40% in the 3' region. These findings may explain the immature termination and therefore lack of 5' ends in the EST clones.

To examine the ability of the hpa gene product to catalyze degradation of heparan sulfate in an in vitro assay the entire open reading frame was expressed in insect cells, using the Baculovirus expression system. Extracts of cells, infected with virus containing the hpa gene, demonstrated a high level of heparan sulfate degradation activity, while cells infected with a similar construct containing no hpa gene had no such activity, nor did non-infected cells. These results are further demonstrated in the following Examples.

Example 2

Degradation of Soluble ECM-Derived HSPG

Monolayer cultures of High Five cells were infected (72 h, 28° C.) with recombinant Bacoluvirus containing the pFasthpa plasmid or with control virus containing an insert free plasmid. The cells were harvested and lysed in heparanase reaction buffer by three cycles of freezing and thawing. The cell lysates were then incubated (18 h, 37° C.) with sulfate labeled, ECM-derived HSPG (peak I), followed by gel filtration analysis (Sepharose 6B) of the reaction mixture.

Figure 2:
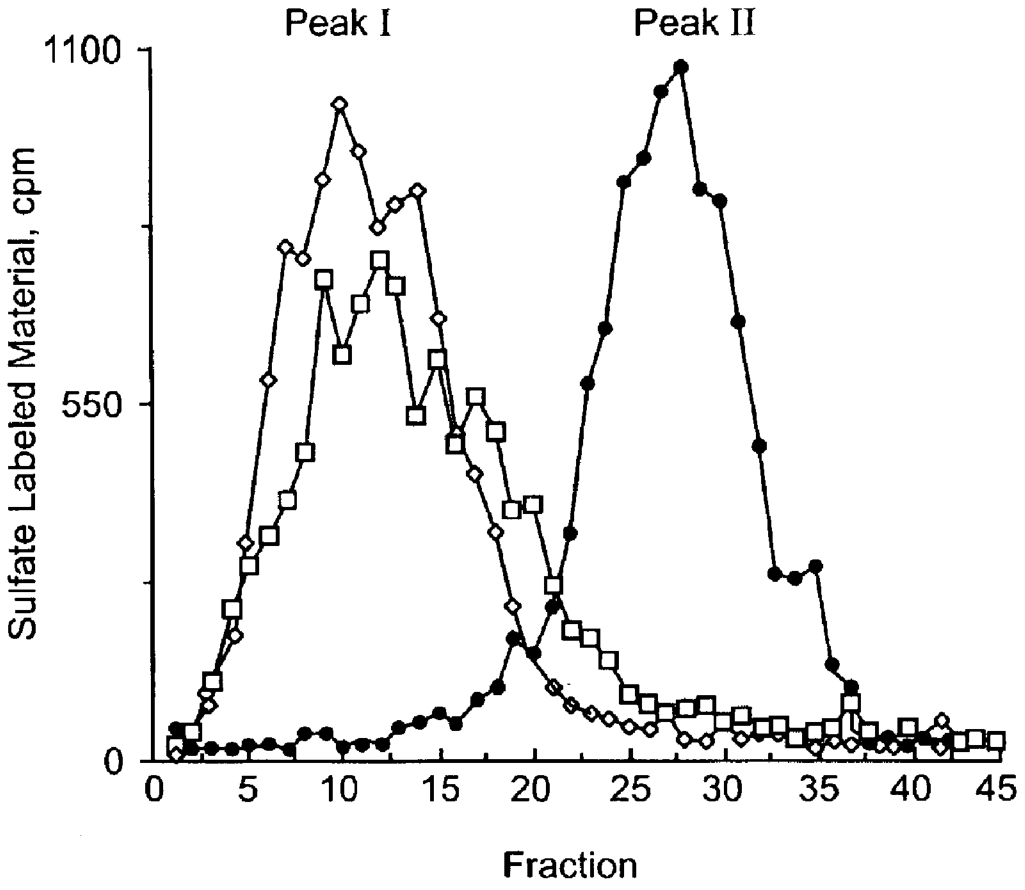
FIG. 2 demonstrates degradation of soluble sulfate labeled HSPG substrate by lysates of High Five cells infected with pFhpa2 virus. Lysates of High Five cells that were infected with pFhpa2 virus (•) or control pF2 virus (□) were incubated (18 h, 37° C.) with sulfate labeled ECM-derived soluble HSPG (peak I). The incubation medium was then subjected to gel filtration on Sepharose 6B. Low molecular weight HS degradation fragments (peak II) were produced only during incubation with the pFhpa2 infected cells, but there was no degradation of the HSPG substrate (◇) by lysates of pF2 infected cells.

As shown in FIG. 2, the substrate alone included almost entirely high molecular weight (Mr) material eluted next to $V_o$ (peak I, fractions 5–20, Kav<0.35). A similar elution pattern was obtained when the HSPG substrate was incubated with lysates of cells that were infected with control virus. In contrast, incubation of the HSPG substrate with lysates of cells infected with the hpa containing virus resulted in a complete conversion of the high Mr substrate into low Mr labeled degradation fragments (peak II, fractions 22–35, 0.5<Kav<0.75).

Fragments eluted in peak II were shown to be degradation products of heparan sulfate, as they were (i) 5- to 6-fold smaller than intact heparan sulfate side chains (Kav approx. 0.33) released from ECM by treatment with either alkaline borohydride or papain; and (ii) resistant to further digestion with papain or chondroitinase ABC, and susceptible to deamination by nitrous acid (6, 11). Similar results (not shown) were obtained with Sf21 cells. Again, heparanase activity was detected in cells infected with the hpa containing virus (pFhpa), but not with control virus (pF). This result was obtained with two independently generated recombinant viruses. Lysates of control not infected High Five cells failed to degrade the HSPG substrate.

In subsequent experiments, the labeled HSPG substrate was incubated with medium conditioned by infected High Five or Sf21 cells.

Figure 3A:
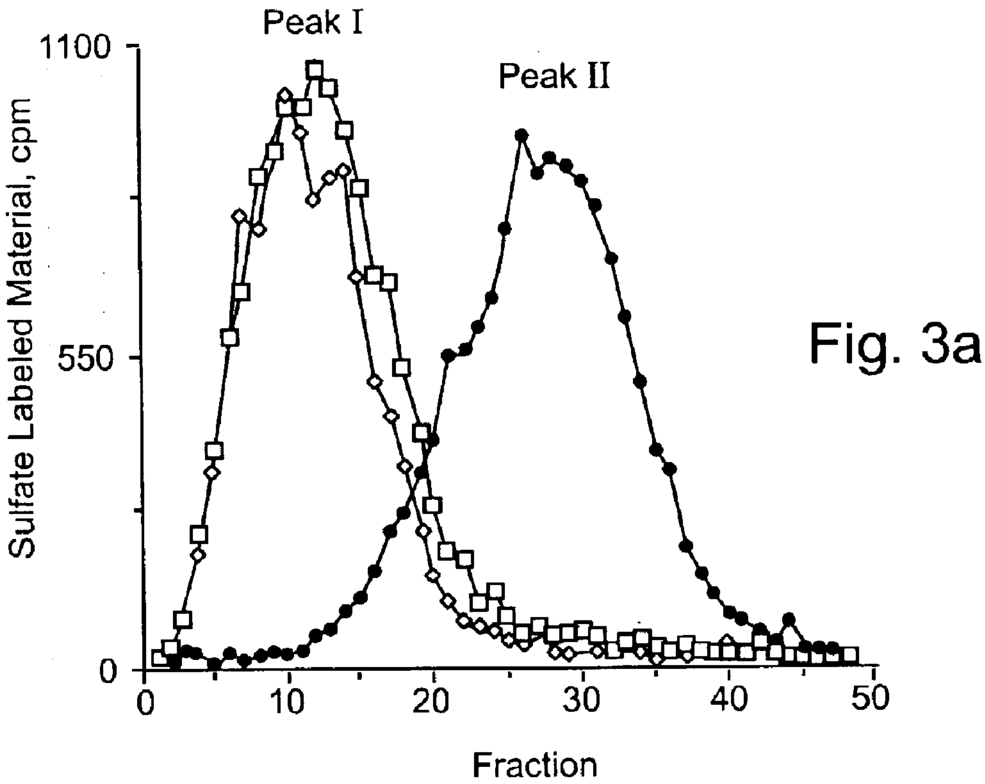
FIGS. 3*a*–*b* demonstrate degradation of soluble sulfate labeled HSPG substrate by the culture medium of pFhpa2 and pFhpa4 infected cells. Culture media of High Five cells infected with pFhpa2 (3*a*) or pFhpa4 (3*b*) viruses (•), or with control viruses (□) were incubated (18 h, 37° C.) with sulfate labeled ECM-derived soluble HSPG (peak I, ◇). The incubation media were then subjected to gel filtration on Sepharose 6B. Low molecular weight HS degradation fragments (peak II) were produced only during incubation with the hpa gene containing viruses. There was no degradation of the HSPG substrate by the culture medium of cells infected with control viruses.
Figure 3B:
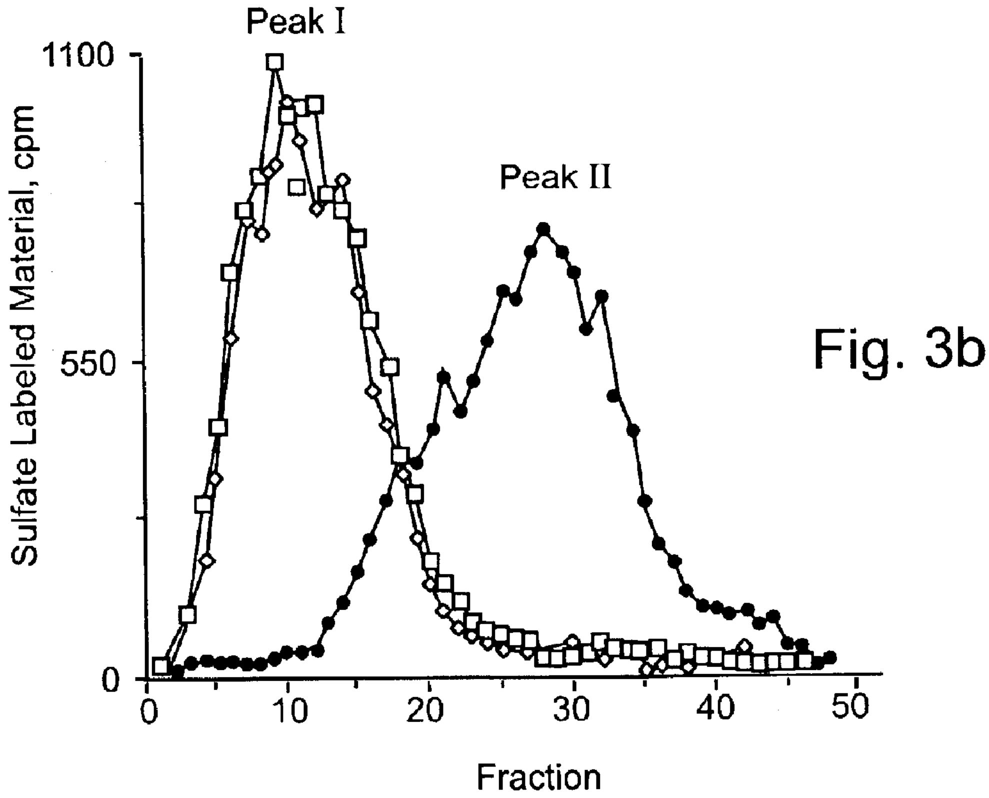

As shown in FIGS. 3*a–b*, heparanase activity, reflected by the conversion of the high Mr peak I substrate into the low Mr peak II which represents HS degradation fragments, was found in the culture medium of cells infected with the pFhpa2 or pFhpa4 viruses, but not with the control pF1 or pF2 viruses. No heparanase activity was detected in the culture medium of control non-infected High Five or Sf21 cells.

Figure 4:
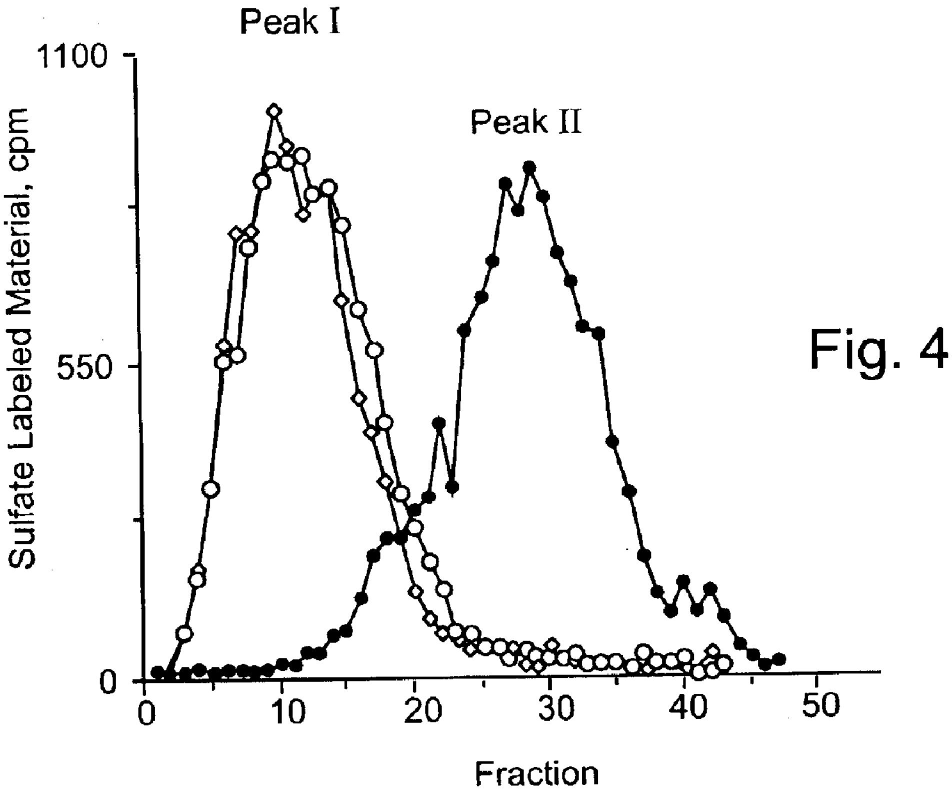
FIG. 4 presents size fractionation of heparanase activity expressed by pFhpa2 infected cells. Culture medium of pFhpa2 infected High Five cells was applied onto a 50 kDa cut-off membrane. Heparanase activity (conversion of the peak I substrate, (◇) into peak II HS degradation fragments)

The medium of cells infected with the pFhpa4 virus was passed through a 50 kDa cut off membrane to obtain a crude estimation of the molecular weight of the recombinant heparanase enzyme. As demonstrated in FIG. 4, all the enzymatic activity was retained in the upper compartment and there was no activity in the flow through (<50 kDa) material. This result is consistent with the expected molecular weight of the hpa gene product.

In order to further characterize the hpa product the inhibitory effect of heparin, a potent inhibitor of heparanase mediated HS degradation (40) was examined.

As demonstrated in FIGS. 5*a–b*, conversion of the peak I substrate into peak II HS degradation fragments was completely abolished in the presence of heparin.

Altogether, these results indicate that the heparanase enzyme is expressed in an active form by insect cells infected with Baculovirus containing the newly identified human hpa gene.

Example 3

Degradation of HSPG in Intact ECM

Next, the ability of intact infected insect cells to degrade HS in intact, naturally produced ECM was investigated. For this purpose, High Five or Sf21 cells were seeded on metabolically sulfate labeled ECM followed by infection (48 h, 28° C.) with either the pFhpa4 or control pF2 viruses. The pH of the medium was then adjusted to pH 6.2–6.4 and the cells further incubated with the labeled ECM for another 48 h at 28° C. or 24 h at 37° C. Sulfate labeled material released into the incubation medium was analyzed by gel filtration on Sepharose 6B.

As shown in FIGS. 6*a–b* and 7*a–b*, incubation of the ECM with cells infected with the control pF2 virus resulted in a constant release of labeled material that consisted almost entirely (>90%) of high Mr fragments (peak I) eluted with or next to $V_o$. It was previously shown that a proteolytic activity residing in the ECM itself and/or expressed by cells is responsible for release of the high Mr material (6). This nearly intact HSPG provides a soluble substrate for subsequent degradation by heparanase, as also indicated by the relatively large amount of peak I material accumulating when the heparanase enzyme is inhibited by heparin (6, 7, 12, FIG. 9). On the other hand, incubation of the labeled ECM with cells infected with the pFhpa4 virus resulted in release of 60–70% of the ECM-associated radioactivity in the form of low Mr sulfate-labeled fragments (peak II, 0.5<Kav<0.75), regardless of whether the infected cells were incubated with the ECM at 28° C. or 37° C. Control intact non-infected Sf21 or High Five cells failed to degrade the ECM HS side chains.

In subsequent experiments, as demonstrated in FIGS. 8*a–b*, High Five and Sf21 cells were infected (96 h, 28° C.) with pFhpa4 or control pF1 viruses and the culture medium incubated with sulfate-labeled ECM. Low Mr HS degradation fragments were released from the ECM only upon incubation with medium conditioned by pFhpa4 infected cells. As shown in FIG. 9, production of these fragments was abolished in the presence of heparin. No heparanase activity was detected in the culture medium of control, non-infected cells. These results indicate that the heparanase enzyme expressed by cells infected with the pFhpa4 virus is capable of degrading HS when complexed to other macromolecular constituents (i.e. fibronectin, laminin, collagen) of a naturally produced intact ECM, in a manner similar to that reported for highly metastatic tumor cells or activated cells of the immune system (6, 7).

Example 4

Purification of Recombinant Human Heparanase

The recombinant heparanase was partially purified from medium of pFhpa4 infected Sf21 cells by Heparin-Sepharose chromatography (FIG. 10*a*) followed by gel filtration of the pooled active fractions over an FPLC Superdex 75 column (FIG. 11*a*). A ~63 kDa protein was observed, whose quantity, as was detected by silver stained SDS-polyacrylamide gel electrophoresis, correlated with heparanase activity in the relevant column fractions (FIGS. 10*b* and 11*b*, respectively). This protein was not detected in the culture medium of cells infected with the control pF1 virus and was subjected to a similar fractionation on heparin-Sepharose (not shown).

Example 5

Expression of the Human hpa cDNA in Various Cell Types, Organs and Tissues

Figure 12A:
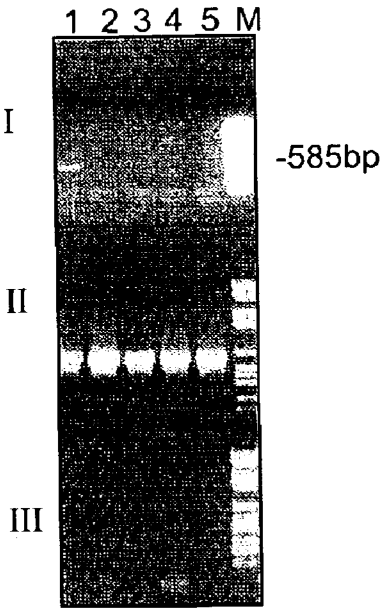
Figure 12B:
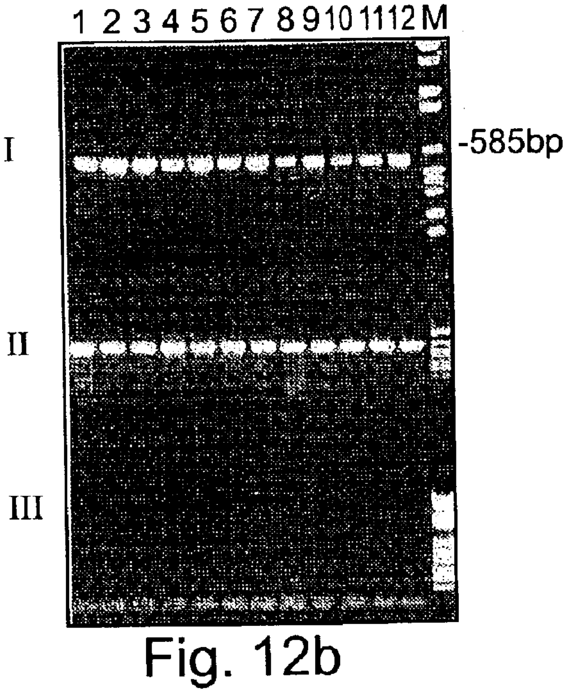
Figure 12C:
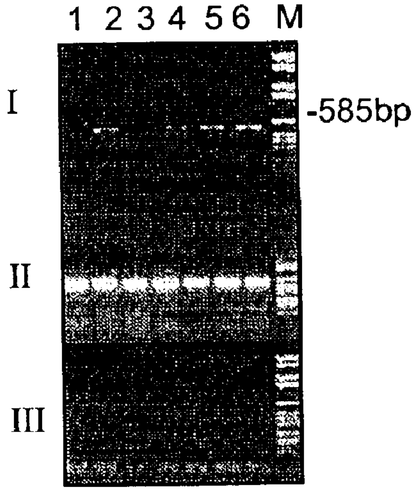
Figure 12D:
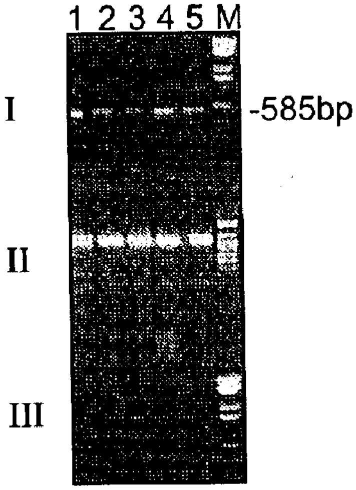
Figure 12E:
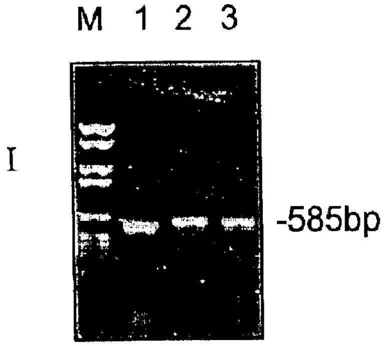

Referring now to FIGS. 12*a–e*, RT-PCR was applied to evaluate the expression of the hpa gene by various cell types and tissues. For this purpose, total RNA was reverse transcribed and amplified. The expected 585 bp long cDNA was clearly demonstrated in human kidney, placenta (8 and 11 weeks) and mole tissues, as well as in freshly isolated and short termed (1.5–48 h) cultured human placental cytotrophoblastic cells (FIG. 12*a*), all known to express a high heparanase activity (41). The hpa transcript was also expressed by normal human neutrophils (FIG. 12*b*). In contrast, there was no detectable expression of the hpa mRNA in embryonic human muscle tissue, thymus, heart and adrenal (FIG. 12*b*). The hpa gene was expressed by several, but not all, human bladder carcinoma cell lines (FIG. 12*c*), SK hepatoma (SK-hep-1), ovarian carcinoma (OV 1063), breast carcinoma (435, 231), melanoma and megakaryocytic (DAMI, CHRF) human cell lines (FIGS. 12*d–e*).

The above described expression pattern of the hpa transcript was determined to be in a very good correlation with heparanase activity levels determined in various tissues and cell types (not shown).

Example 6

Isolation of an Extended 5' End of hpa cDNA from Human SK-hep1 Cell Line

The 5' end of hpa cDNA was isolated from human SK-hep1 cell line by PCR amplification using the Marathon RACE (rapid amplification of cDNA ends) kit (Clontech). Total RNA was prepared from SK-hep1 cells using the TRI-Reagent (Molecular research center Inc.) according to the manufacturer instructions. Poly A+RNA was isolated using the mRNA separator kit (Clonetech).

The Marahton RACE SK-hep1 cDNA composite was constructed according to the manufacturer recommendations. First round of amplification was performed using an adaptor specific primer AP1: 5'-CCATCCTAATACG ACTCACTATAGGGC-3', SEQ ID NO:1, and a hpa specific antisense primer hpl-629: 5'-CCCCAGGAGCAGCA-GCATCAG-3', SEQ ID NO:17, corresponding to nucleotides 119–99 of SEQ ID NO:9. The resulting PCR product was subjected to a second round of amplification using an adaptor specific nested primer AP2: 5'-ACTCAC-TATAGGGCTCGAGCGGC-3', SEQ ID NO:3, and a hpa specific antisense nested primer hpl-666 5'-AGGCTTCGAGCGCAGCAGCAT-3', SEQ ID NO:18, corresponding to nucleotides 83–63 of SEQ ID NO:9. The PCR program was as follows: a hot start of 94° C. for 1 minute, followed by 30 cycles of 90° C.—30 seconds, 68° C.—4 minutes. The resulting 300 bp DNA fragment was extracted from an agarose gel and cloned into the vector pGEM-T Easy (Promega). The resulting recombinant plasmid was designated pHPSK1.

The nucleotide sequence of the pHPSK1 insert was determined and it was found to contain 62 nucleotides of the 5' end of the placenta hpa cDNA (SEQ ID NO:9) and additional 178 nucleotides upstream, the first 178 nucleotides of SEQ ID NOs:13 and 15.

A single nucleotide discrepancy was identified between the SK-hep1 cDNA and the placenta cDNA. The "T" derivative at position 9 of the placenta cDNA (SEQ ID NO:9), is replaced by a "C" derivative at the corresponding position 187 of the SK-hep1 cDNA (SEQ ID NO: 13).

The discrepancy is likely to be due to a mutation at the 5' end of the placenta cDNA clone as confirmed by sequence analysis of sevsral additional cDNA clones isolated from placenta, which like the SK-hep1 cDNA contained C at position 9 of SEQ ID NO:9.

The 5' extended sequence of the SK-hep1 hpa cDNA was assembled with the sequence of the hpa cDNA isolated from human placenta (SEQ ID NO:9). The assembled sequence contained an open reading frame which encodes, as shown in SEQ ID NOs:14 and 15, a polypeptide of 592 amino acids with a calculated molecular weight of 66,407 daltons. The open reading frame is flanked by 93 bp 5' untranslated region (UTR).

Example 7

Isolation of the Upstream Genomic Region of the hpa Gene

The upstream region of the hpa gene was isolated using the Genome Walker kit (Clontech) according to the manufacturer recommendations. The kit includes five human genomic DNA samples each digested with a different restriction endonuclease creating blunt ends: EcoRV, ScaI, DraI, PvuII and SspI.

The blunt ended DNA fragments are ligated to partially single stranded adaptors. The Genomic DNA samples were subjected to PCR amplification using the adaptor specific primer and a gene specific primer. Amplification was performed with Expand High Fidelity (Boehringer Mannheim).

A first round of amplification was performed using the ap1 primer: 5'-G TAATACGACTCACTATAGGGC-3', SEQ ID NO:19, and the hpa specific antisense primer hpl-666: 5'-AGGCTTCGAGCGCAGCAGCAT-3', SEQ ID NO:18, corresponding to nucleotides 83–63 of SEQ ID NO:9. The PCR program was as follows: a hot start of 94° C.—3 minutes, followed by 36 cycles of 94° C.—40 seconds, 67° C.—4 minutes.

The PCR products of the first amplification were diluted 1:50. One μl of the diluted sample was used as a template for a second amplification using a nested adaptor specific primer ap2: 5'-ACTATAGGGCACGCGTGGT-3', SEQ ID NO:20, and a hpa specific antisense primer hpl-690, 5'-CTTGGGCTCACC TGGCTGCTC-3', SEQ ID NO:21, corresponding to nucleotides 62–42 of SEQ ID NO:9. The resulting amplification products were analyzed using agarose gel electrophoresis. Five different PCR products were obtained from the five amplification reactions. A DNA fragment of approximately 750 bp which was obtained from the SspI digested DNA sample was gel extracted. The purified fragment was ligated into the plasmid vector pGEM-T Easy (Promega). The resulting recombinant plasmid was designated pGHP6905 and the nucleotide sequence of the hpa insert was determined.

A partial sequence of 594 nucleotides is shown in SEQ ID NO:16. The last nucleotide in SEQ ID NO:13 corresponds to nucleotide 93 in SEQ ID:13. The DNA sequence in SEQ ID NO:16 contains the 5' region of the hpa cDNA and 501 nucleotides of the genomic upstream region which are predicted to contain the promoter region of the hpa gene.

Example 8

Expression of the 592 Amino Acids HPA Polypeptide in a Human 293 Cell Line

The 592 amino acids open reading frame (SEQ ID NOs:13 and 15) was constructed by ligation of the 110 bp corresponding to the 5' end of the SK-hep1 hpa cDNA with the placenta cDNA. More specifically the Marathon RACE—PCR amplification product of the placenta hpa DNA was digested with SacI and an approximately 1 kb fragment was ligated into a SacI-digested pGHP6905 plasmid. The resulting plasmid was digested with EarI and AatII. The EarI sticky ends were blunted and an approximately 280 bp EarI/blunt-AatII fragment was isolated. This fragment was ligated with pFasthpa digested with EcoRI which was blunt ended using Klenow fragment and further digested with AatII. The resulting plasmid contained a 1827 bp insert which includes an open reading frame of 1776 bp, 31 bp of 3'UTR and 21 bp of 5'UTR. This plasmid was designated pFastLhpa.

A mammalian expression vector was constructed to drive the expression of the 592 amino acids heparanase polypeptide in human cells. The hpa cDNA was excised prom pFastLhpa with BssHII and NotI. The resulting 1850 bp BssHII-NotI fragment was ligated to a mammalian expression vector pSI (Promega) digested with MluI and NotI. The resulting recombinant plasmid, pSIhpaMet2 was transfected into a human 293 embryonic kidney cell line.

Transient expression of the 592 amino-acids heparanase was examined by western blot analysis and the enzymatic activity was tested using the gel shift assay. Both these procedures are described in length in U.S. patent application Ser. No. 09/071,739, filed May 1, 1998, which is incorporated by reference as if fully set forth herein. Cells were harvested 3 days following transfection. Harvested cells were re-suspended in lysis buffer containing 150 mM NaCl, 50 mM Tris pH 7.5, 1% Triton X-100, 1 mM PMSF and protease inhibitor cocktail (Boehringer Mannheim). 40 μg protein extract samples were used for separation on a SDS-PAGE. Proteins were transferred onto a PVDF Hybond-P membrane (Amersham). The membrane was incubated with an affinity purified polyclonal anti heparanase antibody, as described in U.S. patent application Ser. No. 09/071,739. A major band of approximately 50 kDa was observed in the transfected cells as well as a minor band of approximately 65 kDa. A similar pattern was observed in extracts of cells transfected with the pShpa as demonstrated in U.S. patent application Ser. No. 09/071,739. These two bands probably represent two forms of the recombinant heparanase protein produced by the transfected cells. The 65 kDa protein probably represents a heparanase precursor, while the 50 kDa protein is suggested herein to be the processed or mature form.

The catalytic activity of the recombinant protein expressed in the pShpaMet2 transfected cells was tested by gel shift assay. Cell extracts of transfected and of mock transfected cells were incubated overnight with heparin (6 μg in each reaction) at 37° C., in the presence of 20 mM phosphate citrate buffer pH 5.4, 1 mM $CaCl_2$, 1 mM DTT and 50 mM NaCl. Reaction mixtures were then separated on a 10% polyacrylamide gel. The catalytic activity of the recombinant heparanase was clearly demonstrated by a faster migration of the heparin molecules incubated with the transfected cell extract as compared to the control. Faster migration indicates the disappearance of high molecular weight heparin molecules and the generation of low molecular weight degradation products.

Example 9

Chromosomal Localization of the hpa Gene

Chromosomal mapping of the hpa gene was performed utilizing a panel of monochromosomal human/CHO and human/mouse somatic cell hybrids, obtained from the UK HGMP Resource Center (Cambridge, England).

40 ng of each of the somatic cell hybrid DNA samples were subjected to PCR amplification using the hpa primers: hpu565 5'-AGCTCTGTAGATGTGC TATACAC-3', SEQ ID NO:22, corresponding to nucleotides 564–586 of SEQ ID NO:9 and an antisense primer hpl171 5'-GCATCTTA-GCCGTCTTTCTTCG-3', SEQ ID NO:23, corresponding to nucleotides 897–876 of SEQ ID NO:9.

The PCR program was as follows: a hot start of 94° C.—3 minutes, followed by 7 cycles of 94° C.—45 seconds, 66° C.—1 minute, 68° C.—5 minutes, followed by 30 cycles of 94° C.—45 seconds, 62° C.—1 minute, 68 ° C.—5 minutes, and a 10 minutes final extension at 72° C.

The reactions were performed with Expand long PCR (Boehringer Mannheim). The resulting amplification products were analyzed using agarose gel electrophoresis. As demonstrated in FIG. 14, a single band of approximately 2.8 Kb was obtained from chromosome 4, as well as from the control human genomic DNA. A 2.8 kb amplification product is expected based on amplification of the genomic hpa clone (data not shown). No amplification products were obtained neither in the control DNA samples of hamster and mouse nor in somatic hybrids of other human chromosome.

Example 10

Human Genomic Clone Encoding Heparanase

Five plaques were isolated following screening of a human genomic library and were designated L3-1, L5-1, L8-1, L10-1 and L6-1. The phage DNAs were analyzed by Southern hybridization and by PCR with hpa specific and vector specific primers. Southern analysis was performed with three fragments of hpa cDNA: a PvuII-BamHI fragment (nucleotides 32–450, SEQ ID NO:9), a BamHI-NdeI fragment (nucleotides 451–1102, SEQ ID NO:9) and an NdeI-XhoI fragment (nucleotides 1103–1721, SEQ ID NO:9).

Following Southern analysis, phages L3, L6, L8 were selected for further analysis. A scheme of the genomic region and the relative position of the three phage clones is depicted in FIG. 15. A 2 kb DNA fragment containing the gap between phages L6 and L3 was PCR amplified from human genomic DNA with two gene specific primers GHpuL3 and GHp1L6. The PCR product was cloned into the plasmid vector pGEM-T-easy (Promega).

Large scale DNA sequencing of the three Lambda clones and the amplified fragment was performed with Lambda purified DNA by primer walking. A nucleotide sequence of 44,898 bp was analyzed (FIG. 16, SEQ ID NO:42). Comparison of the genomic sequence with that of hpa cDNA revealed 12 exons separated by 11 introns (FIGS. 15 an 16). The genomic organization of the hpa gene is depicted in FIG. 15 (top). The sequence include the coding region from the first ATG to the stop codon which spans 39,113 nucleotides, 2742 nucleotides upstream of the first ATG and 3043 nucleotides downstream of the stop codon. Splice site consensus sequences were identified at exon/intron junctions.

Example 11

Alternative Splicing

Several minor RT-PCR products were obtained from various cell types, following amplification with hpa specific primers. Each one found to contain a deletion of one or two exons. Some of these PCR products contain ORFs, which encode potential shorter proteins.

Table 1 below summarizes the alternative spliced products isolated from various cell lines.

Fragments of similar sizes were obtained following amplification with two cell lines, placenta and platelets.

| Cell type | Nucleotides deleted | Exons deleted | ORF |
|---|---|---|---|
| Platelets | 1047–1267 | 8, 9 | + |
| Platelets | 1154–1267 | 9 | – |
| Platelets | 289–435, 562–735 | 2, 4 | – |
| Sk-hep1, platelets, Zr75 | 562–735 | 4 | + |
| Sk-hep1 (hepatoma) | 561–904 | 4, 5 | – |
| Zr75 (breast carcinoma) | 96–203 | 1 (partial) | + |

Example 12

Mouse and Rat hpa

EST databases were screened for sequences homologous to the hpa gene. Three mouse EST's were identified (accession No. Aa177901, from mouse spleen, Aa067997 from mouse skin, Aa47943 from mouse embryo), assembled into a 824 bp cDNA fragment which contains a partial open reading frame (lacking a 5' end) of 629 bp and a 3' untranslated region of 195 bp (SEQ ID NO:12). As shown in FIG. 13, the coding region is 80% similar to the 3' end of the hpa cDNA sequence. These EST's are probably cDNA fragments of the mouse hpa homolog that encodes for the mouse heparanase.

Searching for consensus protein domains revealed an amino terminal homology between the heparanase and several precursor proteins such as Procollagen Alpha 1 precursor, Tyrosine-protein kinase-RYK, Fibulin-1, Insulin-like growth factor binding protein and several others. The amino terminus is highly hydrophobic and contains a potential trans-membrane domain. The homology to known signal peptide sequences suggests that it could function as a signal peptide for protein localization.

The amino acid sequence of human heparanase was used to search for homologous sequences in the DNA and protein databases. Several human EST's were identified, as well as mouse sequences highly homologous to human heparanase. The following mouse EST's were identified AA177901, AA674378, AA67997, AA047943, AA690179, AI122034, all sharing an identical sequence and correspond to amino acids 336–543 of the human heparanase sequence. The entire mouse heparanase cDNA was cloned, based on the nucleotide sequence of the mouse EST's. PCR primers were designed and a Marathon RACE was performed using a Marathon cDNA library from 15 days mouse embryo (Clontech) and from BL6 mouse melanoma cell line. The mouse hpa homologous cDNA was isolated following several amplification steps. A 1.1 kb fragment was amplified from mouse embryo Marathon cDNA library. The first cycle of amplification was performed with primers mhpl773 and Ap1 and the second cycle with primers mhpl736 and AP2. A 1.1 kb fragment was then amplified from BL6 Marathon cDNA library. The first cycle of amplification was performed with the primers mhpl152 and Ap1, and the second with mhpl83 and AP2. The combined sequence was homologous to nucleotides 157–1702 of the human hpa cDNA, which encode amino acids 33–543. The 5' end of the mouse hpa gene was isolated from a mouse genomic DNA library using the Genome Walker kit (Clontech). An 0.9 kb fragment was amplified from a DraI digested Genome walker DNA library. The first cycle of amplification was performed with primers mhpl114 and Ap1 and the second with primers mhpl103 and AP2. The assembled sequence (SEQ ID NOs:43, 45) is 2396 nucleotides long. It contains an open reading frame of 1605 nucleotides, which encode a polypeptide of 535 amino acids (SEQ ID NOs:44, 45), 196 nucleotides of 3' untranslated region (UTR), and anupstream sequence which includes the promoter region and the 5'-UTR of the mouse hpa cDNA. According to two promoter predicting programs TSSW and TSSG, the transcription start site is localized to nucleotide 431 of SEQ ID NOs:43, 45, 163 nucleotides upstream of the first ATG codon. The 431 upstream genomic sequence contains the promoter region. A TATA box is predicted at position 394 of SEQ ID NOs:43, 45. The mouse and the human hpa genes share an average homology of 78% between the nucleotide sequences and 81% similarity between the deduced amino acid sequences.

Search for hpa homologous sequences, using the Blast 2.0 server revealed two EST's from rat: AI060284 (385 nucleotides, SEQ ID NO:46) which is homologous to the amino terminus (68% similarity to amino acids 12–136) of human heparanase and AI237828 (541 nucleotides, SEQ ID NO:47) which is homologous to the carboxyl terminus (81% similarity to amino acids 500–543) of human heparanase, and contains a 3'-UTR. A comparison between the human heparanase and the mouse and rat homologous sequences is demonstrated in FIG. 17.

Example 13

Prediction of Heparanase Active Site

Homology search of heparanase amino acid sequence against the DNA and the protein databases revealed no significant homologies. The protein secondary structure as predicted by the PHD program consists of alternating alpha helices and beta sheets. The fold recognition server of UCLA predicted alpha/beta barrel structure, with under-threshold confidence.

Five of 15 proteins, which were predicted to have most similar folds, were glycosyl hydrolases from various organisms: 1xyza—xylanase from Clostridium Thermocellum, 1pbga—6-phospho-beta-δ-galactosidase from Lactococcus Lactis, 1amy—alpha-amylase from Barley, 1ecea—endocellulase from Acidothermus Cellulolyticus and 1qbc—hexosaminidase alpha chain, glycosyl hydrolase.

Protein homology search using the bioaccelerator pulled out several proteins, including glycosyl hydrolyses such as beta-fructofuranosidase from Vicia faba (broad bean) and from potato, lactase phlorizin hydrolase from human, xylanases from *Clostridium thermocellum* and from *Streptomyces halstedii* and cellulase from *Clostridium thermocellum*. Blocks 9.3 database pulled out the active site of glycosyl hydrolases family five, which includes cellulases from various bacteria and fungi. Similar active site motif is shared by several lysosomal acid hydrolases (63) and other glycosyl hydrolases. The common mechanism shared by these enzymes involves two glutamic acid residues, a proton donor and a nucleophile.

Despite the lack of an overall homology between the heparanase and other glycosyl hydolases, the amino acid couple Asp-Glu (NE), which is characteristic of the proton donor of glycosyl hydrolyses of the GH-A clan, was found at positions 224–225 of the human heparanase protein sequence. As in other clan members, this NE couple is located at the end of a β sheet.

Considering the relative location of the proton donor and the predicted secondary structure, the glutamic acid that functions as nucleophile is most likely located at position 343, or at positon 396. Identification of the active site and the amino acids directly involved in hydrolysis opens the way for expression of the defined catalytic domain. In addition, it will provide the tools for rational design of enzyme activity either by modification of the microenviroment or catalytic site itself.

Example 14

Expression of hpa Antisense in Mammalian Cell Lines

A mammalian expression vector Hpa2Kepcdna3 was constructed in order to express hpa antisense in mammalian cells. hpa cDNA (1.7 kb EcoRI fragment) was cloned into the plasmid pCDNA3 in 3'>5' (antisense) orientation. The construct was used to transfect MBT2-T50 and T24P cell lines. $2\times10^5$ cells in 35 mm plates were transfected using the Fugene protocol (Boehringer Mannheim). 48 hours after transfection cells were trypsinized and seeded in six well plates. 24 hours later G418 was added to initiate selection. The number of colonies per 35 mm plate following 3 weeks:

| | Antisense | No insert |
|---|---|---|
| T24P | 15 | 60 |
| MBT-T50 | 1 | 6 |

The lower number of colonies obtained after transfection with hpa antisense, as compared with the control plasmid suggests that the introduction of hpa antisense interfere with cell growth. This experiment demonstrates the use of complementary antisense hpa DNA sequence to control heparanase expression in cells. This approach may be used to inhibit expression of heparanase in vivo, in, for example, cancer cells and in other pathological processes in which heparanase is involved.

Example 15

Zoo Blot

Hpa cDNA was used as a probe to detect homologous sequences in human DNA and in DNA of various animals. The autoradiogram of the Southern analysis is presented in FIG. 18. Several bands were detected in human DNA, which correlated with the accepted pattern according to the genomic hpa sequence. Several intense bands were detected in all mammals, while faint bands were detected in chicken. This correlates with the phylogenetic relation between human and the tested animals. The intense bands indicate that hpa is conserved among mammals as well as in more genetically distant organisms. The multiple bands patterns suggest that in all animals, like in human, the hpa locus occupy large genomic region. Alternatively, the various bands could represent homologous sequences and suggest the existence of a gene family, which can be isolated based on their homology to the human hpa reported herein. This conservation was actually found, between the isolated human hpa cDNA and the mouse homologue.

Example 16

Characterization of the hpa Promoter

The DNA sequence upstream of the hpa first ATG was subjected to computational analysis in order to localize the predicted transcription start site and to identify potential transcription factors binding sites. Recognition of human PolII promoter region and start of transcription were predicted using the TSSW and TSSG programs. Both programs identified a promoter region upstream of the coding region. TSSW pointed at nucleotide 2644 and TSSG at 2635 of SEQ ID NO:42. These two predicted transcription start sites are located 4 and 13 nucleotides upstream of the longest hpa cDNA isolated by RACE.

A hpa promoter-GFP reporter vector was constructed in order to investigate the regulation of hpa transcription. Two constructs were made, containing 1.8 kb and 1.1 kb of the hpa promoter region. The reporter vector was transfected into T50-mouse bladder carcinoma cells. Cells transfected with both constructs exhibited green fluorescence, which indicated the promoter activity of the genomic sequence upstream of the hpa-coding region. This reporter vector, enables the monitoring of hpa promoter activity, at various conditions and in different cell types and to characterize the factors involved regulation of hpa expression.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

LIST OF REFERENCES

1. Wight, T. N., Kinsella, M. G., and Qwarnstromn, E. E. (1992). The role of proteoglycans in cell adhesion, migration and proliferation. *Curr. Opin. Cell Biol.*, 4, 793–801.

2. Jackson, R. L., Busch, S. J., and Cardin, A. L. (1991). Glycosaminoglycans: Molecular properties, protein interactions and role in physiological processes. *Physiol. Rev.*, 71, 481–539.

3. Wight, T. N. (1989). Cell biology of arterial proteoglycans. *Arteriosclerosis*, 9, 1–20.

4. Kjellen, L., and Lindahl, U. (1991). Proteoglycans: structures and interactions. *Annu. Rev. Biochem.*, 60, 443–475.

5. Ruoslahti, E., and Yamaguchi, Y. (1991). Proteoglycans as modulators of growth factor activities. *Cell*, 64, 867–869.

6. Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. *Invasion & Metastasis*, 12, 112–127.

7. Vlodavsky, I., Mohsen, M., Lider, O., Ishai-Michaeli, R., Ekre, H. -P., Svahn, C. M., Vigoda, M., and Peretz, T. (1995). Inhibition of tumor metastasis by heparanase inhibiting species of heparin. *Invasion & Metastasis*, 14, 290–302.

8. Nakajima, M., Irimura, T., and Nicolson, G. L. (1988). Heparanase and tumor metastasis. *J. Cell. Biochem.*, 36, 157–167.

9. Nicolson, G. L. (1988). Organ specificity of tumor metastasis: Role of preferential adhesion, invasion and growth of malignant cells at specific secondary sites. *Cancer Met. Rev.*, 7, 143–188.

10. Liotta, L. A., Rao, C. N., and Barsky, S. H. (1983). Tumor invasion and the extracellular matrix. *Lab. Invest.*, 49, 639–649.

11. Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. *Cancer Res.*, 43, 2704–2711.

12. Vlodavsky, I., Ishai-Michaeli, R., Bar-Ner, M., Fridman, R., Horowitz, A. T., Fuks, Z. and Biran, S. (1988). Involvement of heparanase in tumor metastasis and angiogenesis. Is. *J. Med.*, 24, 464–470.

13. Vlodavsky, I., Liu, G. M., and Gospodarowicz, D. (1980). Morphological appearance, growth behavior and migratory activity of human tumor cells maintained on extracellular matrix vs. plastic. *Cell*, 19, 607–616.

14. Gospodarowicz, D., Delgado, D., and Vlodavsky, I. (1980). Permissive effect of the extracellular matrix on cell proliferation in-vitro. *Proc. Natl. Acad. Sci. USA.*, 77, 4094–4098.

15. Bashkin, P., Doctrow, S., Klagsbrun, M., Svahn, C. M., Folkman, J., and Vlodavsky, I. (1989). Basic fibroblast growth factor binds to subendothelial extracellular matrix and is released by heparitinase and heparin-like molecules. *Biochemistry*, 28, 1737–1743.

16. Parish, C. R., Coombe, D. R., Jakobsen, K. B., and Underwood, P. A. (1987). Evidence that sulphated polysaccharides inhibit tumor metastasis by blocking tumor cell-derived heparanase. *Int. J. Cancer*, 40, 511–517.

16a. Vlodavsky, I., Hua-Quan Miao., Benezra, M., Lider, O., Bar-Shavit, R., Schmidt, A., and Peretz, T. (1997). Involvement of the extracellular matrix, heparan sulfate proteoglycans and heparan sulfate degrading enzymes in angiogenesis and metastasis. In: Tumor Angiogenesis. Eds. C. E. Lewis, R. Bicknell & N. Ferrara. Oxford University Press, Oxford UK, pp. 125–140.

17. Burgess, W. H., and Maciag, T. (1989). The heparin-binding (fibroblast) growth factor family of proteins. *Annu. Rev. Biochem.*, 58, 575–606.

18. Folkman, J., and Klagsbrun, M. (1987). Angiogenic factors. *Science*, 235, 442–447.

19. Vlodavsky, I., Folkman, J., Sullivan, R., Fridman, R., Ishai-Michaelli, R., Sasse, J., and Klagsbrun, M. (1987). Endothelial cell-derived basic fibroblast growth factor: Synthesis and deposition into subendothelial extracellular matrix. *.Proc. Natl. Acad. Sci. USA*, 84, 2292–2296.

20. Folkman, J., Klagsbrun, M., Sasse, J., Wadzinski, M., Ingber, D., and Vlodavsky, I. (1980). A heparin-binding angiogenic protein—basic fibroblast growth factor—is stored within basement membrane. *Am. J. Pathol.*, 130, 393–400.

21. Cardon-Cardo, C., Vlodavsky, I., Haimovitz-Friedman, A., Hicklin, D., and Fuks, Z. (1990). Expression of basic fibroblast growth factor in normal human tissues. *Lab. Invest.*, 63, 832–840.

22. Ishai-Michaeli, R., Svahn, C. -M., Chajek-Shaul, T., Komer, G., Ekre, H. -P., and Vlodavsky, I. (1992). Importance of size and sulfation of heparin in release of basic fibroblast factor from the vascular endothelium and extracellular matrix. *Biochemistry*, 31, 2080–2088.

23. Ishai-Michaeli, R., Eldor, A., and Vlodavsky, I. (1990). Heparanase activity expressed by platelets, neutrophils and lymphoma cells releases active fibroblast growth factor from extracellular matrix. *Cell Reg.*, 1,833–842.

24. Vlodavsky, I., Bar-Shavit, R., Ishai-Michaeli, R., Bashkin, P., and Fuks, Z. (1991). Extracellular sequestration and release of fibroblast growth factor: a regulatory mechanism? *Trends Biochem. Sci.*, 16, 268–271.

25. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp327–343. Academic press Inc., Orlando, Fla.

26. Yayon, A., Klagsbrun, M., Esko, J. D., Leder, P., and Ornitz, D. M. (1991). Cell surface, heparin-like molecules are required for binding of basic fibroblast growth factor to its high affinity receptor. *Cell*, 64, 841–848.

27. Spivak-Kroizman, T., Lemmon, M. A., Dikic, I., Ladbury, J. E., Pinchasi, D., Huang, J., Jaye, M., Crumley, G., Schlessinger, J., and Lax, I. (1994). Heparin-induced oligomerization of FGF molecules is responsible for FGF receptor dimerization, activation, and cell proliferation. *Cell*, 79, 1015–1024.

28. Ornitz, D. M., Herr, A. B., Nilsson, M., West, a., J., Svahn, C. -M., and Waksman, G. (1995). FGF binding and FGF receptor activation by synthetic heparan-derived di- and trisaccharides. *Science*, 268, 432–436.

29. Gitay-Goren, H., Soker, S., Vlodavsky, I., and Neufeld, G. (1992). Cell surface associated heparin-like molecules are required for the binding of vascular endothelial growth factor (VEGF) to its cell surface receptors. *J. Biol. Chem.*, 267, 6093–6098.

30. Lider, O., Baharav, E., Mekori, Y., Miller, T., Naparstek, Y., Vlodavsky, I., and Cohen, I. R. (1989). Suppression of experimental autoimmune diseases and prolongation of allograft survival by treatment of animals with heparinoid inhibitors of T lymphocyte heparanase. *J. Clin. Invest.*, 83, 752–756.

31. Lider, O., Cahalon, L., Gilat, D., Hershkovitz, R., Siegel, D., Margalit, R., Shoseyov, O., and Cohn, I. R. (1995). A disaccharide that inhibits tumor necrosis factor α is formed from the extracellular matrix by the enzyme heparanase. *Proc. Natl. Acad. Sci. USA.*, 92, 5037–5041.

31a. Rapraeger, A., Krufka, A., and Olwin, B. R. (1991). Requirement of heparan sulfate for bFGF-mediated fibroblast growth and myoblast differentiation. *Science*, 252, 1705–1708.

32. Eisenberg, S., Sehayek, E., Olivecrona, T., and Vlodavsky, I. (1992). Lipoprotein lipase enhances binding of lipoproteins to heparan sulfate on cell surfaces and extracellular matrix. *J. Clin. Invest.*, 90, 2013–2021.

33. Shieh, M-T., Wundunn, D., Montgomery, R. I., Esko, J. D., and Spear, P. G. J. (1992). Cell surface receptors for herpes simplex virus are heparan sulfate proteoglycans. *J Cell Biol.*, 116, 1273–1281.

33a. Chen, Y., Maguire, T., Hileman, R. E., Fromm, J. R., Esko, J. D., Linhardt, R. J., and Marks, R. M. (1997). Dengue virus infectivity depends on envelope protein binding to target cell heparan sulfate. *Nature Medicine* 3, 866–871.

33b. Putnak, J. R., Kanesa-Thasan, N., and Innis, B. L. (1997). A putative cellular receptor for dengue viruses. *Nature Medicine* 3, 828–829.

34. Narindrasorasak, S., Lowery, D., Gonzalez-DeWhitt, P., Poorman, R. A., Greenberg, B., Kisilevsky, R. (1991). High affinity interactions between the Alzheimer's beta-amyloid precursor protein and the basement membrane form of theparan sulfate proteoglycan. *J. Biol. Chem.*, 266, 12878–83.

35. Ross, R. (1993). The pathogenesis of atherosclerosis: a perspective for the 1990s. *Nature* (*Lond.*)., 362:801–809.

36. Zhong-Sheng, J., Walter, J., Brecht, R., Miranda, D., Mahmood Hussain, M., Innerarity, T. L. and Mahley, W. R. (1993). Role of heparan sulfate proteoglycans in the binding and uptake of apolipoprotein E-enriched remnant lipoproteins by cultured cells. *J. Biol. Chem.*, 268, 10160–10167.

37. Ernst, S., Langer, R., Cooney, Ch. L., and Sasisekharan, R. (1995). Enzymatic degradation of glycosaminoglycans. Critical Reviews in Biochemistry and Molecular Biology, 30(5), 387–444.

38. Gospodarowicz, D., Mescher, A L., Birdwell, C R. (1977). Stimulation of corneal endothelial cell proliferation in vitro by fibroblast and epidermal growth factors. *Exp Eye Res* 25, 75–89.

39. Haimovitz-Friedman, A., Falcone, D. J., Eldor, A., Schirrmacher, V., Vlodavsky, I., and Fuks, Z. (1991) Activation of platelet heparitinase by tumor cell-derived factors. *Blood*, 78, 789–796.

39a. Savitsky, K., Platzer, M., Uziel, T., Gilad, S., Sartiel, A., Rosental, A., Elroy-Stein, O., Siloh, Y. and Rotman, G. (1997). Ataxia-telangiectasia: structural diversity of untranslated sequences suggests complex post-translational regulation of ATM gene expression. Nucleic Acids Res. 25(9), 1678–1684.

40. Bar-Ner, M., Eldor, A., Wasserman, L., Matzner, Y., and Vlodavsky, I. (1987). Inhibition of heparanase mediated degradation of extracellular matrix heparan sulfate by modified and non-anticoagulant heparin species. *Blood*, 70, 551–557.

41. Goshen, R., Hochberg, A., Korner, G., Levi, E., Ishai-Michaeli, R., Elkin, M., de Grot, N., and Vlodavsky, I. (1996). Purification and characterization of placental heparanase and its expression by cultured cytotrophoblasts. *Mol. Human Reprod.*, 2, 679–684.

42. Korb M., Ke Y. and Johnson L. F. (1993) Stimulation of gene expression by introns: conversion of an inhibitory intron to a stimulatory intron by alteration of the splice donor sequence. *Nucleic Acids Res.*, 25;21(25):5901–8.

43. Zheng B., Qiu X. Y., Tan M., Xing Y. N., Lo D., Xue J. L. and Qiu X. F. (1997) Increment of hFIX expression with endogenous intron 1 in vitro. *Cell Res.*, 7(1):21–29.

44. Kurachi S., Hitomi Y., Furukawa M. and Kurachi K. (1995) Role of intron I in expression of the human factor IX gene. *J. Biol. Chem.* 10, 270(10):5276–5281.

45. Shekhar P. V. and Miller F. R. (1994–5) Correlation of differences in modulation of ras expression with metastatic competence of mouse mammary tumor subpopulations. *Invasion Metastasis*, 14(1–6):27–37.

46. Zhou G., Garofalo S., Mukhopadhyay K., Lefebvre V., Smith C. N., Eberspaecher H. and de Crombrugghe B. (1995) A 182 bp fragment of the mouse pro alpha 1(II) collagen gene is sufficient to direct chondrocyte expression in transgenic mice. *J. Cell Sci.*, 108 (Pt 12):3677–3684.

47. Hormuzdi S. G., Penttinen R., Jaenisch R. and Bornstein P. (1998) A gene-targeting approach identifies a function for the first intron in expression of the alpha1(I) collagen gene. *Mol. Cell*, 18(6):3368–3375.

48. Kang Y. K., Lee C. S., Chung A. S. and Lee K. K. (1998) Prolactin-inducible enhancer activity of the first intron of the bovine beta-casein gene. *Mol. Cells*, 30;8(3):259–265.

49. Chow Y. H., O'Brodovich H., Plumb J., Wen Y., Sohn K. J., Lu Z., Zhang F., Lukacs G. L., Tanswell A. K., Hui C. C., Buchwald M. and Hu J. (1997) Development of an epithelium-specific expression cassette with human DNA regulatory elements for transgene expression in lung airways. *Proc. Natl. Acad. Sci. USA*, 23;94(26): 14695–14700.

50. Gottschalk U. and Chan S. (1998) Somatic gene therapy. Present situation and future perspective. *Arzneimittelforschung*, 48(11):1111–1120.

51. Ye S., Cole-Strauss A. C., Frank B. and Kmiec E. B. (1998) Targeted gene correction: a new strategy for molecular medicine. *Mol. Med. Today*, 4(10):431–437.

52. Lai L., and Lien Y. (1999) Homologous recombination based gene *therapy. Exp. Nephrol.*, 7(1):11–14.

53. Yazaki N., Fujita H., Ohta M., Kawasaki T. and Itoh N. (1993) The structure and expression of the FGF receptor-1 mRNA isoforms in rat tissues. *Biochim. Biophys. Acta.*, 20;1172(1–2):37–42.

54. Le Fur N., Kelsall S. R., Silvers W. K. and Mintz B. (1997) Selective increase in specific alternative splice variants of tyrosinase in murine melanomas: a projected basis for immunotherapy. *Proc. Natl. Acad. Sci. USA*, 13;94(10):5332–5337.

55. Miyake H., Okamoto I., Hara I., Gohji K., Yamanaka K., Arakawa S., Kamidono S. and Saya H. (1998) Highly specific and sensitive detection of malignancy in urine samples from patients with urothelial cancer by CD44v8–10/CD44v10 competitive RT-PCR. *Int. J. Cancer*, 18;79(6):560–564.

56. Guriec N., Marcellin L., Gairard B., Calderoli H., Wilk A., Renaud R., Bergerat J. P. and Oberling F. (1996) CD44 exon 6 expression as a possible early prognostic factor in primary node negative breast carcinoma. *Clin. Exp. Metastasis*, 14(5):434–439.

57. Gewirtz A. M., Sokol D. L. and Ratajczak M. Z. (1998) Nucleic acid therapeutics: state of the art and future prospects. Blood, 1;92(3):712–736.

58. Hida K., Shindoh M., Yasuda M., Hanzawa M., Funaoka K., Kohgo T., Amemiya A., Totsuka Y., Yoshida K. and Fujinaga K (1997) Antisense E1AF transfection restrains oral cancer invasion by reducing matrix metalloproteinase activities. *Am. J. Pathol.* 150(6):2125–2132.

59. Shastry B. S. (1998) Gene disruption in mice: models of development and disease. *Mol. Cell. Biochem.* 1998 April;181(1–2):163–179.

60. Carpentier A. F., Rosenfeld M. R., Delattre J. Y., Whalen R. G., Posner J. B. and Dalmau J. (1998) DNA vaccination with HuD inhibits growth of a neuroblastoma in mice. *Clin. Cancer Res.*, 4(11):2819–2824.

61. Lai W. C. and Bennett M. (1998) DNA vaccines. *Crit. Rev. Immunol.*, 18(5):449–484.

62. Welch P. J., Barber J. R., and Wong-Staal F. (1998) Expression of ribozymes in gene transfer systems to modulate target RNA levels. *Curr. Opin. Biotechnol.*, 9(5) :486–496.

63. Durand P., Lehn P., Callebaunt I., Fabrega S., Henrissat B. and Mornon J. P. (1997) Active-site motifs of lysosomal acid hydrolyses: invariant features of clan GH-A glycosyl hydrolases deduced from hydrophobic cluster analysis. Glycobiology, 7(2):277–284.

64. Thuong and Helene (1993) Sequence specific recognition and modification of double helical DNA by oligonucleotides Angev. Chem. Int. Ed. Engl. 32:666

65. Dash P., Lotan I., Knapp M., Kandel E. R. and Goelet P. (1987) Selective elimination of mRNAs in vivo: complementary oligodeoxynucleotides promote RNA degradation by an RNase H-like activity. Proc. Natl. Acad. Sci. USA, 84:7896.

66. Chiang M. Y., Chan H., Zounes M. A., Freier S. M., Lima W. F. and Bennett C. F. (1991) Antisense oligonucleotides inhibit intercellular adhesion molecule 1 expression by two distinct mechanisms. J. Biol. Chem. 266:18162–71.

67. Paterson Paterson B. M, Roberts B. E and Kuff E L. (1977) Structural gene identification and mapping by DNA-mRNA hybrid-arrested cell-free translation. Proc. Natl. Acad. Sci. USA, 74:4370.

68. Cohen (1992) Oligonucleotide therapeutics. Trends in Biotechnology, 10:87.

69. Szczylik et al (1991) Selective inhibition of leukemia cell proliferation by BCR-ABL antisense oligodeoxynucleotides. Science 253:562.

70. Calabretta et al. (1991) Normal and leukemic hematopoietic cell manifest differential sensitivity to inhibitory effects of c-myc antisense oligodeoxynucleotides: an in vitro study relevant to bone marrow purging. Proc. Natl. Acad. Sci. USA 88:2351.

71. Heikhila et al. (1987) A c-myc antisense oligodeoxynucleotide inhibits entry into S phase but not progress from G(0) to G(1). Nature, 328:445.

72. Reed et al. (1990) Antisense mediated inhibition of BCL2 prooncogene expression and leukemic cell growth and survival: comparison of phosphodiester and phosphorothioate oligodeoxynucleotides. Cancer Res. 50:6565.

73. Burch and Mahan (1991) Oligodeoxynucleotides antisense to the interleukin I receptor m RNA block the effects of interleukin I in cultured murine and human fibroblasts and in mice. J. Clin. Invest. 88:1190.

74. Agrawal (1992) Antisense oligonucleotides as antiviral agents. TIBTECH 10:152.

75. Uhlmann et al. (1990) Chem. Rev. 90:544.

76. Cook (1991) Medicinal chemistry of antisense oligonucleotides—future opportunities. Anti-Cancer Drug Design 6:585.

77. Biotechnology research news (1993) Can DNA mimics improve on the real thing? Science 262:1647.

---

What is claimed is:

1. An isolated polynucleotide fragment comprising a polynucleotide sequence encoding a polypeptide having heparanase catalytic activity, wherein said polypeptide shares at least 95% homology with SEQ ID NO:14, as determined using default parameters of a DNA sequence analysis software package developed by the Genetic Computer Group (GCG) at the University of Wisconsin.

2. The polynucleotide fragment of claim 1, wherein said polynucleotide sequence includes nucleotides 63–1691 of SEQ ID NO:9.

3. The polynucleotide fragment of claim 1, wherein said polynucleotide sequence includes nucleotides 63–721 of SEQ ID NO:9.

4. The polynucleotide fragment of claim 1, wherein said polynucleotide sequence includes a segment of SEQ ID NO:9, said segment encodes said polypeptide having said heparanase catalytic activity.

5. The polynucleotide fragment of claim 1, wherein said polypeptide includes an amino acid sequence as set forth in SEQ ID NO:14.

6. The polynucleotide fragment of claim 1, wherein said polypeptide includes a segment of SEQ ID NO:14 said segment harbors said heparanase catalytic activity.

7. The polynucleotide fragment of claim 1, wherein said polynucleotide sequence is selected from the group consisting of double stranded DNA, single stranded DNA and RNA.

8. An isolated polynucleotide sequence as set forth in SEQ ID NO:13.

9. An isolated polynucleotide sequence at least 95% homologous to SEQ ID NO:13, as determined using default parameters of a DNA sequence analysis software package developed by the Genetic Computer Group (GCG) at the University of Wisconsin, wherein said polynucleotide sequence encodes a polypeptide having heparanase catalytic activity.

10. A vector comprising a polynucleotide sequence encoding a polypeptide having heparanase catalytic activity, wherein said polypeptide shares at least 95% homology with SEQ ID NO:14, as determined using default parameters of a DNA sequence analysis software package developed by the Genetic Computer Group (GCG) at the University of Wisconsin.

11. The vector of claim 10, wherein said polynucleotide sequence includes nucleotides 63–1691 of SEQ ID NO:9.

12. The vector of claim 10, wherein said polynucleotide sequence includes nucleotides 63–721 of SEQ ID NO:9.

13. The vector of claim 10, wherein said polynucleotide sequence includes a segment of SEQ ID NO:9, said segment encodes said polypeptide having said heparanase catalytic activity.

14. The vector of claim 10, wherein said polypeptide includes an amino acid sequence as set forth in SEQ ID NO:14.

15. The vector of claim 10, wherein said polypeptide includes a segment of SEQ ID NO:14, said segment harbors said heparanase catalytic activity.

16. The vector of claim 10, wherein said polynucleotide sequence is selected from the group consisting of double stranded DNA, single stranded DNA and RNA.

17. The vector of claim 10, wherein said vector is a baculovirus vector.

18. A host cell comprising an exogenous polynucleotide fragment including a polynucleotide sequence encoding a polypeptide having heparanase catalytic activity, wherein said polypeptide shares at least 95% homology with SEQ ID NO:14, as determined using default parameters of a DNA sequence analysis software package developed by the Genetic Computer Group (GCG) at the University of Wisconsin.

19. The host cell of claim 18, wherein said polynucleotide sequence includes nucleotides 63–1691 of SEQ ID NO:9.

20. The host cell of claim 18, wherein said polynucleotide sequence includes nucleotides 63–721 of SEQ ID NO:9.

21. The host cell of claim 18, wherein said polynucleotide sequence includes a segment of SEQ ID NO:9, said segment encodes said polypeptide having said heparanase catalytic activity.

22. The host cell of claim 18, wherein said polypeptide includes an amino acid sequence as set forth in SEQ ID NO:14.

23. The host cell of claim 18, wherein said polypeptide includes a segment of SEQ ID NO:14 said segment harbors said heparanase catalytic activity.

24. The host cell of claim 18, wherein said polynucleotide sequence is selected from the group consisting of double stranded DNA, single stranded DNA and RNA.

25. A host cell expressing a recombinant heparanase, wherein said recombinant heparanase shares at least 95% homology with SEQ ID NO:14, as determined using default parameter of a DNA sequence analysis software package developed by the Genetic Computer (Group (GCG) at the University of Wisconsin.

26. A heparanase overexpression system comprising a cell overexpressing heparanase catalytic activity, wherein said heparanase catalytic activity is effected by a heparanase sharing at least 95% homology with SEQ ID NO:14, as determined using default parameters of a DNA sequence analysis software package developed by the Genetic Computer Group (GCG) at the University of Wisconsin.

27. The host cell of claim 18, wherein said cell is an insect cell.

* * * * *

SEQUENCE LISTING

```
<160> NUMBER OF SEQ ID NOS: 48

<210> SEQ ID NO 1
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 1

ccatcctaat acgactcact atagggc                                27


<210> SEQ ID NO 2
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 2

gtagtgatgc catgtaactg aatc                                   24


<210> SEQ ID NO 3
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 3

actcactata gggctcgagc ggc                                    23
```

-continued

<210> SEQ ID NO 4
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 4
gcatcttagc cgtctttctt cg 22

<210> SEQ ID NO 5
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 5
tttttttttt ttttt 15

<210> SEQ ID NO 6
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 6
ttcgatccca agaaggaatc aac 23

<210> SEQ ID NO 7
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 7
gtagtgatgc catgtaactg aatc 24

<210> SEQ ID NO 8
<211> LENGTH: 9
<212> TYPE: PRT
<213> ORGANISM: Artificial sequence
<220> FEATURE:
<223> OTHER INFORMATION: Peptide derived from tryptic digestion of human heparenase

<400> SEQUENCE: 8

Tyr Gly Pro Asp Val Gly Gln Pro Arg
1 5

<210> SEQ ID NO 9
<211> LENGTH: 1721
<212> TYPE: DNA
<213> ORGANISM: Homo sapiens

<400> SEQUENCE: 9
ctagagcttt cgactctccg ctgcgcggca gctggcgggg ggagcagcca ggtgagccca 60
agatgctgct gcgctcgaag cctgcgctgc cgccgccgct gatgctgctg ctcctggggc 120
cgctgggtcc cctctcccct ggcgccctgc cccgacctgc gcaagcacag gacgtcgtgg 180
acctggactt cttcacccag gagccgctgc acctggtgag cccctcgttc ctgtccgtca 240
ccattgacgc caacctggcc acggacccgc ggttcctcat cctcctgggt tctccaaagc 300

-continued

```
ttcgtacctt ggccagaggc ttgtctcctg cgtacctgag gtttggtggc accaagacag    360

acttcctaat tttcgatccc aagaaggaat caacctttga agagagaagt tactggcaat    420

ctcaagtcaa ccaggatatt tgcaaatatg gatccatccc tcctgatgtg gaggagaagt    480

tacggttgga atggccctac caggagcaat tgctactccg agaacactac cagaaaaagt    540

tcaagaacag cacctactca agaagctctg tagatgtgct atacactttt gcaaactgct    600

caggactgga cttgatcttt ggcctaaatg cgttattaag aacagcagat ttgcagtgga    660

acagttctaa tgctcagttg ctcctggact actgctcttc caaggggtat aacatttctt    720

gggaactagg caatgaacct aacagtttcc ttaagaaggc tgatattttc atcaatgggt    780

cgcagttagg agaagattat attcaattgc ataaacttct aagaaagtcc accttcaaaa    840

atgcaaaact ctatggtcct gatgttggtc agcctcgaag aaagacggct aagatgctga    900

agagcttcct gaaggctggt ggagaagtga ttgattcagt tacatggcat cactactatt    960

tgaatggacg gactgctacc agggaagatt ttctaaaccc tgatgtattg gacattttta   1020

tttcatctgt gcaaaaagtt ttccaggtgg ttgagagcac caggcctggc aagaaggtct   1080

ggttaggaga aacaagctct gcatatggag gcggagcgcc cttgctatcc gacacctttg   1140

cagctggctt tatgtggctg gataaattgg gcctgtcagc ccgaatggga atagaagtgg   1200

tgatgaggca agtattcttt ggagcaggaa actaccattt agtggatgaa aacttcgatc   1260

ctttacctga ttattggcta tctcttctgt tcaagaaatt ggtgggcacc aaggtgttaa   1320

tggcaagcgt gcaaggttca aagagaagga agcttcgagt ataccttcat tgcacaaaca   1380

ctgacaatcc aaggtataaa gaaggagatt taactctgta tgccataaac ctccataacg   1440

tcaccaagta cttgcggtta ccctatcctt tttctaacaa gcaagtggat aaataccttc   1500

taagaccttt gggacctcat ggattacttt ccaaatctgt ccaactcaat ggtctaactc   1560

taaagatggt ggatgatcaa accttgccac ctttaatgga aaaacctctc cggccaggaa   1620

gttcactggg cttgccagct ttctcatata gtttttttgt gataagaaat gccaaagttg   1680

ctgcttgcat ctgaaaataa aatatactag tcctgacact g                       1721
```

<210> SEQ ID NO 10
<211> LENGTH: 543
<212> TYPE: PRT
<213> ORGANISM: Homo sapiens

<400> SEQUENCE: 10

```
Met Leu Leu Arg Ser Lys Pro Ala Leu Pro Pro Pro Leu Met Leu Leu
1               5                   10                  15

Leu Leu Gly Pro Leu Gly Pro Leu Ser Pro Gly Ala Leu Pro Arg Pro
            20                  25                  30

Ala Gln Ala Gln Asp Val Val Asp Leu Asp Phe Phe Thr Gln Glu Pro
        35                  40                  45

Leu His Leu Val Ser Pro Ser Phe Leu Ser Val Thr Ile Asp Ala Asn
    50                  55                  60

Leu Ala Thr Asp Pro Arg Phe Leu Ile Leu Leu Gly Ser Pro Lys Leu
65                  70                  75                  80

Arg Thr Leu Ala Arg Gly Leu Ser Pro Ala Tyr Leu Arg Phe Gly Gly
                85                  90                  95

Thr Lys Thr Asp Phe Leu Ile Phe Asp Pro Lys Lys Glu Ser Thr Phe
            100                 105                 110

Glu Glu Arg Ser Tyr Trp Gln Ser Gln Val Asn Gln Asp Ile Cys Lys
```

-continued

```
        115                 120                 125

Tyr Gly Ser Ile Pro Pro Asp Val Glu Glu Lys Leu Arg Leu Glu Trp
    130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                165                 170                 175

Ala Asn Cys Ser Gly Leu Asp Leu Ile Phe Gly Leu Asn Ala Leu Leu
            180                 185                 190

Arg Thr Ala Asp Leu Gln Trp Asn Ser Ser Asn Ala Gln Leu Leu Leu
        195                 200                 205

Asp Tyr Cys Ser Ser Lys Gly Tyr Asn Ile Ser Trp Glu Leu Gly Asn
    210                 215                 220

Glu Pro Asn Ser Phe Leu Lys Lys Ala Asp Ile Phe Ile Asn Gly Ser
225                 230                 235                 240

Gln Leu Gly Glu Asp Tyr Ile Gln Leu His Lys Leu Leu Arg Lys Ser
                245                 250                 255

Thr Phe Lys Asn Ala Lys Leu Tyr Gly Pro Asp Val Gly Gln Pro Arg
            260                 265                 270

Arg Lys Thr Ala Lys Met Leu Lys Ser Phe Leu Lys Ala Gly Gly Glu
        275                 280                 285

Val Ile Asp Ser Val Thr Trp His His Tyr Tyr Leu Asn Gly Arg Thr
    290                 295                 300

Ala Thr Arg Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
                325                 330                 335

Lys Lys Val Trp Leu Gly Glu Thr Ser Ser Ala Tyr Gly Gly Gly Ala
            340                 345                 350

Pro Leu Leu Ser Asp Thr Phe Ala Ala Gly Phe Met Trp Leu Asp Lys
        355                 360                 365

Leu Gly Leu Ser Ala Arg Met Gly Ile Glu Val Val Met Arg Gln Val
    370                 375                 380

Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Lys Leu Val Gly Thr
                405                 410                 415

Lys Val Leu Met Ala Ser Val Gln Gly Ser Lys Arg Arg Lys Leu Arg
            420                 425                 430

Val Tyr Leu His Cys Thr Asn Thr Asp Asn Pro Arg Tyr Lys Glu Gly
        435                 440                 445

Asp Leu Thr Leu Tyr Ala Ile Asn Leu His Asn Val Thr Lys Tyr Leu
    450                 455                 460

Arg Leu Pro Tyr Pro Phe Ser Asn Lys Gln Val Asp Lys Tyr Leu Leu
465                 470                 475                 480

Arg Pro Leu Gly Pro His Gly Leu Leu Ser Lys Ser Val Gln Leu Asn
                485                 490                 495

Gly Leu Thr Leu Lys Met Val Asp Asp Gln Thr Leu Pro Pro Leu Met
            500                 505                 510

Glu Lys Pro Leu Arg Pro Gly Ser Ser Leu Gly Leu Pro Ala Phe Ser
        515                 520                 525

Tyr Ser Phe Phe Val Ile Arg Asn Ala Lys Val Ala Ala Cys Ile
    530                 535                 540
```

```
<210> SEQ ID NO 11
<211> LENGTH: 1721
<212> TYPE: DNA
<213> ORGANISM: Homo sapiens
<220> FEATURE:
<221> NAME/KEY: CDS
<222> LOCATION: (63)..(1691)
<223> OTHER INFORMATION:

<400> SEQUENCE: 11

ctagagcttt cgactctccg ctgcgcggca gctggcgggg ggagcagcca ggtgagccca      60

ag atg ctg ctg cgc tcg aag cct gcg ctg ccg ccg ccg ctg atg ctg        107
   Met Leu Leu Arg Ser Lys Pro Ala Leu Pro Pro Pro Leu Met Leu
   1               5                   10                  15

ctg ctc ctg ggg ccg ctg ggt ccc ctc tcc cct ggc gcc ctg ccc cga       155
Leu Leu Leu Gly Pro Leu Gly Pro Leu Ser Pro Gly Ala Leu Pro Arg
                20                  25                  30

cct gcg caa gca cag gac gtc gtg gac ctg gac ttc ttc acc cag gag       203
Pro Ala Gln Ala Gln Asp Val Val Asp Leu Asp Phe Phe Thr Gln Glu
            35                  40                  45

ccg ctg cac ctg gtg agc ccc tcg ttc ctg tcc gtc acc att gac gcc       251
Pro Leu His Leu Val Ser Pro Ser Phe Leu Ser Val Thr Ile Asp Ala
        50                  55                  60

aac ctg gcc acg gac ccg cgg ttc ctc atc ctc ctg ggt tct cca aag       299
Asn Leu Ala Thr Asp Pro Arg Phe Leu Ile Leu Leu Gly Ser Pro Lys
    65                  70                  75

ctt cgt acc ttg gcc aga ggc ttg tct cct gcg tac ctg agg ttt ggt       347
Leu Arg Thr Leu Ala Arg Gly Leu Ser Pro Ala Tyr Leu Arg Phe Gly
80                  85                  90                  95

ggc acc aag aca gac ttc cta att ttc gat ccc aag aag gaa tca acc       395
Gly Thr Lys Thr Asp Phe Leu Ile Phe Asp Pro Lys Lys Glu Ser Thr
                100                 105                 110

ttt gaa gag aga agt tac tgg caa tct caa gtc aac cag gat att tgc       443
Phe Glu Glu Arg Ser Tyr Trp Gln Ser Gln Val Asn Gln Asp Ile Cys
            115                 120                 125

aaa tat gga tcc atc cct cct gat gtg gag gag aag tta cgg ttg gaa       491
Lys Tyr Gly Ser Ile Pro Pro Asp Val Glu Glu Lys Leu Arg Leu Glu
        130                 135                 140

tgg ccc tac cag gag caa ttg cta ctc cga gaa cac tac cag aaa aag       539
Trp Pro Tyr Gln Glu Gln Leu Leu Leu Arg Glu His Tyr Gln Lys Lys
    145                 150                 155

ttc aag aac agc acc tac tca aga agc tct gta gat gtg cta tac act       587
Phe Lys Asn Ser Thr Tyr Ser Arg Ser Ser Val Asp Val Leu Tyr Thr
160                 165                 170                 175

ttt gca aac tgc tca gga ctg gac ttg atc ttt ggc cta aat gcg tta       635
Phe Ala Asn Cys Ser Gly Leu Asp Leu Ile Phe Gly Leu Asn Ala Leu
                180                 185                 190

tta aga aca gca gat ttg cag tgg aac agt tct aat gct cag ttg ctc       683
Leu Arg Thr Ala Asp Leu Gln Trp Asn Ser Ser Asn Ala Gln Leu Leu
            195                 200                 205

ctg gac tac tgc tct tcc aag ggg tat aac att tct tgg gaa cta ggc       731
Leu Asp Tyr Cys Ser Ser Lys Gly Tyr Asn Ile Ser Trp Glu Leu Gly
        210                 215                 220

aat gaa cct aac agt ttc ctt aag aag gct gat att ttc atc aat ggg       779
Asn Glu Pro Asn Ser Phe Leu Lys Lys Ala Asp Ile Phe Ile Asn Gly
    225                 230                 235

tcg cag tta gga gaa gat tat att caa ttg cat aaa ctt cta aga aag       827
Ser Gln Leu Gly Glu Asp Tyr Ile Gln Leu His Lys Leu Leu Arg Lys
240                 245                 250                 255
```

-continued

```
tcc acc ttc aaa aat gca aaa ctc tat ggt cct gat gtt ggt cag cct      875
Ser Thr Phe Lys Asn Ala Lys Leu Tyr Gly Pro Asp Val Gly Gln Pro
                260                 265                 270

cga aga aag acg gct aag atg ctg aag agc ttc ctg aag gct ggt gga      923
Arg Arg Lys Thr Ala Lys Met Leu Lys Ser Phe Leu Lys Ala Gly Gly
            275                 280                 285

gaa gtg att gat tca gtt aca tgg cat cac tac tat ttg aat gga cgg      971
Glu Val Ile Asp Ser Val Thr Trp His His Tyr Tyr Leu Asn Gly Arg
        290                 295                 300

act gct acc agg gaa gat ttt cta aac cct gat gta ttg gac att ttt     1019
Thr Ala Thr Arg Glu Asp Phe Leu Asn Pro Asp Val Leu Asp Ile Phe
    305                 310                 315

att tca tct gtg caa aaa gtt ttc cag gtg gtt gag agc acc agg cct     1067
Ile Ser Ser Val Gln Lys Val Phe Gln Val Val Glu Ser Thr Arg Pro
320                 325                 330                 335

ggc aag aag gtc tgg tta gga gaa aca agc tct gca tat gga ggc gga     1115
Gly Lys Lys Val Trp Leu Gly Glu Thr Ser Ser Ala Tyr Gly Gly Gly
                340                 345                 350

gcg ccc ttg cta tcc gac acc ttt gca gct ggc ttt atg tgg ctg gat     1163
Ala Pro Leu Leu Ser Asp Thr Phe Ala Ala Gly Phe Met Trp Leu Asp
            355                 360                 365

aaa ttg ggc ctg tca gcc cga atg gga ata gaa gtg gtg atg agg caa     1211
Lys Leu Gly Leu Ser Ala Arg Met Gly Ile Glu Val Val Met Arg Gln
        370                 375                 380

gta ttc ttt gga gca gga aac tac cat tta gtg gat gaa aac ttc gat     1259
Val Phe Phe Gly Ala Gly Asn Tyr His Leu Val Asp Glu Asn Phe Asp
    385                 390                 395

cct tta cct gat tat tgg cta tct ctt ctg ttc aag aaa ttg gtg ggc     1307
Pro Leu Pro Asp Tyr Trp Leu Ser Leu Leu Phe Lys Lys Leu Val Gly
400                 405                 410                 415

acc aag gtg tta atg gca agc gtg caa ggt tca aag aga agg aag ctt     1355
Thr Lys Val Leu Met Ala Ser Val Gln Gly Ser Lys Arg Arg Lys Leu
                420                 425                 430

cga gta tac ctt cat tgc aca aac act gac aat cca agg tat aaa gaa     1403
Arg Val Tyr Leu His Cys Thr Asn Thr Asp Asn Pro Arg Tyr Lys Glu
            435                 440                 445

gga gat tta act ctg tat gcc ata aac ctc cat aac gtc acc aag tac     1451
Gly Asp Leu Thr Leu Tyr Ala Ile Asn Leu His Asn Val Thr Lys Tyr
        450                 455                 460

ttg cgg tta ccc tat cct ttt tct aac aag caa gtg gat aaa tac ctt     1499
Leu Arg Leu Pro Tyr Pro Phe Ser Asn Lys Gln Val Asp Lys Tyr Leu
    465                 470                 475

cta aga cct ttg gga cct cat gga tta ctt tcc aaa tct gtc caa ctc     1547
Leu Arg Pro Leu Gly Pro His Gly Leu Leu Ser Lys Ser Val Gln Leu
480                 485                 490                 495

aat ggt cta act cta aag atg gtg gat gat caa acc ttg cca cct tta     1595
Asn Gly Leu Thr Leu Lys Met Val Asp Asp Gln Thr Leu Pro Pro Leu
                500                 505                 510

atg gaa aaa cct ctc cgg cca gga agt tca ctg ggc ttg cca gct ttc     1643
Met Glu Lys Pro Leu Arg Pro Gly Ser Ser Leu Gly Leu Pro Ala Phe
            515                 520                 525

tca tat agt ttt ttt gtg ata aga aat gcc aaa gtt gct gct tgc atc     1691
Ser Tyr Ser Phe Phe Val Ile Arg Asn Ala Lys Val Ala Ala Cys Ile
        530                 535                 540

tgaaaataaa atatactagt cctgacactg                                    1721


<210> SEQ ID NO 12
<211> LENGTH: 824
<212> TYPE: DNA
<213> ORGANISM: Mus musculus
```

-continued

<400> SEQUENCE: 12

```
ctggcaagaa ggtctggttg ggagagacga gctcagctta cggtggcggt gcacccttgc     60
tgtccaacac ctttgcagct ggctttatgt ggctggataa attgggcctg tcagcccaga    120
tgggcataga agtcgtgatg aggcaggtgt tcttcggagc aggcaactac cacttagtgg    180
atgaaaactt tgagccttta cctgattact ggctctctct tctgttcaag aaactggtag    240
gtcccagggt gttactgtca agagtgaaag gcccagacag gagcaaactc cgagtgtatc    300
tccactgcac taacgtctat cacccacgat atcaggaagg agatctaact ctgtatgtcc    360
tgaacctcca taatgtcacc aagcacttga aggtaccgcc tccgttgttc aggaaaccag    420
tggatacgta ccttctgaag ccttcggggc cggatggatt actttccaaa tctgtccaac    480
tgaacggtca aattctgaag atggtggatg agcagaccct gccagctttg acagaaaaac    540
ctctccccgc aggaagtgca ctaagcctgc ctgccttttc ctatggtttt tttgtcataa    600
gaaatgccaa aatcgctgct tgtatatgaa aataaaaggc atacggtacc cctgagacaa    660
aagccgaggg gggtgttatt cataaaacaa aaccctagtt taggaggcca cctccttgcc    720
gagttccaga gcttcgggag ggtggggtac acttcagtat tacattcagt gtggtgttct    780
ctctaagaag aatactgcag gtggtgacag ttaatagcac tgtg                      824
```

<210> SEQ ID NO 13
<211> LENGTH: 1899
<212> TYPE: DNA
<213> ORGANISM: Homo sapiens

<400> SEQUENCE: 13

```
gggaaagcga gcaaggaagt aggagagagc cgggcaggcg gggcggggtt ggattgggag     60
cagtgggagg gatgcagaag aggagtggga gggatggagg gcgcagtggg aggggtgagg    120
aggcgtaacg gggcggagga aaggagaaaa gggcgctggg gctcggcggg aggaagtgct    180
agagctctcg actctccgct gcgcggcagc tggcgggggg agcagccagg tgagcccaag    240
atgctgctgc gctcgaagcc tgcgctgccg ccgccgctga tgctgctgct cctggggccg    300
ctgggtcccc tctcccctgg cgccctgccc cgacctgcgc aagcacagga cgtcgtggac    360
ctggacttct tcacccagga gccgctgcac ctggtgagcc cctcgttcct gtccgtcacc    420
attgacgcca acctggccac ggacccgcgg ttcctcatcc tcctgggttc tccaaagctt    480
cgtaccttgg ccagaggctt gtctcctgcg tacctgaggt ttggtggcac caagacagac    540
ttcctaattt tcgatcccaa gaaggaatca acctttgaag agagaagtta ctggcaatct    600
caagtcaacc aggatatttg caaatatgga tccatccctc ctgatgtgga ggagaagtta    660
cggttggaat ggccctacca ggagcaattg ctactccgag aacactacca gaaaaagttc    720
aagaacagca cctactcaag aagctctgta gatgtgctat acacttttgc aaactgctca    780
ggactggact tgatctttgg cctaaatgcg ttattaagaa cagcagattt gcagtggaac    840
agttctaatg ctcagttgct cctggactac tgctcttcca aggggtataa catttcttgg    900
gaactaggca atgaacctaa cagtttcctt aagaaggctg atattttcat caatgggtcg    960
cagttaggag aagattatat tcaattgcat aaacttctaa gaaagtccac cttcaaaaat   1020
gcaaaactct atggtcctga tgttggtcag cctcgaagaa agacggctaa gatgctgaag   1080
agcttcctga aggctggtgg agaagtgatt gattcagtta catggcatca ctactatttg   1140
aatggacgga ctgctaccag ggaagatttt ctaaaccctg atgtattgga catttttatt   1200
```

-continued

```
tcatctgtgc aaaaagtttt ccaggtggtt gagagcacca ggcctggcaa gaaggtctgg   1260

ttaggagaaa caagctctgc atatggaggc ggagcgccct tgctatccga cacctttgca   1320

gctggcttta tgtggctgga taaattgggc ctgtcagccc gaatgggaat agaagtggtg   1380

atgaggcaag tattctttgg agcaggaaac taccatttag tggatgaaaa cttcgatcct   1440

ttacctgatt attggctatc tcttctgttc aagaaattgg tgggcaccaa ggtgttaatg   1500

gcaagcgtgc aaggttcaaa gagaaggaag cttcgagtat accttcattg cacaaacact   1560

gacaatccaa ggtataaaga aggagattta actctgtatg ccataaacct ccataacgtc   1620

accaagtact tgcggttacc ctatcctttt tctaacaagc aagtggataa ataccttcta   1680

agacctttgg gacctcatgg attactttcc aaatctgtcc aactcaatgg tctaactcta   1740

aagatggtgg atgatcaaac cttgccacct ttaatggaaa aacctctccg gccaggaagt   1800

tcactgggct tgccagcttt ctcatatagt ttttttgtga taagaaatgc caaagttgct   1860

gcttgcatct gaaaataaaa tatactagtc ctgacactg                          1899


<210> SEQ ID NO 14
<211> LENGTH: 592
<212> TYPE: PRT
<213> ORGANISM: Homo sapiens

<400> SEQUENCE: 14

Met Glu Gly Ala Val Gly Gly Val Arg Arg Arg Asn Gly Ala Glu Glu
1               5                   10                  15

Arg Arg Lys Gly Arg Trp Gly Ser Ala Gly Gly Ser Ala Arg Ala Leu
            20                  25                  30

Asp Ser Pro Leu Arg Gly Ser Trp Arg Gly Glu Gln Pro Gly Glu Pro
        35                  40                  45

Lys Met Leu Leu Arg Ser Lys Pro Ala Leu Pro Pro Pro Leu Met Leu
    50                  55                  60

Leu Leu Leu Gly Pro Leu Gly Pro Leu Ser Pro Gly Ala Leu Pro Arg
65                  70                  75                  80

Pro Ala Gln Ala Gln Asp Val Val Asp Leu Asp Phe Phe Thr Gln Glu
                85                  90                  95

Pro Leu His Leu Val Ser Pro Ser Phe Leu Ser Val Thr Ile Asp Ala
            100                 105                 110

Asn Leu Ala Thr Asp Pro Arg Phe Leu Ile Leu Leu Gly Ser Pro Lys
        115                 120                 125

Leu Arg Thr Leu Ala Arg Gly Leu Ser Pro Ala Tyr Leu Arg Phe Gly
    130                 135                 140

Gly Thr Lys Thr Asp Phe Leu Ile Phe Asp Pro Lys Lys Glu Ser Thr
145                 150                 155                 160

Phe Glu Glu Arg Ser Tyr Trp Gln Ser Gln Val Asn Gln Asp Ile Cys
                165                 170                 175

Lys Tyr Gly Ser Ile Pro Pro Asp Val Glu Glu Lys Leu Arg Leu Glu
            180                 185                 190

Trp Pro Tyr Gln Glu Gln Leu Leu Leu Arg Glu His Tyr Gln Lys Lys
        195                 200                 205

Phe Lys Asn Ser Thr Tyr Ser Arg Ser Ser Val Asp Val Leu Tyr Thr
    210                 215                 220

Phe Ala Asn Cys Ser Gly Leu Asp Leu Ile Phe Gly Leu Asn Ala Leu
225                 230                 235                 240

Leu Arg Thr Ala Asp Leu Gln Trp Asn Ser Ser Asn Ala Gln Leu Leu
                245                 250                 255
```

-continued

```
Leu Asp Tyr Cys Ser Ser Lys Gly Tyr Asn Ile Ser Trp Glu Leu Gly
            260                 265                 270

Asn Glu Pro Asn Ser Phe Leu Lys Lys Ala Asp Ile Phe Ile Asn Gly
        275                 280                 285

Ser Gln Leu Gly Glu Asp Tyr Ile Gln Leu His Lys Leu Leu Arg Lys
    290                 295                 300

Ser Thr Phe Lys Asn Ala Lys Leu Tyr Gly Pro Asp Val Gly Gln Pro
305                 310                 315                 320

Arg Arg Lys Thr Ala Lys Met Leu Lys Ser Phe Leu Lys Ala Gly Gly
                325                 330                 335

Glu Val Ile Asp Ser Val Thr Trp His His Tyr Tyr Leu Asn Gly Arg
            340                 345                 350

Thr Ala Thr Arg Glu Asp Phe Leu Asn Pro Asp Val Leu Asp Ile Phe
        355                 360                 365

Ile Ser Ser Val Gln Lys Val Phe Gln Val Val Glu Ser Thr Arg Pro
    370                 375                 380

Gly Lys Lys Val Trp Leu Gly Glu Thr Ser Ser Ala Tyr Gly Gly Gly
385                 390                 395                 400

Ala Pro Leu Leu Ser Asp Thr Phe Ala Ala Gly Phe Met Trp Leu Asp
                405                 410                 415

Lys Leu Gly Leu Ser Ala Arg Met Gly Ile Glu Val Val Met Arg Gln
            420                 425                 430

Val Phe Phe Gly Ala Gly Asn Tyr His Leu Val Asp Glu Asn Phe Asp
        435                 440                 445

Pro Leu Pro Asp Tyr Trp Leu Ser Leu Leu Phe Lys Lys Leu Val Gly
    450                 455                 460

Thr Lys Val Leu Met Ala Ser Val Gln Gly Ser Lys Arg Arg Lys Leu
465                 470                 475                 480

Arg Val Tyr Leu His Cys Thr Asn Thr Asp Asn Pro Arg Tyr Lys Glu
                485                 490                 495

Gly Asp Leu Thr Leu Tyr Ala Ile Asn Leu His Asn Val Thr Lys Tyr
            500                 505                 510

Leu Arg Leu Pro Tyr Pro Phe Ser Asn Lys Gln Val Asp Lys Tyr Leu
        515                 520                 525

Leu Arg Pro Leu Gly Pro His Gly Leu Leu Ser Lys Ser Val Gln Leu
    530                 535                 540

Asn Gly Leu Thr Leu Lys Met Val Asp Asp Gln Thr Leu Pro Pro Leu
545                 550                 555                 560

Met Glu Lys Pro Leu Arg Pro Gly Ser Ser Leu Gly Leu Pro Ala Phe
                565                 570                 575

Ser Tyr Ser Phe Phe Val Ile Arg Asn Ala Lys Val Ala Ala Cys Ile
            580                 585                 590
```

<210> SEQ ID NO 15
<211> LENGTH: 1899
<212> TYPE: DNA
<213> ORGANISM: Homo sapiens
<220> FEATURE:
<221> NAME/KEY: CDS
<222> LOCATION: (94)..(1869)
<223> OTHER INFORMATION:

<400> SEQUENCE: 15

```
gggaaagcga gcaaggaagt aggagagagc cgggcaggcg gggcggggtt ggattgggag     60

cagtgggagg gatgcagaag aggagtggga ggg atg gag ggc gca gtg gga ggg     114
```

-continued

```
                                   Met Glu Gly Ala Val Gly Gly
                                   1               5

gtg agg agg cgt aac ggg gcg gag gaa agg aga aaa ggg cgc tgg ggc       162
Val Arg Arg Arg Asn Gly Ala Glu Glu Arg Arg Lys Gly Arg Trp Gly
        10                  15                  20

tcg gcg gga gga agt gct aga gct ctc gac tct ccg ctg cgc ggc agc       210
Ser Ala Gly Gly Ser Ala Arg Ala Leu Asp Ser Pro Leu Arg Gly Ser
    25                  30                  35

tgg cgg ggg gag cag cca ggt gag ccc aag atg ctg ctg cgc tcg aag       258
Trp Arg Gly Glu Gln Pro Gly Glu Pro Lys Met Leu Leu Arg Ser Lys
40                  45                  50                  55

cct gcg ctg ccg ccg ccg ctg atg ctg ctg ctc ctg ggg ccg ctg ggt       306
Pro Ala Leu Pro Pro Pro Leu Met Leu Leu Leu Leu Gly Pro Leu Gly
                60                  65                  70

ccc ctc tcc cct ggc gcc ctg ccc cga cct gcg caa gca cag gac gtc       354
Pro Leu Ser Pro Gly Ala Leu Pro Arg Pro Ala Gln Ala Gln Asp Val
            75                  80                  85

gtg gac ctg gac ttc ttc acc cag gag ccg ctg cac ctg gtg agc ccc       402
Val Asp Leu Asp Phe Phe Thr Gln Glu Pro Leu His Leu Val Ser Pro
        90                  95                  100

tcg ttc ctg tcc gtc acc att gac gcc aac ctg gcc acg gac ccg cgg       450
Ser Phe Leu Ser Val Thr Ile Asp Ala Asn Leu Ala Thr Asp Pro Arg
    105                 110                 115

ttc ctc atc ctc ctg ggt tct cca aag ctt cgt acc ttg gcc aga ggc       498
Phe Leu Ile Leu Leu Gly Ser Pro Lys Leu Arg Thr Leu Ala Arg Gly
120                 125                 130                 135

ttg tct cct gcg tac ctg agg ttt ggt ggc acc aag aca gac ttc cta       546
Leu Ser Pro Ala Tyr Leu Arg Phe Gly Gly Thr Lys Thr Asp Phe Leu
                140                 145                 150

att ttc gat ccc aag aag gaa tca acc ttt gaa gag aga agt tac tgg       594
Ile Phe Asp Pro Lys Lys Glu Ser Thr Phe Glu Glu Arg Ser Tyr Trp
            155                 160                 165

caa tct caa gtc aac cag gat att tgc aaa tat gga tcc atc cct cct       642
Gln Ser Gln Val Asn Gln Asp Ile Cys Lys Tyr Gly Ser Ile Pro Pro
        170                 175                 180

gat gtg gag gag aag tta cgg ttg gaa tgg ccc tac cag gag caa ttg       690
Asp Val Glu Glu Lys Leu Arg Leu Glu Trp Pro Tyr Gln Glu Gln Leu
    185                 190                 195

cta ctc cga gaa cac tac cag aaa aag ttc aag aac agc acc tac tca       738
Leu Leu Arg Glu His Tyr Gln Lys Lys Phe Lys Asn Ser Thr Tyr Ser
200                 205                 210                 215

aga agc tct gta gat gtg cta tac act ttt gca aac tgc tca gga ctg       786
Arg Ser Ser Val Asp Val Leu Tyr Thr Phe Ala Asn Cys Ser Gly Leu
                220                 225                 230

gac ttg atc ttt ggc cta aat gcg tta tta aga aca gca gat ttg cag       834
Asp Leu Ile Phe Gly Leu Asn Ala Leu Leu Arg Thr Ala Asp Leu Gln
            235                 240                 245

tgg aac agt tct aat gct cag ttg ctc ctg gac tac tgc tct tcc aag       882
Trp Asn Ser Ser Asn Ala Gln Leu Leu Leu Asp Tyr Cys Ser Ser Lys
        250                 255                 260

ggg tat aac att tct tgg gaa cta ggc aat gaa cct aac agt ttc ctt       930
Gly Tyr Asn Ile Ser Trp Glu Leu Gly Asn Glu Pro Asn Ser Phe Leu
    265                 270                 275

aag aag gct gat att ttc atc aat ggg tcg cag tta gga gaa gat tat       978
Lys Lys Ala Asp Ile Phe Ile Asn Gly Ser Gln Leu Gly Glu Asp Tyr
280                 285                 290                 295

att caa ttg cat aaa ctt cta aga aag tcc acc ttc aaa aat gca aaa      1026
Ile Gln Leu His Lys Leu Leu Arg Lys Ser Thr Phe Lys Asn Ala Lys
                300                 305                 310
```

-continued

```
ctc tat ggt cct gat gtt ggt cag cct cga aga aag acg gct aag atg      1074
Leu Tyr Gly Pro Asp Val Gly Gln Pro Arg Arg Lys Thr Ala Lys Met
            315                 320                 325

ctg aag agc ttc ctg aag gct ggt gga gaa gtg att gat tca gtt aca      1122
Leu Lys Ser Phe Leu Lys Ala Gly Gly Glu Val Ile Asp Ser Val Thr
        330                 335                 340

tgg cat cac tac tat ttg aat gga cgg act gct acc agg gaa gat ttt      1170
Trp His His Tyr Tyr Leu Asn Gly Arg Thr Ala Thr Arg Glu Asp Phe
    345                 350                 355

cta aac cct gat gta ttg gac att ttt att tca tct gtg caa aaa gtt      1218
Leu Asn Pro Asp Val Leu Asp Ile Phe Ile Ser Ser Val Gln Lys Val
360                 365                 370                 375

ttc cag gtg gtt gag agc acc agg cct ggc aag aag gtc tgg tta gga      1266
Phe Gln Val Val Glu Ser Thr Arg Pro Gly Lys Lys Val Trp Leu Gly
                380                 385                 390

gaa aca agc tct gca tat gga ggc gga gcg ccc ttg cta tcc gac acc      1314
Glu Thr Ser Ser Ala Tyr Gly Gly Gly Ala Pro Leu Leu Ser Asp Thr
            395                 400                 405

ttt gca gct ggc ttt atg tgg ctg gat aaa ttg ggc ctg tca gcc cga      1362
Phe Ala Ala Gly Phe Met Trp Leu Asp Lys Leu Gly Leu Ser Ala Arg
        410                 415                 420

atg gga ata gaa gtg gtg atg agg caa gta ttc ttt gga gca gga aac      1410
Met Gly Ile Glu Val Val Met Arg Gln Val Phe Phe Gly Ala Gly Asn
    425                 430                 435

tac cat tta gtg gat gaa aac ttc gat cct tta cct gat tat tgg cta      1458
Tyr His Leu Val Asp Glu Asn Phe Asp Pro Leu Pro Asp Tyr Trp Leu
440                 445                 450                 455

tct ctt ctg ttc aag aaa ttg gtg ggc acc aag gtg tta atg gca agc      1506
Ser Leu Leu Phe Lys Lys Leu Val Gly Thr Lys Val Leu Met Ala Ser
                460                 465                 470

gtg caa ggt tca aag aga agg aag ctt cga gta tac ctt cat tgc aca      1554
Val Gln Gly Ser Lys Arg Arg Lys Leu Arg Val Tyr Leu His Cys Thr
            475                 480                 485

aac act gac aat cca agg tat aaa gaa gga gat tta act ctg tat gcc      1602
Asn Thr Asp Asn Pro Arg Tyr Lys Glu Gly Asp Leu Thr Leu Tyr Ala
        490                 495                 500

ata aac ctc cat aac gtc acc aag tac ttg cgg tta ccc tat cct ttt      1650
Ile Asn Leu His Asn Val Thr Lys Tyr Leu Arg Leu Pro Tyr Pro Phe
    505                 510                 515

tct aac aag caa gtg gat aaa tac ctt cta aga cct ttg gga cct cat      1698
Ser Asn Lys Gln Val Asp Lys Tyr Leu Leu Arg Pro Leu Gly Pro His
520                 525                 530                 535

gga tta ctt tcc aaa tct gtc caa ctc aat ggt cta act cta aag atg      1746
Gly Leu Leu Ser Lys Ser Val Gln Leu Asn Gly Leu Thr Leu Lys Met
                540                 545                 550

gtg gat gat caa acc ttg cca cct tta atg gaa aaa cct ctc cgg cca      1794
Val Asp Asp Gln Thr Leu Pro Pro Leu Met Glu Lys Pro Leu Arg Pro
            555                 560                 565

gga agt tca ctg ggc ttg cca gct ttc tca tat agt ttt ttt gtg ata      1842
Gly Ser Ser Leu Gly Leu Pro Ala Phe Ser Tyr Ser Phe Phe Val Ile
        570                 575                 580

aga aat gcc aaa gtt gct gct tgc atc tgaaaataaa atatactagt           1889
Arg Asn Ala Lys Val Ala Ala Cys Ile
    585                 590

cctgacactg                                                           1899


<210> SEQ ID NO 16
<211> LENGTH: 594
<212> TYPE: DNA
<213> ORGANISM: Homo sapiens
```

-continued

<400> SEQUENCE: 16

```
attactatag ggcacgcgtg gtcgacggcc cgggctggta ttgtcttaat gagaagttga     60
taaagaattt tgggtggttg atctctttcc agctgcagtt tagcgtatgc tgaggccaga    120
ttttttcagg caaaagtaaa atacctgaga aactgcctgg ccagaggaca atcagatttt    180
ggctggctca agtgacaagc aagtgtttat aagctagatg ggagaggaag ggatgaatac    240
tccattggag gctttactcg agggtcagag ggatacccgg cgccatcaga atgggatctg    300
ggagtcggaa acgctgggtt cccacgagag cgcgcagaac acgtgcgtca ggaagcctgg    360
tccgggatgc ccagcgctgc tccccgggcg ctcctccccg ggcgctcctc cccaggcctc    420
ccgggcgctt ggatcccggc catctccgca cccttcaagt gggtgtgggt gatttcgtaa    480
gtgaacgtga ccgccaccgg ggggaaagcg agcaaggaag taggagagag ccgggcaggc    540
ggggcggggt tggattggga gcagtgggag ggatgcagaa gaggagtggg aggg          594
```

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17

```
ccccaggagc agcagcatca g                                               21
```

<210> SEQ ID NO 18
<211> LENGTH: 21
<212> TYPE: PRT
<213> ORGANISM: Artificial sequence
<220> FEATURE:
<223> OTHER INFORMATION: Synthetic oligonucleotide

<400> SEQUENCE: 18

```
Ala Gly Gly Cys Thr Thr Cys Gly Ala Gly Cys Gly Cys Ala Gly Cys
1               5                   10                  15

Ala Gly Cys Ala Thr
            20
```

<210> SEQ ID NO 19
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 19

```
gtaatacgac tcactatagg gc                                              22
```

<210> SEQ ID NO 20
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 20

```
actatagggc acgcgtggt                                                  19
```

<210> SEQ ID NO 21
<211> LENGTH: 21
<212> TYPE: DNA

-continued

<213> ORGANISM: Artificial sequence
<220> FEATURE:
<223> OTHER INFORMATION: Synthetic oligonucleotide

<400> SEQUENCE: 21
cttgggctca cctggctgct c 21

<210> SEQ ID NO 22
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 22
agctctgtag atgtgctata cac 23

<210> SEQ ID NO 23
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 23
gcatcttagc cgtctttctt cg 22

<210> SEQ ID NO 24
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 24
gagcagccag gtgagcccaa gat 23

<210> SEQ ID NO 25
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 25
ttcgatccca agaaggaatc aac 23

<210> SEQ ID NO 26
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 26
agctctgtag atgtgctata cac 23

<210> SEQ ID NO 27
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 27
tcagatgcaa gcagcaactt tggc 24

-continued

<210> SEQ ID NO 28
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 28
gcatcttagc cgtctttctt cg 22

<210> SEQ ID NO 29
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 29
gtagtgatgc catgtaactg aatc 24

<210> SEQ ID NO 30
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 30
aggcacccta gagatgttcc ag 22

<210> SEQ ID NO 31
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 31
gaagatttct gtttccatga cgtg 24

<210> SEQ ID NO 32
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 32
ccacactgaa tgtaatactg aagtg 25

<210> SEQ ID NO 33
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 33
cgaagctctg gaactcggca ag 22

<210> SEQ ID NO 34
<211> LENGTH: 22
<212> TYPE: DNA
<213> ORGANISM: Artificial sequence
<220> FEATURE:

-continued

<223> OTHER INFORMATION: Synthetic oligonucleotide

<400> SEQUENCE: 34
gccagctgca aaggtgttgg ac 22

<210> SEQ ID NO 35
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 35
aacacctgcc tcatcacgac ttc 23

<210> SEQ ID NO 36
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 36
gccaggctgg cgtcgatggt ga 22

<210> SEQ ID NO 37
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 37
gtcgatggtg atggacagga ac 22

<210> SEQ ID NO 38
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 38
gtaatacgac tcactatagg gc 22

<210> SEQ ID NO 39
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 39
actatagggc acgcgtggt 19

<210> SEQ ID NO 40
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 40
ccatcctaat acgactcact atagggc 27

-continued

<210> SEQ ID NO 41
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 41
actcactata gggctcgagc ggc 23

<210> SEQ ID NO 42
<211> LENGTH: 44848
<212> TYPE: DNA
<213> ORGANISM: Homo sapiens

<400> SEQUENCE: 42
ggatcttggc tcactgcaat ctctgcctcc catgcaattc ttatgcatca gcctcctgag 60
tagcttggat tataggtctg cgccaccact cctggctaca ccatgttgcc caggctggtc 120
ttgaactctt gggctctagt gatccacccg ccttggcctc ccaaagtgct gggattacag 180
gtgtgagcca tcacacccgg ccccccgttt ccatattagt aactcacatg tagaccacaa 240
ggatgcacta tttagaaaac ttgcaatggt ccacttttca aatcacccaa acatgttaaa 300
gaaattggta tgactgggca tggcacagtg gctcatgcct gcaatcctag cattttgtga 360
ggctgagacg ggcagatcac gaggtcagga gattgagacc atcctgacag acatggtgaa 420
atcccatctc tactaaaaat acaaaacaat tagccggggg tgatggcagg cccctgtagt 480
cccagctact cgggaggctg aggcaggaga atggcgtgaa tccaggaggc agagcttgca 540
gtgagccgag atggtgccac tgcactccag cctgggcgac agagcgagac tccgtctcaa 600
aaaaaaaaaa aaagaaagaa attggtatga ctgttgactc acaacaggag tcaggggcat 660
ggggtggggt gtaagattaa tgtcatgaca aatgtggaaa agaaacttct gtttttccaa 720
ctccacgtct gctaccatat tattacactc ttctggtagt gtggtgttta tgtgtgaatt 780
ttttttcata tgtatacagt aattgtagga tatgaacctg attctagttg caaaactcac 840
tatgagctta gcttttaagt tgcttaagaa taggtagatc tatgcaaata atgataatta 900
ttattattat tttaagagag ggtctcactt tgtcacccag gctggagtgc agtggtgtga 960
ttaagggtca ctgcaacctc cacctcccag gctcaaataa acctcccacc tcagcctccc 1020
cagtagctgg aaccacaggc acgggccacc acgcctggct aattttttgt atttttttgta 1080 gagatggggt ttcatcatgt tgcccaggct gttcttgaat tcctcggctc aagcaatcct 1140
cccaccttgg cctcccaaaa tgctggcatc acaggcatga tggcatcact ggcatcacat 1200
accatgcctg gcctgattta tgcaaattag atatgcattt caaaataatc tatttttatt 1260
tgttgcctta ttggtggtac aatctcaagt ggaaaaatct aagggttttg gtgttatttg 1320
cttactcaac caatatttat tagactctta ctaagcacca acatgatcac atgcctgagc 1380
tatggctagc atagcgtgtg agacaaactt aatctctgtt ttggtggagc atataatcta 1440
gtagatgaag ccaatgttga gcaacatcac aatactaaca aattgaggat gctacgagag 1500
tgtctaacaa attgaggatg ctacgagagt gtctaacaaa ttgaggatgc tatgagagtg 1560
tgtcatggag agctgcctgg agattgagag aaagcttcct tgagggaagt tacatttcag 1620
ctgaaacaca ctgccatctg ctcgaggttt tgtaactgca ttcacatccc gattctgaca 1680
cttcacatcc cgattctgac acttcaccca gttactgtct cagagcttgg gtccgcatgt 1740
gtaaaacaag gacagtatgc acttggcagg gttgtgagaa gggaagagaa cacaagtaaa 1800

-continued

```
gcacctgtat caggcataca gtaggcacta agcgtgcgat gcttgctatg attatacatc   1860
agtgtaagca tcaaggaaaa gctgaagaaa agtctgacca acagcgaaag ataaatgcgc   1920
agaggagaaa tttggcaaag gctccaaatt caggggcagt ccgtactcta cactttgtat   1980
gggggcttca ggtcctgagt tccagacatt ggagcaacta accctttaag attgctaaat   2040
attgtcttaa tgagaagttg ataaagaatt tgggtggtt gatctctttc cagctgcagt   2100
ttagcgtatg ctgaggccag attttttcaa gcaaaagtaa aatacctgag aaactgcctg   2160
gccagaggac aatcagattt tggctggctc aagtgacaag caagtgttta taagctagat   2220
gggagaggaa gggatgaata ctccattgga ggttttactc gagggtcaga gggataccg    2280
gcgccatcag aatgggatct gggagtcgga aacgctgggt tcccacgaga gcgcgcagaa   2340
cacgtgcgtc aggaagcctg gtccgggatg cccagcgctg ctccccgggc gctcctcccc   2400
gggcgctcct ccccaggcct cccgggcgct tggatcccgg ccatctccgc acccttcaag   2460
tgggtgtggg tgatttcgta agtgaacgtg accgccaccg aggggaaagc gagcaaggaa   2520
gtaggagaga gccgggcagg cggggcgggg ttggattggg agcagtggga gggatgcaga   2580
agaggagtgg gagggatgga gggcgcagtg ggaggggtga ggaggcgtaa cggggcggag   2640
gaaaggagaa aagggcgctg gggctcggcg ggaggaagtg ctagagctct cgactctccg   2700
ctgcgcggca gctggcgggg ggagcagcca ggtgagccca agatgctgct gcgctcgaag   2760
cctgcgctgc cgccgccgct gatgctgctg ctcctggggc cgctgggtcc cctctcccct   2820
ggcgccctgc cccgacctgc gcaagcacag gacgtcgtgg acctggactt cttcacccag   2880
gagccgctgc acctggtgag cccctcgttc ctgtccgtca ccattgacgc caacctggcc   2940
acggacccgc ggttcctcat cctcctgggg taagcgccag cctcctggtc ctgtcccctt   3000
tcctgtcctc ctgacaccta tgtctgcccc gccagcggct ctccttcttt tgcgcggaaa   3060
caacttcaca ccggaacctc cccgcctgtc tctccccacc ccacttcccg cctctcattc   3120
tccctctccc tcccttactc tcagacccca aaccgctttt tggggggtat catttaaaaa   3180
atagatttag gggttacaag tgcagttctg ttccatgggt atattgcatt gtggtggcat   3240
ctgggctctt agtgtaactg tcacccgaat gttgtacatt gtatctaata ggtaatttct   3300
catccctcat ccctctccca ccctcccacc ttttggagtc tccagtgtct actattccac   3360
taagtccatg tgtacacatt gtttagcgcc cactctaaat gagccttttt gtttcattca   3420
ttctgtaagt gttgaatagg caccacctaa ggtcaggtat aagtggaaat ttgaaaaaga   3480
aactgcccac ttgccccagt acttccctag ccaagaggag ggaaaccagg caggtgcacc   3540
tgaaggcctg tgagtgcttg atttgctgtg cagtgtagga caagtaagat tgtgcatagc   3600
cttctgtatt taagactgtg ttaggaagat ttctctttct tttcttttct ttttcttttt   3660
tcttttcttt ttttttttta ggcagatgaa aagggcgtca cagaacagga ataaaaatct   3720
aaatattcaa taaatgagac ctaggagact actgcagtga cttacaaagt cctaataaaa   3780
agatgtctct ccaaaatggg gctgcaaaat gtggtgctgc cttatcagct ctaagttttt   3840
tccttacctg agaaagaagg aacctgatgc aggttcaggg ctcctgcccc atgaatgcag   3900
gctgactcca agatggggag ctacagggac aatcccaggt cttctaggcc tcttatttag   3960
gccctgggag cctccagaga tggccacatc ttgaccagcc cagatagagg gaaagatcac   4020
cattatctca cctctgtgtc aaatacctag atgctgtcct ccctgagccc acactatagt   4080
tgccagcgct aatttaatgg gtagtgtact ggttaagaga tggacagacc atcctggctt   4140
gactctcagc tctggcaaag atgagtgact tggtttttcc atatctcttg gccacaccaa   4200
```

-continued

```
ccttgatttc ttcagctgta gaatggaatt tctcaagctt gcctcaagga ttattgcccg   4260
aggatttgat gatatggtaa gagcttctca gtgtttgacc catagtaagt gtttgacgtt   4320
tcaaacgaat tgtttctttc taggacatgg tgagcatttg gtagccattc accggttttc   4380
tgtttctttg gatcatagtt aacctctcct tttccttctg gcactacaat tttctggtgg   4440
ggaagaatcc ttactttctg cccttcccct taaggatagg aagctgatac taggcagcaa   4500
ctagttgggg gataggaaga ttgttccaga gaaatgctga accatagggc tccagatcac   4560
aggaccccag tcttagcttg ctggggtgtg gggtgggggg gggcggttac tgaacatggg   4620
tatgaagtag atgtccattt actgaaatgt gaggacctga ggcctcttct attgctgtag   4680
ccagcatatt ccccaacctc tccccaagaa aggacagatg gggggttcccc cctggagtaa   4740
caggtccaaa agaaaaaaca tacagtggga cttccaggat ctgggcctga tcacccagca   4800
gtcaagctcc ccgcaattga ctaacacccc cctaacacgt agaaattcca atctgcaatt   4860
tagtgaggat gataccttta ttcttcttaa atacatctct tcatttccca gagcaccctt   4920
ttttcccctc ctctgcacct ttttgttaaa gactggagta taatgaaata ccaagagagc   4980
ataacatgtg atacataaaa ctttttttct ggtttacaaa acagttcatt cttgtccata   5040
cgtgcttctc tccaaggctg gctgctgtct gttccagccc gcttcgcttg gagaggccat   5100
ctgccatacc tgctccccag acgcatcgac aagcacaccc agagtgttat ctgctaagac   5160
ctaaaagagg gaggaacccc ctctcctcat ctaagaccta gcttctaaat tagagtgtga   5220
gggtccatct ccccaggagg ggcacagggc ccaaacagcc cagccatctc agaagacaac   5280
actaagcttt gtaggggtcc acagtagagg agagtaagac gcctgttgtt taatttatta   5340
cagttcctca aaagtgaaga tgtgtgggcg ggatggcaag agctgagcag acgaaagctg   5400
aaggaataag gaaagagagg aggacacaaa cagctgacac ttcctcagtt cttgtcattt   5460
gcctggccct gttctaagca ccttctaggt attaatccat ttagtcttgg ctacaacact   5520
gtgagtaact agttttgtca cccccatttt aaaaatgaag aaagtgaggc tcagggaggt   5580
taagtaactt ggccacagtt tgaaactaga ctctgatcac atgagataat agtgcccata   5640
aaaagggaaa gcagattata ttttttaaag gaaagagagt aggatatggt agaaaaagat   5700
tgtttggaaa ggaattgaga gattgatata atgaaaagaa gcattcacat gagagtaaca   5760
gtatcagggc ccaaaccttc atctaaggta cttcaaagag gcctaagcaa acttagtcac   5820
tggcgtggtt ctagtctcca tgatggcaaa tacattgtgt acagcccaac tccacacaaa   5880
acttaaatac caatgataga gcaatctaaa atttgaaaga aaaaatcttt caatttgtcg   5940
tcttcccaga gggacttaat caagaaacca atcaaaatac ttcctaagcc taactgtgtg   6000
cagaactcca aagagagccc agccctaaat caacactgtc caatggaaat ataatataat   6060
gtgggcctca tatgcaaggt catatgtaat tttaaatttt ctagtagcca tattaaaaag   6120
gtaaaaagaa acaagtgaaa ttaattttaa taattttatt tagttcaata gatccaaaat   6180
gttttctcag catgtaatca atataaaaat attaatgagg tatttattat tccttttctc   6240
aaaccaagtc tattctataa tctggcgtgt attatttaca gcacttctca gactatattt   6300
ctttctttct tttttttttc cgagacaatt ttgctcttgt cacccaagct agagtacaat   6360
ggcgttacct cggctcactg caacctccgc ctcccgggtt caagttattc tcctgcctca   6420
gtctcccaag tagctgggac tagaggcatg caccaccacg cctggctaat tgtgtatttt   6480
tagtagagac agggtttcac catgttggcc aggctaatct caaactcctg agctcaggtg   6540
```

-continued

```
atatgcccac ctcggcctcc caaagtgttg ggattacagg cgtgagccac tgcacccggc   6600
ctcagattaa ctatatttca agcgttcagt agccacatgt agctagtgct atggtagtgg   6660
acagtacaga tctgcatttc aattaagaca cgtatacaag catagttcac taatgcacgg   6720
taaaaaaaag tatagtgctg agtcggtggt agaaatccta aatactgcag agcaaaagtg   6780
gtacgaacag caatctcagt gataatgcaa ccatgcttgc ttttcattgc aatttgctta   6840
ttttccttca gcaaagttca tccatttttg ccaattcaat aaatatttac tgataaaaac   6900
tttcaatatt agattcttgc atcttcatag acagagttgc ttttcacatt tagaaaatta   6960
cttatcaatg ttaaacacac gttttgataa ccagtgttgg aaagaggtgc agactcccca   7020
tgtgcctatt gatggcagaa atattcacag ccaaagggaa acaaagggct ggggacaatc   7080
acacacctca tgtctcctaa ctcctgggaa gtgctgtccc tctgattgag ctcttattat   7140
tgccttcccc actaaccctg tccactgtgc cctggagccc tttgcagggt tacctgctct   7200
gtcctcctca cagaatatct cctctacctc cttgtccaag ctacaacttg gctattctct   7260
gatgacactg tcttccctgt agccctttttg agtaatggct gcatattctc ccatagtcca   7320
gttcttttcc tgttctccag tctggcttct ggatgacagc ccactagttt gaactccata   7380
ctgctatagt tcaagtccct tttgacttgt taccttgggc aaattacctc cttttgttca   7440
ggttccttgt ttgtaaaatg acgataataa tgccatttgc ttcagtgggt tattttgaaa   7500
ttgagtgaaa gaaggcgggt agcttcccta cacgctcagt gtagactagc ctgatgtgca   7560
ttacgggtga tgccatgact cagtgtgttt tcctcatctc cacatctggc tctcatccag   7620
tgctcctgct tacggcactc tgtccccctc ttacttactc cccctttatta actgaagact   7680
ggcactgatc tcacagtttc ctctccactt cctagtctca ccatcatcct agatgacttc   7740
aagtcaccta gataaactgt ctcagtttct tcactcacat tttttataa cagataatgt   7800
tacactcaag ttgtaacaga accagcttat ccagctcatg aaatgtatgc atttcatctc   7860
aactctgtat tcagtgacat cctgtgggta tctggaaatc agccatggtg agaatattta   7920
ccatggaaat tggcaaatac taaaaagcag agcacctttt tttctgagag ccagaccata   7980
gctcttctac tccatagcac ccatcataac aatttttaaa tacctccact gaacagcttc   8040
ttcctctctc tacttcttcc atatctgatt tgagcttctt aatttatcat gtgaaccact   8100
cttgtaataa taaccccaaa tccctgttcc attgttcttc ctgctaaaat actaaacctg   8160
gtttagtcca accatatttt ctctctttgg aatctacagg gtggcccaaa aacctggaaa   8220
tggaaaaata ttacttatta attttaatgt atattaataa gccattttaa tgcttcattt   8280
ccagtctcag tggccaccct gtatagctgg gctattgagc tcttgcggga ggagggagtg   8340
gacagtctcc cagccacaca gactgatgtt gcaccaaaca ttttttagct tccagacttc   8400
cctggccctt agtgttaccc ttaactctcc atttctctgc ctttcacatt ctctactttt   8460
taaaaatctc tgactccacc ttcaccttat cattcttagc acatgaccat acttctgctt   8520
cccaaagaaa atgagcaatt acttcctttt ccttttcctc ctgtcatcaa atctgcagac   8580
atgtcatgcc taagtccagc tttcctcctt tctctgatct cagtctgctt cttccatttc   8640
tgccctgaat cccgtcccct ccccaacccc caaggacttc gctctatcag tcacctcttc   8700
cctctcctgt atcttcaact cctcccattt tactggcttc ttcctcaagc ctttccccaa   8760
gcctttccca tctcaattac ctcctcgcac atgcctctgc agaaaccacc ccgtttcttc   8820
cctcccctcg gcagcctgtt cttcctgttc tgccctcatg atggcaccat cattgtgtca   8880
ctaaaatcaa tctctccgac atcatcaatg gccttccttt gttgggaaac ctaataaaca   8940
```

-continued

```
ctttatctta tttggtcttt gttatgggtt gaatgaggtt accccgaaat ccatattaga   9000
agtcctaacc cccagtacct cagaatgtga ctttatttgg gaatagggtc attgcagacg   9060
ttattagtta ggatgaggtc atactggaat gtgatgggct gcttatctaa tatgactgat   9120
gtccttataa caaggagaaa tttggagaca gacacgcaca tagggagaat accatgtgat   9180
gacaggagtt atggagttgg agtcaaaaag ctatgggaac ttaggagaaa gacctggaac   9240
aaatcctttc ctgcgcctag agagggagta tggccctgcc actaccttga attcaacgtt   9300
tcggcttttc aaaactgtaa gacaatacat ttctgttgtt caaaccaatt agtttgcagt   9360
actctgcgac tgcagcccta acaaactaat acagtctctt ggaggcattt ggcaaggttg   9420
acaatggaag cactttctta cccctttagg tctgtcgcct ttcttgttgg ggggtgtttt   9480
ctaacaattc ctctccatct ctctctctct agtttgtctt aaacattggt gttcttcaga   9540
cttctgacct aggccttctt ttcacttcac atattcccct gggtggtctc acccacttcc   9600
agaaattact taaattactg ctcatgcagt actgtgctgg aaactgttta acaactggct   9660
ctctgggaag aggggagact ggttgatggt ttttgctgat ttctgtggtg taaatactcc   9720
ctccatggcc aattccaaac tgccaacagt ttaacaactg gctcacaaat tttctccaaa   9780
tttaacattt ggctttcaca ggccaacaac gtggtacagc caactccagc acacctctgc   9840
ttttgtgtca gagagaagta acttattttt gtacaaaagg taaaataaaa acacctgcag   9900
gccccctttt tttccttaac aaactgctct agaaatagaa tagctgaagc ttcttttatg   9960
cattcatctg ttatttccat gtcactgtgg tggtgggatt atttttcctt tatttttctt  10020
gtatatggtt gaaatactgt acctttgatc agttttagtt ttatggcatg ttttgcaccc  10080
atattaaatc tagtttttgt cagagggcgt caatattatt ttctcaaaac aagaaaatat  10140
ttcattgcaa aggagacaaa caaaaaggtc cttaatacca aaactttgaa atgtgatttc  10200
ttgtacttgg cagtgtccaa gtggtaaacc caaacagtat tgggttttca ttttgttcag  10260
gaaagtcttt gtctggcagc gacttaccct tacatcaggc gggccttgct cattcattca  10320
cttaagtatt tattaaacac cagcggtgtg ccaagtactt atctaggtat cgggtagatt  10380
ctgataagtc agtcaggtcc ctgctctcag ggagcttgca gcagagatgg gggctgcaat  10440
agagagtaag ccaaggaaat gaaaaaggaa gttgatttca gagagtgatg aatgctatga  10500
agaaaatgaa ggcagcgcag tgtgatggag agtgacccaa ggtggtacag tttgtacctc  10560
taaggaccag actgtgaccc aggtcactca cagatgcccg tcatgtgatg ccacagcaac  10620
ttttccaggt gctcgtttcc tcccacttcc cagtctcttg cccagccgcg actgcttaca  10680
aatacagcta gaggaatcta aatgaggttc ctctatcatc aaacccaatc aaaatgccaa  10740
ggaacagaat cagtgcctgg ctgaaggcag tggaacaggg ccagcctgga gtggttctct  10800
ctgaggaagt tcctcatctt ggttttaggg ccataccttg tgacctgtga gctaggggtt  10860
gccagtccct gacatttcta ctgaggactc gcctgtctat attcccggcc tgtatgtgtc  10920
tcctgagttc cagacacaca gggcgaagcg cctgatggat ggaagtatgt tttttggtgt  10980
tccattggta tctcaaattc tacaaaactt agtgcccctt ctcctccctg ttcctcccca  11040
tcttcagtct atcacctgtt cctcatccag caaatgatat taccatcttc caaggagctt  11100
cccaggagta atccttgact cctcctcaac atccaattaa taatcaaatc taggccaggt  11160
acaatagctc acgcctataa tcccagcact ttgggaggct gaggcaggtg gatcatttga  11220
ggccaggagt tcaagaccag cctggccaac aaggtgaaac ctgtctcatt taaaaaaagt  11280
```

-continued

```
tattttaaaa actcaaatct attatttcta cctctaagtg tgtcttgaat ttatccatct  11340
ctctccatct ctgagctgtt accttacctc agtccatcac gttttgtcta cgttaacatg  11400
accagagtct tgttcttagt ctggtgaggt cactccagct gcttcagatc cttccatggc  11460
tcaccgttgc cctcatataa agttggcact cctggacatg tggcttacgg ggccctccgt  11520
gatgtggccc tatttgcttc tccattctgt tctctcccag cctctctgcc cccatctcta  11580
ggcaccaacc acacccttct gctcgtcaat ggtgccagct tctcttctat ctctggtctt  11640
tggacagact tttcccttca cctggaatgc tttcttcaat cctaccccac tctctttaat  11700
ctagataagg tttattcttt ttgaatgtct agcagtgaaa ccatttcccc tgaaaaacct  11760
tctctaacca accccctacc ctcagcccaa ggtctagatt aggagtccct ctgaatgttt  11820
ccatagcatt tttaaagaat tgcctattta cttgttcgta tctatcacta aactacaaat  11880
tgtatgagaa cagccactat ctctgcctgg ttcaccattc atctccagca actagcataa  11940
tgcctggcag agtcagcctg caacaaatat ttgttgaata aattaacaga tggctttatc  12000
tccttaagta aatcttgctt ttttcaccta ttaaaacaga cgcacaggcc aggtgtggtg  12060
gcccatgcct gtaatcccag cactttggca ggctgaggtg ggcggatcac ctgaggtcag  12120
gagttcaaga ccagcctggc caacatggtg aaaccccatc tctaataaaa atacaaaaat  12180
tagctgggca tggtggtggg tgcgtatagt cccagctact agggaggctg aggcaagaga  12240
atcgcttgaa cccaggaggc agaggtggca gtgagccgag atcatgccac tgtactccag  12300
cctggatgac agagaccctg tctcaaaaca cacacacaca cacacacaca cacacacaca  12360
cacacacaca cacacacacc aagttgtata atttaaaata taacgtgctt gttatggaac  12420
acttgtaaaa tacaggaaag taatgaaaaa gtctaccatc tagctcacca cataatgacc  12480
attgctatca tcctggcata attctctcct gtatataaat atatattctt ttattgttaa  12540
aattacacta tgagtactat ttatttattt tactgtggca aaatgcgcaa aacataaaat  12600
cttgccattt taaggtatgc agtttggtgc attcaccaca ctcacattgt tgtgcaaata  12660
tcaccactat ctatctcaga acttcttcgt cttcccaaac tgaaactctg tacccattaa  12720
acaatagtgc atcctctgtt ttcccctccc tacaatttat ttttatttgg gtttgtacca  12780
aactgaaaat agctgcttct tccttactta gttcagatta gcatttccat ttatttagcc  12840
gtggttttga ggatgccatg acagatgcca tccttcctag agctctttgg ggctgtcagg  12900
tatttcagtc agggtgaatt cgggttgata acattttaaa atctcacttt attctgaggt  12960
tcctagtgtc agagcccacc gtatttttag ggactcccaa gttacaaaca aaaatatggt  13020
gaggaggaat cactgaagtt ttaacacaag agacttacat tttgttcaat ttctatcttt  13080
tagtttattt cctaagcata aagaaatact ttgaaaattt tacatagcat tatacatatt  13140
taattaagca tgagcacatc ttaaaacttt aaattttaga tcagatcttt aattcctagg  13200
atattaagag gtactggcaa tttggccagg tgtggtggtt cacgcctata atcccaacac  13260
tttgggaggg tgaagtgggc gaattgctag agcccaggag gtggaggctg caatggcctg  13320
agatcacgcc atcgtactcc agcctggatg atgagaatga aatcctgtct caaaaaaaaa  13380
aaaaaaaaaa aaaagaagaa gaagaagtat tggcaatcag tgctccagga ataatttcct  13440
gacttgaaat aaacctacat gtagacaaac taattaggcc attccaagag ttgctagcat  13500
tggtttaata tgttttcaga gcattccagg aagcagtgtg gccagcattg catgtttgat  13560
acttcagaaa tgtatgacag gtgtttctct tacccaggtc ttctgttttc ttagttttgc  13620
tcatgtaaat atttatgaac atcctcatct ttttgaggga agggattata gatcattcta  13680
```

-continued

```
attccatttt ctagcatttg gtaccattct aagcacatga taggcaccca tttggagcat  13740
ttttggcttg acagaatatg catttagaat tgttcaaatt agaggtgtca gtgatgggaa  13800
ttagaatact atataattct aagtcatttg acttaaatac aaaagaatga ttttccttgg  13860
tggggaatgg tgaagggagg caggagttaa gaagaggaga agagatccta agtcatttat  13920
aaacttctct ggaaagacag gtgtgtgaag actttttaaa aagtcattca ccaaattgtg  13980
tgtgtgtgtg tgtgtgtgtt ttaaatagac tttatttttt agagcagttt taggttcaca  14040
gcaaaattga atgcaaggac agagatttcc cataaacccc ctgcccacac acatgcatag  14100
cctccctcat tatcaacatc cccaccagag aggtgtttgt tctagttgat gaacctacac  14160
tgacacatca ttatcaccca aagtccatag ttcacggcag ggttcactgt cggtgtacat  14220
tctatgggtt tgagcaaatg tataatgaca tgtatccacc attatagtaa catacagagt  14280
attttcagtg ccctgcaaat cccctgttct ccacctattc atccctccct ctctgcattt  14340
ccacccccag cccctggtaa ccgctgatct ttttactgtc ccatagtttc ggacgatcta  14400
tttttcagac agacacagag ctgtctttcc cttagtttct attctatcat ttctttctcc  14460
ccatccatca taaaaggcta tgagtttttt ttaagtgttg aacaccatcc tacttgtcaa  14520
gttaaaacat aagctcctgg ctgggtacag tggctcatgc ctgtaatctc agcattttgg  14580
gaggctgtgg cagaagcatc acttgaagcc agaagtttga gaccagcctg ggcaacatag  14640
caagacccca tccctccaca cacaaacaca cacacacaca cacacacaca cacacacaca  14700
cacacacaca cacaaaaaca agctcttgcc agaattagag ctacaaattg ccctcaggtt  14760
cctagaagat cagtccttca attagattca gattgagatg cttcctcttt taaacaatga  14820
ttccctttct atcatgccca ataagaaaac aaataaaaat taaacaatac tgcctgtaat  14880
ctcagctacc caggaggcag aagcagaact gcttcaaccc ggcaagcaga agttgcagtg  14940
aagtgagatc gcgccactgc actccagcct gggaaacaga gcaagattct gtctcaaaaa  15000
caaaacaatg tgatttcctc ctctaagtcc tgcacaggga aatgttaaga aataggtcca  15060
ccaggaaaga aggaagtaag aatgtttgac tagattgtct tggaaaaaat agttatactt  15120
tcttgcttgt cttcctaaca gttctccaaa gcttcgtacc ttggccagag gcttgtctcc  15180
tgcgtacctg aggtttggtg gcaccaagac agacttccta attttcgatc ccaagaagga  15240
atcaaccttt gaagagagaa gttactggca atctcaagtc aaccagggtg aaaattttta  15300
aagattcact ctatatttta attaacgtca gtccgtcatg agaatgcttt gagaaaactg  15360
ttatttctca cacctaacaa ttaatgagat taacttcctc tcccctcatc tgacctgtgg  15420
aggaatctga acaagaggag gaggcagtgg gcaggtttcc ttatcatgat gtttgtcatg  15480
ttcagtgtga ggcctcacaa aaaaaaaaaa aaaaaaaaaa ggcgtcctgg atataactga  15540
gagctcattg tacagtaaat attaataaaa cagtgattgt agctgaagga tagaactgct  15600
tggagggagc aagtgggtag aatcgcgtca aactaaagag catttctagc caaagacaca  15660
atgatagatt gaaggatatt tattctaaat atagaatatg ggtgaacgag atctgtggac  15720
ttctgggctc caacgttaga ttctgatttt agcaagcttg tcaggggatt ctgatattga  15780
aaggctgtgg ccttcacctg agaaacctgc cctagggggc catgaaaatt tgtcctgtct  15840
ttcagaagtg ctatcagaca tcaaatggaa gttaaatcgt atcttaacaa ttactaggat  15900
gggcgcagtg actcacacct gtaatcccaa cactttggga ggctgaggca ggaggatcac  15960
ttgagcccag gagttcggga ccagcctggg caacatagag agacgttgtc tctatttttt  16020
```

-continued

```
aataatttaa agagaaaaaa atactgaaaa tattgtatac accactgaat tataataatg  16080
tgtatataat gtatatattc attatgagga atatttgatt atttcatata ttatatcttt  16140
tccttctgtt tattttatcc agttatgaag tatttagaac aattcatcag taattggggc  16200
taaattgaca gaatagtaat cagagaaaat agaaaaagac agatgggtta tctttgaata  16260
ccaggttgga gttgtttatg ggtttgtttt ttgttttggg ggcgtttttt tagacagagt  16320
cccactctgt tgcccaggct ggagtgcagt ggcacaagca tggcccactg catccttgac  16380
ctcttgggct caagcaatct tcccacctta gcctcctgag tagctgggac cacaggtgca  16440
tgtcaccaca cccagctaat ttttttattt tttgtagaga cagtctttct atgttatcca  16500
ggctgatctc aaactcctgc actcaagtga tccccctgcc ttggcgtccc aaagtattgg  16560
gattataggc atagccacca cacccaacct agtttctatt tagacttggc cctttcccac  16620
cagtcatttg tgtccaaaag atctcataaa tgtagacagg aaactgtcct ttgctcatca  16680
gttttcttca tcctgtgtct agggggatgg tcggtggggg aaactggggt tatgcaagtt  16740
cctctgaaac atcctctgtg agcccaggga tggatgaggc accagccgcc agcgagtcag  16800
tgtgcagctt tccagaaagg aagtcatcag ccagtcagcc ggccctggca gccagcaccc  16860
ggcaaccctg ctgtcttgtg ataaagaaat ggtctgcctg acaggatggt gtggattttt  16920
ctttttttctt tttttttttt ttgagacagg gtctggctct gtcgcccagg ctggagtgca  16980
atggcgggat cttggctcac tgcagcctct gcctcccagg ctcaaggcat cctcccacct  17040
cggtctcccg agtagctggg accacaggca cacaccacca cgcccaacta agttttcgta  17100
tttttagtag aggcagggtt ttactatgtt gtccaggcta gtctcaaact cctgagctca  17160
agctatccat ctgccttggc ctcccaaaga gctggaatta caagcgtgag ccactgtgcc  17220
tgaccagggt ggattttttc aagtgcacat gttgtggtcc cagaagctct gatggtacca  17280
aattccaagc gaaaaaaagt caatggttcc cacccatcct acctcccatg atggcaagag  17340
gaaatcacca cactgcagat acagtccatg taaaacaaat tgctatggat tttgaaagtg  17400
aaccttaaga gaactgcact atgttttctt cattagagtt ctctggtaat ttccagcttt  17460
tttttttttt ttttttagac agtgtctcgc tttgtcgccc agtgtcaccc aggctggagt  17520
gcagtgacgt gatctcggct cactgcaacc tccgcctcgt gggttgaagt gattctcctg  17580
cctcagcctc ctgagtagct gtattttagt agagacgagg tttcaccatt tggccaggct  17640
ggtctcgaac tcctgacctc aagtgattcg cccatctcag cctcccaaag tgctgggatt  17700
acaggtgtga gccactgcac ccggccagta atttcaagct tctgaggagc cctttgaatt  17760
gttaaataac ttgtagctat gtccaacata tccatgttca gtgtatgttc gatatttctt  17820
aggaaacctg cccttggttg ttttctttgt ggtaattcat gagccggcaa atttgacatg  17880
tgttacagaa tataccttttt ctctgctctc ctacctcata accagaactt aattatcctg  17940
ctttagtcac ataaatagct aactaaataa atatatgaga tttcagtctg ctcactgtga  18000
aaatagacct tctaaatgat ctcttccact tgcagatatt tgcaaatatg gatccatccc  18060
tcctgatgtg gaggagaagt tacggttgga atggccctac caggagcaat tgctactccg  18120
agaacactac cagaaaaagt tcaagaacag cacctactca agtaagaaat gaaaggcacc  18180
ctagagatgt tccagcccca aagatatttg aataggttgg actcgggcac caatctagca  18240
agtcctacgg aagttgtata aagctgaaaa tactgaagca tttcccaaat gggaaatcct  18300
aaactcaaaa cttgcttttt ggtttttttg tttgtttgtt ttttcttcat ctgacattgc  18360
ttagtagtca cagaatgaaa gataaatcaa tcattcatga tctaacaatg accttcagtg  18420
```

-continued

```
ctctaaaaaa ctacggagtc aaggaaaaca tgaatatatt cctcatgtaa aattaaaata  18480
cagacatata aagggcaaaa catgaacatc attcatacct tgaggtccgt ccccctccca  18540
gaaataaccc ccagtatgcc ttggtttaga gcattaagca ggagggccct gagtcactcc  18600
agacagtctt gaccaccaag cagcattctc tttttgtttc ctctgtggct tttgcaaaca  18660
cagggctagc tcagctaccc attagtatgt tttcagtcac taaaacagtc ttccagtctt  18720
caaattagga tgacattgtc acatggggct ttaaagcaag tgaaacaagg aacccccttt  18780
tttttttttt ttgagatgga atctcactct tgtcgcccag cctggagtgc aatggcgcaa  18840
tcttggctca ctgcaacctc cacctcccag gttcaagaga ttctcctgcc ttagcctcct  18900
attcattatg aggaatattt gattattcag ttcctgtagg gtaaagatat tacccccgat  18960
catattattg attattgagt agctgagatt acaggtgcct gccaccacga ccggctaatt  19020
ttttgtattt tttagtagag acagggtttc accatgttgg ccaggctcca ggctcgtctc  19080
gaactcctga cctcaggtga tccacccacc tcagcctccc aaagttctgg gattacaggc  19140
gtgagccacc actcctggcc acaatccttt tttaactatg aaatatattt ttatctgaag  19200
tttgatgttt atacccaact gagggatgat gttcccatat ctcagttaaa gaaataacct  19260
gctcagatac ttcaagctct tcttttgact tttgaaaata aatgatcttg aagttactat  19320
actttgtttg ggttagttaa cattatttaa agtatattat tttaattaat tatctttgta  19380
agattttact gtatactacc tggagttcaa tgtatcagat ggatttcaaa tttatgtaca  19440
ttttttatgt atatggtaca gaaaaaaatg tgatccataa gaaatcagaa aatagcgcat  19500
atgctaatag ctaatgttgt cctctaaaaa acttattttt gcatttttaa gaggggggata  19560
tactctgaca ctttaataag tgtaattaat tattgactgg aatttggcat gaggcagggc  19620
catttcagat cccattaaag gaatgacaca taccagagaa ccacagaagt aaggccacat  19680
ttgtaataaa tcattatagc tctgctagga gaagacccag ttgtattagg taattaatgg  19740
atttgctctt aaaacacatg tcccggaaga tataggtgag tcttgggggg ccgcattaaa  19800
cattatacca atgtatctta catttctaag aaagttttac tactttacag gatctttctg  19860
ttaccaaaat ggaaggtttc caactccagg acttggcttt catagttcct acaccagggg  19920
aaatgccttc ctttgctaac tatgcaacca ggttagttag tgtaagtcca gccaccctgt  19980
tggcaatgct aaaaggtaca acaaacacag aattttattt gcatttgtaa acatttgatt  20040
tctggctcga aattttcagt tttcatgggc acgtcatgga aacagaaatc ttctgtgttt  20100
agtttgggca cctactcatt gtagtgacaa atatttcaga agccaatagg ggattccaca  20160
aattgttctg aacctgtggc tgagactggt aatggctgag tgacatgggg acataccaca  20220
aaagaagagg tagcaaaagg ctgctgagat aaggacatgt tcattgctta gctagtggcc  20280
tgcaccctta aaacacatgt cccaggctgg gtgctgtggc tcacgcctgt aatcccagca  20340
ctttgggagg ctgaggcggg tggattacct gaggtcagga gttcgagacc aacctggcca  20400
acatagtgaa acctcatttc tactaaaaat acaaaaatta gccaggcatg gtggcgggcg  20460
cctgtagtcc cagctactca ggaggcaggc aggagaatta cttgaatctg ggaggcagag  20520
gttgtggtga gccgagattg cgccaccgca cgctagcctg ggcgacaaag tgagactctg  20580
tctcaaaaaa acaaaaacaa aaaacaaaca aacaaaaaac aacaacaaca aaaaaacggg  20640
tatcccagaa gatacaggta agttttctaa cacaggtcct cttgtatggt gcgttccact  20700
taagtagaag atgacaaaaa catttgtcat gagaatatag actcacattt taaacctgtt  20760
```

-continued

```
tgagcaggaa aaggaagcaa tgttacagat gtaattctgg gtgtgactgc agaaaggatg  20820
actcccttat taaagtagtc atcctgagtg agctaactct ttgtacttcc tcttctcctc  20880
ctgttcccct catcacccca ttcttccgtt gcctacaccc aggcccacat tggatgctga  20940
catagactta catggtacag tccaagggaa agatctgcca ttttttcaa tgtgtcatct  21000
tggttatctt cattccaagg atctctccac tctttataca gtaagagatg agagtctgga  21060
aaggattggg aataagataa tgaattgtaa gttttaaatt gttcttcgta ttttggggaa  21120
ggagtaggct aggtggtcct tctgtttttt ttttgttttt ttttttaaag tagatgtggc  21180
cagacgtggt ggctcacgcc tgtaatccca gcactttgag aggctgaggc aggtggatca  21240
cttgatgtca ggagttcaag accagcctgg ccaacacagt gaaaccccgt ctttactaaa  21300
aatacaaaaa ctagccgggc ttggtggcgt ccacctgtag tcccagctac tgcagaggtg  21360
gaggcaggag aatcacttga acccgggagg tggaggttgc agtgagccaa gatcatgcca  21420
ttgtactcca gcctgggcga cagaacaata ctctgtctca aaaaaaaaga gaaaagaaaa  21480
gaaaaaaaga atggatttga actcagtcgt caatagcctc tattccagga gatgttacag  21540
ttgattatgt tatagggggt gtataataga atttcgagct atgtaaattc caagtgcatt  21600
tggaagaatg aagaaatgga ggaagggtaa agtatgagtg caagcattcc aggtttttttg  21660
aaaatgctat aatctttgtt cagggctagt acaaagtgct atttagctgt aagggttttt  21720
tgtgatttac agacagtttt cacatgtgtc atttcaacct tggttttatg gcgaaggcat  21780
gtgatggtgc ttgtcccagg actttagatc catatctgag gttcctgtcg ggcaaagata  21840
ttacccctga tcatattata gtctataagt gggagagttg tgcctggagc tcaagtctta  21900
tgatttctga tccagggcac ttcctacaac atgattttgc aatataaaag cctataatgt  21960
gtgactaaag caggtcactc accccttgta acagactcta gtaatggtac tgccaccaaa  22020
cggctgcgtg atattgggca aagacttacc ttatttgaat ctcagtttcc tcctagaaaa  22080
atgagggtgg aggttaagca taggctgatg atcctaaagc ctccatactg ccctaaactg  22140
tggctctaag atccagtaga atgctgggtc acaggactct agggagcttt tcaaacccaa  22200
atgtctgtca ttccttgatg gtaggcagca gtttatggaa gtgggcgaca cagcaaatat  22260
caaaatacct aaagcagctt gcaagagttg tttctgccta gtggtcttta tagttaatat  22320
taaatagtta attttttttt tttttgagac agagtcttgc tctgttaccc aggctgcagt  22380
gcagtggcac aatctcggct cactgcaacc tccacctccc gggtttgagc aattctgtct  22440
cagcctccca agtagctggg actacaggtg catgccactg cacccagcta atttttgtat  22500
ttttagtaga gacggggttt caccatattg ggcaggctgg tctcgaactc ttgacctcag  22560
gtgatccacc tgcctcagcc tcccaaagtg ctgggattac aggcatgagc cactgcaccc  22620
agcttaaata gctaatattt aatattattc tatagttatt caagtaattc aggccaaaga  22680
cttagaaaca aaacaaaaag ccacttttaa ggagaaaggg tgtaagtttg ccagatagat  22740
agagatcttt cttttttaac tacaagagtt caggaatgaa ttactcttta acaaacgact  22800
atagatatac atgaaaattg gaaggactta ttatgcatat gataatcaat ttaaagacaa  22860
cacttaaaat tatattgttg ccactctcaa aaagtggtaa tagaacagct aatggtttaa  22920
aaagcagagt acagaagttc ccaaacttat ggcaccttaa tatcgcagaa aactttttaa  22980
agcatgccta ggccacaaaa aatacctgta ttttgattat taaattgtaa ggtctacaca  23040
acctaatagt aataggtcca atagtaatgc tgtccaatag atgttgatgt ttttttcctt  23100
gcaaacttaa aagatcctac agtgcctctg taaatagcac tgcctggtta gagttgaatt  23160
```

-continued

```
tcagataaat aattttttc atgttaatta tttttctttt ctttactttt tttttgttt  23220
ttttgttttt ttgtttttt ttttgagaca gggtctcatt ctgttgccca ggctgctgtg  23280
caatggcatg atcatggctc actgcagcct tgacctccct gggctcaggt gatcctccca  23340
cctcagcctc ccaagtagct agctgggact acaggtgctt accatcatgc ccggctaatt  23400
tttgtgtttt ttgtagagat gtggttttgc catgttgccc aggctggtct tgaactcctg  23460
ggctcaagtg atccgcccgc ctcggcctcc caaagtgcta ggatgacagg catgagccac  23520
tgcacctggc ccctgggcga agtatttctt aatggttaca taggacatac actaaacatt  23580
atttattgtc tatatgaagt tcaagtttaa ctaggtgccc tgcactttta gttgctaaat  23640
cctgtagctg tacccatgca ttcactggtg ctccccagct tgccttgcac agagtttgga  23700
aaccatagtc ctataactct aggccaattt tttaatgtaa aatttgattc attttaaatt  23760
aataaataat aacaggaatt tttttaaaaa ttgttttaaa tataattaaa attatcaaaa  23820
tattttttaa ctgaacttgt gactagagat atttagatta tgaagagtgg ggtttatgct  23880
aactaatgac agtctggcta tgcatgtgga gcactgagct ataaattgtg gcttccccaa  23940
ttctcctgat gtcacttgaa caaaacctaa gtgtcagacc agagcttctg gtatcttcca  24000
tgggatttca ttcaacagct ggagcaaatg aagtcagatt gatttttttt aatttgtcca  24060
attttgttgt ctcaaaaaca taattataat catttattag aactagaatt tcttcagttt  24120
aacaacagaa atagttattc attatgaaaa gcgaatctgg aggccttcat tgtggtgcca  24180
atctaaccat taaattgtga cgtttttctt ttaggaagct ctgtagatgt gctatacact  24240
tttgcaaact gctcaggact ggacttgatc tttggcctaa atgcgttatt aagaacagca  24300
gatttgcagt ggaacagttc taatgctcag ttgctcctgg actactgctc ttccaagggg  24360
tataacattt cttgggaact aggcaatggt gagtacccca gggaacaatt cattaataag  24420
gagattcccc actagcatta tttcttttct tttctttttc ttttcttttt tttttttttt  24480
gagacagagt ctcgcactgc tgcccaggct ggagtgcagt ggcgccacct cggctcactt  24540
gaagctctgc ctcccaaaac gccattctcc tgcctcagcc tcccgagtag ctgggactac  24600
aggcacccgc caccgcgccc ggctaatttt tttttttttt tttttttttt ttttttttgca  24660
tttttagtag agacggggtt tcaccgtgtt agccaggatg gtcttgatct cctgacctcg  24720
tgatctgccc tcctcggcct cccaaagtgc tgggattaca ggcgtgagcc accaggcccg  24780
gctagcatta tttcttatga cacttttttt tttttttga gacggagtct cgctctgtcg  24840
cccaggctgg agtgcagtgg cgccatctcg gctcactgca agctccacct cccaggttca  24900
cgccattctc ctgcctcagc ctcccgagta gctgggacta cacgcacccg ccaccacgcc  24960
cggctaattt ttttgtattt ttagtagaga cggggtttca ccgtgttagc caggatggtc  25020
tctatatcct gaccccatga tctgcccgcc tcggcctccc aaagtggtgg gattacaggc  25080
gtgagccact gcgcccggcc aacactcttt ttattattag caaatatact tctgcctggg  25140
cacattcttg caagtgctca acaatgcaac ttttggaagt gcatgtggca gaaactcctg  25200
ctgtatttat tccagaacct attattgcta atcccagttt atgttacatt tgaagtgaga  25260
accagttgga gccagcaacg ttcccagctc caaagttccc ttgagatttt cagaatcact  25320
taaccctatt atgcttggca acctggactc agcaaaactg ggaagtcagc agtttgtttt  25380
attcatccct tcctttctca gtttctcaaa tgtgtcagtt aatctcagta accccattgc  25440
aaccttcatt acctgcccaa gcggtctaga acttgccagt atagaatcct acgtgggtca  25500
```

-continued

```
agctcctgac tgtctccttc ttcactcttt ttttgcaaag aacttgtaaa ttttaactat  25560
aagtattcat gattcgccac atttattcaa aacatagagt gctttttcca catatcagcc  25620
aatggaaata aggattaaat gggaaatgaa atgtagtaat aggataagca caagtcttct  25680
tcctgctcaa actttttttt tttttttttt cagacaagat cttgctctgt tacccaggct  25740
ggagtgcagt ggcgtgttca tagctcaatg taacctccaa ctcctgggct catgcaatct  25800
ctcacacctc agccccctga ttagctagga ctacactatg cctagccaat ttttttttctt  25860
ttgtctggtt gtgttgccca ggctgtctcg atctcctggc ctcaagtaat cctcctgcct  25920
cggccttcta aagtgctggg attataggca tgagccactg tgcccggtct caaacctttt  25980
tttccaaagt aaatgaagtt attagatatg gaatatagtc tagttcccag atatccatat  26040
ccattggttt attaccctca ttattaactt caaattgttt aatagaccct catatctcag  26100
ttatacagtt aaaatttttg ttttgttttt ctggagtatc ttatttataa ctatgagttt  26160
tactttactt atttatttta ttttttgaga cagacgcttg ctctgtcact caggctggag  26220
tgcggttgcg tgatcatggc tcactatggc ctcgaccttc tgggctcaag tgatcctctc  26280
cctcagcctc ccaagctgag actacaggca tgcaccacca catctagcta attttttttt  26340
ttccccatgg aacaaggctt tactatgtta cccagagtgg tctcaaactc ctggcctcag  26400
gggatcctcc tgtctcagcc taccaaaatg ctgggattac aggcatgagc catagcgcca  26460
gacctggttt tacttttctt gactttgaat tacaagtttt tgtaatttgg aaaatgtttt  26520
gttgctttta aatactgctg tatgtttgct tttaaataca acatttctcg atatatattt  26580
tgagaattgc tgtctttcag aacctaacag tttccttaag aaggctgata ttttcatcaa  26640
tgggtcgcag ttaggagaag attttattca attgcataaa cttctaagaa agtccacctt  26700
caaaaatgca aaactctatg gtcctgatgt tggtcagcct cgaagaaaga cggctaagat  26760
gctgaagagg taggaactag aggatgcaga atcactttac ttttcttctt tttccttttg  26820
agacagagtc tcactctgtc agccagactg gagtgcagtg gtacaatcat ggctcactgc  26880
aacttcgacc tcccaggctc aagcaatcct cccatctcag tcccacaaat agctgggact  26940
acaggtgcac atcaccacac ctggctactt taaaaaaatt tttttgtaga gatggggtct  27000
ccctgtgttg cccaggctgg tctcttgaat tcctgtgctc aagccatcct tccacctcag  27060
cctcccagag tgccaggatt acaggcatga gccaccacac ccagccacca cttttcttaa  27120
aaaaaaaaaa agattctctc tggtagacaa tcctcaatag tccacatgtt attaaacaat  27180
ctgctgcctg aatacatgat ttaccaaaaa aaggaaattt tgacgggttc agaatatcaa  27240
gggatctgag gcaaatgtca cctatgataa aatttgctat caaaattagg aagtttgtgt  27300
ttacctgatc ctaaagcagt aaccagccca tttctaggga ataaaactct catgcgtata  27360
ttgtgcatat atatgtatta tatgactgag tgataataaa attttttttc tagcttcctg  27420
aaggctggtg gagaagtgat tgattcagtt acatggcatc agtaagtatg tctcctattc  27480
ttaatactag gaaagtaagg ctagctttat ttattaccta gtattcaaaa agttagttca  27540
tttaactgcc aattgactgc agttcaaata agaaacaaat agtgtctcaa gtagcactgt  27600
actccaattt taatattaat aaaaaaaatt ttaagttatt ttaaataatg tagtggtttc  27660
tataaagatc actttataca gaagaacagt gccaattaac ccatggaaca tataagtagc  27720
taaaaccaat tgcttgccaa agaaccagta acccaggagt acatgtcctt gccactgtgt  27780
tttttcaaga cagagtaact gatttctagt tacttgcata gaatggactc ctcctcataa  27840
ctcccttcca tcttggtctt tccctagtag aacttctacc ttttttagt aacaggtgag  27900
```

-continued

```
tgggagaggt aagaaggaga ataaggtcag caattaacct aaaagcagaa agtaaaattt  27960
gttatttttt ttctgaatat tttctgtgta atttagctac tatttgaatg gacggactgc  28020
taccagggaa gattttctaa accctgatgt attggacatt tttatttcat ctgtgcaaaa  28080
agttttccag gtaatagtct ttttaaactt tttaatgtaa aaccagaatc cttattttat  28140
agtctagcta gttctaaatt ctataggtat gtatatttac atgtttttct aattttagag  28200
aacaagcact atgacttatc cactgttagt tttcccctta gcattgggtc ttaccccatg  28260
tacgtgatta gaaatttgaa atatttccaa tagcctttag tagaattaac tcacatagat  28320
gataagaatg ggttggttca cttcatgttc cttccacagc ctactatttc aataaaagaa  28380
agtttcccaa gacctaaatg actatgaaca tattttataa ctatatagga ggggtgggtc  28440
taggaataca aagttttgaa tgctgttaat cttcaacacc acagttgaaa ccacaggtca  28500
gctttttgc aattaccatg gatacttttc tgttctatag gtggttgaga gcaccaggcc  28560
tggcaagaag gtctggttag gagaaacaag ctctgcatat ggaggcggag cgcccttgct  28620
atccgacacc tttgcagctg gctttatgtg agtgaagcag cgctggcctt aggggtcaga  28680
gtgcagctct tctccatcct tctattctgc tgaaatagct ccccagccaa aaagcagatc  28740
aaagaccgtt tcagtggctg agccccaaaa ttcatgccag attttgcaag aaaatgattt  28800
actaaagctt gagggacatc tttaacaagt gttccaaatt aatcactata aggatgaatt  28860
gtttcagaaa ttttggcctt taattatggc ccataaatat gtcaagtagt ccttactcta  28920
aagaagtaca ctgtaaaaga atgcatatag ccggatatgg tagttccctg taatcccaat  28980
actttgggag gccaaggtgg gaggattgct tgagcccagg agtttgaggc tgcagtgagt  29040
tatgatggtg ccactgcact ctagactggg caacagagtg agactgtctt ttttttccc  29100
ctctgtcacc cagactggag ggcagtggca cgatctcacc tcactgcaac ctctgcctcc  29160
cggattgaag cgattctcct gcctcagcgt cctgagtagc tgggactaca ggagtatcac  29220
cgcactgggc taatttttgt atttttagta gagacggggt tttgacatgt tgcccaggct  29280
ggtctgaaac ccatgagctc aagtgatctg cctacctcag ccttccaaaa tgctgggatt  29340
acggacatga gctaccacgc ccggccacac cctgtctctt aaaaaaaaaa aaaatgcaag  29400
ttagagcata ttacagcttt gtctctcagg aggatactta gtgtatgtag ctataattca  29460
tagattccca agaagtttag agcctaaagt atgaggtccc accagagggg ctatcattaa  29520
atttaaagat ttgttaaatc atctcattgt ccaacaccac aaacttgatt gctttaaaat  29580
actggtttag ttacatttag taactctatt agtgctttta atctatactg ctatatcctc  29640
acattgagat tttttttctt ttctcttcca tcttcattct tttttctctc atcctcattc  29700
ttataagcct agaatacatc acaaatcctt tatgcccatg gaagcaagag gaataaagaa  29760
tggagatgtt tgttttgcca ttaactaaag atctggggtg tcggggagaa gggggataga  29820
gaaggagaag tgggaagagg tgtccataat agcttaggtg caattctgct tattttacat  29880
tttacccccg ctgactgcca ctttttcttc agccctcaca cattgtttgt gcagggacct  29940
cataggacca ggaattgtct atagaggtgg gaatttgtct caccctgaaa gggatacctc  30000
tagcatggta atagtcttct aggatttgtt atcatatgga aagatgtaaa gggagggatt  30060
ctgctgctgc tgctgctgct gcatgcagtt gccatttcat ttaaatgact tatttataat  30120
tgatgacact tttctggctt cctgttaatt cctccctcaa agatcaataa accagaacca  30180
ggcatggtgg catgcacttg tggtcctgta accacccaac aggttcacct tgcctgctgt  30240
```

-continued

```
ctagatagag ccaattatca agacagggga attgcaaagg agaaagagta atttatgcag  30300
agccagctgt gcaggagacc agagttttat tattactcaa atcagtctcc ccgaacattc  30360
gaggatcaga gcttttaagg ataatttggc cggtaggggc ttaggaagtg gagagtgctg  30420
gttggtcagg ttggagatgg aatcacaggg agtggaagtg aggttttctt gctgtcttct  30480
gttcctggat gggatggcag aactggttgg gccagattac cggtctgggt ggtctcaaat  30540
gatccaccca gttcagggtc tgcaagatat ctcaagcact gatcttaggt tttacaacag  30600
tgatgttatc cccaggaaca atttggggag gttcagactc ttggagccag aggctgcatt  30660
atccctaaac cgtaatctct aatgttgtag ctaatttgtt agtcctgcaa aggtagactt  30720
gtccccaggc aagaaggggg tcttttcaga aaagggctat tatcattttt gtttcagagt  30780
caaaccatga actgaatttc ttcccaaagt tagttcagcc tacacccagg aatgaagaag  30840
gacagcttaa aggttagaag caagatggag tcaatgaggt ctgatctctt tcactgtcat  30900
aatttcctca gttataattt ttgcaaaggc ggtttcagtc ccagctactt gggaggctga  30960
gacaggagga ttaatggagc ccaggagttt gaggttgcag agagctatga tcacgccact  31020
gcactccagc ctgggtgaca gagtgagacc ctgtctctaa ataaataaat aagtaaataa  31080
ataaatacat aaataaaatc aagatggtgt gcaattagaa ttgagcgatt ttgtttccaa  31140
acctcaagaa agcttggtct tgctctgtcc caggtggctg gataaattgg gcctgtcagc  31200
ccgaatggga atagaagtgg tgatgaggca agtattcttt ggagcaggaa actaccattt  31260
agtggatgaa aacttcgatc ctttacctgt aagtgaccat tattttccta attctagtgg  31320
agtagattaa agtcaactca ggacctctgg tgttaacctc ctatgaacag tcagtcctct  31380
cagtaactag ccaaatcatg agatgatgaa ttagaaggag ccttagatag catccaatct  31440
aacatttttt tgtgtgtttg aagagaagaa atcaagagct aggaataact ttttaaaggt  31500
aagccatttg cagtatagtg tggattttgt ttaaaagggg ataatttgaa attttatgac  31560
tcattataca agacaaaata agttggattt tcaaatgttt tacaaagtaa atcaaagtta  31620
taattgccta cagtacgcaa agcttcaaaa catttttttat gttatgaaat tgtaatttat  31680
ttaaccttaa aatgagccag taccatgtgt ttgcttaaaa atctcatgct aagaatttac  31740
tatgttgtta ataatcttca agatatttat gaataaagtc ttatttctaa tccttcctcc  31800
aactgtatct ggtgctaaat caggaaatgt ttcttcccaa aaagcctcgt ggaagatctg  31860
tatgtctaaa tatatgtcag ggataataca gatgtagccc tgcgaagcat gaccttgatt  31920
tttatagtct aaaatgtcat ttgcagatat ctattttcta agaataattc ctaaaagaat  31980
tatttgaatg ttgtaggaaa gctaagaaat tttgcaaaga gcgtacgtga aaatataagc  32040
taggcttttg tggtttgtgg atagacttcc caacaaaatt gctttttatc tatagtgatc  32100
caagcttgtg gaacatatta gtcatctttt tttagaaaat tcttagaaaa gtgatcttgc  32160
aaaaatggaa tttatctttc cccaagtata ttctgtcatg tatagagtta aactaagcat  32220
agtaatttca ccagacaaac attcaaaatc tactcctgac ctttttatct catccaaatt  32280
ttcccagggc ccagacataa acctttgcct tacgaactct ttgtatatgc actaaatatg  32340
cttctccttc aaggttctca gtcagctaga aaaatgtgca agagtaaatg gtacccttct  32400
cacttgtaga tccaagagaa ttagacttaa actcactcta catgtctgtg actttatttt  32460
atttgcatga cagtcctgtg aggtggcaag gcaggtatct tggatccatt ttttagataa  32520
ggaagttcaa attgagaaga ggttgcatga tttacaggaa gccatactgt agtcctatgt  32580
tactcttaaa aatcccattc aaatcctgct tctgaggcct gcatactttc taccctacca  32640
```

-continued

```
gtcattgacc catgcttatg tctcctttga aaacattgat tccactcttg tctccagtga  32700
aaaagtggaa tttaagcaga gaaacaaaag ccatttgtct tgttaagtct actttccctc  32760
tactttcaag aaggaaagtt ggggtatgtg ttgaatggtg atttatttat ttatttatta  32820
ttttaaaaat tgatacaagg tcttactgta ttgtgcaggc tggtctcaaa ctcctgggct  32880
caagtgatca tcccacctca gcctcccagt gttgggatta cagcatgaac cattgtgccc  32940
accaccgatc cgcagttttt taagaaaaac ttttactata gaaaatttta atcatataca  33000
aaatacagag gaaagtatat gaacccactt taggagacta gaatatgcca ccccaaaata  33060
tgccactttg gcataaggat tatttcgagc taaaggcaac tgggaagaaa cacatagaag  33120
aaaagttctc tgtccttctc catttgccta aaagcaggac atgaatctta aaagtccccc  33180
tccttccctt tctaccagga aaaacaagag ttaatcactg aagataactt cagaccctta  33240
tcagtgtaga gatggcacta gaagaatcta tattacatac tcatttattt tccttcccac  33300
aacttgccac cccagagact aaaaatcctt ttcctttgtc atgtctcttg tccaaaaatt  33360
tgctctataa gctggagttc taagccacct ctttgagaat tacttgttcc ctggtatttt  33420
ctgttaacat acatgtatta atatacatgt taacaagctt ctgtttgttt ttctcctgtt  33480
ttctgtcttg ttacagaggt ccatcccaac taagaactaa agagtaggag gaaaatataa  33540
tttcctcctg catactttga tcttgtttaa tccgtaaccc ttcccacttt tcacctccta  33600
cctattagat tactttgaag caaatttcag atatattact ttatctataa atatttcagt  33660
atgtgctagg tgtggtggct cacacctgta atcccaacac tttgggaagc tgaggcagga  33720
ggatcacttg agcccaggag ttcaagacca gctacggcaa caaaaaatca aaaacttatc  33780
tgggcatggt ggcacatgcc tgtggtccca gctacatgag aggctgaggc aggaggatcg  33840
ctttagccca ggaggttgag gctgcagtaa gctgcattca caccactgca ctccagcctg  33900
ggtgacagag taagaccatg tctcaaaaaa atacatattt tagtatgtat cctttttgta  33960
aaaacacaat acttttatca tactttaaat aataacaata attccttagt atcaccaaat  34020
attttgtcag tgtctcacat tttccttatt gtctaaaata ttgttgatag ttattcaaat  34080
cagaatccaa acaaggtcca tatattacat ttggttgaca agtctcttaa gtttgttcat  34140
ctttaagttc ttcctccctc tctttcatct cttgtaattt attaatgtga aaaaacaggt  34200
aatttgttct atagtatttc ctacattata gagtttgcta catttattcc ctatgatatc  34260
atttagcatg ttcctctgtc ccctgtgttt cctgtaaact ggtagttata cctagaagct  34320
tgagtttatt caggttttta attgtatttt ttttgcaaga attctttatt atctgcttct  34380
ggaagcacag aatgtctggt tgtgtctggt tttgatcttg acagctactg atgaccattg  34440
cctaatccat tactttattg gggtgggggg aataaggttt taaaataaat ttttttttaaa  34500
gatttttttta actgttattt tgagacagtg tctcatttcg tttcccaggc tggagtgcag  34560
tggcacaatc acggctcact gcagccttga cctcctggga tcaggtgatc ttctcacctc  34620
agcctcctgg gtacctggaa ctacaggtgc acaccaccac acctggctaa ttttttgtat  34680
tttgtgtaca gaaggggttt catcatgttt cccagactgg tcttgaactc ctgggttcaa  34740
gtgatctacc cacttcagct tcccaaaatc ctgggattac actttggcca ccgtgcctgg  34800
cctaaatgaa attatttgtc tctaaacaga cagaagtttt actttaaaaa tttgtctttg  34860
tgtgtacatg tgtttgtgta tgtgtgtgtg tctaaaagtt tggctttgag ctttgctttg  34920
aattcttgga tgaacaataa ccaagaatac ttaaactctg atcattcttg acagatatcc  34980
```

-continued

```
cctacaggct atggcctttt gaattgtgtc ctccagtgat aaaaagcagc aagcacgata  35040
ctgctctcag attcatggtg gtcacatgtg aggtgaaaaa aaaaaaaaag atgaatccta  35100
tttaaatgcc cccaggataa cagtgatact ctttgtagga taactatttg cttgccactg  35160
gtttcattaa ataaggacat aagtaaagat ctatttttgt ctctttctcc ccaaccacca  35220
caactaggat tattggctat ctcttctgtt caagaaattg gtgggcacca aggtgttaat  35280
ggcaagcgtg caaggttcaa agagaaggaa gcttcgagta taccttcatt gcacaaacac  35340
tgacaagtaa gtatgaaaca caccctttac caatcatcaa gttttagtgg gtaagcctgt  35400
aactttactc aaacaccctg ttgcatgtgt ctatacattg cataagtata ggcagttgca  35460
atttagtaaa gttttataca acgattttat tttattttat ttttagaaga aaaatgctac  35520
ttttgttgtt gttgtttttt gagacggggc ctcgctcgtc acccaggctg gagtgcagtg  35580
gtgcaatctc agctcactgc aacctccgcc tcccgggttc aagtgattct tgaagaggag  35640
aacaataata acaacaatat tattttcaaa agttgtgacc gcagtttctg gagttgagaa  35700
gacatcgaga tttttgtagc ctcatactct tgctttaggt agcaaaaaat gttcctaaat  35760
ctcaggaata ttctctagat aggtttcaat ctatcattcc tgataagatg atgctgaaat  35820
actaattcta gccaaaaaag accagctacc atttccgatt gttggggact gggaactctg  35880
gatagtgagg accccagtag gaagtagcga ggggaatggt ttgaatggat aaattcataa  35940
aaaatgtcag tagatttaat tttcttatac atttcagtct ttttataagg ctaggaaaag  36000
cccctgtttt tatggtttat aatttgaatt cacatgaacc cacaaaattt gccttttacc  36060
ttcctatgtc tgaaaatgga tagtctggct ggcctcttaa caacccagct ggcagagctg  36120
tgaggatctc agtgtgctct agcccagaca ttggtagcat gaacggcaac atttttaatt  36180
gtgttttcaa aataggagca cactagcggt ctaaaacgat cataaaagaa ggatactaag  36240
agggcccact gtcattatgg atcctaatac ttaggatgca ttatggattg tcattatgga  36300
tactaatact taggatcaca tttgtaattg agtttttaat tgcttaaatt agatacatat  36360
ttctattaag ttaacctctt tgcttttagt ccaaggtata aagaaggaga tttaactctg  36420
tatgccataa acctccataa tgtcaccaag tacttgcggt taccctatcc tttttctaac  36480
aagcaagtgg ataaatacct tctaagacct ttgggacctc atggattact ttccaagtaa  36540
gtaattttcc ttgttcattc caaactttca ataaatttat tggtgtttat cagaatagag  36600
agtttggaca gggagcaaaa gacaaagtca actatatcaa gttctaataa ttcttaatat  36660
tcaggaaatt tatgtatgaa tacttactaa tatgagtata actcatccta agagtctaaa  36720
gcaaaaggat gtgaacacaa actagcagtt atcttagaga ataagtttgc atttcaaaat  36780
aacttgacat atcaagatcc actcaacgca tttaaattat ttactctaaa aagacataat  36840
tcttggtaac acattcacta aagcaaaata tacctttata taattgctat caaaggtatg  36900
tgggttggta taaaatatca taccatgtga gatcagtgtg attcctttac agcattaatt  36960
tttattggtt agagtaagaa aaagaatagc tagagtatat ttcttaagta gattctcata  37020
cactttggtt tcaaaaacca attattgact acatcttata aaagcctgta ttcaatggag  37080
tgccaaaaaa tgactatgag tcttaaagag ttaggcatat aaatatttta aggtttctgt  37140
tcaatgtatg ttggaaggag ttcctttctc atgactattc tcatattgga gcataaaaag  37200
agtttacagg cttggcgcag tggctcatgc ctgtaatccc aatactttgg gaagctgaag  37260
caggcagatc acttcagccc aggagtttga gaccagcctg ggcaatatgg caaaactctc  37320
tctacaaaat ataccaaaat tagccaggcg tggtggtgca tgcctgtagt cccagctact  37380
```

-continued

```
tgggaagctg aggtgggagg attgcttgag cccagggggg tcatggctgc agtgagctgt  37440
gatggtgcct ctgtcaccca gcctgggtga cagagtgaga ccctgtctca aaaaaataaa  37500
taaataaaaa ttaagagttt acaaaattct caccatctcc tcccatcttt gcaaatgcca  37560
cataagtgat gtgttccagg actattagcc tcggaacctg aggcagtaca gtaagcacgc  37620
tttctccaaa gtcctgtccc ccacagacaa acattattta cactgggtac tgctctttta  37680
ttttttcccc tctatgcttt attttactat aactataatc atataacatg taataggaaa  37740
aaggcagggt cgggggagag atccagaagt cttcccaaga gcctttccaa catagcctct  37800
gtagacattt tttctttctt cttttttttt tttttttttt ttctgagaca gagtctcact  37860
ctgttgtcca ggctagagtg cagtggcgtg atctaggctc actgcaacct ccgcctcctg  37920
ggttcaagca attctcccac ctcagcctcc ctagtagctg ggattagagg catgcatcac  37980
cacgcctggc taatttttgt atttttagta gagatgaggt ttcaccatgt gggccaggct  38040
ggtcttgaac tcctgacctc aagtgatcca cctgccttag cctcccaaag tgctaggatt  38100
acacgagtga gccaccgtgc cctgccccta ttacattctg atcacacatt tcatgtttta  38160
taattggaaa actggtgaaa ttatagacaa tgttttgttc ccctaaattc tctttgatga  38220
gtatatatta cttacactct tctgtcttta aaattttgca aaatagtatc ctagataagt  38280
ttatgagtgc acagtctgta cgcttactca tattaatgac ctcggagagt taaacaacag  38340
tcacctttaa aaattattac tatcattatc attattttg aggcgggggt ctcattctgt  38400
ctcccaggct ggagagtagt ggtgcggtca cagctcactg cagccaccgc tacctgggct  38460
caagtgatcc ttcctcctca gccttctgag tagctgagac cacaggctta tgctaccaca  38520
cctggctaat tttttaactt tttgtagaga cgatgtctca ttatgttgcc caggctggtc  38580
tcaaactcct aagctcaagt gatcttcctc agcctcccaa agtgctggga ttacaggcat  38640
gaaaaactgc acccagccct aaaaattatt agggtcctgc atagtaagac tttaataaat  38700
atttaaatga acatctggtt tttttaaaaa aaaaatagag acaaggtctc actatattgc  38760
ccaagctggt ctcgaactcc tggactcacg caatcctgct gccttagccg cccaaagtgc  38820
tgggattaca ggcatgaccc acctcatctg ggctgagtga acatattttt aacataaagg  38880
ccgtatttta tatttatctc atacattttg cccagcatcc ccatttccgc cgaatctgtt  38940
gcttgctaat tccttccagc ttcatttcat ctgaaatttg acaaacatct tctatttctt  39000
tgtcgtcatg ttattgactt cagaatataa aataaaacac tatacccaaa ttaaacccca  39060
ccctcattgc ccagcctgat gtgaaaataa tcagcataca ttaagcttac ccttgatata  39120
tgtgtagcat cttttagata aatatacagc tgattaagca atatagcctg atggtataat  39180
atcttgccca tgtacctcat cttatctcca gcaggattaa ttcacagtga tcagatttac  39240
ctttaaactt tgtagcaaaa tatcctctcc aaaagcatat ctaaaacttt tgtgtgtact  39300
cttgcaagtt tcttaatttc atgcagaaca ggctcttacc actgttagct ggagatattt  39360
tcaagaccta tttttgtttg tggtttcctg atgatggtca tggcatttcc cccttcactc  39420
catctaaaaa ttgaggtgat acaggctttt aaacaaaacc aactcatata gactgagtac  39480
aactgcaatg caggcatgct aacctctgct acaatcatgg gcgtgctatt gatatgtctt  39540
aagttacaga acacagggct gagcgtctca ttaggtcaaa atgtaaacca gtttttctgc  39600
tcactgatgc ttaatgagga cagggtgtga gagatttctt taaggaaaac aaatatataa  39660
taatgctaca tggaaaaata tctaacatta gagaattaag taaataaact aatatactca  39720
```

-continued

```
caccatggaa tcttgtgcag acattaaaat tatgtagtgg atggatgttt aatggtgtga  39780
gaaaaagtta ggatgtgctg gggtgggggg aagaatcaag ttttaagaaa atacagtata  39840
cccatactta agtaaaaaaa aaaaaaaagg tatgtacagt catgtgttgc ttaatgatgg  39900
ggatacattc cgagaaatgt gtcgataggt gatttcatcc ttgtgtgaac atcatagagt  39960
gaacttacac aaacctagat ggtctagcct actatgtatc taggctatat gactagcctg  40020
ttgctcctag gctacaaacc tgtaaagcat gttactgtag cgaatataca aatacttaac  40080
acaatggcaa gctatcattg tgttaagtag ttgtgtatct aaacatatct aaaacataga  40140
aaactaatgt gttgtgctac aatgttacaa tgactatgac attgctaggc aataggaatt  40200
ataattttat ccttttatgg aaccacactt atatatgcgg tccatggtgg accaaaacat  40260
ccttatgtgg catatgactg tatacatgta cacaaaaaat agatgaaaga atgaatatac  40320
atcaaaatat ttaaaatggt tataatgact taggttactt ttatttatct tagtaataat  40380
aatgatgata gataatactt ttatagtgtt tactatataa aagacactgt tataagtgtt  40440
ctacatactt tacatgtatt acctaaatga tataaatata actctgacag taactaatct  40500
tatacgttct cttttctttt tttttttttt cttttttttag acagaatctt gctctaccag  40560
gctggagtgc agggtgcaat ctcggctcac tgcaacctcc gcctcccagg ttcaaacgat  40620
tctcatgtct cagcctcctg agtagctggg actacaggca cacaccacca tgcccggcta  40680
atttttgtat ttttgggtag agatggagtt ttgccatgtt ggccaggctg atcttgaact  40740
cctggcctca agtgatctgc ctgcctcagc ctcccaaagt gctgggatta caggtgtgaa  40800
ccactgtgct cggcctaatc ttacaagttt tcaatattta aagagtgcta actttgttga  40860
caatataaaa catatttgag aaaaagagat ataagcatct tatttagaat tatgaaaata  40920
tcaatagacc tacagccgac taaagctttt cttcataagc tcttgcctat attgattcgc  40980
tcctgtgaat atgcattaat ttgatttaaa taataagtat gtataagaaa taacactttt  41040
ccttaatttt taagaacgtt caacagtttt taatttgaat tccaatagtg aaatacatag  41100
aaaatataaa attttctgta gtttagccaa attgtttttg tttcaccaca gcattctacc  41160
aaaatttctt aataacagta agaaaatgaa tgcatacctc ctgcagggag aggggagtta  41220
ggcagtttat gggcatagtt acaagtgaga aatttcattg gctaccattt acgctaaatt  41280
cataaaaact gcattcaatt ctatatatct attttcttta cataaaaaag gtttcaatta  41340
ttggccatta aataaaatag ccaccattcc agaagttgtg tcatgtttat ccttttttata  41400
ccaccatcat attgcctatt atatagattg tgtgtgttcc attttctgta atgggccaga  41460
cagtaagtat ttctggcttt ggagtccata tggtctctat cataactact catctctgcc  41520
attgtagctt aaagattatc taggtcaaat gcctaagtga tatagtgttg aaatacaagt  41580
tatataatat aggctgccac aaaaaaaaat ttatttggtc taaaaaagat ttcatgactt  41640
ttgtagcagc atgggtgggg catgcaccac ttggttaact cggtgtatct ttctcctttg  41700
cagatctgtc caactcaatg gtctaactct aaagatggtg gatgatcaaa ccttgccacc  41760
tttaatggaa aaacctctcc ggccaggaag ttcactgggc ttgccagctt tctcatatag  41820
tttttttgtg ataagaaatg ccaaagttgc tgcttgcatc tgaaaataaa atatactagt  41880
cctgacactg aatttttcaa gtatactaag agtaaagcaa ctcaagttat aggaaaggaa  41940
gcagatacct tgcaaagcaa ctagtgggtg cttgagagac actgggacac tgtcagtgct  42000
agatttagca cagtattttg atctcgctag gtagaacact gctaataata atagctaata  42060
ataccttgtt ccaaatactg cttagcattt tgcatgtttt acttttatct aaagttttgt  42120
```

-continued

```
tttgttttat tatttattta tttatttatt ttgagacaga atctctctct gtcacccagg  42180
ctggagtgcc atggtgcgat cttggctcac tgcaacttta agcaattctc ctgcctcagc  42240
ttcctgagta gctgggatta taggcgtgtg ccaccacgcc cagctacttt ctatattttt  42300
tgtagagatg gagtttcgcc atattggcca agctggtctc gaactcctgt cctcgaactc  42360
ctgtcctcaa gtgatccacc cgcctcagcc tctcaaagtg ctgggattac aggtgtgagc  42420
caccacaccc agcagtgttt tatttttgag acagggtatc attctgttgc ccaggcttga  42480
gtgcagtggt gcaatcatag atcactgcag ccttttaact cctgggctca agtcatcctc  42540
ctgcttagcc tcccaagtag ctaggaccac agacacatgc catcacactt ggctattttt  42600
aaaaaatttt ttgtagagat ggggtctcgc tatgttaccc aaactggtcc tgaactcctg  42660
gactcaattg atcctcccac cttggccttc caggtgctgg gatttctttg ggagtacagc  42720
atggtacagc aggagatcat ttgatgttac ctctgtgcag tgttgctagt cagcgaaaga  42780
ctataatacc tgtggggaca gcgattagcc accacaacca gtctttattt aaagttatta  42840
aaaatggctg ggcgcagtgg ctcacacctg taatcctagc actttgggag gccgaggcag  42900
atggatcacc tgacgtgagg aatttgagac cagcctggcc aacatggtga aaccccatct  42960
ctactaaaaa atacaaaaat tagctgggtg tggtcctgta gtcccagcta cttgggaggc  43020
tggggcagga gaattacttg aacccaggag gcagaggttg cagtgagccg agattgtgcc  43080
actgcactcc agcctgggtg acagagagag attccatctc aaaaaaacaa gttattaaaa  43140
atgtatatga atgctcctaa tatggtcagg aagcaaggaa gcgaaggata tattatgagt  43200
tttaagaagg tgcttagctg tatatttatc tttcaaaatg tattagaaga ttttagaatt  43260
ctttccttca tgtgccatct ctacaggcac ccatcagaaa aagcatactg ccgttaccgt  43320
gaaactggtt gtaaaagaga aactatctat ttgcacctta aaagacagct agattttgct  43380
gattttcttc tttcggtttt ctttgtcagc aataatatgt gagaggacag attgttagat  43440
atgatagtat aaaaaatggt taatgacaat tcagaggcga ggagattctg taaacttaaa  43500
attactataa atgaaattga tttgtcaaga ggataaattt tagaaaacac ccaatacctt  43560
ataactgtct gttaatgctt gctttttctc tacctttctt ccttgtttca gttgggaagc  43620
ttttggctgc aagtaacaga aactcctaat tcaaatggct taagcaataa ggaaatgtat  43680
attcccacat aactagacgt tcaaacaggc caggctccag cacttcagta cgtcaccagg  43740
gatctgggtt cttcccagct ctctgctctg ccatctttag cgctggcttc attctcagac  43800
tctggtagca tgatggctgt agctgtttca tgggcccctt caaacctcat agcaaccaga  43860
ggaagaaaat gagccatttt ttgagtctcc ttcatagact tgaataactc tttttcagag  43920
cttctcacag caaacctctc ctcatgtctc ctcatgtctt attgttcaga aatgggtaat  43980
gtggccattt caccagtcac tgccaacaac aacgaggttc ctataattgt ctctgagtaa  44040
ccctttggaa tggagagggt gttggtcagt ctacaaactg aacactgcag ttctgcgctt  44100
tttaccagtg aaaaaatgta attattttcc cctcttaagg attaatattc ttcaaatgta  44160
tgcctgttat ggatatagta tctttaaaat tttttatttt aatagcttta ggggtacaca  44220
ctttttgctt acaggggtga attgtgtagt ggtgaagact cggcttttaa tgtacttgtc  44280
acctgagtga tgtacattgt acccaatagg taatttttca tccattaccc tccttccgcc  44340
ctcttccctt ctgagtctcc aacatccctt ataccactgt gtatgttctt gtgtacctac  44400
agctaagctt ccacttataa gtgagaacat gcagtatttg gttttccatt cctgagttac  44460
```

-continued

```
ttcccttagg ataacagccc ccagttccgt ccaagttgct gcaaaataca ttattcttct  44520

ttatggctga gtaatagtcc atggtacata tataccacat tttctttatc cacttatcag  44580

ttgatggaca cttaggttaa ttccattcaa tttcattcaa tttaagtata tttgtaagga  44640

gctaaagctg aaaattaaat tttagatctt tcaatactct taaattttat atgtaagtgg  44700

tttttatatt ttcacatttg aaataaagta atttttataa ccttgatatt gtatgactat  44760

tcttttagta atgtaaagcc tacagactcc tacatttgga accactagtg tgttgtttca  44820

ccccttgtta tactatcagg atcctcga                                    44848
```

<210> SEQ ID NO 43
<211> LENGTH: 2396
<212> TYPE: DNA
<213> ORGANISM: Mus musculus

<400> SEQUENCE: 43

```
tttctagttg cttttagcca atgtcggatc aggtttttca agcgacaaag agatactgag    60

atcctgggca gaggacatcc tagctcggtc agatttgggc aggctcaagt gaccagtgtc   120

ttaaggcaga agggagtcgg ggtagggtct ggctgaaccc tcaaccgggg cttttaactc   180

agggtctagt cctggcgcca aatggatggg acctagaaaa ggtgacagag tgcgcaggac   240

accaggaagc tggtcccacc cctgcgcggc tcccgggcgc tccctcccca ggcctccgag   300

gatcttggat tctggccacc tccgcaccct ttggatgggt gtggatgatt tcaaaagtgg   360

acgtgaccgc ggcggagggg aaagccagca cggaaatgaa agagagcgag gaggggaggg   420

cggggagggg agggcgctag ggagggactc ccgggagggg tgggagggat ggagcgctgt   480

gggagggtac tgagtcctgg cgccagaggc gaagcaggac cggttgcagg gggcttgagc   540

cagcgcgccg gctgccccag ctctcccggc agcgggcggt ccagccaggt gggatgctga   600

ggctgctgct gctgtggctc tgggggccgc tcggtgccct ggcccagggc gcccccgcgg   660

ggaccgcgcc gaccgacgac gtggtagact tggagtttta caccaagcgg ccgctccgaa   720

gcgtgagtcc ctcgttcctg tccatcacca tcgacgccag cctggccacc gacccgcgct   780

tcctcacctt cctgggctct ccaaggctcc gtgctctggc tagaggctta tctcctgcat   840

acttgagatt tggcggcaca aagactgact tccttatttt tgatccggac aaggaaccga   900

cttccgaaga aagaagttac tggaaatctc aagtcaacca tgatatttgc aggtctgagc   960

cggtctctgc tgcggtgttg aggaaactcc aggtggaatg gcccttccag gagctgttgc  1020

tgctccgaga gcagtaccaa aaggagttca agaacagcac ctactcaaga agctcagtgg  1080

acatgctcta cagttttgcc aagtgctcgg ggttagacct gatctttggt ctaaatgcgt  1140

tactacgaac cccagactta cggtggaaca gctccaacgc ccagcttctc cttgactact  1200

gctcttccaa gggttataac atctcctggg aactgggcaa tgagcccaac agtttctgga  1260

agaaagctca cattctcatc gatgggttgc agttaggaga agactttgtg gagttgcata  1320

aacttctaca aaggtcagct ttccaaaatg caaaactcta tggtcctgac atcggtcagc  1380

ctcgagggaa gacagttaaa ctgctgagga gtttcctgaa ggctggcgga gaagtgatcg  1440

actctcttac atggcatcac tattacttga atggacgcat cgctaccaaa gaagattttc  1500

tgagctctga tgcgctggac acttttattc tctctgtgca aaaaattctg aaggtcacta  1560

aagagatcac acctggcaag aaggtctggt tgggagagac gagctcagct tacggtggcg  1620

gtgcaccctt gctgtccaac acctttgcag ctggctttat gtggctggat aaattgggcc  1680

tgtcagccca gatgggcata gaagtcgtga tgaggcaggt gttcttcgga gcaggcaact  1740
```

-continued

```
accacttagt ggatgaaaac tttgagcctt tacctgatta ctggctctct cttctgttca   1800

agaaactggt aggtcccagg gtgttactgt caagagtgaa aggcccagac aggagcaaac   1860

tccgagtgta tctccactgc actaacgtct atcacccacg atatcaggaa ggagatctaa   1920

ctctgtatgt cctgaacctc cataatgtca ccaagcactt gaaggtaccg cctccgttgt   1980

tcaggaaacc agtggatacg taccttctga agccttcggg gccggatgga ttactttcca   2040

aatctgtcca actgaacggt caaattctga agatggtgga tgagcagacc ctgccagctt   2100

tgacagaaaa acctctcccc gcaggaagtg cactaagcct gcctgccttt tcctatggtt   2160

tttttgtcat aagaaatgcc aaaatcgctg cttgtatatg aaaataaaag gcatacggta   2220

cccctgagac aaaagccgag gggggtgtta ttcataaaac aaaaccctag tttaggaggc   2280

cacctccttg ccgagttcca gagcttcggg agggtggggt acacttcagt attacattca   2340

gtgtggtgtt ctctctaaga agaatactgc aggtggtgac agttaatagc actgtg       2396
```

```
<210> SEQ ID NO 44
<211> LENGTH: 535
<212> TYPE: PRT
<213> ORGANISM: Mus musculus

<400> SEQUENCE: 44

Met Leu Arg Leu Leu Leu Leu Trp Leu Trp Gly Pro Leu Gly Ala Leu
1               5                   10                  15

Ala Gln Gly Ala Pro Ala Gly Thr Ala Pro Thr Asp Asp Val Val Asp
            20                  25                  30

Leu Glu Phe Tyr Thr Lys Arg Pro Leu Arg Ser Val Ser Pro Ser Phe
        35                  40                  45

Leu Ser Ile Thr Ile Asp Ala Ser Leu Ala Thr Asp Pro Arg Phe Leu
    50                  55                  60

Thr Phe Leu Gly Ser Pro Arg Leu Arg Ala Leu Ala Arg Gly Leu Ser
65                  70                  75                  80

Pro Ala Tyr Leu Arg Phe Gly Gly Thr Lys Thr Asp Phe Leu Ile Phe
                85                  90                  95

Asp Pro Asp Lys Glu Pro Thr Ser Glu Glu Arg Ser Tyr Trp Lys Ser
            100                 105                 110

Gln Val Asn His Asp Ile Cys Arg Ser Glu Pro Val Ser Ala Ala Val
        115                 120                 125

Leu Arg Lys Leu Gln Val Glu Trp Pro Phe Gln Glu Leu Leu Leu Leu
    130                 135                 140

Arg Glu Gln Tyr Gln Lys Glu Phe Lys Asn Ser Thr Tyr Ser Arg Ser
145                 150                 155                 160

Ser Val Asp Met Leu Tyr Ser Phe Ala Lys Cys Ser Gly Leu Asp Leu
                165                 170                 175

Ile Phe Gly Leu Asn Ala Leu Leu Arg Thr Pro Asp Leu Arg Trp Asn
            180                 185                 190

Ser Ser Asn Ala Gln Leu Leu Leu Asp Tyr Cys Ser Ser Lys Gly Tyr
        195                 200                 205

Asn Ile Ser Trp Glu Leu Gly Asn Glu Pro Asn Ser Phe Trp Lys Lys
    210                 215                 220

Ala His Ile Leu Ile Asp Gly Leu Gln Leu Gly Glu Asp Phe Val Glu
225                 230                 235                 240

Leu His Lys Leu Leu Gln Arg Ser Ala Phe Gln Asn Ala Lys Leu Tyr
                245                 250                 255
```

-continued

```
Gly Pro Asp Ile Gly Gln Pro Arg Gly Lys Thr Val Lys Leu Leu Arg
            260                 265                 270

Ser Phe Leu Lys Ala Gly Gly Glu Val Ile Asp Ser Leu Thr Trp His
        275                 280                 285

His Tyr Tyr Leu Asn Gly Arg Ile Ala Thr Lys Glu Asp Phe Leu Ser
    290                 295                 300

Ser Asp Ala Leu Asp Thr Phe Ile Leu Ser Val Gln Lys Ile Leu Lys
305                 310                 315                 320

Val Thr Lys Glu Ile Thr Pro Gly Lys Lys Val Trp Leu Gly Glu Thr
                325                 330                 335

Ser Ser Ala Tyr Gly Gly Gly Ala Pro Leu Leu Ser Asn Thr Phe Ala
            340                 345                 350

Ala Gly Phe Met Trp Leu Asp Lys Leu Gly Leu Ser Ala Gln Met Gly
        355                 360                 365

Ile Glu Val Val Met Arg Gln Val Phe Phe Gly Ala Gly Asn Tyr His
    370                 375                 380

Leu Val Asp Glu Asn Phe Glu Pro Leu Pro Asp Tyr Trp Leu Ser Leu
385                 390                 395                 400

Leu Phe Lys Lys Leu Val Gly Pro Arg Val Leu Leu Ser Arg Val Lys
                405                 410                 415

Gly Pro Asp Arg Ser Lys Leu Arg Val Tyr Leu His Cys Thr Asn Val
            420                 425                 430

Tyr His Pro Arg Tyr Gln Glu Gly Asp Leu Thr Leu Tyr Val Leu Asn
        435                 440                 445

Leu His Asn Val Thr Lys His Leu Lys Val Pro Pro Pro Leu Phe Arg
    450                 455                 460

Lys Pro Val Asp Thr Tyr Leu Leu Lys Pro Ser Gly Pro Asp Gly Leu
465                 470                 475                 480

Leu Ser Lys Ser Val Gln Leu Asn Gly Gln Ile Leu Lys Met Val Asp
                485                 490                 495

Glu Gln Thr Leu Pro Ala Leu Thr Glu Lys Pro Leu Pro Ala Gly Ser
            500                 505                 510

Ala Leu Ser Leu Pro Ala Phe Ser Tyr Gly Phe Phe Val Ile Arg Asn
        515                 520                 525

Ala Lys Ile Ala Ala Cys Ile
    530                 535
```

<210> SEQ ID NO 45
<211> LENGTH: 2396
<212> TYPE: DNA
<213> ORGANISM: Mus musculus
<220> FEATURE:
<221> NAME/KEY: CDS
<222> LOCATION: (594)..(2198)
<223> OTHER INFORMATION:

<400> SEQUENCE: 45

```
tttctagttg cttttagcca atgtcggatc aggtttttca agcgacaaag agatactgag     60

atcctgggca gaggacatcc tagctcggtc agatttgggc aggctcaagt gaccagtgtc    120

ttaaggcaga agggagtcgg ggtagggtct ggctgaaccc tcaaccgggg cttttaactc    180

agggtctagt cctggcgcca aatggatggg acctagaaaa ggtgacagag tgcgcaggac    240

accaggaagc tggtcccacc cctgcgcggc tcccgggcgc tccctcccca ggcctccgag    300

gatcttggat tctggccacc tccgcaccct ttggatgggt gtggatgatt tcaaaagtgg    360

acgtgaccgc ggcggagggg aaagccagca cggaaatgaa agagagcgag gaggggaggg    420
```

-continued

```
cggggagggg agggcgctag ggagggactc ccgggagggg tgggagggat ggagcgctgt    480

gggagggtac tgagtcctgg cgccagaggc gaagcaggac cggttgcagg gggcttgagc    540

cagcgcgccg gctgccccag ctctcccggc agcgggcggt ccagccaggt ggg atg       596
                                                           Met
                                                           1

ctg agg ctg ctg ctg ctg tgg ctc tgg ggg ccg ctc ggt gcc ctg gcc      644
Leu Arg Leu Leu Leu Leu Trp Leu Trp Gly Pro Leu Gly Ala Leu Ala
            5                   10                  15

cag ggc gcc ccc gcg ggg acc gcg ccg acc gac gac gtg gta gac ttg      692
Gln Gly Ala Pro Ala Gly Thr Ala Pro Thr Asp Asp Val Val Asp Leu
        20                  25                  30

gag ttt tac acc aag cgg ccg ctc cga agc gtg agt ccc tcg ttc ctg      740
Glu Phe Tyr Thr Lys Arg Pro Leu Arg Ser Val Ser Pro Ser Phe Leu
    35                  40                  45

tcc atc acc atc gac gcc agc ctg gcc acc gac ccg cgc ttc ctc acc      788
Ser Ile Thr Ile Asp Ala Ser Leu Ala Thr Asp Pro Arg Phe Leu Thr
50                  55                  60                  65

ttc ctg ggc tct cca agg ctc cgt gct ctg gct aga ggc tta tct cct      836
Phe Leu Gly Ser Pro Arg Leu Arg Ala Leu Ala Arg Gly Leu Ser Pro
                70                  75                  80

gca tac ttg aga ttt ggc ggc aca aag act gac ttc ctt att ttt gat      884
Ala Tyr Leu Arg Phe Gly Gly Thr Lys Thr Asp Phe Leu Ile Phe Asp
            85                  90                  95

ccg gac aag gaa ccg act tcc gaa gaa aga agt tac tgg aaa tct caa      932
Pro Asp Lys Glu Pro Thr Ser Glu Glu Arg Ser Tyr Trp Lys Ser Gln
        100                 105                 110

gtc aac cat gat att tgc agg tct gag ccg gtc tct gct gcg gtg ttg      980
Val Asn His Asp Ile Cys Arg Ser Glu Pro Val Ser Ala Ala Val Leu
    115                 120                 125

agg aaa ctc cag gtg gaa tgg ccc ttc cag gag ctg ttg ctg ctc cga     1028
Arg Lys Leu Gln Val Glu Trp Pro Phe Gln Glu Leu Leu Leu Leu Arg
130                 135                 140                 145

gag cag tac caa aag gag ttc aag aac agc acc tac tca aga agc tca     1076
Glu Gln Tyr Gln Lys Glu Phe Lys Asn Ser Thr Tyr Ser Arg Ser Ser
                150                 155                 160

gtg gac atg ctc tac agt ttt gcc aag tgc tcg ggg tta gac ctg atc     1124
Val Asp Met Leu Tyr Ser Phe Ala Lys Cys Ser Gly Leu Asp Leu Ile
            165                 170                 175

ttt ggt cta aat gcg tta cta cga acc cca gac tta cgg tgg aac agc     1172
Phe Gly Leu Asn Ala Leu Leu Arg Thr Pro Asp Leu Arg Trp Asn Ser
        180                 185                 190

tcc aac gcc cag ctt ctc ctt gac tac tgc tct tcc aag ggt tat aac     1220
Ser Asn Ala Gln Leu Leu Leu Asp Tyr Cys Ser Ser Lys Gly Tyr Asn
    195                 200                 205

atc tcc tgg gaa ctg ggc aat gag ccc aac agt ttc tgg aag aaa gct     1268
Ile Ser Trp Glu Leu Gly Asn Glu Pro Asn Ser Phe Trp Lys Lys Ala
210                 215                 220                 225

cac att ctc atc gat ggg ttg cag tta gga gaa gac ttt gtg gag ttg     1316
His Ile Leu Ile Asp Gly Leu Gln Leu Gly Glu Asp Phe Val Glu Leu
                230                 235                 240

cat aaa ctt cta caa agg tca gct ttc caa aat gca aaa ctc tat ggt     1364
His Lys Leu Leu Gln Arg Ser Ala Phe Gln Asn Ala Lys Leu Tyr Gly
            245                 250                 255

cct gac atc ggt cag cct cga ggg aag aca gtt aaa ctg ctg agg agt     1412
Pro Asp Ile Gly Gln Pro Arg Gly Lys Thr Val Lys Leu Leu Arg Ser
        260                 265                 270

ttc ctg aag gct ggc gga gaa gtg atc gac tct ctt aca tgg cat cac     1460
Phe Leu Lys Ala Gly Gly Glu Val Ile Asp Ser Leu Thr Trp His His
```

-continued

```
    275                 280                 285

tat tac ttg aat gga cgc atc gct acc aaa gaa gat ttt ctg agc tct      1508
Tyr Tyr Leu Asn Gly Arg Ile Ala Thr Lys Glu Asp Phe Leu Ser Ser
290                 295                 300                 305

gat gcg ctg gac act ttt att ctc tct gtg caa aaa att ctg aag gtc      1556
Asp Ala Leu Asp Thr Phe Ile Leu Ser Val Gln Lys Ile Leu Lys Val
                310                 315                 320

act aaa gag atc aca cct ggc aag aag gtc tgg ttg gga gag acg agc      1604
Thr Lys Glu Ile Thr Pro Gly Lys Lys Val Trp Leu Gly Glu Thr Ser
            325                 330                 335

tca gct tac ggt ggc ggt gca ccc ttg ctg tcc aac acc ttt gca gct      1652
Ser Ala Tyr Gly Gly Gly Ala Pro Leu Leu Ser Asn Thr Phe Ala Ala
        340                 345                 350

ggc ttt atg tgg ctg gat aaa ttg ggc ctg tca gcc cag atg ggc ata      1700
Gly Phe Met Trp Leu Asp Lys Leu Gly Leu Ser Ala Gln Met Gly Ile
    355                 360                 365

gaa gtc gtg atg agg cag gtg ttc ttc gga gca ggc aac tac cac tta      1748
Glu Val Val Met Arg Gln Val Phe Phe Gly Ala Gly Asn Tyr His Leu
370                 375                 380                 385

gtg gat gaa aac ttt gag cct tta cct gat tac tgg ctc tct ctt ctg      1796
Val Asp Glu Asn Phe Glu Pro Leu Pro Asp Tyr Trp Leu Ser Leu Leu
                390                 395                 400

ttc aag aaa ctg gta ggt ccc agg gtg tta ctg tca aga gtg aaa ggc      1844
Phe Lys Lys Leu Val Gly Pro Arg Val Leu Leu Ser Arg Val Lys Gly
            405                 410                 415

cca gac agg agc aaa ctc cga gtg tat ctc cac tgc act aac gtc tat      1892
Pro Asp Arg Ser Lys Leu Arg Val Tyr Leu His Cys Thr Asn Val Tyr
        420                 425                 430

cac cca cga tat cag gaa gga gat cta act ctg tat gtc ctg aac ctc      1940
His Pro Arg Tyr Gln Glu Gly Asp Leu Thr Leu Tyr Val Leu Asn Leu
    435                 440                 445

cat aat gtc acc aag cac ttg aag gta ccg cct ccg ttg ttc agg aaa      1988
His Asn Val Thr Lys His Leu Lys Val Pro Pro Pro Leu Phe Arg Lys
450                 455                 460                 465

cca gtg gat acg tac ctt ctg aag cct tcg ggg ccg gat gga tta ctt      2036
Pro Val Asp Thr Tyr Leu Leu Lys Pro Ser Gly Pro Asp Gly Leu Leu
                470                 475                 480

tcc aaa tct gtc caa ctg aac ggt caa att ctg aag atg gtg gat gag      2084
Ser Lys Ser Val Gln Leu Asn Gly Gln Ile Leu Lys Met Val Asp Glu
            485                 490                 495

cag acc ctg cca gct ttg aca gaa aaa cct ctc ccc gca gga agt gca      2132
Gln Thr Leu Pro Ala Leu Thr Glu Lys Pro Leu Pro Ala Gly Ser Ala
        500                 505                 510

cta agc ctg cct gcc ttt tcc tat ggt ttt ttt gtc ata aga aat gcc      2180
Leu Ser Leu Pro Ala Phe Ser Tyr Gly Phe Phe Val Ile Arg Asn Ala
    515                 520                 525

aaa atc gct gct tgt ata tgaaaataaa aggcatacgg tacccctgag             2228
Lys Ile Ala Ala Cys Ile
530                 535

acaaaagccg agggggtgt tattcataaa acaaaaccct agtttaggag gccacctcct   2288

tgccgagttc cagagcttcg ggagggtggg gtacacttca gtattacatt cagtgtggtg   2348

ttctctctaa gaagaatact gcaggtggtg acagttaata gcactgtg                2396
```

<210> SEQ ID NO 46
<211> LENGTH: 385
<212> TYPE: DNA
<213> ORGANISM: Rattus norvegicus

<400> SEQUENCE: 46

-continued

```
cggccgctgc tgctgctgtg gctctggggg cggctccgtg ccctgaccca aggcactccg     60

gcggggaccg cgccgaccaa agacgtggtg gacttggagt tttacaccaa gaggctattc    120

caaagcgtga gtccctcgtt cctgtccatc accatcgacg ccagtctggc caccgaccct    180

cggttcctca ccttcctgag ctctccacgg cttcgagccc tgtctagagg cttatctcct    240

gcgtacttga gatttggcgg caccaagact gacttcctta tttttgatcc caacaacgaa    300

cccacctctg aagaaagaag ttactggcaa tctcaagaca acaatgatat ttgcgggtct    360

gaccgggtct ccgctgacgt gttga                                          385
```

<210> SEQ ID NO 47
<211> LENGTH: 541
<212> TYPE: DNA
<213> ORGANISM: Rattus norvegicus
<220> FEATURE:
<221> NAME/KEY: misc_feature
<222> LOCATION: (507)..(507)
<223> OTHER INFORMATION: Any nucleotide

<400> SEQUENCE: 47

```
aaatcaggac atatccttca cttatttgcc tcttggtcat attggaggca tttgtattca     60

tttttaataa ccctcaaaat agtgcatgca aagtgctaag cgtcatttgc cacatggtgc    120

cattaactgt caccacctgc agtggtctac ttagagaaca ccgcactgga tgttaacact    180

gaagcgcgtg ccccgccctc ccgaggctct ggatccagcg ttgaagcttg ccccgccctc    240

ccgaggctct ggatccagca ctggagcatg ccccgccctc ccgaggctct ggagcttgct    300

aaggagtccg ctccctaccg ctggggtttt gctttattct tatgaatgac acccctgacc    360

gctttcgtct caggggtact gtaatgcctt ttattttcat atacaagctg cgattttggc    420

atttcttatg acaaaaaacc cataggaaaa ggcgggcacg cttagtgagc ttcctgcggg    480

gagaggtttt tctgttagag ctggcanggt ctgctcatcg accatcttca ggcctcgtgc    540

c                                                                    541
```

<210> SEQ ID NO 48
<211> LENGTH: 532
<212> TYPE: PRT
<213> ORGANISM: Rattus norvegicus
<220> FEATURE:
<221> NAME/KEY: misc_feature
<222> LOCATION: (127)..(488)
<223> OTHER INFORMATION: Xaa can be any naturally occurring amino acid
<220> FEATURE:
<221> NAME/KEY: misc_feature
<222> LOCATION: (497)..(497)
<223> OTHER INFORMATION: Xaa can be any naturally occurring amino acid

<400> SEQUENCE: 48

```
Leu Leu Leu Leu Trp Leu Trp Gly Arg Leu Arg Ala Leu Thr Gln Gly
1               5                   10                  15

Thr Pro Ala Gly Thr Ala Pro Thr Lys Asp Val Val Asp Leu Glu Phe
            20                  25                  30

Tyr Thr Lys Arg Leu Phe Gln Ser Val Ser Pro Ser Phe Leu Ser Ile
        35                  40                  45

Thr Ile Asp Ala Ser Leu Ala Thr Asp Pro Arg Phe Leu Thr Phe Leu
    50                  55                  60

Ser Ser Pro Arg Leu Arg Ala Leu Ala Arg Gly Leu Ser Pro Ala Tyr
65                  70                  75                  80

Leu Arg Phe Gly Gly Thr Lys Thr Asp Phe Leu Ile Phe Asp Pro Asn
```

-continued

```
                85                  90                  95

Asn Glu Pro Thr Ser Glu Glu Arg Ser Tyr Trp Gln Ser Gln Asp Asn
            100                 105                 110

Asn Asp Ile Cys Gly Ser Asp Arg Val Ser Ala Asp Val Leu Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Leu Lys Met Val Asp Glu Gln Thr
                485                 490                 495

Xaa Pro Ala Leu Thr Glu Lys Pro Leu Pro Ala Gly Ser Ser Leu Ser
            500                 505                 510
```

-continued

```
Val Pro Ala Phe Ser Tyr Gly Phe Phe Val Ile Arg Asn Ala Lys Ile
        515                 520                 525

Ala Ala Cys Ile
    530
```